US012331295B2

(12) United States Patent
Maori et al.

(10) Patent No.: US 12,331,295 B2
(45) **Date of Patent: *Jun. 17, 2025**

(54) MODIFYING THE SPECIFICITY OF PLANT NON-CODING RNA MOLECULES FOR SILENCING GENE EXPRESSION

(71) Applicant: Tropic Biosciences UK Limited, Norwich (GB)

(72) Inventors: Eyal Maori, Cambridge (GB); Yaron Galanty, Cambridge (GB); Cristina Pignocchi, Norwich (GB); Angela Chaparro Garcia, Norwich (GB); Ofir Meir, Norwich (GB)

(73) Assignee: TROPIC BIOSCIENCES UK LIMITED, Norwich (GB)

( * ) Notice: Subject to any disclaimer, the term of this patent is extended or adjusted under 35 U.S.C. 154(b) by 4 days.

This patent is subject to a terminal disclaimer.

(21) Appl. No.: 18/152,718

(22) Filed: Jan. 10, 2023

(65) Prior Publication Data

US 2023/0279414 A1 Sep. 7, 2023

Related U.S. Application Data

(62) Division of application No. 16/648,748, filed as application No. PCT/IB2018/057160 on Sep. 18, 2018, now Pat. No. 11,555,199.

(30) Foreign Application Priority Data

Sep. 19, 2017 (GB) ..................................... 1715113
Sep. 19, 2017 (GB) ..................................... 1715116
Nov. 23, 2017 (GB) ..................................... 1719516

(51) Int. Cl.
*C12N 15/11* (2006.01)
*C12N 9/22* (2006.01)
*C12N 15/113* (2010.01)
*C12N 15/82* (2006.01)
*C12N 15/85* (2006.01)
*C12N 15/90* (2006.01)

(52) U.S. Cl.
CPC .............. *C12N 15/113* (2013.01); *C12N 9/22* (2013.01); *C12N 15/8213* (2013.01); *C12N 15/8279* (2013.01); *C12N 15/85* (2013.01); *C12N 15/902* (2013.01); *C12N 15/8218* (2013.01); *C12N 2310/11* (2013.01); *C12N 2310/141* (2013.01); *C12N 2310/20* (2017.05)

(58) Field of Classification Search
None
See application file for complete search history.

(56) References Cited

U.S. PATENT DOCUMENTS 3,791,932 A 2/1974 Schuurs et al.
3,839,153 A 10/1974 Schuurs et al.
3,850,578 A 11/1974 Mcconnell
3,850,752 A 11/1974 Schuurs et al.
3,853,987 A 12/1974 Dreyer
3,867,517 A 2/1975 Ling
3,879,262 A 4/1975 Schuurs et al.
3,901,654 A 8/1975 Gross
3,935,074 A 1/1976 Rubenstein et al.
3,984,533 A 10/1976 Uzgiris
3,996,345 A 12/1976 Ullman et al.
4,034,074 A 7/1977 Miles
4,098,876 A 7/1978 Piasio et al.
4,666,828 A 5/1987 Gusella et al.
4,683,202 A 7/1987 Mullis
4,801,531 A 1/1989 Frossard
4,855,237 A 8/1989 Morinaga et al.
4,873,316 A 10/1989 Meade et al.
4,879,219 A 11/1989 Wands et al.
4,945,050 A 7/1990 Sanford et al.
5,011,771 A 4/1991 Bellet et al.
5,015,580 A 5/1991 Christou et al.
5,192,659 A 3/1993 Simons et al.
5,272,057 A 12/1993 Smulson et al.
5,281,521 A 1/1994 Trojanowski et al.
(Continued)

FOREIGN PATENT DOCUMENTS

CN 105647962 A 6/2016
CN 105802991 A 7/2016
(Continued)

OTHER PUBLICATIONS

Jacobs et al (2015 BMC Technology 15:1-10 (Year: 2015), provided by Applicant.*
Kawahara et al (2007 Science 315:1137-1140 (Year: 2007), provided by Applicant.*
Bhattacharya and Cui (2017 Journal of Integrative Bioinformatics 2017:1-7 (Year: 2017), provided by Applicant.*
(Continued)

*Primary Examiner* — Brent T Page
(74) *Attorney, Agent, or Firm* — Morrison & Foerster LLP

(57) ABSTRACT

A method of modifying a gene encoding or processed into a non-coding RNA molecule having no RNA silencing activity in a plant cell is disclosed. The method comprising introducing into the plant cell a DNA editing agent conferring a silencing specificity of the non-coding RNA molecule towards a target RNA of interest. A method of modifying a gene encoding or processed into a RNA silencing molecule in a plant cell is also disclosed. The method comprising introducing into the plant cell a DNA editing agent which redirects the silencing specificity of the non-coding RNA molecule towards a target RNA of interest. Plant cells, plant seeds, plants, and methods of generating plants are also disclosed.

19 Claims, 20 Drawing Sheets
(18 of 20 Drawing Sheet(s) Filed in Color)
Specification includes a Sequence Listing.

(56) References Cited

U.S. PATENT DOCUMENTS

| | | | |
|---|---|---|---|
| 5,302,523 | A | 4/1994 | Coffee et al. |
| 5,316,931 | A | 5/1994 | Donson et al. |
| 5,384,253 | A | 1/1995 | Krzyzek et al. |
| 5,464,764 | A | 11/1995 | Capecchi et al. |
| 5,464,765 | A | 11/1995 | Coffee et al. |
| 5,486,359 | A | 1/1996 | Caplan et al. |
| 5,487,992 | A | 1/1996 | Capecchi et al. |
| 5,508,184 | A | 4/1996 | Negrutiu et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,591,616 | A | 1/1997 | Hiei et al. |
| 5,693,507 | A | 12/1997 | Daniell et al. |
| 5,693,512 | A | 12/1997 | Finer et al. |
| 5,824,877 | A | 10/1998 | Hinchee et al. |
| 5,886,164 | A | 3/1999 | Bird et al. |
| 5,981,840 | A | 11/1999 | Zhao et al. |
| 6,160,208 | A | 12/2000 | Lundquist et al. |
| 6,384,301 | B1 | 5/2002 | Martinell et al. |
| 6,399,861 | B1 | 6/2002 | Anderson et al. |
| 6,403,865 | B1 | 6/2002 | Koziel et al. |
| 8,021,867 | B2 | 9/2011 | Smith et al. |
| 8,119,381 | B2 | 2/2012 | Smith et al. |
| 8,124,369 | B2 | 2/2012 | Smith et al. |
| 8,129,134 | B2 | 3/2012 | Smith et al. |
| 8,133,697 | B2 | 3/2012 | Smith et al. |
| 8,143,015 | B2 | 3/2012 | Smith et al. |
| 8,143,016 | B2 | 3/2012 | Smith et al. |
| 8,148,098 | B2 | 4/2012 | Smith et al. |
| 8,163,514 | B2 | 4/2012 | Smith et al. |
| 8,304,222 | B1 | 11/2012 | Smith et al. |
| 11,555,199 | B2 | 1/2023 | Maori et al. |
| 2005/0203047 | A1 | 9/2005 | Thomann et al. |
| 2008/0293143 | A1 | 11/2008 | Lin et al. |
| 2010/0293671 | A1 | 11/2010 | Huang et al. |
| 2015/0047062 | A1 | 2/2015 | Lai et al. |
| 2015/0082478 | A1 | 3/2015 | Cigan et al. |
| 2016/0076093 | A1 | 3/2016 | Shendure et al. |
| 2016/0264994 | A1 | 9/2016 | Lawrence et al. |
| 2016/0289675 | A1 | 10/2016 | Ryan et al. |
| 2020/0102570 | A1 | 4/2020 | Maori et al. |
| 2020/0109408 | A1 | 4/2020 | Maori et al. |
| 2020/0248196 | A1 | 8/2020 | Maori et al. |
| 2020/0270604 | A1 | 8/2020 | Maori et al. |
| 2021/0222185 | A1 | 7/2021 | Maori et al. |
| 2021/0238618 | A1 | 8/2021 | Maori et al. |
| 2022/0154187 | A1 | 5/2022 | Maori et al. |
| 2022/0186219 | A1 | 6/2022 | Maori et al. |
| 2022/0220494 | A1 | 7/2022 | Maori et al. |
| 2023/0340512 | A1 | 10/2023 | Maori et al. |
| 2024/0309401 | A1 | 9/2024 | Maori et al. |

FOREIGN PATENT DOCUMENTS

| | | | |
|---|---|---|---|
| CN | 105899658 | A | 8/2016 |
| CN | 106367435 | B | 2/2017 |
| EP | 194809 | B1 | 3/1991 |
| EP | 264166 | B1 | 8/1996 |
| EP | 1020519 | A1 | 7/2000 |
| EP | 3266872 | A1 | 1/2018 |
| JP | 2016520317 | A | 7/2016 |
| JP | 2017532035 | A | 11/2017 |
| WO | WO-1987006261 | A1 | 10/1987 |
| WO | WO-1996000232 | A1 | 1/1996 |
| WO | WO-2003032713 | A2 | 4/2003 |
| WO | WO-2005111211 | A2 | 11/2005 |
| WO | WO-2006040763 | A2 | 4/2006 |
| WO | WO-2007048628 | A2 | 5/2007 |
| WO | WO-2008148223 | A1 | 12/2008 |
| WO | WO-2009046384 | A1 | 4/2009 |
| WO | WO-2011026644 | A2 | 3/2011 |
| WO | WO-2013126963 | A1 | 9/2013 |
| WO | WO-2014079896 | A1 | 5/2014 |
| WO | WO-2014107763 | A1 | 7/2014 |
| WO | WO-2014186686 | A2 | 11/2014 |
| WO | WO-2014191518 | A1 | 12/2014 |
| WO | WO-2015089613 | A1 | 6/2015 |
| WO | WO-2015123339 | A1 | 8/2015 |
| WO | WO-2016022400 | A1 | 2/2016 |
| WO | WO-2016057800 | A1 | 4/2016 |
| WO | WO-2016100333 | A1 | 6/2016 |
| WO | WO-2016196887 | A1 | 12/2016 |
| WO | WO-2017036351 | A1 | 3/2017 |
| WO | WO-2017123910 | A1 | 7/2017 |
| WO | WO-2018152633 | A1 | 8/2018 |
| WO | WO-2018178987 | A1 | 10/2018 |
| WO | WO-2018183878 | A1 | 10/2018 |
| WO | WO-2018220581 | A1 | 12/2018 |
| WO | WO-2018220582 | A1 | 12/2018 |
| WO | WO-2019005884 | A1 | 1/2019 |
| WO | WO-2019058253 | A1 | 3/2019 |
| WO | WO-2019058255 | A1 | 3/2019 |
| WO | WO-2020178099 | A1 | 9/2020 |
| WO | WO-2020183419 | A1 | 9/2020 |

OTHER PUBLICATIONS

Albani et al., (1997). "The wheat transcriptional activator SPA: a seed-specific bZIP protein that recognizes the GCN4-like motif in the bifactorial endosperm box of prolamin genes," Plant Cell, 9:171-184.

An et al., (1996). "Strong, constitutive expression of the *Arabidopsis* ACT2/ACT8 actin subclass in vegetative tissues," Plant J., 10(1);107-121.

Bartel, (2004). "MicroRNAs: genomics, biogenesis, mechanism, and function," Cell, 116(2):281-297.

Basak et al. "Targeting Non-Coding RNAs in Plant With the CRISPR-Cas Technology Is A Challenge Yet Worth Accepting", Frontiers in Plant Science, XP055528168, 6: 1001-l 1001-8, Published Online Nov. 19, 2015.

Bhattacharya et al., (2017). "Systematic Prediction of the Impacts of Mutations in MicroRNA Seed Sequences," Journal of Integrative Bioinformatics, 14:1-7.

Borges et al., (2015). "The expanding world of small RNAs in plants," Nature Reviews Molecular Cell Biology, 16:727-741, 35 pages.

Bortesi et al. "The CRISPR/Cas9 System for Plant Genome Editing and Beyond", Biotechnology Advances, 33(1): 41-52, Available Online Dec. 20, 2014.

Camargo Ramirez. "Function of Micro RN As in Plant Innate Immunity", Universitat Autonoma de Barcelona, PhHD Thesis, XP55550787, 209 Pages, Mar. 2017.

Carbonell et al. "New Generation of Artificial MicroRNA and Synthetic Trans- Acting Small Interfering RNA Vectors for Efficient Gene Silencing in *Arabidopsis*", Plant Physiology, 165(1): 15-29, May 2014.

Cermak et al., (2011). "Efficient design and assembly of custom TALEN and other TAL effector-based constructs for DNA targeting," Nucleic Acids Research, 39(12):e82, 11 pages.

Certo et al., (2012). "Coupling endonucleases with DNA end-processing enzymes to drive gene disruption," Nature Methods, 9:973-975, 10 pages.

Cheng et al. "Positional Cloning of Quantitative Trait Nucelotides for Blood Pressure and Cardiac QT-Interval by Targeted CRISPR/Cas9 Editing of A Novel Long Non-Coding RNA", PLOS Genetics, XP055528205, 13(8): el006961-1-el006961-20, Published Online Aug. 21, 2017. Fig.I.

Chiang et al., (2016). "CRISPR-Cas9D10A Nickase-Based Genotypic and Phenotypic Screening to Enhance Genome Editing", Scientific Reports, 6:24356, 17 pages.

Cho et al. "Heritable Gene Knockout in Caenorhabditis Elegans by Direct Injection of Cas9-SgRNA Ribonucleoproteins", Genetics, 195(3): 1177-1180, Nov. 2013.

Dai et al. "Exploiting *Drosophila* Genetics to Understand MicroRNA Function and Regulation", Current Topics in Developmental Biology, XP055550050, 99(Chap.8): 201-235, Jan. 2012.

De Pater et al., (1992). "The promoter of the rice gene GOS2 is active in various different monocot tissues and binds rice nuclear factor ASF-1," Plant J, 2(6):837-844.

(56) References Cited

OTHER PUBLICATIONS

Dowdy "Overcoming Cellular Barriers for RNA Therapeutics", Nature Biotechnology, 35(3): 1-8, Published Online Feb. 27, 2017.
Faisal et al., (2017). "Downregulation of the DST Transcription Factor Using Artificial microRNA to Increase Yield, Salt and Drought Tolerance in Rice," American Journal of Plant Sciences, 8(9):2219-2237.
Fan et al., (2015). "Efficient CRISPR/Cas9-mediated Targeted Mutagenesis in Populus in the First Generation," Sci Rep., 5(12217), 7 pages.
Fei "Functional Analysis of MicroRNA Triggers of Phased SIRNA Biogenesis in Plants", A Dissertation Submitted to the Faculty of the University of Delaware in Partial Fulfillment of the Requirements for the Degree of Doctor of Philosophy in Plant and Soil Sciences, XP055529765, p. 1-133, Summer 2016. p. 79-82.
Fujiki et al., (2008). "Development of a new cucumber mosaic virus-based plant expression vector with truncated 3a movement protein," Virology, 381(1):136-142.
Gallego-Giraldo et al., (2011). "Selective lignin downregulation leads to constitutive defense response expression in alfalfa (*Medicago sativa* L.)," New Phytologist, 190(3):627-639.
Garcia-Ruiz et al., (2010). "*Arabidopsis* RNA-Dependent RNA Polymerases and Dicer-Like Proteins in Antiviral Defense and Small Interfering RNA Biogenesis during Turnip Mosaic Virus Infection," The Plant Cell, 22:481-496.
Gaspar et al. "Long-Term Persistence of A Polyclonal T Cell Repertoire After Gene Therapy for X-Linked Severe Combined Immunodeficiency", Science Translational Medicine, 3(97): 97ra79-1-97ra79-7, Aug. 24, 2011.
Gutschner et al. "Noncoding RNA Gene Silencing Through Genomic Integration of RNA Destabilizing Elements Using Zinc Finger Nucleases", Genome Research, XP055197552, 21(11): 1944-1954, Published Online Aug. 15, 2011. p. 1953, Figs.2-4.
Ha et al. "Regulation of MicroRNA Biogenesis", Nature Reviews Molecular Cell Biology, XP055440474, 15(8): 509-524, Published Online Jul. 16, 2014.
Holen, (2006). "Efficient prediction of siRNAs with siRNA rules 1.0: An open-source JAVA approach to siRNA algorithms," RNA, 12:1620-1625.
Holoch et al., (2015). "RNA-mediated epigenetic regulation of gene expression," Nat Rev Genet., 16(2):71-84, 34 pages.
Howe et al. "Insertional Mutagenesis Combined With Acquired Somatic Mutations Causes Leukomogenesis Following Gene Therapy of SCID-XI Patients", The Journal of Clinical Investigation, 118(9): 3143-3150, Published Online Aug. 7, 2008.
Hu et al., (2015). "Down-regulation of Fusarium oxysporum endogenous genes by Host-Delivered RNA interference enhances disease resistance," Front Chem., 3:1-10.
Huo et al. "Lentiviral CRISPR/Cas9 Vector Mediated MIR-21 Gene Editing Inhibits the Epithelial to Mesenchymal Transition in Ovarian Cancer Cells", Journal of Cancer, XP055550172, 8(1): 57-64, Published Online Jan. 1, 2017.
International Preliminary Report on Patentability Dated Apr. 2, 2020 From the International Bureau of WIPO Re. Application No. PCT/IB2018/057143. (12 Pages).
International Preliminary Report on Patentability Dated Apr. 2, 2020 From the International Bureau of WIPO Re. Application No. PCT/IB2018/057160. (11 Pages).
International Search Report and the Written Opinion Dated Feb. 20, 2019 From the International Searching Authority Re. Application No. PCT/IB2018/057143. (25 Pages).
International Search Report and the Written Opinion Dated May 20, 2020 From the International Searching Authority Re. Application No. PCT/IB2020/052245. (15 Pages).
International Search Report and the Written Opinion Dated Feb. 25, 2019 From the International Searching Authority Re. Application No. PCT/IB2018/057160.(23 Pages).
International Search Report and the Written Opinion Dated May 25, 2020 From the International Searching Authority Re. Application No. PCT/IB2020/052248. (17 Pages).
Invitation to Pay Additional Fees, Communication Relating to the Result of the Partial International Search and the Provisional Opinion Dated Jun. 15, 2020 From the International Searching Authority Re. Application No. PCT/IB2020/052241. (20 Pages).
Invitation to Pay Additional Fees, Communication Relating to the Results of the Partial International Search and the Provisional Opinion Dated Dec. 21, 2018 From the International Searching Authority Re. Application No. PCT/IB2018/057143. (19 Pages).
Invitation to Pay Additional Fees, Communication Relating to the Results of the Partial International Search and the Provisional Opinion Dated Dec. 21, 2018 From the International Searching Authority Re. Application No. PCT/IB2018/057160. (18 Pages).
Jacobs et al. "Targeted Genome Modifications in Soybean With CRISPR/Cas9", CRISPR/Cas9, BMC Biotechnology, XP021219338, 15, 16: 1-10, Mar. 12, 2015.
Jiang et al. "Small Indels Induced by CRISPR/Cas9 in the 5' Region of MicroRNA Lead to Its Depletion and Drosha Processing Retardance", RNA Biology, 11(10): 1243-1249, Oct. 2014.
Jinek et al., (2012). "A Programmable Dual-RNA-Guided DNA Endonuclease in Adaptive Bacterial Immunity," Science, 337:816-821.
Jing et al. "CRISPR/CAS9-Mediated Genome Editing ofMiRNA-155 Inhibits Proinflammatory Cytokine Production by RA W264.7 Cells", Biomed Research International, XP055549680, 2015(Art.ID 326042): 1-7, Published Online Nov. 30, 2015.
Kawahara et al., (2007). "Redirection of silencing targets by adenosine-to-inosine editing of miRNAs," Science 315:1137-1140.
Kim et al., "Highly efficient RNA-guided genome editing in human cells via delivery of purified Cas9 ribonucleoproteins" Genome Res. (2014) 24:1012-1019.
Kozomara et al., (2014). "miRBase: annotating high confidence microRNAs using deep sequencing data," Nucleic Acids Res, 42:D68-D73.
Kukowska-Latallo et al., (1996). "Efficient transfer of genetic material into mammalian cells using Starburst polyamidoamine dendrimers," Proc. Natl. Acad. Sci. USA, 93:4897-4902.
Kumar et al., (2015). "The CRISPR-Cas system for plant genome editing: advances and opportunities," J Exp Bot, 66(1):47-57.
Lataniotis et al. "CRISPR/Cas9 Editing Reveals Novel Mechanisms of Clustered MicroRNA Regulation and Function", Scientific Reports, XP055528159, 7(8585): 1-14, Published Online Aug. 17, 2017.
Lawrenson et al., (2015). "Induction of targeted, heritable mutations in barley and Brassica oleracea using RNA-guided Cas9 nuclease," Gen Biol, 16:258, 13 pages.
Lewis et al., (2005). "Conserved Seed Pairing, Often Flanked by Adenosines, Indicates that Thousands of Human Genes are MicroRNA Targets," Cell, 120:15-20.
Lorenz et al., (2011). "ViennaRNA Package 2.0.," Algorithms for Molecular Biology, 6(26), 14 pages.
Mae et al., (2005). "Internalisation of cell-penetrating peptides into tobacco protoplasts," Biochimica et Biophysica Acta., 1669(2):101-107.
Mao et al. "Manipulating Plant RNA-Silencing Pathways to Improve the Gene Editing Efficiency of CRISPR/Cas9 Systems", Genome Biology, XP055694770, 19(1): 149-1-149-15, Sep. 28, 2018.
Mathur et al., (1995). "A simple method for isolation, liquid culture, transformation and regeneration of Arabidopsis thaliana protoplasts," Plant Cell Rep., 14:221-226.
McElroy et al., (1990). "Isolation of an efficient actin promoter for use in rice transformation," Plant Cell, 2:163-171.
Meister et al. "Mechanisms of Gene Silencing by Double-Stranded RNA", Nature, XP055153799, 431(7006): 343-349, Sep. 16, 2004.
Miller et al., (2011). "A TALE nuclease architecture for efficient genome editing," Nat Biotechnol., 29(2):143-148.
Miura et al. "CRISPR/Cas9-Based Generation of Knockdown Mice by Intronic Insertion of Artificial MicroRNA Using Longer Single-Stranded DNA", Scientific Reports, XP055333089, 5: 12799-1-12799-11, Published Online Aug. 5, 2015. Figs.2-4.
Molnar et al., (2009). "Highly specific gene silencing by artificial microRNAs in the unicellular alga Chlamydomonas reinhardtii," Plant J., 58(1):165-174.

(56) References Cited

OTHER PUBLICATIONS

Müller et al., (1993). "The nitrogen response of a barley C-hordein promoter is controlled by positive and negative regulation of the GCN4 and endosperm box," Plant J., 4:343-355.
Narayanan et al. In Vivo Mutagenesis of MiRNA Gene Families Using A Scalable Multiplexed CRISPR/Cas9 Nuclease System:, Scientific Reports, 6(32386): 1-9, Published Online Aug. 30, 2016.
Ohta, (1986). "High-efficiency genetic transformation of maize by a mixture of pollen and exogenous DNA," Proc. Natl. Acad. Sci. USA, 83:715-719.
Opsahl-Ferstad et al., (1997). "ZmEsr, a novel endosperm-specific gene expressed in a restricted region around the maize embryo," Plant J., 12:235-246.
Paddison et al., (2002). "Stable suppression of gene expression by RNAi in mammalian cells," Proc. Natl. Acad. Sci. USA., 99:1443-1448.
Pan et al., (2017). "SlbZIP38, a Tomato bZIP Family Gene Downregulated by Abscisic Acid, Is a Negative Regulator of Drought and Salt Stress Tolerance," Genes, 8(12):402, 17 pages.
Park et al., (2015). "Cas-Designer: a web-based tool for choice of CRISPR-Cas9 target sites," Bioinformatics, 31(24):4014-4016.
Patents Act 1977: Patents Rules 2007: Preliminary Examination Report Under Section 15A Dated Oct. 9, 2017 From the Intellectual Property Office fo the United Kingdom of Great Britain Re. Application No. 1715113.5. (2 Pages).
Patents Act 1977: Patents Rules 2007: Preliminary Examination Report Under Section 15A Dated Sep. 26, 2017 From the Intellectual Property Office fo the United Kingdom of Great Britain Re. Application No. 1715116.8. (2 Pages).
Patents Act 1977: Search Report Under Section 17(5) Dated Jun. 13, 2018 From the Intellectual Property Office of the United Kingdom of Great Britain Re. Application No. 1715113.5. (4 Pages).
Patents Act 1977: Search Report Under Section 17(5) Dated Jun. 13, 2018 From the Intellectual Property Office of the United Kingdom of Great Britain Re. Application No. 1715116.8. (5 Pages).
Porteus "Genome Editing: A New Approach to Human Therapeutics", Annual Review of Pharmacology and Toxicology, Review in Advance, 56: 29.1-29.28, Oct. 28, 2015.
Potrykus, (1991). "Gene Transfer to Plants: Assessment of Published Approaches and Results," Annu. Rev. Plant. Physiol., Plant. Mol. Biol., 42:205-225.
Qi et al. "High-Efficiency CRISPR/Cas9 Multiplex Gene Editing Using the Glycine tRNA-Processing System-Based Strategy in Maize", BMC Biotechnology, XP055515108, 16(1): 58-1-58-8, Published Online Aug. 11, 2016. Fig.3.
Rafalski et al., (1984). "Developmentally regulated plant genes: the nucleotide sequence of a wheat gliadin genomic clone," EMBO J., 3:1409-1415.
Ramirez et al., (2011). "Enhanced disease resistance to Botrytis cinerea in myb46 *Arabidopsis* plants is associated to an early down-regulation of CesA genes," Plant Signal Behav., 6(6):911-913.
Reyon et al., (2012). "FLASH Assembly of TALENs Enables High-Throughput Genome Editing," Nature Biotechnology, 30(5):460-465, 23 pages.
Rybak-Wolf et al. "A Variety of Dicer Substrates in Human and C.Elegans", Cell, 159(5):1153-1167, Nov. 20, 2014.
Sato et al., (1996). "A rice homeobox gene, OSH1, is expressed before organ differentiation in a specific region during early embryogenesis," Proc. Natl. Acad. Sci. USA, 93:8117-8122.
Schwab et al. "Highly Specific Gene Silencing by Artificial MicroRNAs in *Arabidopsis*", The Plant Cell (2006) vol. 18, 1121-1133.
Scofield et al., (1987). "Nucleotide Sequence of a Member of the Napin Storage Protein Family from *Brassica* Napus," J. Biol. Chem., 262(25)B158:12202-12208.
Senis et al. "A Therapeutic Anti-Hepatitis C Virus ShmiRNA Integrated Into the MiR-122 Genomic Locus Mediates A Potent Anti-Viral Response", Human Gene Therapy, XP055529717, 25(11): A51-A52, # OR081, Nov. 15, 2014.
Senis et al. "TALEN/CRISPR-Mediated Engineering of A Promoterless Anti-Viral RNAi Hairpin Into An Endogenous MiRNA Locus—Supplementary Information", Retrieved From the Internet, XP055696419, p. 1-32, Sep. 9, 2016.
Senis et al. "TALEN/CRISPR-Mediated Engineering of A Promoterless Anti-Viral RNAi Hairpin Into An Endogenous MiRNA Locus", Nucleic Acids Research, XP055527360, 45(1): e3-1-e3-17, Published Online Sep. 9, 2016.
Sheen, (1993). "Protein phosphatase activity is required for light-inducible gene expression in maize," EMBO J., 12(9):3497-3505.
Shmakov et al., (2015). "Discovery and Functional Characterization of Diverse Class 2 CRISPR-Cas Systems," Mol Cell., 60(3):385-397.
Strat et al., (2006). "Specific and nontoxic silencing in mammalian cells with expressed long dsRNAs," Nucleic Acids Research, 34(13):3803-3810.
Svitashev et al., (2015). "Targeted Mutagenesis, Precise Gene Editing, and Site-Specific Gene Insertion in Maize Using Cas9 and Guide RNA," Plant Physiology, 169(2):931-945.
Takaiwa et al., (1987). "A rice glutelin gene family—a major type of glutelin mRNAs can be divided into two classes," Mol. Gen. Genet., 208:15-22.
Takamatsu et al. (1987). "Expression of bacterial chloramphenicol acetltransferase gene in tobacco plants mediated by TMV-RNA," EMBO J., 6:307-311.
Takamatsu et al., (1990). "Production of enkephalin in tobacco protoplasts using tobacco mosaic virus RNA vector," FEBS Letters, 269:73-76.
Tiwari et al., (2014). "Artificial microRNA mediated gene silencing in plants: progress and perspectives," Plant Mol Biol., 86: 1-18.
Toriyama et al., (1988). "Transgenic Rice Plants After Direct Gene Transfer into Protoplasts," Bio/Technology, 6:1072-1074.
Tran et al., (2004). "Control of specific gene expression in mammalian cells by co-expression of long complementary RNAs," FEBS Lett., 573:127-134.
Truscott et al. "Novel Regulation and Functional Interaction of Polycistronic MiRNAs", RNA, XP055530916, 22(1): 129-138, Nov. 9, 2015.
Twell et al., (1989). "Isolation and expression of an anther-specific gene from tomato," Mol. Gen Genet., 217:240-245.
Uknes et al., (1992). "Acquired resistance in *Arabidopsis*," Plant Cell, 4:645-656.
Valvekens et al., (1988). "Agrobacterium tumefaciens-mediated transformation of *Arabidopsis thaliana* root explants by using kanamycin selection," Proc Natl Acad Sci USA, 85(15):5536-5540.
Van der Meer et al., (1990). "Promoter analysis of the chalcone synthase (chsA) gene of Petunia hybrida: a 67 bp promoter region directs flower-specific expression," Plant Mol. Biol., 15:95-109.
Verma et al., (2014). "Lignin genetic engineering for improvement of wood quality: Applications in paper and textile industries, fodder and bioenergy production," South African Journal of Botany, 91, pp. 107-125.
Vicente-Carbajosa et al., (1998). "Barley BLZ1: a bZIP transcriptional activator that interacts with endosperm-specific gene promoters," Plant J., 13:629-640.
Wang et al. "Construction and Characterization of A Synthetic MicroRNA Cluster for Multiplex RNA Interference in Mammalian Cells", ACS Synthetic Biology, XP055368273, 5(11): 1193-1200, Published Online Dec. 7, 2015. Fig.5.
Wang et al., (2009). "Shoot-Specific Down-Regulation of Protein Farnesyltransferase (Alpha-Subunit) for Yield Protection against Drought in Canola," Mol Plant., 2(1): 191-200.
Wu et al., (1998). "Genomic Cloning of 18 kDa Oleosin and Detection of Triacylglycerols and Oleosin Isoforms in Maturing Rice and Postgerminative Seedlings," J. Biochem., 123:386-391.
Wu et al., (1998). "Promoters of Rice Seed Storage Protein Genes Direct Endosperm- Specific Gene Expression in Transgenic Rice," Plant Cell Physiology, 39(8):885-889.
Xiao et al., (2014). "CasOT: a genome-wide Cas9/gRNA off-target searching tool," Bioinformatics, 30:1180-1182.
Yoon et al., (2018). "Downregulation of stress-associated protein 1 (PagSAP1) increases salt stress tolerance in poplar (Populus alba x P. glandulosa)," Trees 32:823-833.

(56) References Cited

OTHER PUBLICATIONS

Zetsche et al., (2015). "Cpf1 is a single RNA-guided endonuclease of a class 2 CRISPR-Cas system," Cell, 163(3):759-771.
Zhang et al. "Next Generation Insect-Resistant Plants: RNAi-Mediated Crop Protection", Trends in Biotechnology, XP085171385, 35(9): 871-882, Sep. 2017.
Zhang et al., (2010). "Short biodegradable polyamines for gene delivery and transfection of brain capillary endothelial cells," J Control Release, 143(3):359-366, 22 pages.
Zhang et al., (2014). "tasiRNAdb: a database of ta-siRNA regulatory pathways," Bioinformatics, 30(7):1045-1046.
Zhao et al., (2014). "Sequence-specific inhibition of microRNA via CRISPR/CRISPRi system," Scientific Reports, 4(3943), 5 pages.
Zhou et al. "CRISPR-Cas9 Based Genome Editing Reveals New Insights Into MicroRNA Function and Regulation in Rice", Frontiers in Plant Science, XP055528166, 8: 1598-1-1598-12, Published Online Sep. 13, 2017. Fig.4.
Zielezinski et al., (2015). "mirEX 2.0—an Integrated Environment for Expression Profiling of Plant microRNAs." BMC Plant Biology 15:144, 9 pages.
Zuris et al. "Cationic Lipid-Mediated Delivery of Proteins Enables Efficient Protein-Based Genome Editing In Vitro and In Vivo", Nature Biotechnology, 33(1): 73-80, Published Online Oct. 30, 2014.
Akatsuka et al., (2007). "Minor histocompatibility antigens as targets for immunotherapy using allogeneic immune reactions," Cancer Science, 98(8):1139-1146.
Alison, (2003). "Tissue-based stem cells: ABC transporter proteins take centre stage," J Pathol., 200(5):547-550.
Allen et al., (2005). "microRNA-Directed Phasing during Trans-Acting siRNA Biogenesis in Plants," Cell, 121:207-221.
Axtell et al., (2006). "A Two-Hit Trigger for siRNA Biogenesis in Plants," Cell, 127:565-577.
Bauer et al., (2015). "Generation of genomic deletions in mammalian cell lines via CRISPR/Cas9," J Vis Exp., 83:e52118, 10 pages.
Berlin et al., (2014). "Mapping the HLA ligandome landscape of acute myeloid leukemia: a targeted approach toward peptide-based immunotherapy," Leukemia, 29(3):647-659.
Bi, (2018). "Dissertation: Gene editing of rice miRNA and argonaute genes, Chapter 1: Introduction: Gene Editing With Talens And Crispr/Cas In Rice " Iowa State University, 24 pages.
Borralho et al., (2007). "Inhibition of Fas expression by RNAi modulates 5-fluorouracil-induced apoptosis in HCT116 cells expressing wild-type p53," Biochimica et Biophysica Acta., 1772:40-47.
Braley-Mullen et al., (2000). "Early requirement for B cells for development of spontaneous autoimmune thyroiditis in NOD.H-2h4 mice," J Immunol., 165(12):7262-7269.
Burke et al., (2019). "RNA Interference in the Tobacco Hornworm, Manduca sexta, Using Plastid-Encoded Long Double-Stranded RNA," Front. Plant Sci., 10:313, 10 pages.
Byrne et al., (1989). "Multiplex gene regulation: a two-tiered approach to transgene regulation in transgenic mice," PNAS USA, 86:5473-5477.
Carlson et al., (2012). "Efficient TALEN-mediated gene knockout in livestock," PNAS USA, 109(43), 17382-17387.
Chang et al., (2006). "Lessons from Nature: microRNA-based shRNA libraries," Nat Methods, 3(9):707-14.
Chen et al., (2010). "22-Nucleotide RNAs trigger secondary siRNA biogenesis in plants," PNAS USA, 107(34):15269-15274.
Chen et al., (2019). "CRISPR/Cas genome editing and precision plant breeding in agriculture," Annual Review of Plant Biology, 70(28):1-28, 31 pages.
Chipuk et al., (2004). "Direct Activation of Bax by p53 Mediates Mitochondrial Membrane Permeabilization and Apoptosis," Science, 303(5660):1010-1014.
Christian et al., (2010). "Targeting DNA double-strand breaks with TAL effector nucleases," Genetics, 186(2):757-761, 13 pages.
Cong et al., (2013). "Multiplex genome engineering using CRISPR/Cas systems," Science, 339(6121):819-823, 9 pages.
Cunha-Neto et al., (1996). "Autoimmunity in Chagas' disease. Identification of cardiac myosin-B13 Trypanosoma cruzi protein crossreactive T cell clones in heart lesions of a chronic Chagas' cardiomyopathy patient," J Clin Invest., 98(8):1709-1712.
De Freitas Lima et al., (2017). "Molecular mechanisms of biomass increase in plants," Biotechnology Research and Innovation, 1:14-25.
Demeter et al., (1991). "Production of tumor necrosis factor-alpha by B-cell chronic lymphocytic leukemia and hairy cell leukemia cells: considerations regarding bone remodeling in the chronic B-cell leukemias," Blood, 77(5):1127-1128.
DiCarlo et al., (2013). "Genome engineering in *Saccharomyces cerevisiae* using CRISPR-Cas systems," Nucleic Acids Research, 41(7):4336-4343.
Dobin et al., (2013). "STAR: ultrafast universal RNA-seq aligner," Bioinformatics, 29(1):15-21.
Dominici et al., (2001). "Bone marrow mesenchymal cells: biological properties and clinical applications," J. Biol. Regul. Homeost. Agents, 15:28-37.
Dossa et al., (2018). "Development of T-cell immunotherapy for hematopoietic stem cell transplantation recipients at risk of leukemia relapse," Blood, American Society Of Hematology, 131(1):108-120.
Elison et al., (2017). "A Precise Genome Editing Method Reveals Insights Into the Activity of Eukaryotic Promoters", Cell Reports, 18(1):275-286.
Eventov-Friedman et al., (2006). "Embryonic pig pancreatic tissue transplantation for the treatment of diabetes," PLoS Med., 3(7):e215, 13 pages.
Gaj et al., (2013). "ZFN, TALEN, and CRISPR/Cas-based methods for genome engineering," Trends In Biotechnology, 31(7):397-405.
Griffiths-Jones, (2004). "The microRNA Registry," Nucleic Acids Res, 32:D109-D111.
Hiemstra et al., (2001). "Cytomegalovirus in autoimmunity: T cell crossreactivity to viral antigen and autoantigen glutamic acid decarboxylase," PNAS, 98(7):3988-3991.
Hwang et al., (2013). "Efficient In Vivo Genome Editing Using RNA-Guided Nucleases," Nature Biotechnology, 31(3):227-229, 12 pages.
Inglis et al., (2018). "Fast and inexpensive protocols for consistent extraction of high-quality DNA and RNA from challenging plant and fungal samples for high-throughput SNP genotyping and sequencing applications," PLoS ONE, 13(10):1-14.
Jaubert et al., (2011). "ARGONAUTE2 Mediates RNA-Silencing Antiviral Defenses against Potato virus X in Arabidopsis," Plant Physiology, 156(3):1556-1564.
Jinek et al., (2013). "RNA-programmed genome editing in human cells," eLife, 2:e00471, 9 pages.
Kawase et al., (2008). "Identification of human minor histocompatibility antigens based on genetic association with highly parallel genotyping of pooled DNA," Blood, 111(6):3286-3294.
Kelly, (1990). "T cell regulation of autoimmune interstitial nephritis," J Am Soc Nephrol., 1(2):140-149.
Kim et al., (1996). "Hybrid restriction enzymes: zinc finger fusions to Fok I cleavage domain," PNAS USA, 93(3):1156-1160.
Korkuc et al., (2014). "Characterization and identification of cis-regulatory elements in *Arabidopsis* 10 based on single-nucleotide polymorphism information," Plant Physiol., 164(1):181-200.
Krek et al., (2005). "Combinatorial microRNA target predictions," Nat Genet, 37(5):495-500.
Krenn et al., (2000). "Histopathology and molecular pathology of synovial B-lymphocytes in rheumatoid arthritis," Histol Histopathol., 15(3):791-798.
Lambirth et al., (2015). "CONTRAILS: A tool for rapid identification of transgene integration sites in complex, repetitive genomes using low-coverage paired-end sequencing," Genomics Data, 6:175-181.
Landgraf et al., (2016). "Scarless Gene Tagging With One-Step Transformation and Two-Step Selection in *Saccharomyces* Cerevisiae and Schizosaccharomyces Pombe," PLOS ONE, 11(10): e0163950, 24 pages.
Langmead et al., (2012). "Fast gapped-read alignment with Bowtie 2," Nat. Methods, 9:357-359.

(56) References Cited

OTHER PUBLICATIONS

Liu et al., (2007). "High 20 efficiency thermal asymmetric interlaced PCR for amplification of unknown flanking sequences," BioTechniques, 43(5):649-656.
Liu et al., (2017). "CRISPR-p. 2.0: An Improved CRISPR-Cas9 Tool for Genome Editing in Plants," Molecular Plant, 10(3):530-532.
Maheshwari et al., (1986). "I: Isolation and Regeneration of Protoplasts from Higher Plants," Differentiation of Protoplasts and of Transformed Plant Cells, 3-36.
Mahfouz et al., (2011). "De novo-engineered transcription activator-like effector (TALE) hybrid nuclease with novel DNA binding specificity creates double-strand breaks," PNAS USA, 108(6):2623-2628.
Mali et al., (2013). "RNA-guided human genome engineering via Cas9," Science, 339(6121):823-826, 8 pages.
Manns, (2000). "Antibodies to soluble liver antigen: specific marker of autoimmune hepatitis," J Hepatol., 33(2):326-328.
Mans et al., (2015). "CRISPR/Cas9: A Molecular Swiss Army Knife for Simultaneous Introduction of Multiple Genetic Modifications in *Saccharomyces* Cerevisiae", FEMS Yeast Research, 15(2):fov004, 15 pages.
Martin, (2011). "Cutadapt Removes Adapter Sequences From High-Throughput Sequencing Reads," EMBnet journal, 17(1):10-12.
Mchale et al., (2013). "A 22-nt artificial microRNA mediates widespread RNA silencing in *Arabidopsis*," Plant Journal, 76(3):519-529.
McQuin et al., (2018). "CellProfiler 3.0: Next-generation image processing for biology," PLoS Biology, 16(7):e2005970, 17 pages.
Miroshnichenko et al., (2020). "Enhancement of resistance to PVY in intragenic marker-free potato plants by RNAi-mediated silencing of elF4E translation initiation factors," PCTOC, 140:691-705.
Mutis, (2018). "Targeting Alloreactive Donor T-Cells to Hematopoietic System-Restricted Minor Histocompatibility Antigens to Dissect Graft-versus-Leukemia Effects from Graft-versus-Host Disease after Allogeneic Stem Cell Transplantation," International Journal Of Hematology, 78(3):208-212.
Nakade et al., (2017). "Cas9, Cpf1 and C2c1/2/3-What's next?" Bioengineered, 8(3):265-273.
Neuhaus et al., (1987). "Transgenic rapeseed plants obtained by the microinjection of DNA into microspore-derived embryoids," Theor. Appl. Genet., 75:30-36.
Notarianni et al., (1991). "Derivation of pluripotent, embryonic cell lines from the pig and sheep," J Reprod Fertil Suppl., 43:255-260.
Peragine et al., (2004). "SGS3 and SGS2/SDE1/RDR6 are required for juvenile development and the production of trans-acting siRNAs in *Arabidopsis*," Genes & Development, 18:2368-2379.
Pinkert et al., (1987). "An albumin enhancer located 10 kb upstream functions along with its promoter to direct efficient, liver-specific expression in transgenic mice," Genes Dev., 1:268-276.
Potrykus et al., (1985). "Direct gene transfer to cells of a graminaceous monocot," Mol. Gen. Genet., 199:183-8.
Qin et al., (2007). "Disruption of phytoene desaturase gene results in albino and dwarf phenotypes in *Arabidopsis* by impairing chlorophyll, carotenoid, and gibberellin biosynthesis," Cell Res, 17:471-82.
Rees et al., (2018). "Base editing: precision chemistry on the genome and transcriptome of living cells," Nat Rev Genet., 19:770-788.
Renaudineau et al., (1999). "Anti-Endothelial Cell Antibodies in Systemic Sclerosis," Clin Diagn Lab Immunol., 6(2):156-160.
Rose et al., (2005). "Functional polarity is introduced by Dicer processing of short substrate RNAs," Nucleic Acids Research, 33(13):4140-4156.
Rubinstein et al., (1981). "Convenient assay for interferons," J Virol., 37(2):755-758.
Santos et al., (2016). "Promoter Analysis in Banana," Banana: Genomics and Transgenic Approaches for Genetic Improvement, pp. 157-179, 28 pages.
Schmittgen et al., (2008). "Analyzing real-time PCR data by the comparative CT method," Nat Protoc., 3(6):1101-1108.
Semple et al., (1996). "Differences in serum cytokine levels in acute and chronic autoimmune thrombocytopenia purpura: relationship to platelet phenotype and antiplatelet T-cell reactivity," Blood, 87(10):4245-4254.
Sindhu et al., (2009). "Effective and specific in planta RNAi in cyst nematodes: expression interference of four parasitism genes reduces parasitic success," Journal of Experimental Botany, 60(1):315-324.
Soderström et al., (1994). "Autoimmune T cell repertoire in optic neuritis and multiple sclerosis: T cells recognising multiple myelin proteins are accumulated in cerebrospinal fluid," J Neurol Neurosurg Psychiatry, 57(5):544-551.
Stadinski et al., (2019). "A temporal thymic selection switch and ligand binding kinetics constrain neonatal Foxp3+Tregcell development," Nature Immulogy, 20(8):1046-1058.
Sweeney et al., (2019). "The Graft-Versus-Leukemia Effect in AML," Frontiers In Oncology, 9:1217, 19 pages.
Takano et al., (2021). "ACCase-inhibiting herbicides: mechanism of action, resistance evolution and stewardship," Scientia Agricola, 78(1):e20190102, 11 pages.
Tang et al., (2010). "RNA Interference and Its Applications on Silencing of Insecticide-resistant Genes in Insects," Cotton Science, 22(6):617-624. English abstract.
Taniguchi et al., (2002). "Convergence of the fanconi anemia and ataxia telangiectasia signaling pathways," Cell, 109:459-472.
Telem et al., (2013). "Cisgenics—a sustainable approach for crop improvement," Curr Genomics, 14(7):468-476.
Thomson et al., (1995). "Isolation of a primate embryonic stem cell line," PNAS USA, 92:7844-7848.
Thomson et al., (1996). "Pluripotent cell lines derived from common marmoset (Callithrix jacchus) blastocysts," Biol Reprod., 55:254-259.
Thorvaldsdóttir et al., (2012). "Integrative Genomics Viewer (IGV): high-performance genomics data visualization and exploration," Brief Bioinform., 14(2):178-192.
Tisch et al., (1994). "Antigen-specific immunotherapy: is it a real possibility to combat T-cell-mediated autoimmunity?" PNAS USA, 91(2):437-438.
Touriño et al., (2008). "High expression of foreign proteins from a biosafe viral vector derived from Turnip mosaic virus," Spanish Journal of Agricultural Research, 6(SPEC.ISS.)48-58.
Tranel et al., (2002). "Resistance of weeds to ALS-inhibiting herbicides: What have we learned'?" Weed Science, 50(6):700-712.
Vazquez et al., (2004). "Endogenous trans-Acting siRNAs Regulate the Accumulation of *Arabidopsis* mRNAs," Molecular Cell, 16:69-79.
Vincent et al., (1998). "Antibodies affecting ion channel function in acquired neuromyotonia, in seropositive and seronegative myasthenia gravis, and in antibody-mediated arthrogryposis multiplex congenita," Ann NY Acad Sci., 841:482-496.
Voswinkel et al., (2001). "B lymphocyte involvement in ankylosing spondylitis: the heavy chain variable segment gene repertoire of B lymphocytes from germinal center-like foci in the synovial membrane indicates antigen selection," Arthritis Res., 3(3):189-195, 9 pages.
Wang et al., (2017). "Systematic characterization of A-to-I RNA editing hotspots in microRNAs across human cancers," Genome Research, 27:1112-1125, 14 pages.
Wang et al., (2018). "When MicroRNAs meet RNA editing in cancer: a nucleotide change can make a difference," Bioessays, 40(2):1700188, 14 pages.
Weeks et al., (2016). "Use of designer nucleases for targeted gene and genome editing in plants," Plant Biotechnology Journal, 14(2):483-495.
Winoto et al., (1989). "A novel, inducible and T cell-specific enhancer located at the 3' end of the T cell receptor alpha locus," EMBO J., 8(3):729-733.
Xia et al., (2014). "Characterization of Small Interfering RNAs Derived from Sugarcane Mosaic Virus in Infected Maize Plants by Deep Sequencing," PLoS ONE, 9(5):e97013, 8 pages.

(56) References Cited

OTHER PUBLICATIONS

Yang et al., (2004). "A natural variant of a host RNA-dependent RNA polymerase is associated with increased susceptibility to viruses by Nicotiana benthamiana," PNAS, 101(16):6297-6302.
Yang et al., (2018). "CRISPR/Cas9-mediated noncoding RNA editing in human cancers," RNA Biology, 15(1):35-43.
Yee et al., (2015). "Animal Models Of Cancer Biology," Cancer Growth Metastasis, 8(Suppl 1):115-118, 4 pages.
Yeh et al., (2015). "Down-Regulation of Cytokinin Oxidase 2 Expression Increases Tiller No. and Improves Rice Yield," Rice, 8:36, 13 pages.
Yi et al., (2015). "PNRD: a plant non-coding RNA database," Nucleic Acids Research, 43(D1):D982-D989.
Yoshikawa et al., (2005). "A pathway for the biogenesis of trans-acting siRNAs in *Arabidopsis*," Genes & Development, 19:2164-2175.
Yu et al., (2010). "AHAS herbicide resistance endowing mutations: effect on AHAS functionality and plant growth," J Exp Bot, 61(14):3925-3934.
Zhao et al., (2017). "Methods of MicroRNA Promoter Prediction and Transcription Factor Mediated Regulatory Network," Biomed Res Int, 2017:7049406, 9 pages.
Zhu et al., (1994). "Cloning and functional expression of a cDNA encoding coffee bean alpha-galactosidase," GENE, 140(2):227-231.
Zong et al., (2017). "Precise base editing in rice, wheat and maize with a Cas9-cytidine deaminase fusion," Nature Biotechnology, 35:438-440, 4 pages.
Richardson et al., (2016). "Enhancing homology-directed genome editing by catalytically active and inactive CRISPR-Cas9 using asymmetric donor DNA," Nat Biotechnol, 34(3):339-44, 7 pages.

* cited by examiner

FIG. 8

| Crops | Dak Lak | | Gia Lai | | Kon Tum | |
|---|---|---|---|---|---|---|
| | *R. similis* | *P. coffeae* | *R. similis* | *P. coffeae* | *R. similis* | *P. coffeae* |
| Banana | 0 | + | 0 | + | 0 | + |
| Coffee | + | + | + | + | 0 | 0 |
| Pepper | 0 | 0 | 0 | 0 | 0 | 0 |
| Durian | 0 | 0 | 0 | 0 | 0 | + |
| Citrus | 0 | 0 | 0 | 0 | 0 | + |
| Pineapple | 0 | 0 | 0 | + | 0 | 0 |
| Ginger | 0 | 0 | 0 | - | 0 | 0 |
| Longan | 0 | + | 0 | - | 0 | 0 |
| Mango | 0 | 0 | 0 | 0 | 0 | 0 |

+: Nematode was found 0: No nematode was found -: No sample was collected (a) AtmiR390
SEQ ID NO: 404

(b) SWAP5 (*GFP*)
SEQ ID NO: 405

(c) SWAP6 (*GFP*)
SEQ ID NO: 406

(d) SWAP7 (*PDS3*)
SEQ ID NO: 407

(e) SWAP8 (*PDS3*)
SEQ ID NO: 408

(f) SWAP11 (*ADH1*)
SEQ ID NO: 409

(g) SWAP12 (*ADH1*)
SEQ ID NO: 410

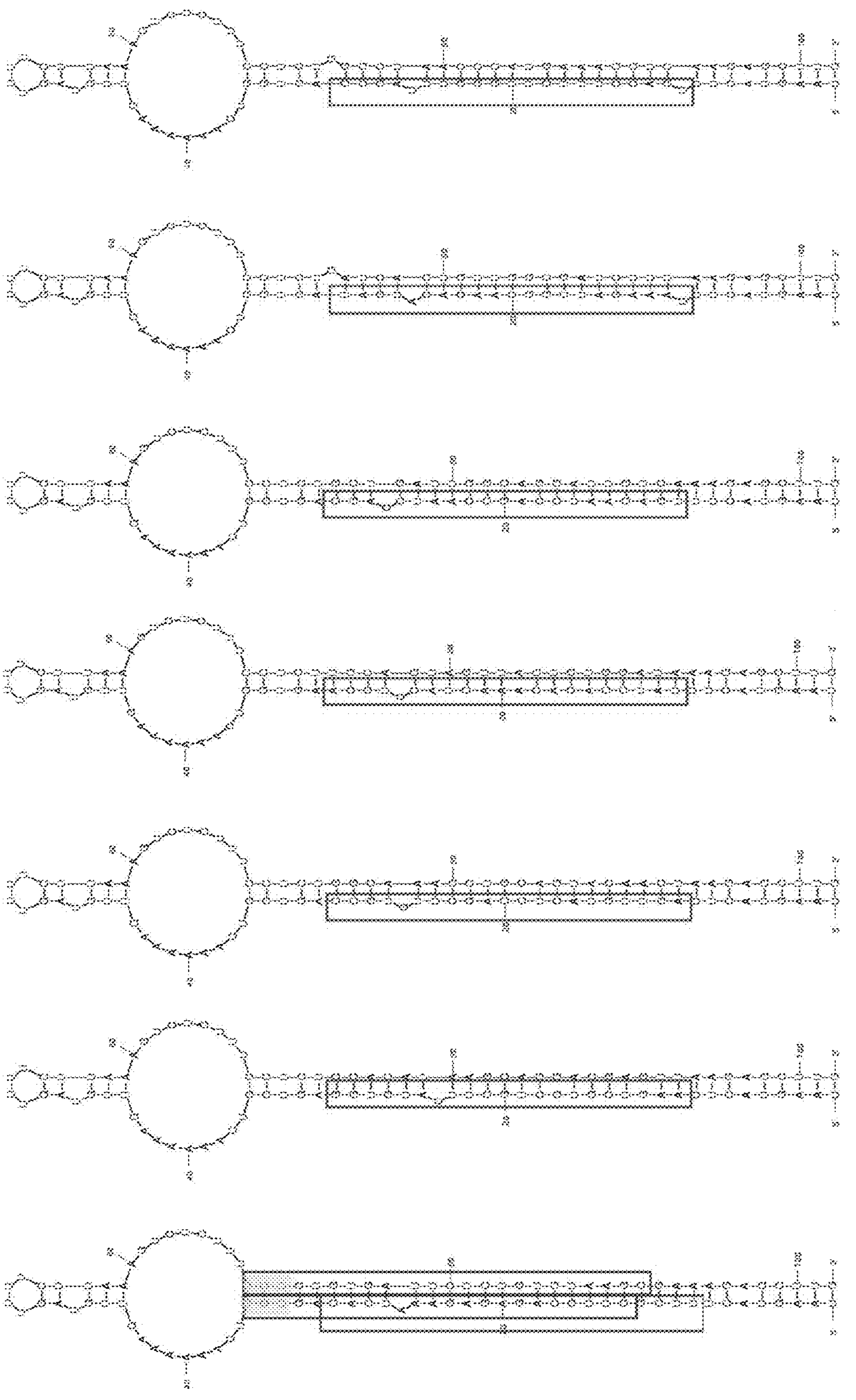
FIG. 13A (a) AtmiR173 SEQ ID NO: 411
FIG. 13B (b) SWAP1 (*GFP*) SEQ ID NO: 412
FIG. 13C (c) SWAP2 (*GFP*) SEQ ID NO: 413
FIG. 13D (d) SWAP3 (*PDS3*) SEQ ID NO: 414
FIG. 13E (e) SWAP4 (*PDS3*) SEQ ID NO: 415
FIG. 13F (f) SWAP9 (*ADH1*) SEQ ID NO: 416
FIG. 13G (g) SWAP10 (*ADH1*) SEQ ID NO: 417

Wild-type tasiRNA precursor
SEQ ID NO: 403

GEiGS-based on tasiRNA precursor (small nt change)
SEQ ID NO: 401

GEiGS-based on tasiRNA precursor (large nt change)
SEQ ID NO: 402

FIG. 14A

```
                                                              SEQ ID NO: 373
(a) AtTAS1c  3'------ACCAGAAGCGAACATCTCTTTTTAGTGTTGTTTTGTTACGACAAAGTAGAGCTTTTGTAGGCATTGGGTTGCTTTAGTTTCTTCTCCTGCCCTTC------5'
                     |||||||| |||||||||||||
miR173          5'- TTCGCTTGCAGAGAGAAATCAC- 3'    SEQ ID NO: 374
```

FIG. 14B

```
                                                              SEQ ID NO: 375
(b) GFP      3'------AACTTCTTCAGCACGACGAAGTACACCAGCCCCATCGCCGACTTCGTGACGTGCGGCATCCAGTCCCACCAGTGCTCCCACCCGGTCCCGTGCCC------5'
                     |||||||||||||||||||||
SWAP1           5'- aaGtcgtgctgcttcAtgtgg- 3'    SEQ ID NO: 376
                                                              SEQ ID NO: 377
GFP          3'-----ACAACATCAACATGAGGTCGAACACGGGGTCCTACAACGGCAGGAGGAACTTCAGCTACGGGAAGTCGAGCTACGCCAAGTGGTCCCACAGCGGG-----5'
                     |||||||||||||||||||||
SWAP2           5'- agttgTaCtccagcttgTgcC- 3'    SEQ ID NO: 378
```

FIG. 14C

```
                                                              SEQ ID NO: 379
(c) AtPDS3   3'-----AACCTTATAGGTGTGTTTGATGGACGTTTCCTGGTCGTCATGAGGAGGAGGAACAAGAACAGAATTCGCGAACTCTTCACCCTTGGGATTTCGAT-----5'
                     |||||||||||||||||||||
SWAP3           5'- TatCcacacaAactAccTgca- 3'    SEQ ID NO: 380
                                                              SEQ ID NO: 381
AtPDS3       3'-----ACGTCAACTGTTAGGTCGGTTAGGTCGTGGTCGTTAATGTTGAAAGTTTCCGAATCGTCCTGCTCCTCGTGATGCCTTCCTACGTCTATTTGATC-----5'
                     |||||||||||||||||||||
SWAP4           5'- TgacaatccAGccaAtccagC- 3'    SEQ ID NO: 382
```

FIG. 14D

```
                                                              SEQ ID NO: 383
(d) AtADH1   3'-----GAGGCCATTTCTAGCCGTTGTGTACTAGAGGACCGACTTCTAGTCAGTGAGGAAGAGGTTGTGAGAGTTGTTAGGGAGGTCGAAGTACCGGCTT-----5'
                     |||||||||||||||||||||
SWAP9           5'- TaaagatcgGcaAcAcATgAt- 3'    SEQ ID NO: 384
                                                              SEQ ID NO: 385
AtADH1       3'-----TGTGAAACTGGAAAGAACCCAAATCGGTGTAAGTTTCAACGAGGATTGGGTCATCTGTTTGGTGTTGACTGTTATGTCTGGAACAGTTCTCCTC-----5'
                     |||||||||||||||||||||
SWAP10          5'- TgaCcTttcttGgGtttagcC- 3'    SEQ ID NO: 386
```

FIG. 15A

SEQ ID NO: 387

(a) *AtTAS3* 3'--------------CTGATTTTCGAGTCTATCCTATTGTGGCGAAATAGTAACTTTGACCTTACGGCTTCTTTTTGAGTTACAGAGTCGTGTCGCCTAGGT------5' miR390 5'- AAGCTCAGGAGGGATAGCGCC-3' SEQ ID NO: 388

FIG. 15B

SEQ ID NO: 389

(b) *GFP* 3'--------------AACTTCTTCAGCACGACGAAGTACACCAGCCCCATCGCCGACTTCGTGACGTGCGGCATCCAGTCCCACCAGTGCTCCCACCCGGTC------5'

SWAP5 5'- AAGtcgtGctGcttcAtgtgg-3' SEQ ID NO: 390

SEQ ID NO: 391

*GFP* 3'--------------ACAACATCAACATGAGGTCGAACACGGGGTCCTACAACGGCAGGAGGAACTTCAGCTACGGGAAGTCGAGCTACGCCAAGTGGTCCC------5'

SWAP6 5'- AgttgtActccaGcTtGtGCC-3' SEQ ID NO: 392

FIG. 15C

SEQ ID NO: 393

(c) *AtPDS3* 3'--------------AACCTTATAGGTGTGTTTGATGGACGTTTCCTGGTCGTCATGAGGAGGAGGAACAAGAACAGAATTCGCGAACTCTTCACCCTTGGG------5'

SWAP7 5'- tAtCcacacAaactacctGCa-3' SEQ ID NO: 394

SEQ ID NO: 395

*AtPDS3* 3'--------------ACGTCAACTGTTAGGTCGGTTAGGTCGTGGTCGTTAATGTTGAAAGTTTCCGAATCGTCCTGCTCCTCGTGATGCCTTCCTACGTCT------5'

SWAP8 5'- tgaCaatccAGccAatcCagC-3' SEQ ID NO: 396

FIG. 15D

SEQ ID NO: 397

(d) *AtADH1* 3'--------------GAGGCCATTTCTAGCCGTTGTGTACTAGAGGACCGACTTCTAGTCAGTGAGGAAGAGGTTGTGAGAGTTGTTAGGGAGGTCGAAGTA------5'

SWAP11 5'- tAaagatcGgcaacacatGat- 3' SEQ ID NO: 398

SEQ ID NO: 399

*AtADH1* 3'--------------TGTGAAACTGGAAAGAACCCAAATCGGTGTAAGTTTCAACGAGGATTGGGTCATCTGTTTGGTGTTGACTGTTATGTCTGGAACAGTTC------5'

SWAP12 5'- tgaCctttcttGGgTttagCC- 3' SEQ ID NO: 400

ADH1 GEiGS SELECTION

MODIFYING THE SPECIFICITY OF PLANT NON-CODING RNA MOLECULES FOR SILENCING GENE EXPRESSION

RELATED APPLICATIONS

This application is a divisional application of U.S. patent application Ser. No. 16/648,748, filed on Mar. 19, 2020, which is a National Phase of PCT Application No. PCT/IB2018/057160, having an International filing date of Sep. 18, 2018, which claims the benefit of priority of Great Britain Patent Application No. 1719516.5 filed on Nov. 23, 2017, and Great Britain Patent Application Nos. 1715116.8 and 1715113.5 both filed on Sep. 19, 2017. The contents of the above applications are all incorporated by reference as if fully set forth herein in their entirety.

REFERENCE TO AN ELECTRONIC SEQUENCE LISTING

The contents of the electronic sequence listing (251502011910seqlist.xml; Size: 672,147 bytes; and Date of Creation: Dec. 20, 2022) is herein incorporated by reference in its entirety.

FIELD AND BACKGROUND OF THE INVENTION

The present invention, in some embodiments thereof, relates to modifying genes that encode or are processed into non-coding RNA molecules, including RNA silencing molecules and, more particularly, but not exclusively, to the use of same for silencing endogenous or exogenous target gene-expression of interest in plants.

RNA silencing or RNA interference (RNAi), the endogenous co- or post-transcriptional genetic regulatory mechanism in which RNA molecules inhibit gene expression or translation, is generally mediated by non-coding RNA molecules including microRNAs (miRNAs), small interfering RNAs (siRNAs), trans-acting siRNA (ta-siRNA), piwi-interacting RNAs (piRNA), antisense RNA, etc. Recently, additional non-coding RNAs have been implicated to harbour a RNA silencing activity including transfer RNA (tRNA), small nuclear RNA (snoRNA), small nucleolar RNA (snoRNA) and repeats-derived RNA. These canonical and non-canonical RNA silencing molecules differ in their substrates, biogenesis, effector proteins and modes of target down regulation.

Moreover, Argonaute proteins, in complex with small RNAs, form the core of the RNA-induced silencing complex (RISC), the RNA-interference (RNAi) effector complex. The Argonaute superfamily segregates into two clades, termed Ago and Piwi. Ago proteins (e.g. Ago1 and Ago2) typically complex with miRNAs and siRNAs, while Piwi proteins (e.g. Piwi, Ago3 and Aubergine (Aub)) typically complex with piRNA.

Small interfering RNAs (siRNAs) are double-stranded RNA molecules of 20-25 nucleotides (nt) in length, which interfere with the expression of specific genes with complementary nucleotide sequences by degrading their transcript during or after transcription resulting in no translation.

MicroRNAs (miRNAs) are small endogenous non-coding RNAs (ncRNAs) of 20 to 24 nt in length, originating from long self-complementary precursors. Mature miRNAs regulate gene expression in two ways; (i) by inhibiting translation or (ii) by degrading coding mRNAs by perfect or near-perfect complement with the target transcript. The majority of plant target mRNAs contain a single miRNA-complementary site, which results in the target mRNAs being cleaved and degraded by the RNA silencing molecule and RNA decay machinery.

Piwi-interacting RNAs (piRNAs) are small non-coding RNAs which are the product of long single stranded precursor molecules, and which are generated without a dicing step. piRNAs are typically 26 to 31 nt in length and are mostly antisense. piRNAs form RNA-protein complexes through interactions with Piwi proteins. Antisense piRNAs are typically loaded into Piwi or Aub.

Transacting siRNA (tasiRNA) are a class of small interfering RNA (siRNA) that repress gene expression through post-transcriptional gene silencing. Their biogenesis is primed by association of miRNAs to tasiRNA precursors, which recruits RNA-dependent RNA-polymerases (RdRp) that synthesize dsRNA from the tasiRNA precursor template. Next, such dsRNA is processed by DICER-LIKE 4 (DCL4) into about 21-nucleotide "phased" intervals mature tsaiRNAs.

Recent advances in genome editing techniques have made it possible to alter DNA sequences in living cells. By editing only a few of the billions of nucleotides in the cells of plants, these new techniques might be the most effective way to get crops to grow better in harsh climates (crop performance and abiotic stress) and enhance resistance to biotic stress (insects, viruses, bacteria, beetles, nematodes etc.). There are limited approaches to achieve resistance to pests using genome editing technologies such as CRISPR/Cas9: plant susceptible genes knock-out (such as the well-known MLO genes), by introduction of stop codons, frame shifts, insertions, deletions etc.; or up regulation of resistance genes, like R genes, by modification of regulatory elements like promoters, microRNA binding sites etc. Nevertheless, approaches that target specifically the pathogen are limited to transgenic CRISPR applications.

Previous work on genome editing of RNA molecules in various organisms (e.g. murine, human, shrimp, plants), focused on knocking-out miRNA activity or changing their binding site in target RNAs, for example:

Zhao et al., [Zhao et al., *Scientific Reports* (2014) 4:3943] provided a miRNA inhibition strategy employing the CRISPR system in murine cells. Zhao used a specifically designed gRNAs to cut a miRNA gene at a single site by Cas9, resulting in knockdown of the miRNA in murine cells.

Jiang et al. [Jiang et al., *RNA Biology* (2014) 11 (10): 1243-9] used CRISPR/Cas9 to deplete human miR-93 from a cluster by targeting its 5' region in HeLa cells. Various small indels were induced in the targeted region containing the Drosha processing site (i.e. the position at which Drosha, a double-stranded RNA-specific RNase HI enzyme, binds, cleaves and thereby processes primary miRNAs (pri-miRNAs) into pre-miRNA in the nucleus of a host cell) and seed sequences (i.e. the conserved heptametrical sequences which are essential for the binding of the miRNA to mRNA, typically situated at positions 2-7 from the miRNA 5'-end). According to Jiang et al. even a single nucleotide deletion led to complete knockout of the target miRNA with high specificity.

With regard to plant genome editing, Bortesi and Fischer [Bortesi and Fischer, *Biotechnology Advances* (2015) 33: 41-52] discussed the use of CRISPR-Cas9 technology in plants compared to ZFNs and TALENs, and Basak and Nithin [Basak and Nithin, *Front Plant Sci.* (2015) 6: 1001] demonstrated the use of CRISPR-Cas9 technology for knockdown of protein-coding genes in model plants such as *Arabidopsis* and tobacco and crops like wheat, maize, and rice.

In addition to disruption of miRNA activity or target binding sites, gene silencing using artificial microRNAs (amiRNAs)-mediated gene silencing of endogenous and exogenous target genes were used [Tiwari et al. *Plant Mol Biol* (2014) 86: 1]. Similar to microRNAs, amiRNAs are single-stranded, approximately 21 nt long, and designed by replacing the mature miRNA sequences of duplex within pre-miRNAs [Tiwari et al. (2014) supra]. These amiRNAs are introduced as a transgene within an artificial expression cassette (including a promoter, terminator etc.) [Carbonell et al., *Plant Physiology* (2014) pp. 113.234989], are processed via small RNA biogenesis and silencing machinery and downregulate target expression. According to Schwab et al. [Schwab et al. *The Plant Cell* (2006) Vol. 18, 1121-1133], amiRNAs are active when expressed under tissue-specific or inducible promoters and can be used for specific gene silencing in plants, especially when several related, but not identical, target genes need to be downregulated.

Senis et al. [Senis et al., *Nucleic Acids Research* (2017) Vol. 45(1): e3] disclose engineering of a promoterless anti-viral amiRNA into an endogenous miRNA locus. Specifically, Senis et al. insert a amiRNA precursor transgene (hairpin pri-amiRNA) adjacent to a naturally occurring miRNA gene (e.g. miR122) by homology-directed DNA recombination that is induced by sequence-specific nuclease such as Cas9 or TALEN. This approach uses promoter- and terminator-free amiRNAs by utilizing transcriptionally active DNA that expresses natural miRNA (miR122), that is, the endogenous promoter and terminator drove and regulated the transcription of the inserted amiRNA transgene.

Various DNA-free methods of introducing RNA and/or proteins into cells have been previously described. For example, RNA transfection using electroporation and lipofection has been described in U.S. Patent Application No. 20160289675. Direct delivery of Cas9/gRNA ribonucleoprotein (RNP) complexes to cells by microinjection of Cas9 protein and gRNA complexes was described by Cho [Cho et al., "Heritable gene knockout in *Caenorhabditis elegans* by direct injection of Cas9-sgRNA ribonucleoproteins," *Genetics* (2013) 195:1177-1180]. Delivery of Cas9 protein/gRNA complexes via electroporation was described by Kim [Kim et al., "Highly efficient RNA-guided genome editing in human cells via delivery of purified Cas9 ribonucleoproteins" *Genome Res*. (2014) 24:1012-1019]. Delivery of Cas9 protein-associated gRNA complexes via liposomes was reported by Zuris [Zuris et al., "Cationic lipid-mediated delivery of proteins enables efficient protein-based genome editing in vitro and in vivo" *Nat Biotechnol*. (2014) doi: 10.1038/nbt.3081].

SUMMARY OF THE INVENTION

According to an aspect of some embodiments of the present invention, there is provided a method of modifying a gene encoding or processed into a non-coding RNA molecule having no RNA silencing activity in a plant cell, the method comprising introducing into the plant cell a DNA editing agent conferring a silencing specificity of the non-coding RNA molecule towards a target RNA of interest, thereby modifying the gene encoding or processed into the non-coding RNA molecule.

According to an aspect of some embodiments of the present invention, there is provided a method of modifying a gene encoding or processed into a non-coding RNA molecule having no RNA silencing activity in a plant cell, the method comprising introducing into the plant cell a DNA editing agent conferring a silencing specificity of the non-coding RNA molecule towards a target RNA of interest.

According to an aspect of some embodiments of the present invention, there is provided a method of modifying a gene encoding or processed into a RNA silencing molecule to a target RNA in a plant cell, the method comprising introducing into the plant cell a DNA editing agent which redirects a silencing specificity of the RNA silencing molecule towards a second target RNA, the target RNA and the second target RNA being distinct, thereby modifying the gene encoding the RNA silencing molecule.

According to an aspect of some embodiments of the present invention, there is provided a method of modifying a gene encoding or processed into a RNA silencing molecule to a target RNA in a plant cell, the method comprising introducing into the plant cell a DNA editing agent which redirects a silencing specificity of the RNA silencing molecule towards a second target RNA, the target RNA and the second target RNA being distinct.

According to an aspect of some embodiments of the present invention, there is provided a plant cell generated according to the method of some embodiments of the invention.

According to an aspect of some embodiments of the present invention, there is provided a plant comprising the plant cell of some embodiments of the invention.

According to an aspect of some embodiments of the present invention, there is provided a method of producing a plant with reduced expression of a target gene, the method comprising: (a) breeding the plant of some embodiments of the invention; and (b) selecting for progeny plants that have reduced expression of the target RNA of interest or the second target RNA, or progeny that comprises a silencing specificity in the non-coding RNA molecule towards a target RNA of interest, and which do not comprise the DNA editing agent, thereby producing the plant with reduced expression of a target gene.

According to an aspect of some embodiments of the present invention, there is provided a method of generating a plant with increased stress tolerance, increased yield, increased growth rate or increased yield quality, the method comprising modifying a gene encoding or processed into a non-coding RNA molecule or into a RNA silencing molecule in a plant cell according to some embodiments of the invention, wherein the target RNA of interest is of a gene of the plant conferring sensitivity to stress, decreased yield, decreased growth rate or decreased yield quality thereby generating the plant.

According to an aspect of some embodiments of the present invention, there is provided a method of generating a pathogen tolerant or resistant plant, the method comprising modifying a gene encoding or processed into a non-coding RNA molecule or into a RNA silencing molecule in a plant cell according to some embodiments of the invention, wherein the target RNA of interest is of a gene of the plant conferring sensitivity to the pathogen, thereby generating the pathogen tolerant or resistant plant.

According to an aspect of some embodiments of the present invention, there is provided a method of generating a pathogen tolerant or resistant plant, the method comprising modifying a gene encoding or processed into a non-coding RNA molecule or into a RNA silencing molecule in a plant cell according to some embodiments of the invention, wherein the target RNA of interest is of a gene of the pathogen, thereby generating the pathogen tolerant or resistant plant.

According to an aspect of some embodiments of the present invention, there is provided a method of generating a pest tolerant or resistant plant, the method comprising modifying a gene encoding or processed into a non-coding RNA molecule or into a RNA silencing molecule in a plant cell according to some embodiments of the invention, wherein the target RNA of interest is of a gene of the pest, thereby generating the pest tolerant or resistant plant.

According to an aspect of some embodiments of the present invention, there is provided a method of generating a pest tolerant or resistant plant, the method comprising modifying a gene encoding or processed into a non-coding RNA molecule or into a RNA silencing molecule in a plant cell according to some embodiments of the invention, wherein the target RNA of interest is of a gene of the plant conferring sensitivity to the pest, thereby generating the pest tolerant or resistant plant.

According to an aspect of some embodiments of the present invention, there is provided a method of generating a herbicide resistant plant, the method comprising modifying a gene encoding or processed into a non-coding RNA molecule or into a RNA silencing molecule in a plant cell according to some embodiments of the invention, wherein the target RNA of interest is of a gene of the plant conferring sensitivity to the herbicide, thereby generating the herbicide resistant plant.

According to an aspect of some embodiments of the present invention, there is provided a plant generated according to the method of some embodiments of the invention.

According to an aspect of some embodiments of the present invention, there is provided a seed of the plant of some embodiments of the invention.

According to some embodiments of the invention, the gene encoding or processed into the non-coding RNA molecule is endogenous to the plant cell.

According to some embodiments of the invention, the gene encoding the RNA silencing molecule is endogenous to the plant cell.

According to some embodiments of the invention, modifying the gene encoding or processed into the non-coding RNA molecule comprises imparting the non-coding RNA molecule with at least 45% complementarity towards the target RNA of interest.

According to some embodiments of the invention, modifying the gene encoding the RNA silencing molecule comprises imparting the RNA silencing molecule with at least 45% complementarity towards the second target RNA.

According to some embodiments of the invention, the silencing specificity of the non-coding RNA molecule is determined by measuring a RNA or protein level of the target RNA of interest.

According to some embodiments of the invention, the silencing specificity of the RNA silencing molecule is determined by measuring a RNA level of the second target RNA.

According to some embodiments of the invention, the silencing specificity of the non-coding RNA molecule or the RNA silencing molecule is determined phenotypically.

According to some embodiments of the invention, determined phenotypically is effected by determination of at least one plant phenotype selected from the group consisting of plant a leaf coloring, a flower coloring, a growth rate, a plant size, a crop yield, a fruit trait, a biotic stress resistance, and an abiotic stress resistance.

According to some embodiments of the invention, the silencing specificity of the non-coding RNA molecule is determined genotypically.

According to some embodiments of the invention, the plant phenotype is determined prior to a plant genotype.

According to some embodiments of the invention, the plant genotype is determined prior to a plant phenotype.

According to some embodiments of the invention, the non-coding RNA molecule or the RNA silencing molecule is processed from a precursor.

According to some embodiments of the invention, the non-coding RNA molecule or the RNA silencing molecule is a RNA interference (RNAi) molecule.

According to some embodiments of the invention, the RNAi molecule is selected from the group consisting of a small interfering RNA (siRNA), a short hairpin RNA (shRNA), a microRNA (miRNA), a Piwi-interacting RNA (piRNA) and trans-acting siRNA (tasiRNA).

According to some embodiments of the invention, the non-coding RNA molecule is selected from the group consisting of a small nuclear RNA (snRNA), a small nucleolar RNA (snoRNA), a long non-coding RNA (lncRNA), a ribosomal RNA (rRNA), transfer RNA (tRNA), a repeat-derived RNA, and a transposable element RNA.

According to some embodiments of the invention, the RNA molecule or RNAi molecule is designed such that a sequence of the RNAi molecule is modified to preserve originality of structure and to be recognized by cellular RNAi factors.

According to some embodiments of the invention, modifying the gene is effected by a modification selected from the group consisting of a deletion, an insertion, a point mutation and a combination thereof.

According to some embodiments of the invention, the modification is in a stem region of the non-coding RNA molecule or the RNA silencing molecule.

According to some embodiments of the invention, the modification is in a loop region of the non-coding RNA molecule or the RNA silencing molecule.

According to some embodiments of the invention, the modification is in a non-structured region of the non-coding RNA molecule or the RNA silencing molecule.

According to some embodiments of the invention, the modification is in a stem region and a loop region of the non-coding RNA molecule or the RNA silencing molecule.

According to some embodiments of the invention, the modification is in a stem region and a loop region and in non-structured region of the non-coding RNA molecule or the RNA silencing molecule.

According to some embodiments of the invention, the modification is an insertion.

According to some embodiments of the invention, the modification is a deletion.

According to some embodiments of the invention, the modification is a point mutation.

According to some embodiments of the invention, the modification comprises a modification of at most 200 nucleotides.

According to some embodiments of the invention, the method further comprises introducing into the plant cell donor oligonucleotides.

According to some embodiments of the invention, the DNA editing agent comprises at least one gRNA operatively linked to a plant expressible promoter.

According to some embodiments of the invention, the DNA editing agent does not comprise an endonuclease.

According to some embodiments of the invention, the DNA editing agent comprises an endonuclease.

According to some embodiments of the invention, the DNA editing agent is of a DNA editing system selected from the group consisting of a meganuclease, a zinc finger nucleases (ZFN), a transcription-activator like effector nuclease (TALEN) and CRISPR.

According to some embodiments of the invention, the endonuclease comprises Cas9.

According to some embodiments of the invention, the DNA editing agent is applied to the cell as DNA, RNA or RNP.

According to some embodiments of the invention, the DNA editing agent is linked to a reporter for monitoring expression in a plant cell.

According to some embodiments of the invention, the reporter is a fluorescent protein.

According to some embodiments of the invention, the target RNA of interest or the second target RNA is endogenous to the plant cell.

According to some embodiments of the invention, the target RNA of interest or the second target RNA is exogenous to the plant cell.

According to some embodiments of the invention, the plant cell is a protoplast.

According to some embodiments of the invention, the breeding comprises crossing or selfing.

According to some embodiments of the invention, the plant is non-genetically modified (non-GMO).

According to some embodiments of the invention, the plant is selected from the group consisting of a crop, a flower and a tree.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
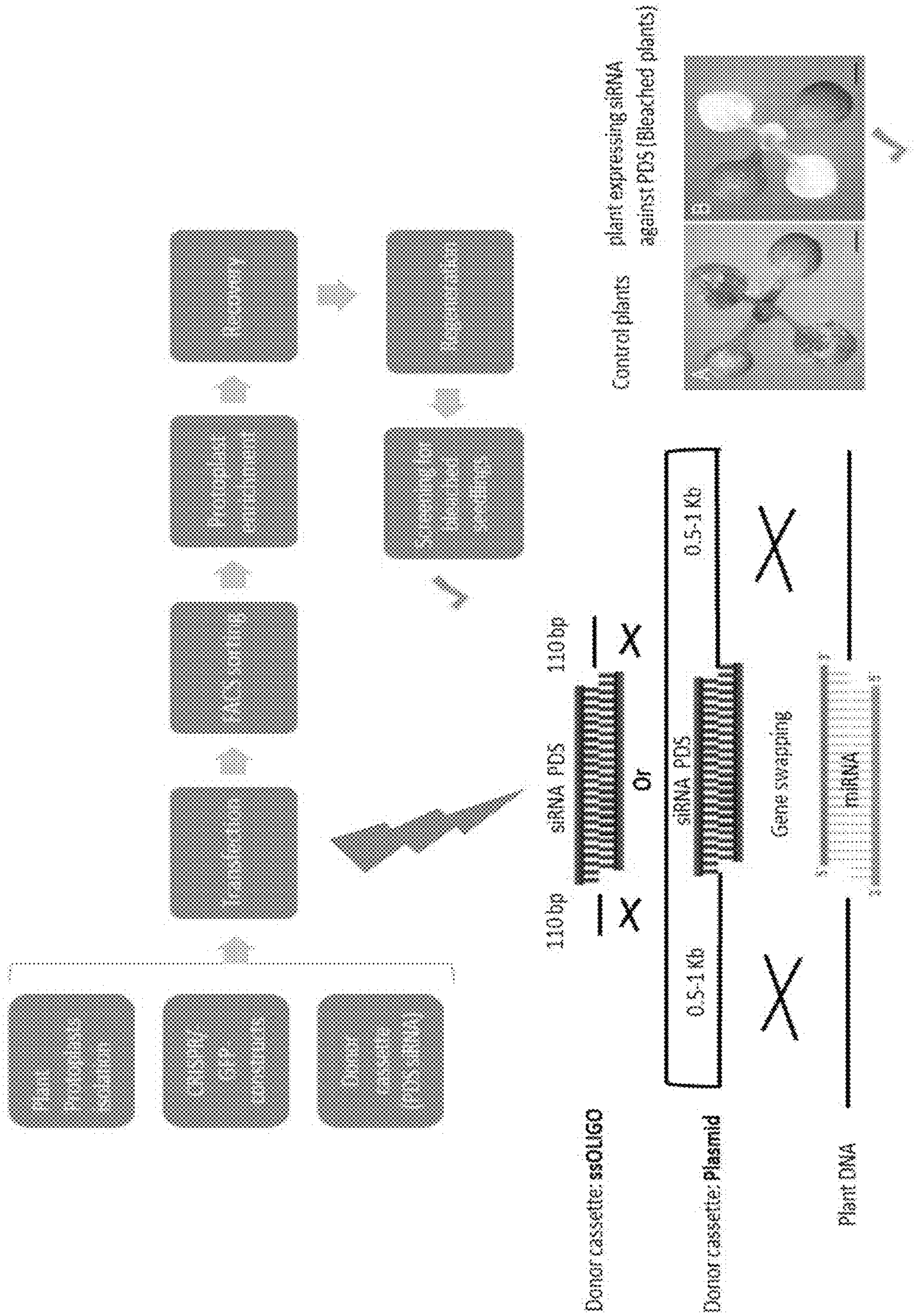

FIG. 1 is an embodiment flow chart of Genome Editing Induced Gene Silencing (GEiGS) replacement of endogenous miRNA with siRNA targeting the PDS gene, hence inducing gene silencing of the endogenous PDS gene. To introduce the modification, a 2-component system is being used. First, a CRISPR/CAS9 system, in a GFP containing vector, generates a cleavage in the chosen loci, through designed specific guide RNAs to promote homologous DNA repair (HDR) in the site. Second, A DONOR sequence, with the desired modification of the miRNA sequence, to target the newly assigned genes, is introduced as a template for the HDR. This system is being used in protoplast transformation, enriched by FACS due to the GFP signal in the CRISPR/CAS9 vector, recovered, and regenerated to plants.

Figure 2B:
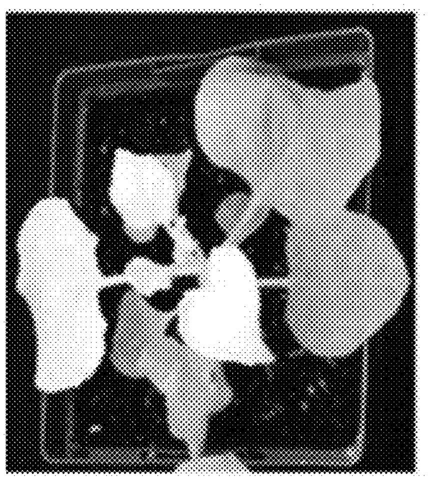
Figure 2A:
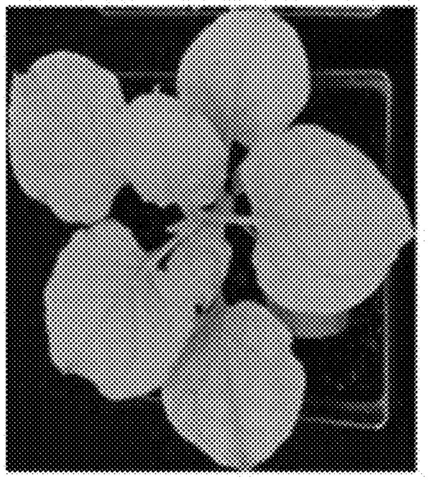
Figure 2C:
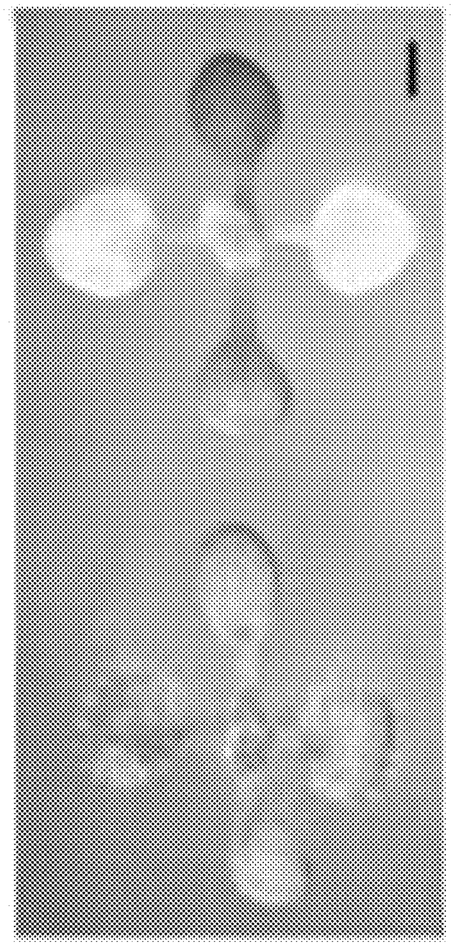

FIGS. 2A-C are photographs illustrating that silencing of the PDS gene causes photobleaching. Silencing of the PDS gene in *Nicotiana* (FIGS. 2A-B) and *Arabidopsis* (FIG. 2C) plants causes photobleaching in *N. benthamiana* (FIG. 2B) and *Arabidopsis* (FIG. 2C, right side). Photographs were taken 3½ weeks after PDS silencing.

Figures 3A, 3B, 3C, 3D:
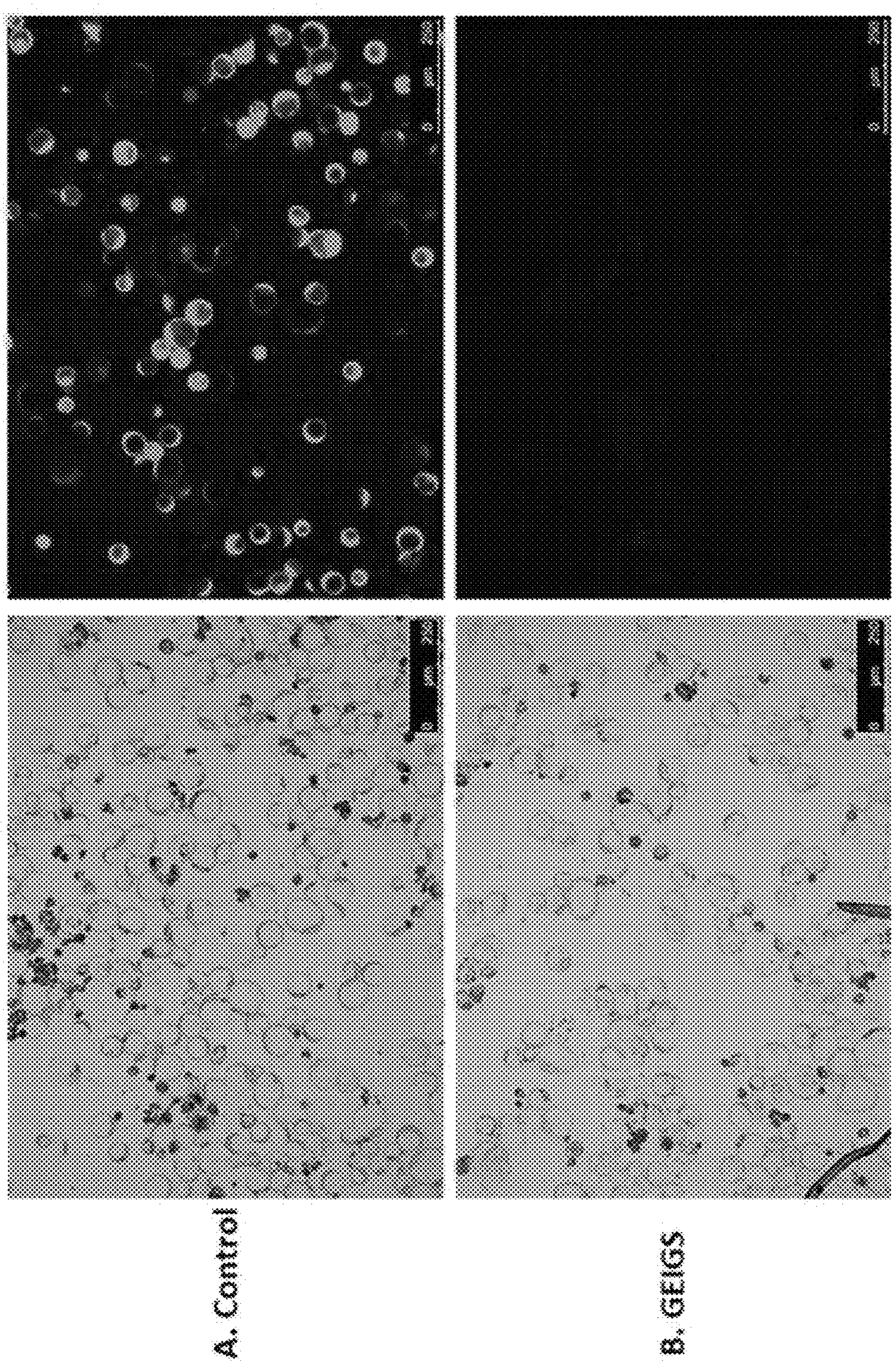

FIG. 3A-D are photographs of knock down of GFP expression levels in *Arabidopsis* using GEiGS. *Arabidopsis* protoplasts expressing GFP are illustrated as control (FIGS. 3A-B) compared to protoplasts edited using GEiGS to express GFP siRNA (FIGS. 3C-D). Of note, GEiGS protoplasts or plants are silenced for expression of GFP protein.

Figure 4:
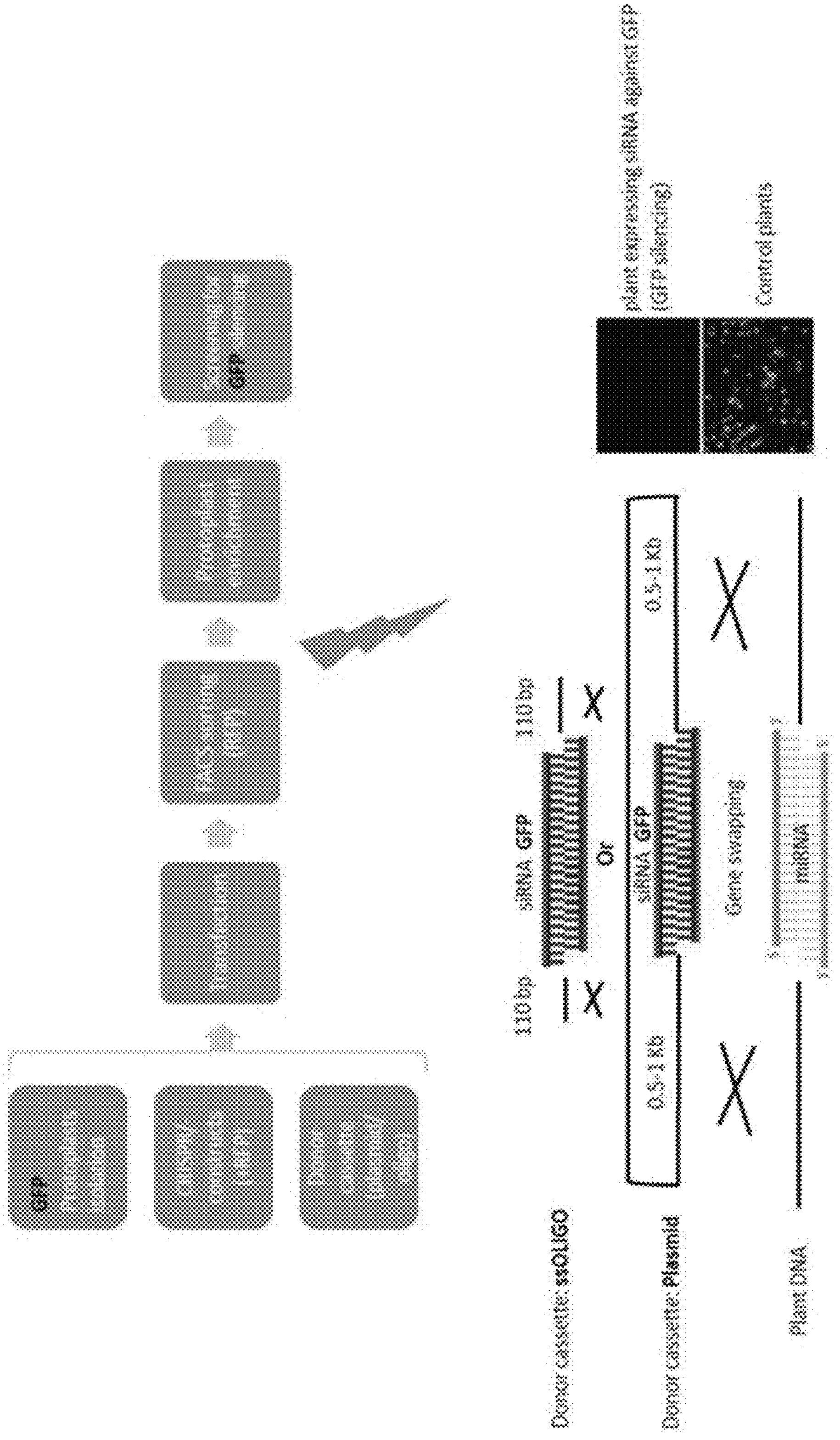

FIG. 4 is an embodiment flow chart of GEiGS replacement of endogenous miRNA with siRNA targeting GFP, generating *Arabidopsis* plants with active RNAi against GFP. To introduce the modification, a CRISPR/CAS9 system, in a RFP containing vector, generates a cleavage in the chosen loci, through designed specific guide RNAs to promote homologous DNA repair (HDR) in the site. Second, A DONOR sequence, with the desired modification of the miRNA sequence, to target the GFP gene, is introduced as a template for the HDR. This system is being used in GFP expressing protoplasts. Enrichment of putatively modified cells by FACS due to the RFP signal in the CRISPR/CAS9 vector, is being carried out and recovered. Regenerated plants are being analysed for intensity of GFP signal.

Figure 5:
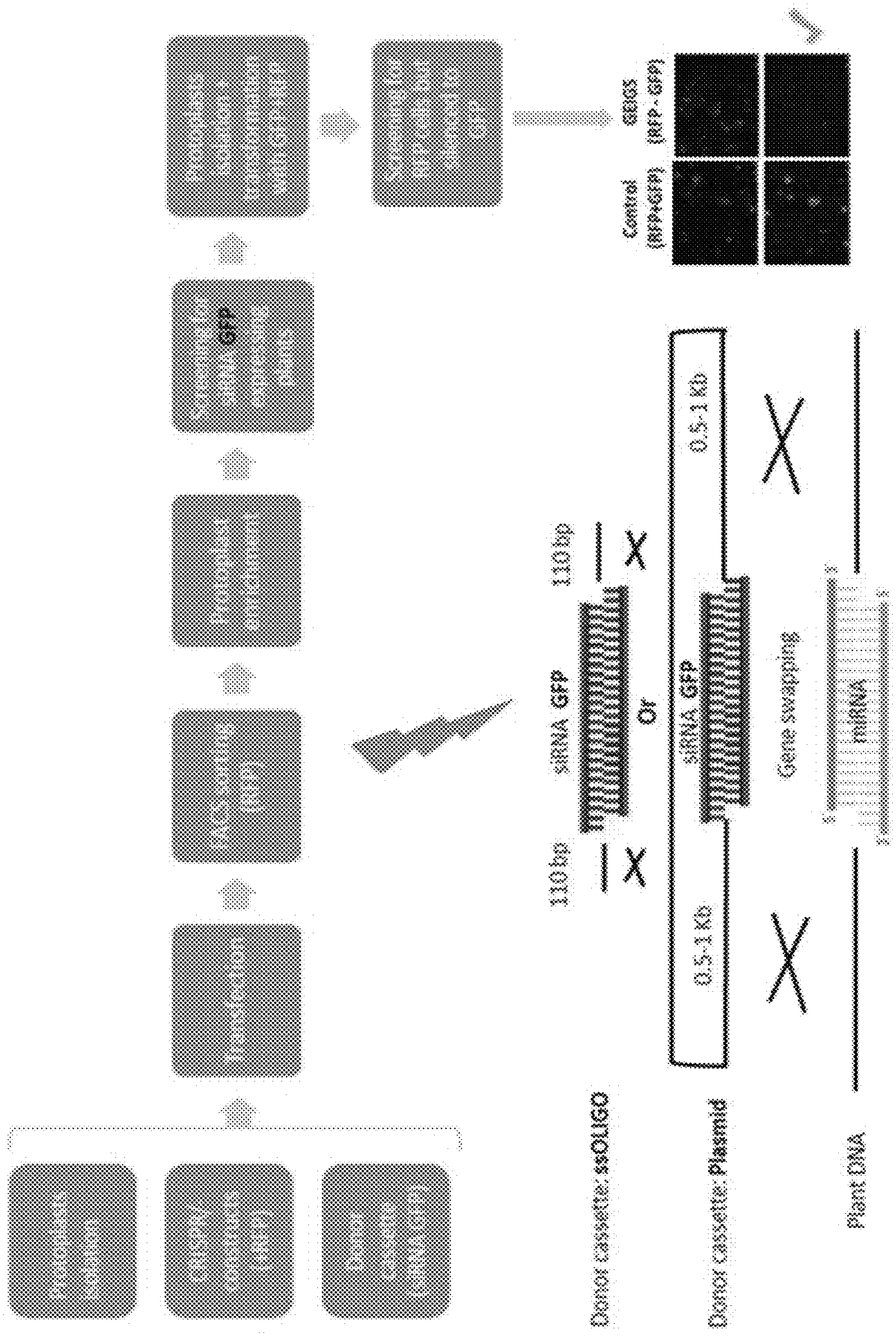

FIG. 5 is an embodiment flow chart of GEiGS replacement of endogenous miRNA with siRNA targeting GFP, generating *Arabidopsis* plants with GEiGS-directed RNAi against GFP. Of note, GEiGS plants are silenced for GFP expression after plant transformation. RFP is being used for the enrichment of cells with transient presence of CRISPR/CAS9 vector.

Figure 6:
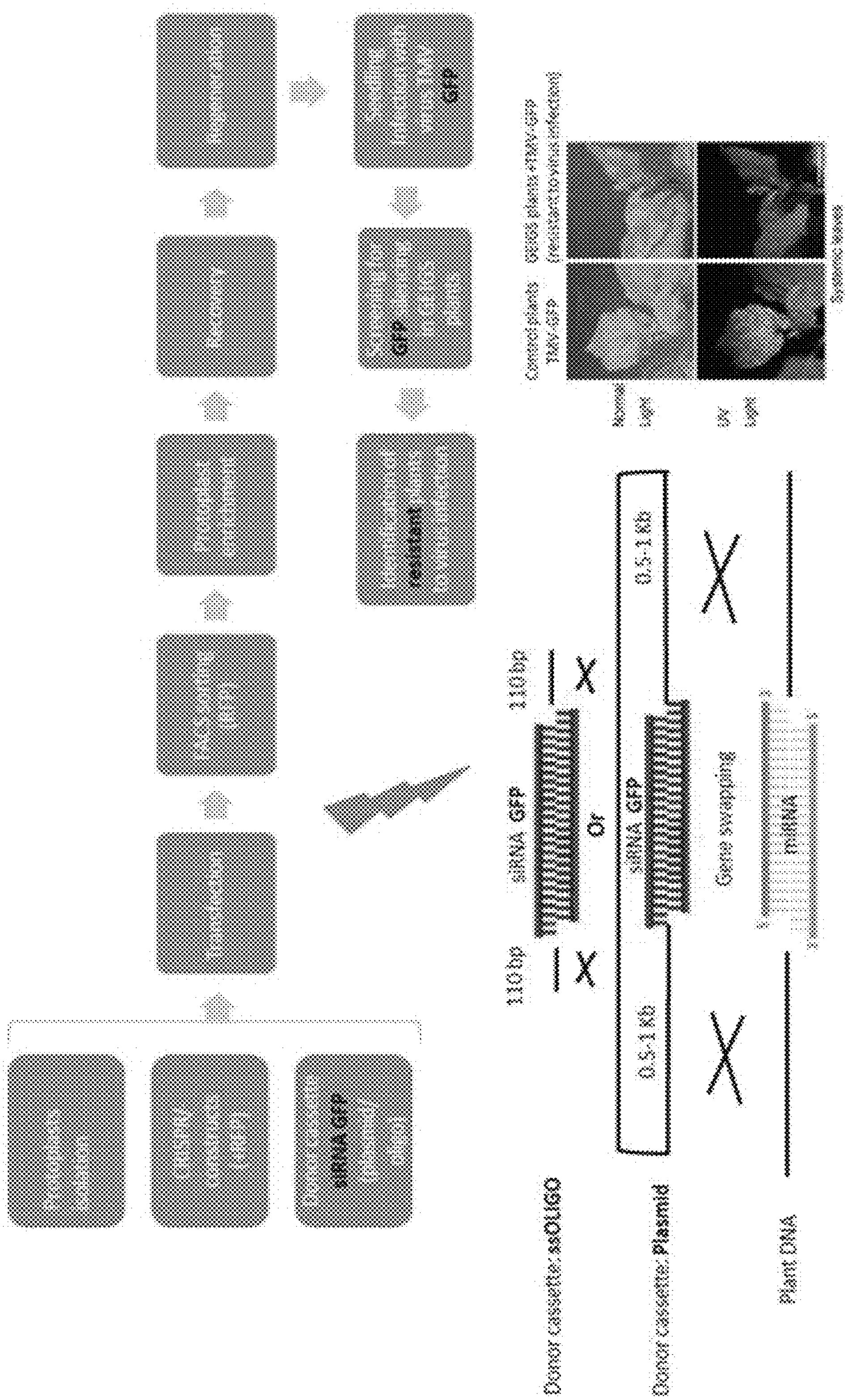

FIG. 6 is an embodiment flow chart of GEiGS replacement of endogenous miRNA with siRNA targeting GFP, generating plants resistant to viral infection e.g. TMV infection (i.e. exogenous gene). RFP is being used for the enrichment of cells with transient presence of CRISPR/CAS9 vector.

Figure 7:

FIG. 7 is a photograph of lodging banana plants suffering from Toppling Disease caused by the burrowing nematode, *Radopholus similis.*

FIG. 8 is a table illustrating the occurrence of *Radopholus similis* and *Pratylenchus coffeae* on different crops in Tay Nguyen area.

Figure 9:
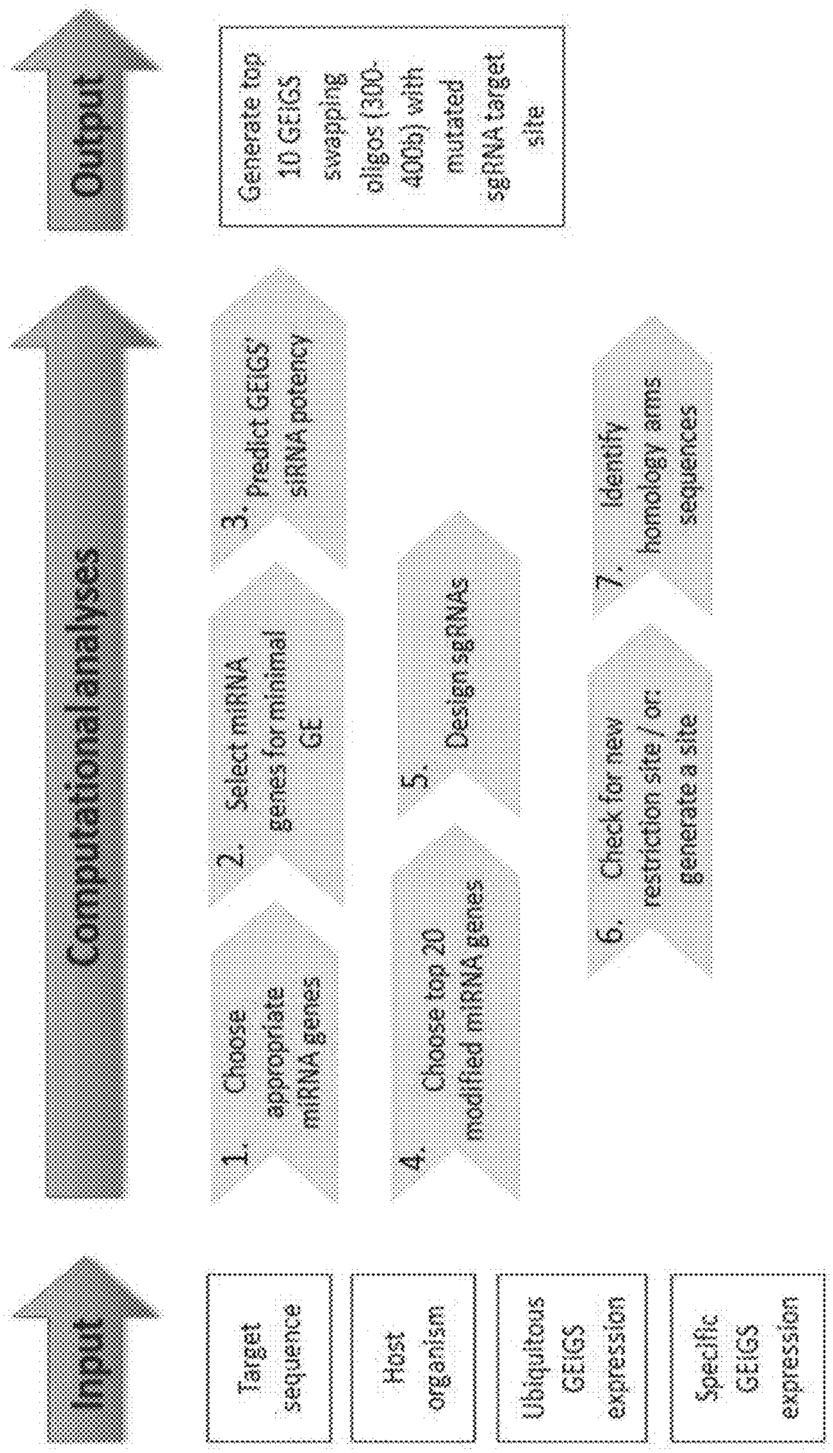

FIG. 9 is an embodiment flow chart of computational pipeline to generate GEiGS templates. The computational GEiGS pipeline applies biological metadata and enables an automatic generation of GEiGS DNA donor templates that are used to minimally edit endogenous non-coding RNA genes (e.g. miRNA genes), leading to a new gain of function, i.e. redirection of their silencing capacity to target gene expression of interest.

Figure 10:
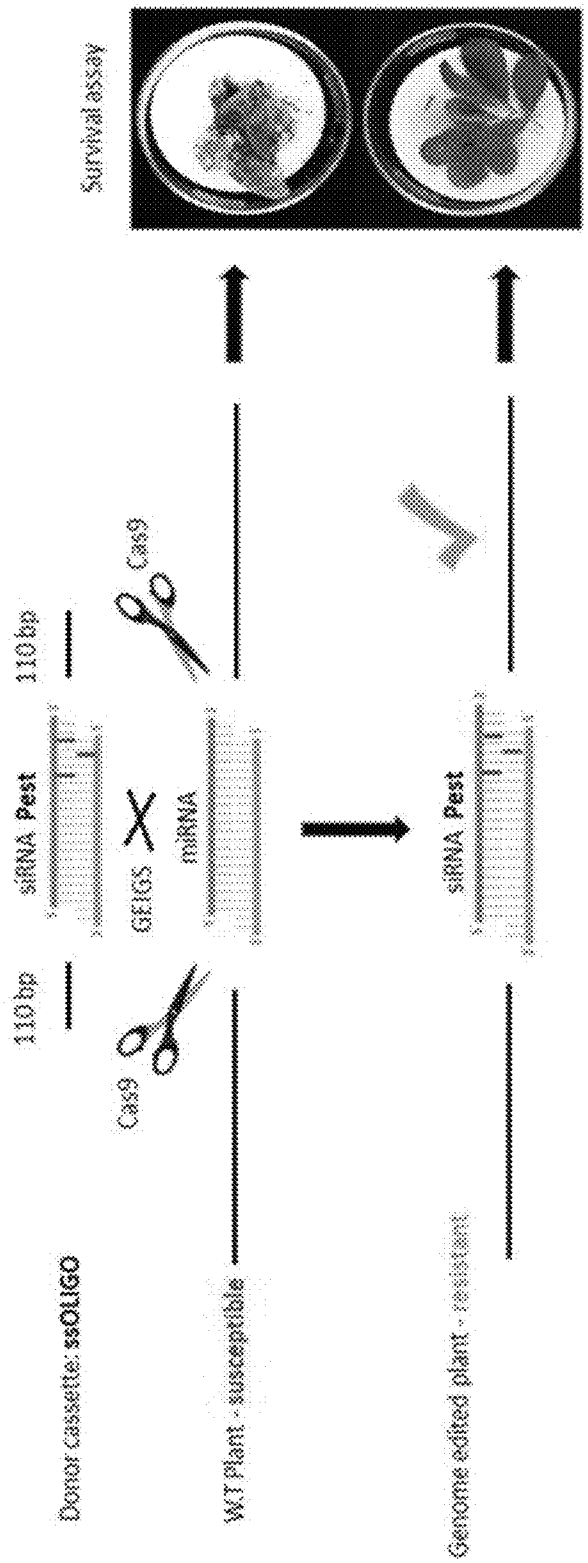

FIG. 10 is an embodiment flow chart illustrating design of resistant plant to pests targeting any desired exogenous pest gene. GEiGS replacement of endogenous miRNA with siRNA targeting pathogen/pest essential gene, generating plants resistant to pathogen/pest infection.

Figure 11:
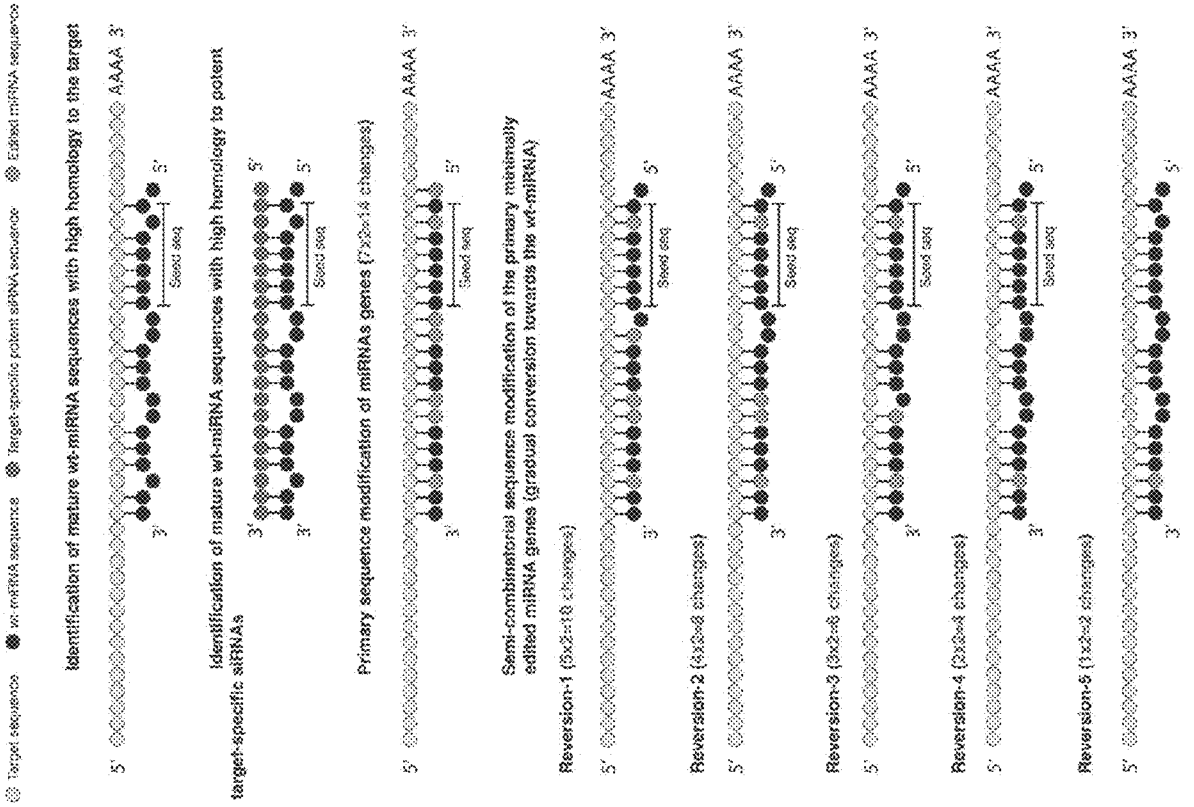

FIG. 11 is an embodiment drawing illustrating the main stages required to design RNA silencing molecule and with minimally edited miRNA gene bases.

Figures 12A, 12B, 12C, 12D, 12E, 12F, 12G:
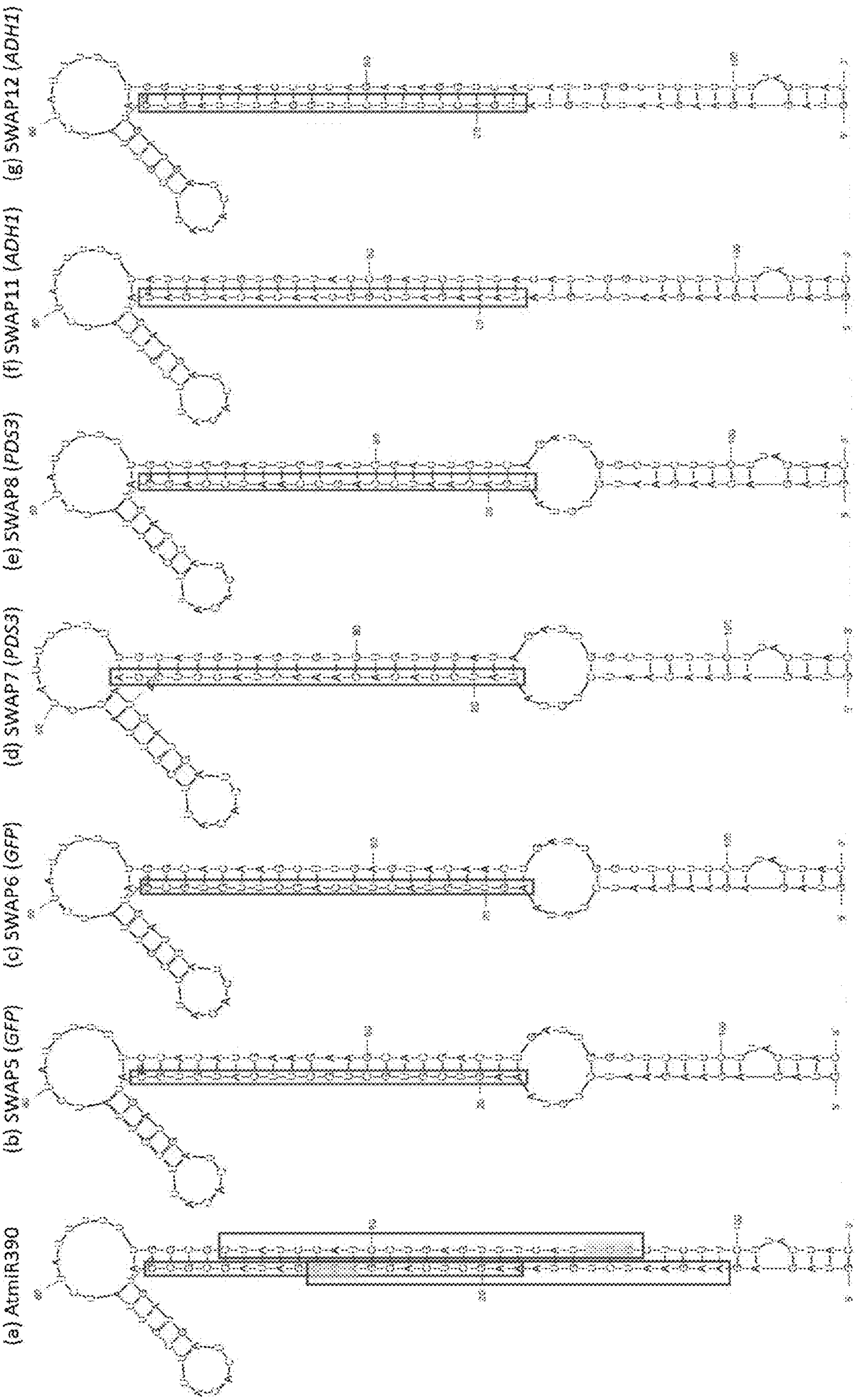

FIGS. 12A-G illustrate primary transcripts of miR-390 and modified miR390—structure and targeted sequences. Secondary structure representation of primary transcripts of miR390, and its modified versions—(FIG. 12A) wild type; (FIGS. 12B-C) modified version to target GFP; (FIGS. 12D-E) modified version to target AtPDS3; (FIGS. 12F-G) modified version to target AtADH1. Mature miRNA/siRNAs are outlined in red, exhibiting structure conservation through design. The regions targeted for manipulation by CRISPR/CAS9 system are outlined in purple and the NGG sequence is highlighted in yellow (FIG. 12A).

FIGS. 13A-G illustrate primary transcripts of miR-173 and modified miR173-structure and targeted sequences. Secondary structure representation of primary transcripts of miR173, and its modified versions—(FIG. 13A) wild type; (FIGS. 13B-C) modified version to target GFP; (FIG. 13D-E) modified version to target AtPDS3; (FIG. 13F-G) modified version to target AtADH1. Mature miRNA/siRNAs are outlined in red, exhibiting structure conservation through design. The regions targeted for manipulation by CRISPR/CAS9 system are outlined in purple and the NGG sequence is highlighted in yellow (FIG. 13A).

Figure 13H:

FIG. 13H illustrates embodiment examples of GEiGS oligo designs in which the precursor structure does not play a role in the biogenesis, hence, it is not required to be maintained. Design based on the *Brassica rapa* bnTAS3B tasiRNA. From top to bottom: wild-type tasiRNA, GEiGS design with minimal sequence changes, and GEiGS design with maximal sequence changes. The selections of non-coding RNA precursors that give rise to mature small RNA molecules are highlighted in green. Sequence differences between the GEiGS oligos and the wild type sequence are highlighted in red. Of note, tasiRNA biogenesis, unlike miRNAs and tRNAs, does not rely on the precursor secondary structure.

FIGS. 14A-D illustrate gene targeting by miR-173 and its modified versions. (FIG. 14A) Wild type miR-173 target the TAS1c transcript by sequence complementarity of the mature miRNA to a sequence in the gene (in red). The newly modified miRNAs (SWAPs 1, 2, 3, 4, 9 and 10) were designed to target (FIG. 14B) GFP, (FIG. 14C) AtPDS3 and (FIG. 14D) AtADH1 by sequence complementarity to their sequence (in red). Modified nucleotide from wt sequence, are written in lowercase.

FIGS. 15A-D illustrate gene targeting by miR-390 and its modified versions. (FIG. 15A) Wild type miR-390 target the TAS3 transcript by sequence complementarity of the mature miRNA to a sequence in the gene (in red). The newly modified miRNAs (SWAPs 5, 6, 7, 8, 11 and 12) were designed to target (FIG. 15B) GFP, (FIG. 15C) AtPDS3 and (FIG. 15D) AtADH1 by sequence complementarity to their sequence (in red). Modified nucleotide from wt sequence, are written in lowercase.

Figure 16:
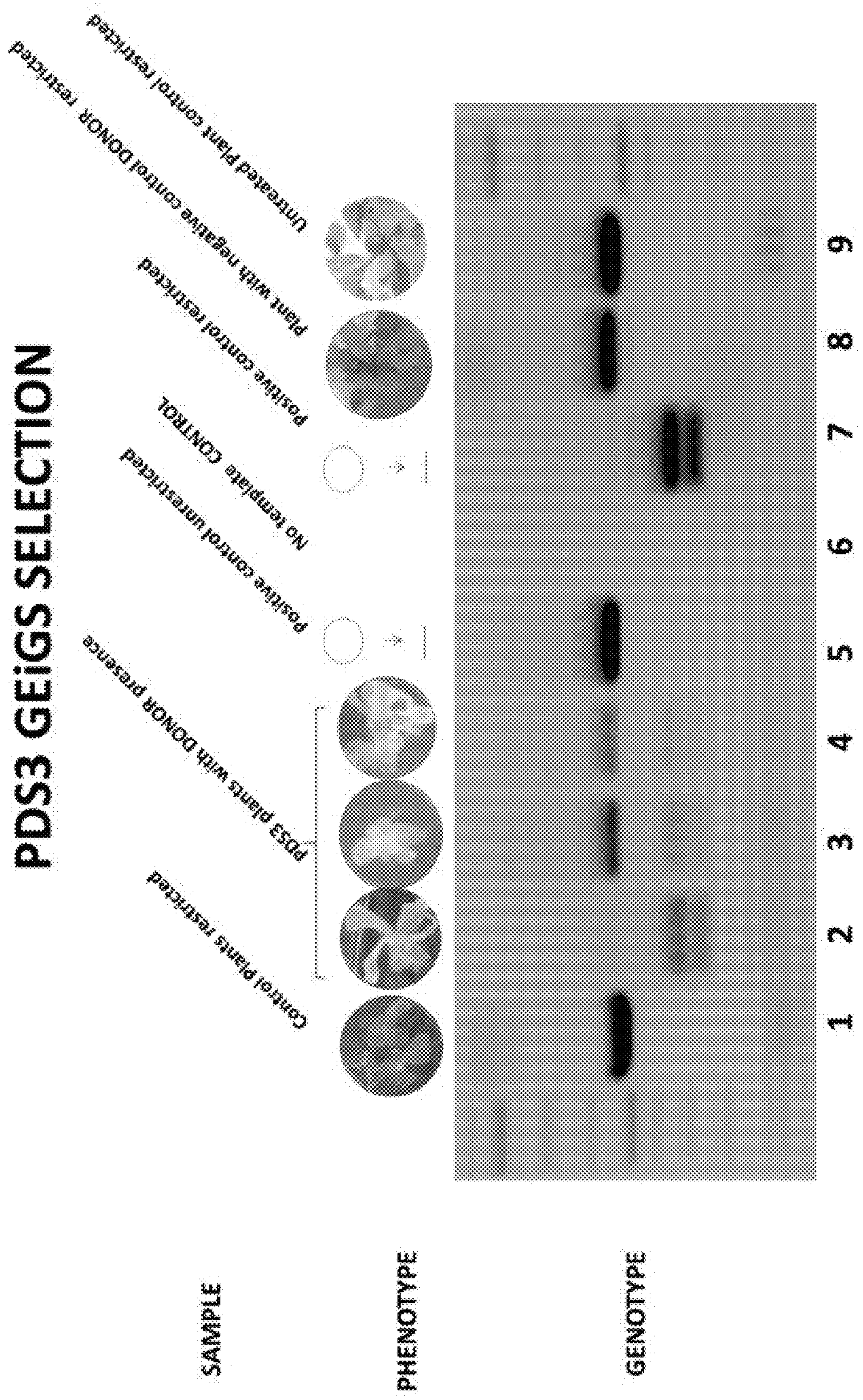

FIG. 16 illustrates PDS3 Phenotype/Genotype: bleached phenotype plants were selected and genotyped through internal amplicon PCR followed by restriction digest analysis with BtsαI (NEB) in order to verify donor presence vs. wild type sequence. Lane 1: Treated plants with NO DONOR, restricted, Lanes 2-4: PDS3 treated plants containing DONOR restricted, Lane 5: Positive plasmid DONOR control unrestricted, Lane 6: Water no template control, Lane 7: Positive Plasmid DONOR restricted, Lane 8: Plants bombarded with negative DONOR restricted, Lane 9: Untreated control plants restricted. Subsequent external PCR amplification of the amplicon was processed and sequenced in order to validate the insertion.

Figure 17:
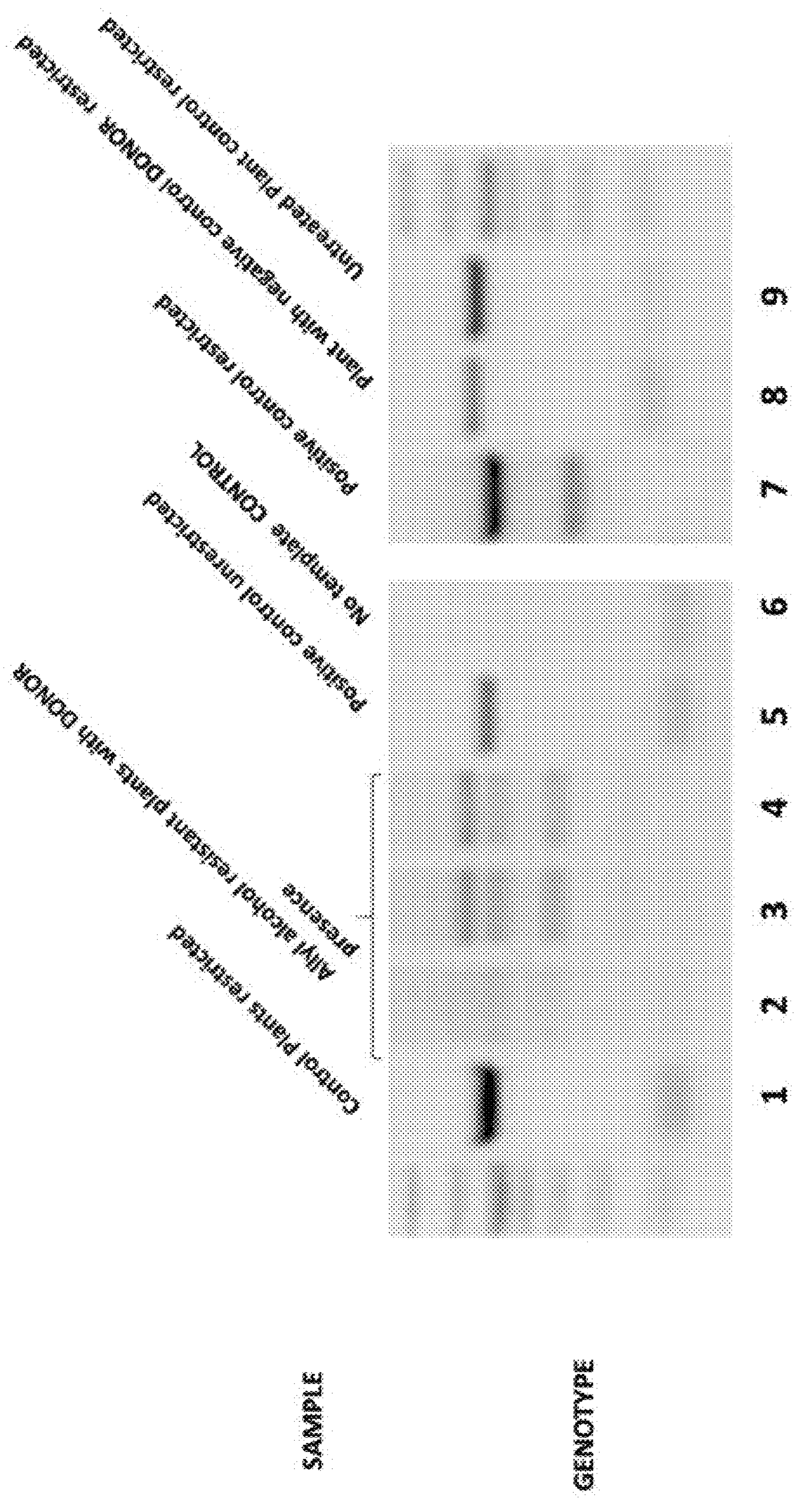

FIG. 17 illustrates ADH1 Phenotype/Genotype: Plants were selected through Allyl alcohol resistance and genotyped through internal amplicon PCR followed by BccI (NEB) restriction digest in order to verify donor presence. Lane 1: Allyl alcohol sensitive control plant restricted, Lane 2-4: Allyl alcohol resistant plants containing DONOR restricted, Lane 5: Positive plasmid DONOR control unrestricted, Lane 6: no template control, Lane 7: Positive Plasmid DONOR restricted, Lane 8: Plant bombarded with non-specific DONOR restricted, Lane 9: Non Allyl alcohol treated control restricted.

Figure 18:
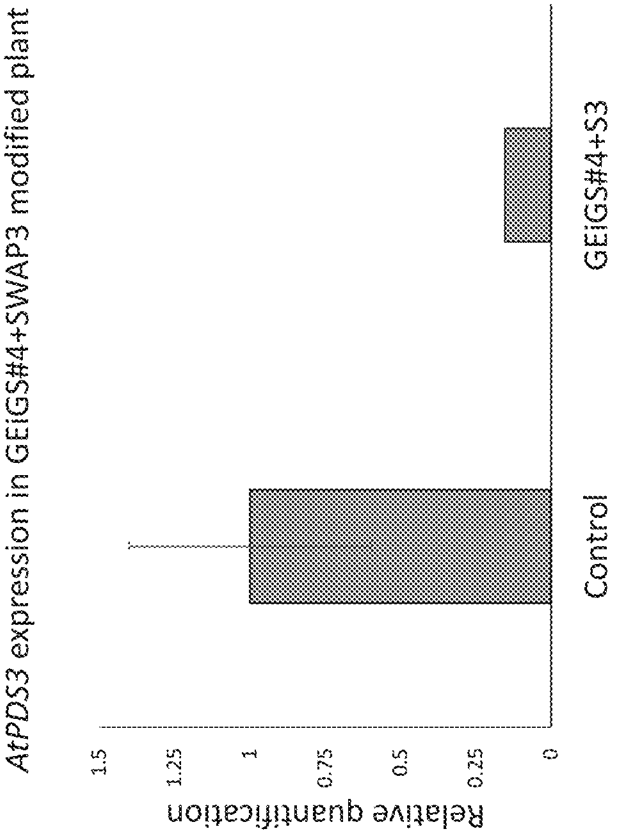

FIG. 18 is a graph illustrating gene expression analysis in miR-173 modified plant targeting AtPDS3 transcript. Analysis of AtPDS3 expression was carried out through qRT-PCR, in regenerating bombarded plants with GEiGS #4 and SWAP3 compared to plants bombarded with GEiGS #5 and SWAP1 and 2 (GFP). Of note, a reduction of 82% in gene expression level, on the average, was observed, when miR-173 was modified to target AtPDS3, compared to control plants (Error bars present SD; p-value <0.01 calculated on Ct values).

Figure 19:
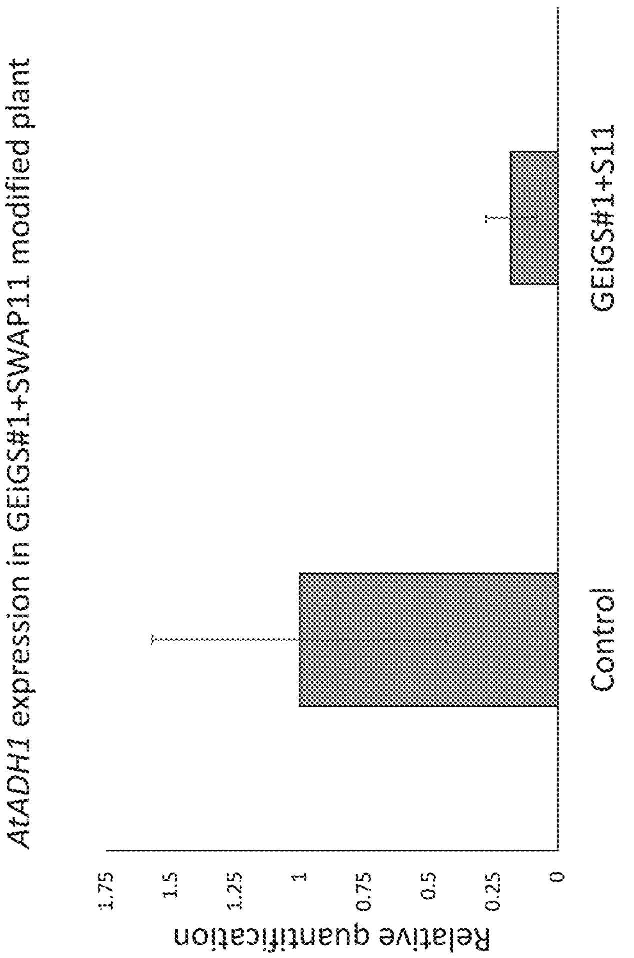

FIG. 19 is a graph illustrating gene expression analysis in miR-390 modified plant targeting AtPDS3 transcript. Analysis of AtADH1 expression was carried out through qRT-PCR, in regenerating bombarded plants with GEiGS #1 and SWAP11, compared to plants bombarded with GEiGS #5 and SWAP1 and 2 (GFP). Of note, a reduction of 82% in gene expression level, on the average, was observed, when miR-390 was modified to target AtADH1, compared to control plants (Error bars represent SD; p-value <0.01 calculated on Ct values).

DESCRIPTION OF SPECIFIC EMBODIMENTS OF THE INVENTION

The present invention, in some embodiments thereof, relates to modifying genes that encode or are processed into non-coding RNA molecules, including RNA silencing molecules and, more particularly, but not exclusively, to the use of same for silencing endogenous or exogenous target RNA of interest in plants.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

Previous work on genome editing of RNA molecules in various organisms (e.g. murine, human, plants), focused on disruption of miRNA activity or target binding sites using transgenesis. Genome editing in plants has further concentrated on the use of CRISPR-Cas9 technology, ZFNs and TALENs, for knockdown of genes or insertions in model plants. Furthermore, gene silencing in plants using artificial microRNAs transgenes to silence endogenous and exogenous target genes were described [Molnar A et al. Plant J. (2009) 58(1):165-74. doi: 10.1111/j.1365-313X.2008.03767.x. Epub 2009 Jan. 19; Borges and Martienssen, *Nature Reviews Molecular Cell Biology|AOP, pub-*

*lished online* 4 Nov. 2015; doi:10.1038/nrm4085]. The artificial miRNAs transgenes are introduced into plant cells within an artificial expression cassette (including a promoter, terminator, selection marker, etc.) and downregulate target expression.

While reducing the present invention to practice, the present inventors have devised a gene editing technology directed to non-coding RNA molecules (e.g. endogenous) designed to target and interfere with a non-natural target gene of interest (endogenous or exogenous to the plant cell). The gene editing technology described herein does not implement the classical molecular genetic and transgenic tools comprising expression cassettes that have a promoter, terminator, selection marker.

As is shown herein below and in the examples section which follows, the present inventors have designed a Genome Editing Induced Gene Silencing (GEiGS) platform capable of utilizing a plant cell's endogenous non-coding RNA molecules including e.g. RNA silencing molecules (e.g. siRNA, miRNA, piRNA, tasiRNA, tRNA, rRNA, antisense RNA, snRNA, snoRNA etc.) and modifying them to target and down regulate any RNA target of interest (see Exemplary flowchart in FIG. 1). Using GEiGS, the present method enables screening of potential non-coding RNA molecules, editing nucleotides in these endogenous RNA molecules, and thereby redirecting their specificity to effectively and specifically target and down regulate any RNA of interest including, endogenous and/or exogenous RNA encoded by pathogens and pests (see Exemplary flowchart in FIG. 9). Taken together, GEiGS can be utilized as a novel non-GMO technology for increasing crop yield, crop growth rate, crop quality as well as for crop protection against stress, pathogens, pests and herbicides.

Thus, according to an aspect of the invention there is provided a method of modifying a gene encoding or processed into a non-coding RNA molecule having no RNA silencing activity in a plant cell, the method comprising introducing into the plant cell a DNA editing agent conferring a silencing specificity of the non-coding RNA molecule towards a target RNA of interest, thereby modifying the gene encoding or processed into the non-coding RNA molecule.

According to another aspect of the invention there is provided a method of modifying a gene encoding or processed into a RNA silencing molecule to a target RNA in a plant cell, the method comprising introducing into the plant cell a DNA editing agent which redirects the specificity of the RNA silencing molecule towards a second target RNA, the target RNA and the second target RNA being distinct, thereby modifying the gene encoding the RNA silencing molecule.

The term "plant" as used herein encompasses whole plants, a grafted plant, ancestors and progeny of the plants and plant parts, including seeds, shoots, stems, roots (including tubers), rootstock, scion, and plant cells, tissues and organs. The plant may be in any form including suspension cultures, embryos, meristematic regions, callus tissue, leaves, gametophytes, sporophytes, pollen, and microspores. Plants that may be useful in the methods of the invention include all plants which belong to the superfamily Viridiplantee, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp. *Dolichos* spp., *Dorycnium rectum, Echinochloa pyramidalis, Ehraffia* spp., *Eleusine coracana, Eragrestis* spp., *Erythrina* spp., *Eucalypfus* spp., *Euclea schimperi, Eulalia vi/losa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, banana, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of some embodiments of the invention.

According to a specific embodiment, the plant is a crop, a flower or a tree.

According to a specific embodiment, the plant is a woody plant species e.g., *Actinidia chinensis* (Actinidiaceae), Manihotesculenta (Euphorbiaceae), Firiodendron *tulipifera* (Magnoliaceae), *Populus* (Salicaceae), Santalum album (Santalaceae). *Ulmus* (Ulmaceae) and different species of the Rosaceae (Malus, *Prunus, Pyrus*) and the Rutaceae (*Citrus, Microcitrus*), Gymnospermae e.g., *Picea glauca* and *Pinus taeda*, forest trees (e.g., Betulaceae, Fagaceae, Gymnospermae and tropical tree species), fruit trees, shrubs or herbs, e.g., (banana, cocoa, coconut, coffee, date, grape and tea) and oil palm.

According to a specific embodiment, the plant is of a tropical crop e.g., coffee, macadamia, banana, pineapple, taro, papaya, mango, barley, beans, cassava, chickpea, cocoa (chocolate), cowpea, maize (corn), millet, rice, *sorghum*, sugarcane, sweet potato, tobacco, taro, tea, yam.

"Grain," "seed," or "bean," refers to a flowering plant's unit of reproduction, capable of developing into another such plant. As used herein, the terms are used synonymously and interchangeably.

According to a specific embodiment, the plant is a plant cell e.g., plant cell in an embryonic cell suspension.

According to a specific embodiment, the plant cell is a protoplast.

The protoplasts are derived from any plant tissue e.g., fruit, flowers, roots, leaves, embryos, embryonic cell suspension, calli or seedling tissue.

As used herein, the term "non-coding RNA molecule" refers to a RNA sequence that is not translated into an amino acid sequence and does not encode a protein.

According to one embodiment, the non-coding RNA molecule is typically subject to the RNA silencing processing mechanism or activity. However, also contemplated herein are a few changes in nucleotides (e.g. for miRNA up to 24 nucleotides) which may elicit a processing mechanism that results in RNA interference or translation inhibition.

According to a specific embodiment, the non-coding RNA molecule is endogenous (naturally occurring, e.g. native) to the cell. It will be appreciated that the non-coding RNA molecule can also be exogenous to the cell (i.e. externally added and which is not naturally occurring in the cell).

According to some embodiments, the non-coding RNA molecule comprises an intrinsic translational inhibition activity.

According to some embodiments, the non-coding RNA molecule comprises an intrinsic RNAi activity.

According to some embodiments, the non-coding RNA molecule does not comprise an intrinsic translational inhibition activity or an intrinsic RNAi activity (i.e. the non-coding RNA molecule does not have an RNA silencing activity).

According to an embodiment of the invention, the non-coding RNA molecule is specific to a target RNA (e.g., a natural target RNA) and does not cross inhibit or silence a second target RNA or target RNA of interest unless designed to do so (as discussed below) exhibiting 100% or less global homology to the target gene, e.g., less than 99%, 98%, 97%, 96%, 95%, 94%, 93%, 92%, 91%, 90%, 89%, 88%, 87%, 86%, 85%, 84%, 83%, 82%, 81% global homology to the target gene; as determined at the RNA or protein level by RT-PCR, Western blot, Immunohistochemistry and/or flow cytometry, sequencing or any other detection methods.

According to one embodiment, the non-coding RNA molecule is a RNA silencing or RNA interference (RNAi) molecule.

The term "RNA silencing" or RNAi refers to a cellular regulatory mechanism in which non-coding RNA molecules (the "RNA silencing molecule" or "RNAi molecule") mediate, in a sequence specific manner, co- or post-transcriptional inhibition of gene expression or translation.

According to one embodiment, the RNA silencing molecule is capable of mediating RNA repression during transcription (co-transcriptional gene silencing).

According to a specific embodiment, co-transcriptional gene silencing includes epigenetic silencing (e.g. chromatic state that prevents functional gene expression).

According to one embodiment, the RNA silencing molecule is capable of mediating RNA repression after transcription (post-transcriptional gene silencing).

Post-transcriptional gene silencing (PTGS) typically refers to the process (typically occurring in the cell cytoplasm) of degradation or cleavage of messenger RNA (mRNA) molecules which decrease their activity by preventing translation. For example, and as discussed in detail below, a guide strand of a RNA silencing molecule pairs with a complementary sequence in a mRNA molecule and induces cleavage by e.g. Argonaute 2 (Ago2).

Co-transcriptional gene silencing typically refers to inactivation of gene activity (i.e. transcription repression) and typically occurs in the cell nucleus. Such gene activity repression is mediated by epigenetic-related factors, such as e.g. methyl-transferases, that methylate target DNA and histones. Thus, in co-transcriptional gene silencing, the association of a small RNA with a target RNA (small RNA-transcript interaction) destabilizes the target nascent transcript and recruits DNA- and histone-modifying enzymes (i.e. epigenetic factors) that induce chromatin remodeling into a structure that repress gene activity and transcription. Also, in co-transcriptional gene silencing, chromatin-associated long non-coding RNA scaffolds may recruit chromatin-modifying complexes independently of small RNAs. These co-transcriptional silencing mechanisms form RNA surveillance systems that detect and silence inappropriate transcription events, and provide a memory of these events via self-reinforcing epigenetic loops [as described in D. Hoch and D. Moazed, RNA-mediated epigenetic regulation of gene expression, *Nat Rev Genet.* (2015) 16(2): 71-84].

According to an embodiment of the invention, the RNAi biogenesis/processing machinery generates the RNA silencing molecule.

According to an embodiment of the invention, the RNAi biogenesis/processing machinery generates the RNA silencing molecule, but no specific target has been identified.

According to one embodiment, the non-coding RNA molecule is a capable of inducing RNA interference (RNAi).

Following is a detailed description of non-coding RNA molecules which comprise an intrinsic RNAi activity (e.g. are RNA silencing molecules) that can be used according to specific embodiments of the present invention.

According to one embodiment, the non-coding RNA molecule or the RNA silencing molecule is processed from a precursor.

According to one embodiment, the non-coding RNA molecule or the RNA silencing molecule is processed from a single stranded RNA (ssRNA) precursor.

According to one embodiment, the non-coding RNA molecule or the RNA silencing molecule is processed from a duplex-structured single-stranded RNA precursor.

According to one embodiment, the non-coding RNA molecule or the RNA silencing molecule is processed from a dsRNA precursor (e.g. comprising perfect and imperfect base pairing).

According to one embodiment, the non-coding RNA molecule or the RNA silencing molecule is processed from a non-structured RNA precursor.

According to one embodiment, the non-coding RNA molecule or the RNA silencing molecule is processed from a protein-coding RNA precursor.

According to one embodiment, the non-coding RNA molecule or the RNA silencing molecule is processed from a non-coding RNA precursor.

According to one embodiment, the dsRNA can be derived from two different complementary RNAs, or from a single RNA that folds on itself to form dsRNA.

Perfect and imperfect based paired RNA (i.e. double stranded RNA; dsRNA), siRNA and shRNA—The presence of long dsRNAs in cells stimulates the activity of a ribonuclease III enzyme referred to as dicer. Dicer (also known as endoribonuclease Dicer or helicase with RNase motif) is an enzyme that in plants is typically referred to as Dicer-like (DCL) protein. Different plants have different numbers of DCL genes, thus for example, *Arabidopsis* genome typically has four DCL genes, rice has eight DCL genes, and maize genome has five DCL genes. Dicer is involved in the processing of the dsRNA into short pieces of dsRNA known as short interfering RNAs (siRNAs). siRNAs derived from dicer activity are typically about 21 to about 23 nucleotides in length and comprise about 19 base pair duplexes with two 3' nucleotides overhangs.

Accordingly, some embodiments of the invention contemplate modifying a gene encoding a dsRNA to redirect a silencing specificity (including silencing activity) towards a second target RNA (i.e. RNA of interest).

According to one embodiment dsRNA precursors longer than 21 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

The term "siRNA" refers to small inhibitory RNA duplexes (generally between 18-30 base pairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is suggested to result from providing Dicer with a substrate (27 mer) instead of a product (21 mer) and that this improves the rate or efficiency of entry of the siRNA duplex into RISC.

It has been found that position, but not the composition, of the 3'-overhang influences potency of a siRNA and asymmetric duplexes having a 3'-overhang on the antisense strand are generally more potent than those with the 3'-overhang on the sense strand (Rose et al., 2005).

The strands of a double-stranded interfering RNA (e.g., a siRNA) may be connected to form a hairpin or stem-loop structure (e.g., a shRNA). Thus, as mentioned, the RNA silencing molecule of some embodiments of the invention may also be a short hairpin RNA (shRNA).

The term short hairpin RNA, "shRNA", as used herein, refers to a RNA molecule having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

The RNA silencing molecule of some embodiments of the invention need not be limited to those molecules containing only RNA, but further encompasses chemically-modified nucleotides and non-nucleotides.

Various types of siRNAs are contemplated by the present invention, including trans-acting siRNAs (Ta-siRNAs), repeat-associated siRNAs (Ra-siRNAs) and natural-antisense transcript-derived siRNAs (Nat-siRNAs).

According to one embodiment, silencing RNA includes "piRNA" which is a class of Piwi-interacting RNAs of about 26 and 31 nucleotides in length. piRNAs typically form RNA-protein complexes through interactions with Piwi proteins, i.e. antisense piRNAs are typically loaded into Piwi proteins (e.g. Piwi, Ago3 and Aubergine (Aub)).

miRNA—According to another embodiment the RNA silencing molecule may be a miRNA.

The term "microRNA", "miRNA", and "miR" are synonymous and refer to a collection of non-coding single-stranded RNA molecules of about 19-24 nucleotides in length, which regulate gene expression. miRNAs are found in a wide range of organisms (e.g. insects, mammals, plants, nematodes) and have been shown to play a role in development, homeostasis, and disease etiology.

Initially the pre-miRNA is present as a long non-perfect double-stranded stem loop RNA that is further processed by Dicer into a siRNA-like duplex, comprising the mature guide strand (miRNA) and a similar-sized fragment known as the passenger strand (miRNA*). The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually becomes incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-8 of the miRNA (referred as "seed sequence").

A number of studies have looked at the base-pairing requirement between miRNA and its mRNA target for achieving efficient inhibition of translation (reviewed by Bartel 2004, Cell 116-281). Computational studies, analyzing miRNA binding on whole genomes have suggested a specific role for bases 2-8 at the 5' of the miRNA (also referred to as "seed sequence") in target binding but the role of the first nucleotide, found usually to be "A" was also recognized (Lewis et al. 2005 Cell 120-15). Similarly, nucleotides 1-7 or 2-8 were used to identify and validate targets by Krek et al. (2005, Nat Genet 37-495). The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

It will be appreciated that the pre-miRNA sequence may comprise from 45-90, 60-80 or 60-70 nucleotides while the pri-miRNA sequence may comprise from 45-30,000, 50-25,000, 100-20,000, 1,000-1,500 or 80-100 nucleotides.

According to one embodiment, the miRNA comprises miR-390a (as set forth in SEQ ID NO: 28).

According to one embodiment, the miRNA comprises miR-173 (as set forth in SEQ ID NO: 29).

Antisense—Antisense is a single stranded RNA designed to prevent or inhibit expression of a gene by specifically hybridizing to its mRNA. Downregulation of a target RNA can be effected using an antisense polynucleotide capable of specifically hybridizing with an mRNA transcript encoding the target RNA.

As mentioned, the non-coding RNA molecule may not comprise a canonical (intrinsic) RNAi activity (e.g. is not a canonical RNA silencing molecule, or its target has not been identified). Such non-coding RNA molecules include the following:

According to one embodiment, the non-coding RNA molecule is a transfer RNA (tRNA). The term "tRNA" refers to a RNA molecule that serves as the physical link between nucleotide sequence of nucleic acids and the amino acid sequence of proteins, formerly referred to as soluble RNA or sRNA. tRNA is typically about 76 to 90 nucleotides in length.

According to one embodiment, the non-coding RNA molecule is a ribosomal RNA (rRNA). The term "rRNA" refers to the RNA component of the ribosome i.e. of either the small ribosomal subunit or the large ribosomal subunit.

According to one embodiment, the non-coding RNA molecule is a small nuclear RNA (snRNA or U-RNA). The terms "sRNA" or "U-RNA" refer to the small RNA molecules found within the splicing speckles and Cajal bodies of the cell nucleus in eukaryotic cells. snRNA is typically about 150 nucleotides in length.

According to one embodiment, the non-coding RNA molecule is a small nucleolar RNA (snoRNA). The term "snoRNA" refers to the class of small RNA molecules that primarily guide chemical modifications of other RNAs, e.g. rRNAs, tRNAs and snRNAs. snoRNA is typically classified into one of two classes: the C/D box snoRNAs are typically about 70-120 nucleotides in length and are associated with methylation, and the H/ACA box snoRNAs are typically about 100-200 nucleotides in length and are associated with pseudouridylation.

Similar to snoRNAs are the scaRNAs (i.e. Small Cajal body RNA genes) which perform a similar role in RNA maturation to snoRNAs, but their targets are spliceosomal snRNAs and they perform site-specific modifications of spliceosomal snRNA precursors (in the Cajal bodies of the nucleus).

According to one embodiment, the non-coding RNA molecule is an extracellular RNA (exRNA). The term "exRNA" refers to RNA species present outside of the cells from which they were transcribed (e.g. exosomal RNA).

According to one embodiment, the non-coding RNA molecule is a long non-coding RNA (lncRNA). The term "lncRNA" or "long ncRNA" refers to non-protein coding transcripts typically longer than 200 nucleotides.

According to one embodiment, non-limiting examples of non-coding RNA molecules include, but are not limited to, microRNA (miRNA), piwi-interacting RNA (piRNA), short interfering RNA (siRNA), short-hairpin RNA (shRNA), trans-acting siRNA (tasiRNA), small nuclear RNA (snRNA or URNA), small nucleolar RNA (snoRNA), Small Cajal body RNA (scaRNA), transfer RNA (tRNA), ribosomal RNA (rRNA), extracellular RNA (exRNA), repeat-derived RNA, transposable element RNA and long non-coding RNA (lncRNA).

According to one embodiment, non-limiting examples of RNAi molecules include, but are not limited to, small interfering RNA (siRNA), short hairpin RNA (shRNA), microRNA (miRNA), Piwi-interacting RNA (piRNA) and trans-acting siRNA (tasiRNA).

As mentioned above, the methods of some embodiments of the invention are utilized to redirect a silencing activity and/or specificity of the non-coding RNA molecule (or to generate a silencing activity and/or specificity if the non-coding RNA molecule does not have an intrinsic capability to silence a RNA molecule) towards a second target RNA or towards a target RNA of interest.

According to one embodiment, the target RNA and the second target RNA are distinct.

According to one embodiment, the method of modifying a gene encoding or processed into a RNA silencing molecule to a target RNA in a plant cell comprises introducing into the plant cell a DNA editing agent which redirects a silencing activity and/or specificity of the RNA silencing molecule towards a second target RNA, the target RNA and the second target RNA being distinct, thereby modifying the gene encoding the RNA silencing molecule.

As used herein, the term "redirects a silencing specificity" refers to reprogramming the original specificity of the non-coding RNA (e.g. RNA silencing molecule) towards a non-natural target of the non-coding RNA (e.g. RNA silencing molecule). Accordingly, the original specificity of the non-coding RNA is abolished (i.e. loss of function) and the new specificity is towards a RNA target distinct of the natural target (i.e. RNA of interest), i.e., gain of function. It will be appreciated that only gain of function occurs in cases that the non-coding RNA has no silencing activity.

As used herein, the term "target RNA" refers to a RNA sequence naturally bound by a non-coding RNA molecule. Thus, the target RNA is considered by the skilled artisan as a substrate for the non-coding RNA.

As used herein, the term "second target RNA" refers to a RNA sequence (coding or non-coding) not naturally bound by a non-coding RNA molecule. Thus, the second target RNA is not a natural substrate of the non-coding RNA.

As used herein, the term "target RNA of interest" refers to a RNA sequence (coding or non-coding) to be silenced by the designed non-coding RNA molecule.

As used herein, the phrase "silencing a target gene" refers to the absence or observable reduction in the level of mRNA and/or protein products from the target gene (e.g. due to co- and/or post-transcriptional gene silencing). Thus, silencing of a target gene can be by 5%, 10%, 20%, 30%, 40%, 50%, 60%, 70%, 80%, 90%, 95% or 100% as compared to a target gene not targeted by the designed non-coding RNA molecule of the invention.

The consequences of silencing can be confirmed by examination of the outward properties of a plant cell or whole plant or other organism that take up the designed non-coding RNA from the plant or by biochemical techniques (as discussed below).

It will be appreciated that the designed non-coding RNA molecule of some embodiments of the invention can have some off-target specificity effect/s provided that it does not affect an agriculturally valuable trait (e.g., biomass, yield etc.).

According to one embodiment, the second target RNA or target RNA of interest is endogenous to the plant cell. Exemplary endogenous second target RNA or target RNA of interest include, but are not limited to, a product of a gene conferring sensitivity to stress, to infection, to herbicides, or a product of a gene related to plant growth rate, crop yield, as further discussed herein below.

According to one embodiment, the second target RNA or target RNA of interest is exogenous to the plant cell (also referred to herein as heterologous). In such a case, the second target RNA or target RNA of interest is a product of a gene that is not naturally part of the plant genome. Exemplary exogenous second target RNA include, but are not limited to, a product of a gene of a plant pathogen such as, but not limited to, an insect, a virus, a bacteria, a fungi, a nematode, as further discussed herein below. An exogenous target RNA (coding or non-coding) may comprise a nucleic acid sequence which shares sequence identity with an endogenous RNA sequence (e.g. may be partially homologous to an endogenous nucleic acid sequence) of the plant.

The specific binding of an endogenous non-coding RNA molecule with a target RNA can be determined by computational algorithms (such as BLAST) and verified by methods including e.g. Northern blot, In Situ hybridization, QuantiGene Plex Assay etc.

By use of the term "complementarity" or "complementary" is meant that the non-coding RNA molecule (or at least a portion of it that is present in the processed small RNA form, or at least one strand of a double-stranded polynucleotide or portion thereof, or a portion of a single strand polynucleotide) hybridizes under physiological conditions to the target RNA, or a fragment thereof, to effect regulation or function or suppression of the target gene. For example, in some embodiments, a non-coding RNA molecule has 100 percent sequence identity or at least about 30, 40, 45, 50, 55, 60, 65, 70, 75, 80, 83, 84, 85, 86, 87, 88, 89, 90, 91, 92, 93, 94, 95, 96, 97, 98, or 99 percent sequence identity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 150, 200, 300, 400, 500 or more contiguous nucleotides in the target RNA (or family members of a given target gene).

As used herein, a non-coding RNA molecules, or their processed small RNA forms, are said to exhibit "complete complementarity" when every nucleotide of one of the sequences read 5' to 3' is complementary to every nucleotide of the other sequence when read 3' to 5'. A nucleotide sequence that is completely complementary to a reference nucleotide sequence will exhibit a sequence identical to the reverse complement sequence of the reference nucleotide sequence.

Methods for determining sequence complementarity are well known in the art and include, but not limited to, bioinformatics tools which are well known in the art (e.g. BLAST, multiple sequence alignment).

According to one embodiment, if the non-coding RNA molecule is or processed into a siRNA, the complementarity is in the range of 90-100% (e.g. 100%) to its target sequence.

According to one embodiment, if the non-coding RNA molecule is or processed into a miRNA or piRNA the complementarity is in the range of 33-100% to its target sequence.

According to one embodiment, if the non-coding RNA molecule is a miRNA, the seed sequence complementarity (i.e. nucleotides 2-8 from the 5') is in the range of 85-100% (e.g. 100%) to its target sequence.

According to one embodiment, the non-coding RNA can be further processed into a small RNA form (e.g. pre-miRNA is processed into a mature miRNA). In such a case, homology is measured based on the processed small RNA form (e.g. the mature miRNA sequence).

As used herein, the term "small RNA form" refers to the mature small RNA being capable of hybridizing with a target RNA (or fragment thereof). According to one embodiment, the small RNA form has a silencing activity.

According to one embodiment, the complementarity to the target sequence is at least about 33% of the processed small RNA form (e.g. 33% of the 21-28 nt). Thus, for example, if the non-coding RNA molecule is a miRNA, 33% of the mature miRNA sequence (e.g. 21 nt) comprises seed complementation (e.g. 7 nt out of the 21 nt).

According to one embodiment, the complementarity to the target sequence is at least about 45% of the processed small RNA form (e.g. 45% of the 21-28 nt). Thus, for example, if the non-coding RNA molecule is a miRNA, 45% of the mature miRNA sequence (e.g. 21 nt) comprises seed complementation (e.g. 9-10 nt out of the 21 nt).

According to one embodiment, the non-coding RNA molecule (i.e. prior to modification) is typically selected as one having about 10%, 20%, 30%, 33%, 40%, 50%, 60%, 70%, 80%, 85%, 90%, 95%, 96%, 97%, 98% or up to 99% complementarity towards the sequence of the second target RNA or target RNA of interest.

According to a specific embodiment, the non-coding RNA molecule (i.e. prior to modification) is typically selected as one having no more than 99% complementarity towards the sequence of the second target RNA or target RNA of interest.

According to a specific embodiment, the non-coding RNA molecule (i.e. prior to modification) is typically selected as one having no more than 98% complementarity towards the sequence of the second target RNA or target RNA of interest.

According to a specific embodiment, the non-coding RNA molecule (i.e. prior to modification) is typically selected as one having no more than 97% complementarity towards the sequence of the second target RNA or target RNA of interest.

According to a specific embodiment, the non-coding RNA molecule (i.e. prior to modification) is typically selected as one having no more than 96% complementarity towards the sequence of the second target RNA or target RNA of interest.

According to a specific embodiment, the non-coding RNA molecule (i.e. prior to modification) is typically selected as one having no more than 95% complementarity towards the sequence of the second target RNA or target RNA of interest.

According to a specific embodiment, the non-coding RNA molecule (i.e. prior to modification) is typically selected as one having no more than 94% complementarity towards the sequence of the second target RNA or target RNA of interest.

According to a specific embodiment, the non-coding RNA molecule (i.e. prior to modification) is typically selected as one having no more than 93% complementarity towards the sequence of the second target RNA or target RNA of interest.

According to a specific embodiment, the non-coding RNA molecule (i.e. prior to modification) is typically selected as one having no more than 92% complementarity towards the sequence of the second target RNA or target RNA of interest.

According to a specific embodiment, the non-coding RNA molecule (i.e. prior to modification) is typically selected as one having no more than 91% complementarity towards the sequence of the second target RNA or target RNA of interest.

According to a specific embodiment, the non-coding RNA molecule (i.e. prior to modification) is typically selected as one having no more than 90% complementarity towards the sequence of the second target RNA or target RNA of interest.

According to a specific embodiment, the non-coding RNA molecule (i.e. prior to modification) is typically selected as one having no more than 85% complementarity towards the sequence of the second target RNA or target RNA of interest.

According to a specific embodiment, the non-coding RNA molecule (i.e. prior to modification) is typically selected as one having no more than 50% complementarity towards the sequence of the second target RNA or target RNA of interest.

According to a specific embodiment, the non-coding RNA molecule (i.e. prior to modification) is typically selected as one having no more than 33% complementarity towards the sequence of the second target RNA or target RNA of interest.

According to one embodiment, the non-coding RNA molecule (e.g. RNA silencing molecule) is designed so as to comprise at least about 33%, 40%, 45%, 50%, 55%, 60%, 70%, 80%, 85%, 90%, 91%, 92%, 93%, 94%, 95%, 96%, 97%, 98%, 99% or even 100% complementarity towards the sequence of the second target RNA or target RNA of interest.

According to a specific embodiment, the non-coding RNA molecule (e.g. RNA silencing molecule) is designed so as to comprise a minimum of 33% complementarity towards the second target RNA or target RNA of interest (e.g. 85-100% seed match).

According to a specific embodiment, the non-coding RNA molecule (e.g. RNA silencing molecule) is designed so as to comprise a minimum of 40% complementarity towards the second target RNA or target RNA of interest.

According to a specific embodiment, the non-coding RNA molecule (e.g. RNA silencing molecule) is designed so as to comprise a minimum of 45% complementarity towards the second target RNA or target RNA of interest.

According to a specific embodiment, the non-coding RNA molecule (e.g. RNA silencing molecule) is designed so as to comprise a minimum of 50% complementarity towards the second target RNA or target RNA of interest.

According to a specific embodiment, the non-coding RNA molecule (e.g. RNA silencing molecule) is designed so as to comprise a minimum of 45% complementarity towards the second target RNA or target RNA of interest.

According to a specific embodiment, the non-coding RNA molecule (e.g. RNA silencing molecule) is designed so as to comprise a minimum of 60% complementarity towards the second target RNA or target RNA of interest.

According to a specific embodiment, the non-coding RNA molecule (e.g. RNA silencing molecule) is designed so as to comprise a minimum of 70% complementarity towards the second target RNA or target RNA of interest.

According to a specific embodiment, the non-coding RNA molecule (e.g. RNA silencing molecule) is designed so as to comprise a minimum of 80% complementarity towards the second target RNA or target RNA of interest.

According to a specific embodiment, the non-coding RNA molecule (e.g. RNA silencing molecule) is designed so as to comprise a minimum of 85% complementarity towards the second target RNA or target RNA of interest.

According to a specific embodiment, the non-coding RNA molecule (e.g. RNA silencing molecule) is designed so as to comprise a minimum of 90% complementarity towards the second target RNA or target RNA of interest.

According to a specific embodiment, the non-coding RNA molecule (e.g. RNA silencing molecule) is designed so as to comprise a minimum of 91% complementarity towards the second target RNA or target RNA of interest.

According to a specific embodiment, the non-coding RNA molecule (e.g. RNA silencing molecule) is designed so as to comprise a minimum of 92% complementarity towards the second target RNA or target RNA of interest.

According to a specific embodiment, the non-coding RNA molecule (e.g. RNA silencing molecule) is designed so as to comprise a minimum of 93% complementarity towards the second target RNA or target RNA of interest.

According to a specific embodiment, the non-coding RNA molecule (e.g. RNA silencing molecule) is designed so as to comprise a minimum of 94% complementarity towards the second target RNA or target RNA of interest.

According to a specific embodiment, the non-coding RNA molecule (e.g. RNA silencing molecule) is designed so as to comprise a minimum of 95% complementarity towards the second target RNA or target RNA of interest.

According to a specific embodiment, the non-coding RNA molecule (e.g. RNA silencing molecule) is designed so as to comprise a minimum of 96% complementarity towards the second target RNA or target RNA of interest.

According to a specific embodiment, the non-coding RNA molecule (e.g. RNA silencing molecule) is designed so as to comprise a minimum of 97% complementarity towards the second target RNA or target RNA of interest.

According to a specific embodiment, the non-coding RNA molecule (e.g. RNA silencing molecule) is designed so as to comprise a minimum of 98% complementarity towards the second target RNA or target RNA of interest.

According to a specific embodiment, the non-coding RNA molecule (e.g. RNA silencing molecule) is designed so as to comprise a minimum of 99% complementarity towards the second target RNA or target RNA of interest.

According to a specific embodiment, the non-coding RNA molecule (e.g. RNA silencing molecule) is designed so as to comprise 100% complementarity towards the second target RNA or target RNA of interest.

In order to induce silencing activity and/or specificity of a non-coding RNA molecule or redirect a silencing activity and/or specificity of a non-coding RNA molecule (e.g. RNA silencing molecule) towards a second target RNA or target RNA of interest, the gene encoding a non-coding RNA molecule (e.g. RNA silencing molecule) is modified using a DNA editing agent.

Following is a description of various non-limiting examples of methods and DNA editing agents used to introduce nucleic acid alterations to a gene encoding a non-coding RNA molecule (e.g. RNA silencing molecule) and agents for implementing same that can be used according to specific embodiments of the present disclosure.

Genome Editing using engineered endonucleases—this approach refers to a reverse genetics method using artificially engineered nucleases to typically cut and create specific double-stranded breaks (DSBs) at a desired location(s) in the genome, which are then repaired by cellular endogenous processes such as, homologous recombination (HR) or non-homologous end-joining (NHEJ). NHEJ directly joins the DNA ends in a double-stranded break (DSB) with or without minimal ends trimming, while HR utilizes a homologous donor sequence as a template (i.e. the sister chromatid formed during S-phase) for regenerating/copying the missing DNA sequence at the break site. In order to introduce specific nucleotide modifications to the genomic DNA, a donor DNA repair template containing the desired sequence must be present during HR (exogenously provided single stranded or double stranded DNA).

Genome editing cannot be performed using traditional restriction endonucleases since most restriction enzymes recognize a few base pairs on the DNA as their target and these sequences often will be found in many locations across the genome resulting in multiple cuts which are not limited to a desired location. To overcome this challenge and create site-specific single- or double-stranded breaks (DSBs), several distinct classes of nucleases have been discovered and bioengineered to date. These include the meganucleases, Zinc finger nucleases (ZFNs), transcription-activator like effector nucleases (TALENs) and CRISPR/Cas9 system.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location.

This can be exploited to make site-specific double-stranded breaks (DSBs) in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence.

Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (DSBs) (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break (DSB).

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break (DSB). Repair of these double-stranded breaks (DSBs) through the non-homologous end-joining (NHEJ) pathway often results in small deletions or small sequence insertions (Indels). Since each repair made by NHEJ is unique, the use of a single nuclease pair can produce an allelic series with a range of different insertions or deletions at the target site.

In general NHEJ is relatively accurate (about 85% of DSBs in human cells are repaired by NHEJ within about 30 min from detection) in gene editing erroneous NHEJ is relied upon as when the repair is accurate the nuclease will keep cutting until the repair product is mutagenic and the recognition/cut site/PAM motif is gone/mutated or that the transiently introduced nuclease is no longer present.

The deletions typically range anywhere from a few base pairs to a few hundred base pairs in length, but larger deletions have been successfully generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break (DSB) can be repaired via homologous recombination (HR) to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers are typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, CA).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, CA).

T-GEE system (TargetGene's Genome Editing Engine)—A programmable nucleoprotein molecular complex containing a polypeptide moiety and a specificity conferring nucleic acid (SCNA) which assembles in-vivo, in a target cell, and is capable of interacting with the predetermined target nucleic acid sequence is provided. The programmable nucleoprotein molecular complex is capable of specifically modifying and/or editing a target site within the target nucleic acid sequence and/or modifying the function of the target nucleic acid sequence. Nucleoprotein composition comprises (a) polynucleotide molecule encoding a chimeric polypeptide and comprising (i) a functional domain capable of modifying the target site, and (ii) a linking domain that is capable of interacting with a specificity conferring nucleic acid, and (b) specificity conferring nucleic acid (SCNA) comprising (i) a nucleotide sequence complementary to a region of the target nucleic acid flanking the target site, and (ii) a recognition region capable of specifically attaching to the linking domain of the polypeptide. The composition enables modifying a predetermined nucleic acid sequence target precisely, reliably and cost-effectively with high specificity and binding capabilities of molecular complex to the target nucleic acid through base-pairing of specificity-conferring nucleic acid and a target nucleic acid. The composition is less genotoxic, modular in their assembly, utilize single platform without customization, practical for independent use outside of specialized core-facilities, and has shorter development time frame and reduced costs.

CRISPR-Cas system and all its variants (also referred to herein as "CRISPR")—Many bacteria and archea contain endogenous RNA-based adaptive immune systems that can degrade nucleic acids of invading phages and plasmids. These systems consist of clustered regularly interspaced short palindromic repeat (CRISPR) nucleotide sequences that produce RNA components and CRISPR associated (Cas) genes that encode protein components. The CRISPR RNAs (crRNAs) contain short stretches of homology to the DNA of specific viruses and plasmids and act as guides to direct Cas nucleases to degrade the complementary nucleic acids of the corresponding pathogen. Studies of the type U CRISPR/Cas system of *Streptococcus pyogenes* have shown that three components form a RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. *Science* (2012) 337: 816-821).

It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded breaks (DSBs) in a variety of different species (Cho et al., 2013; Cong et al., 2013; DiCarlo et al., 2013; Hwang et al., 2013a,b; Jinek et al., 2013; Mali et al., 2013).

The CRISPR/Cas system for genome editing contains two distinct components: a gRNA and an endonuclease e.g. Cas9.

The gRNA (also referred to herein as short guide RNA (sgRNA)) is typically a 20-nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break (DSB). Just as with ZFNs and TALENs, the double-stranded breaks (DSBs) produced by CRISPR/Cas can undergo homologous recombination or NHEJ and are susceptible to specific sequence modification during DNA repair.

The Cas9 nuclease has two functional domains: RuvC and HNH, each cutting a different DNA strand. When both of these domains are active, the Cas9 causes double strand breaks (DSBs) in the genomic DNA.

A significant advantage of CRISPR/Cas is that the high efficiency of this system is coupled with the ability to easily create synthetic gRNAs. This creates a system that can be readily modified to target modifications at different genomic sites and/or to target different modifications at the same site. Additionally, protocols have been established which enable simultaneous targeting of multiple genes. The majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is mostly repaired by single strand break repair mechanism involving proteins such as but not only, PARP (sensor) and XRCC1/LIG III complex (ligation). If a single strand break (SSB) is generated by topoisomerase I poisons or by drugs that trap PARP1 on naturally occurring SSBs then these could persist and when the cell enters into S-phase and the replication fork encounter such SSBs they will become single ended DSBs which can only be repaired by HR. However, two proximal, opposite strand nicks introduced by a Cas9 nickase are treated as a double-strand break, in what is often referred to as a 'double nick' CRISPR system. A double-nick, which is basically non-parallel DSB, can be repaired like other DSBs by HR or NHEJ depending on the desired effect on the gene target and the presence of a donor sequence and the cell cycle stage (HR is of much lower abundance and can only occur in S and G2 stages of the cell cycle). Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that are not likely to change the genomic DNA, even though these events are not impossible.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publicly available tools available to help choose and/or design target sequences as well as lists of bioinformatically determined unique gRNAs for different genes in different species such as, but not limited to, the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and a Cas endonuclease (e.g. Cas9) should be expressed or present (e.g., as a ribonucleoprotein complex) in a target cell. The insertion vector can contain both cassettes on a single plasmid or the cassettes are expressed from two separate plasmids. CRISPR plasmids are commercially available such as the px330 plasmid from Addgene (75 Sidney St, Suite 550A•Cambridge, MA 02139). Use of clustered regularly interspaced short palindromic repeats (CRISPR)-associated (Cas)-guide RNA technology and a Cas endonuclease for modifying plant genomes are also at least disclosed by Svitashev et al., 2015, Plant Physiology, 169 (2): 931-945; Kumar and Jain, 2015. J Exp Bot 66: 47-57; and in U.S. Patent Application Publication No. 20150082478, which is specifically incorporated herein by reference in its entirety. Cas endonucleases that can be used to effect DNA editing with gRNA include, but are not limited to, Cas9, Cpf1 (Zetsche et al., 2015, Cell. 163(3):759-71), C2c1, C2c2, and C2c3 (Shmakov et al., Mol Cell. 2015 Nov. 5; 60(3):385-97).

According to a specific embodiment, the CRISPR comprises a short guide RNA (sgRNA) comprising a nucleic acid sequence selected from the group consisting of SEQ ID NOs: 1-4 or SEQ ID NOs: 235-366.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, introduced into the cells, and positive selection is performed to isolate homologous recombination mediated events. The DNA carrying the homologous sequence can be provided as a plasmid, single or double stranded oligo. These homologous recombinants contain a local duplication that is separated by intervening vector sequence, including the selection cassette. In the second step, targeted clones are subjected to negative selection to identify cells that have lost the selection cassette via intra-chromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After the system components have been introduced to the cell and positive selection applied, HR mediated events could be identified. Next, a second targeting vector that contains a region of homology with the desired mutation is introduced into targeted clones, and negative selection is applied to remove the selection cassette and introduce the mutation. The final allele contains the desired mutation while eliminating unwanted exogenous sequences.

According to a specific embodiment, the DNA editing agent comprises a DNA targeting module (e.g., gRNA).

According to a specific embodiment, the DNA editing agent does not comprise an endonuclease.

According to a specific embodiment, the DNA editing agent comprises a nuclease (e.g. an endonuclease) and a DNA targeting module (e.g., gRNA).

According to a specific embodiment, the DNA editing agent is CRISPR/Cas, e.g. gRNA and Cas9.

According to a specific embodiment, the DNA editing agent is TALEN.

According to a specific embodiment, the DNA editing agent is ZFN.

According to a specific embodiment, the DNA editing agent is meganuclease.

According to one embodiment, the DNA editing agent is linked to a reporter for monitoring expression in a plant cell.

According to one embodiment, the reporter is a fluorescent reporter protein.

The term "a fluorescent protein" refers to a polypeptide that emits fluorescence and is typically detectable by flow cytometry, microscopy or any fluorescent imaging system, therefore can be used as a basis for selection of cells expressing such a protein.

Examples of fluorescent proteins that can be used as reporters are, without being limited to, the Green Fluorescent Protein (GFP), the Blue Fluorescent Protein (BFP) and the red fluorescent proteins (e.g. dsRed, mCherry, RFP). A non-limiting list of fluorescent or other reporters includes proteins detectable by luminescence (e.g. luciferase) or colorimetric assay (e.g. GUS). According to a specific embodiment, the fluorescent reporter is a red fluorescent protein (e.g. dsRed, mCherry. RFP) or GFP.

A review of new classes of fluorescent proteins and applications can be found in Trends in Biochemical Sciences [Rodriguez, Erik A.; Campbell, Robert E.; Lin, John Y.; Lin, Michael Z.; Miyawaki, Atsushi: Palmer, Amy E.; Shu, Xiaokun; Zhang, Jin; Tsien, Roger Y. "*The Growing and Glowing Toolbox of Fluorescent and Photoactive Proteins*". *Trends in Biochemical Sciences*. doi:10.1016/j.tibs.2016.09.010].

According to another embodiment, the reporter is an endogenous gene of a plant. An exemplary reporter is the phytoene desaturase gene (PDS3) which encodes one of the important enzymes in the carotenoid biosynthesis pathway. Its silencing produces an albino/bleached phenotype. Accordingly, plants with reduced expression of PDS3 exhibit reduced chlorophyll levels, up to complete albino and dwarfism. Additional genes which can be used in accordance with the present teachings include, but are not limited to, genes which take part in crop protection. Exemplary genes are described in Table 1B, below.

According to another embodiment, the reporter is an antibiotic selection marker. Examples of antibiotic selection markers that can be used as reporters are, without being limited to, neomycin phosphotransferase II (nptII) and hygromycin phosphotransferase (hpt). Additional marker genes which can be used in accordance with the present teachings include, but are not limited to, gentamycin acetyltransferase (accC3) resistance and bleomycin and phleomycin resistance genes.

It will be appreciated that the enzyme NPTII inactivates by phosphorylation a number of aminoglycoside antibiotics such as kanamycin, neomycin, geneticin (or G418) and paromomycin. Of these, kanamycin, neomycin and paromomycin are used in a diverse range of plant species.

According to another embodiment, the reporter is a toxic selection marker. An exemplary toxic selection marker that can be used as a reporter is, without being limited to, allyl alcohol selection using the Alcohol dehydrogenase (ADH1) gene. ADH1, comprising a group of dehydrogenase enzymes which catalyse the interconversion between alcohols and aldehydes or ketones with the concomitant reduction of NAD+ or NADP+, breaks down alcoholic toxic substances within tissues. Plants harbouring reduced ADH1 expression exhibit increase tolerance to allyl alcohol. Accordingly, plants with reduced ADH1 are resistant to the toxic effect of allyl alcohol.

Regardless of the DNA editing agent used, the method of the invention is employed such that the gene encoding the non-coding RNA molecule (e.g. RNA silencing molecule) is modified by at least one of a deletion, an insertion or a point mutation.

According to one embodiment, the modification is in a structured region of the non-coding RNA molecule or the RNA silencing molecule.

According to one embodiment, the modification is in a stem region of the non-coding RNA molecule or the RNA silencing molecule.

According to one embodiment, the modification is in a loop region of the non-coding RNA molecule or the RNA silencing molecule.

According to one embodiment, the modification is in a stem region and a loop region of the non-coding RNA molecule or the RNA silencing molecule.

According to one embodiment, the modification is in a non-structured region of the non-coding RNA molecule or the RNA silencing molecule.

According to one embodiment, the modification is in a stem region and a loop region and in non-structured region of the non-coding RNA molecule or the RNA silencing molecule.

According to a specific embodiment, the modification comprises a modification of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the modification comprises a modification of at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e.g. RNA silencing molecule).

According to one embodiment, the modification can be in a consecutive nucleic acid sequence (e.g. at least 5, 10, 20, 30, 40, 50, 100, 150, 200 bases).

According to one embodiment, the modification can be in a non-consecutive manner, e.g. throughout a 20, 50, 100, 150, 200, 500, 1000 nucleic acid sequence.

According to a specific embodiment, the modification comprises a modification of at most 200 nucleotides.

According to a specific embodiment, the modification comprises a modification of at most 150 nucleotides.

According to a specific embodiment, the modification comprises a modification of at most 100 nucleotides.

According to a specific embodiment, the modification comprises a modification of at most 50 nucleotides.

According to a specific embodiment, the modification comprises a modification of at most 25 nucleotides.

According to a specific embodiment, the modification comprises a modification of at most 20 nucleotides.

According to a specific embodiment, the modification comprises a modification of at most 15 nucleotides.

According to a specific embodiment, the modification comprises a modification of at most 10 nucleotides.

According to a specific embodiment, the modification comprises a modification of at most 5 nucleotides.

According to one embodiment, the modification depends on the structure of the RNA silencing molecule.

Accordingly, when the RNA silencing molecule contains a non-essential structure (i.e. a secondary structure of the RNA silencing molecule which does not play a role in its proper biogenesis and/or function) or is purely dsRNA (i.e. the RNA silencing molecule having a perfect or almost perfect dsRNA), a few modifications (e.g. 20-30 nucleotides, e.g. 1-10 nucleotides, e.g. 5 nucleotides) are introduced in order to redirect the silence specificity of the RNA silencing molecule.

According to another embodiment, when the RNA silencing molecule has an essential structure (i.e. the proper biogenesis and/or activity of the RNA silencing molecule is dependent on its secondary structure), larger modifications (e.g. 10-200 nucleotides, e.g. 50-150 nucleotides, e.g., more than 30 nucleotides and not exceeding 200 nucleotides, 30-200 nucleotides, 35-200 nucleotides, 35-150 nucleotides, 35-100 nucleotides) are introduced in order to redirect the silence specificity of the RNA silencing molecule.

According to one embodiment, the modification is such that the recognition/cut site/PAM motif of the RNA silencing molecule is modified to abolish the original PAM recognition site.

According to a specific embodiment, the modification is in at least 1, 2, 3, 4, 5, 6, 7, 8, 9, 10 or more nucleic acids in a PAM motif.

According to one embodiment, the modification comprises an insertion.

According to a specific embodiment, the insertion comprises an insertion of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the insertion comprises an insertion of at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e.g. RNA silencing molecule).

According to a specific embodiment, the insertion comprises an insertion of at most 200 nucleotides.

According to a specific embodiment, the insertion comprises an insertion of at most 150 nucleotides.

According to a specific embodiment, the insertion comprises an insertion of at most 100 nucleotides.

According to a specific embodiment, the insertion comprises an insertion of at most 50 nucleotides.

According to a specific embodiment, the insertion comprises an insertion of at most 25 nucleotides.

According to a specific embodiment, the insertion comprises an insertion of at most 20 nucleotides.

According to a specific embodiment, the insertion comprises an insertion of at most 15 nucleotides.

According to a specific embodiment, the insertion comprises an insertion of at most 10 nucleotides.

According to a specific embodiment, the insertion comprises an insertion of at most 5 nucleotides.

According to one embodiment, the modification comprises a deletion.

According to a specific embodiment, the deletion comprises a deletion of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the deletion comprises a deletion of at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e.g. RNA silencing molecule).

According to a specific embodiment, the deletion comprises a deletion of at most 200 nucleotides.

According to a specific embodiment, the deletion comprises a deletion of at most 150 nucleotides.

According to a specific embodiment, the deletion comprises a deletion of at most 100 nucleotides.

According to a specific embodiment, the deletion comprises a deletion of at most 50 nucleotides.

According to a specific embodiment, the deletion comprises a deletion of at most 25 nucleotides.

According to a specific embodiment, the deletion comprises a deletion of at most 20 nucleotides.

According to a specific embodiment, the deletion comprises a deletion of at most 15 nucleotides.

According to a specific embodiment, the deletion comprises a deletion of at most 10 nucleotides.

According to a specific embodiment, the deletion comprises a deletion of at most 5 nucleotides.

According to one embodiment, the modification comprises a point mutation.

According to a specific embodiment, the point mutation comprises a point mutation of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the point mutation comprises a point mutation in at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e.g. RNA silencing molecule).

According to a specific embodiment, the point mutation comprises a point mutation in at most 200 nucleotides.

According to a specific embodiment, the point mutation comprises a point mutation in at most 150 nucleotides.

According to a specific embodiment, the point mutation comprises a point mutation in at most 100 nucleotides.

According to a specific embodiment, the point mutation comprises a point mutation in at most 50 nucleotides.

According to a specific embodiment, the point mutation comprises a point mutation in at most 25 nucleotides.

According to a specific embodiment, the point mutation comprises a point mutation in at most 20 nucleotides.

According to a specific embodiment, the point mutation comprises a point mutation in at most 15 nucleotides.

According to a specific embodiment, the point mutation comprises a point mutation in at most 10 nucleotides.

According to a specific embodiment, the point mutation comprises a point mutation in at most 5 nucleotides.

According to one embodiment, the modification comprises a combination of any of a deletion, an insertion and/or a point mutation.

According to one embodiment, the modification comprises nucleotide replacement (e.g. nucleotide swapping).

According to a specific embodiment, the swapping comprises swapping of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the nucleotide swap comprises a nucleotide replacement in at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e.g. RNA silencing molecule).

According to a specific embodiment, the nucleotide swapping comprises a nucleotide replacement in at most 200 nucleotides.

According to a specific embodiment, the nucleotide swapping comprises a nucleotide replacement in at most 150 nucleotides.

According to a specific embodiment, the nucleotide swapping comprises a nucleotide replacement in at most 100 nucleotides.

According to a specific embodiment, the nucleotide swapping comprises a nucleotide replacement in at most 50 nucleotides.

According to a specific embodiment, the nucleotide swapping comprises a nucleotide replacement in at most 25 nucleotides.

According to a specific embodiment, the nucleotide swapping comprises a nucleotide replacement in at most 20 nucleotides.

According to a specific embodiment, the nucleotide swapping comprises a nucleotide replacement in at most 15 nucleotides.

According to a specific embodiment, the nucleotide swapping comprises a nucleotide replacement in at most 10 nucleotides.

According to a specific embodiment, the nucleotide swapping comprises a nucleotide replacement in at most 5 nucleotides.

According to one embodiment, the gene encoding the non-coding RNA molecule (e.g. RNA silencing molecule) is modified by swapping a sequence of an endogenous RNA silencing molecule (e.g. miRNA) with a RNA silencing sequence of choice (e.g. siRNA).

According to a specific embodiment, the sequence of a siRNA used for gene swapping of an endogenous RNA silencing molecule (e.g. miRNA) comprising a nucleic acid sequence selected from the group consisting of SEQ ID NOs: 5-12 or SEQ ID NOs: 103-234.

According to one embodiment, the guide strand of the non-coding RNA molecule (e.g. RNA silencing molecule such as miRNA precursors (pri/pre-miRNAs) or siRNA precursors (dsRNA)) is modified to preserve originality of structure and keep the same base pairing profile.

According to one embodiment, the passenger strand of the non-coding RNA molecule (e.g. RNA silencing molecule such as miRNA precursors (pri/pre-miRNAs) or siRNA precursors (dsRNA)) is modified to preserve originality of structure and keep the same base pairing profile.

As used herein, the term "originality of structure" refers to the secondary RNA structure (i.e. base pairing profile). Keeping the originality of structure is important for correct and efficient biogenesis/processing of the non-coding RNA (e.g. RNA silencing molecule such as siRNA or miRNA) that is structure- and not purely sequence-dependent.

According to one embodiment, the non-coding RNA (e.g. RNA silencing molecule) is modified in the guide strand (silencing strand) as to comprise about 50-100% complementarity to the target RNA (as discussed above) while the passenger strand is modified to preserve the original (unmodified) non-coding RNA structure.

According to one embodiment, the non-coding RNA (e.g. RNA silencing molecule) is modified such that the seed sequence (e.g. for miRNA nucleotides 2-8 from the 5' terminal) is complimentary to the target sequence.

According to a specific embodiment, the RNA silencing molecule (i.e. RNAi molecule) is designed such that a sequence of the RNAi molecule is modified to preserve originality of structure and to be recognized by cellular RNAi processing and executing factors.

According to a specific embodiment, the non-coding RNA molecule (i.e. rRNA, tRNA, lncRNA, snoRNA, etc.) is designed such that a sequence of the RNAi molecule is modified to be recognized by cellular RNAi processing and executing factors.

The DNA editing agent of the invention may be introduced into plant cells using DNA delivery methods (e.g. by expression vectors) or using DNA-free methods.

According to one embodiment, the gRNA (or any other DNA recognition module used, dependent on the DNA editing system that is used) can be provided as RNA to the cell.

Thus, it will be appreciated that the present techniques relate to introducing the DNA editing agent using transient DNA or DNA-free methods such as RNA transfection (e.g. mRNA+gRNA transfection), or Ribonucleoprotein (RNP) transfection (e.g. protein-RNA complex transfection, e.g. Cas9/gRNA ribonucleoprotein (RNP) complex transfection).

For example, Cas9 can be introduced as a DNA expression plasmid, in vitro transcript (i.e. RNA), or as a recombinant protein bound to the RNA portion in a ribonucleoprotein particle (RNP). gRNA, for example, can be delivered either as a DNA plasmid or as an in vitro transcript (i.e. RNA).

Any method known in the art for RNA or RNP transfection can be used in accordance with the present teachings, such as, but not limited to microinjection [as described by Cho et al., "Heritable gene knockout in *Caenorhabditis elegans* by direct injection of Cas9-sgRNA ribonucleoproteins," *Genetics* (2013) 195:1177-1180, incorporated herein by reference], electroporation [as described by Kim et al., "Highly efficient RNA-guided genome editing in human cells via delivery of purified Cas9 ribonucleoproteins" *Genome Res.* (2014) 24:1012-1019, incorporated herein by reference], or lipid-mediated transfection e.g. using liposomes [as described by Zuris et al., "Cationic lipid-mediated delivery of proteins enables efficient protein-based genome editing in vitro and in vivo" *Nat Biotechnol.* (2014) doi: 10.1038/nbt.3081, incorporated herein by reference]. Additional methods of RNA transfection are described in U.S. Patent Application No. 20160289675, incorporated herein by reference in its entirety.

One advantage of RNA transfection methods of the invention is that RNA transfection is essentially transient and vector-free. A RNA transgene can be delivered to a cell and expressed therein, as a minimal expressing cassette without the need for any additional sequences (e.g. viral sequences).

According to one embodiment, the DNA editing agent of the invention is introduced into the plant cell using expression vectors.

The "expression vector" (also referred to herein as "a nucleic acid construct", "vector" or "construct") of some embodiments of the invention includes additional sequences which render this vector suitable for replication in prokaryotes, eukaryotes, or preferably both (e.g., shuttle vectors).

Constructs useful in the methods according to some embodiments of the invention may be constructed using recombinant DNA technology well known to persons skilled in the art. The nucleic acid sequences may be inserted into vectors, which may be commercially available, suitable for transforming into plants and suitable for transient expression of the gene of interest in the transformed cells. The genetic construct can be an expression vector wherein the nucleic acid sequence is operably linked to one or more regulatory sequences allowing expression in the plant cells.

According to one embodiment, in order to express a functional DNA editing agent, in cases where the cleaving module (nuclease) is not an integral part of the DNA recognition unit, the expression vector may encode the cleaving module as well as the DNA recognition unit (e.g. gRNA in the case of CRISPR/Cas).

Alternatively, the cleaving module (nuclease) and the DNA recognition unit (e.g. gRNA) may be cloned into separate expression vectors. In such a case, at least two different expression vectors must be transformed into the same plant cell.

Alternatively, when a nuclease is not utilized (i.e. not administered from an exogenous source to the cell), the DNA recognition unit (e.g. gRNA) may be cloned and expressed using a single expression vector.

Typical expression vectors may also contain a transcription and translation initiation sequence, transcription and translation terminator and optionally a polyadenylation signal.

According to one embodiment, the DNA editing agent comprises a nucleic acid agent encoding at least one DNA recognition unit (e.g. gRNA) operatively linked to a cis-acting regulatory element active in plant cells (e.g., promoter).

According to one embodiment, the nuclease (e.g. endonuclease) and the DNA recognition unit (e.g. gRNA) are encoded from the same expression vector. Such a vector may comprise a single cis-acting regulatory element active in plant cells (e.g., promoter) for expression of both the nuclease and the DNA recognition unit. Alternatively, the nuclease and the DNA recognition unit may each be operably linked to a cis-acting regulatory element active in plant cells (e.g., promoter).

According to one embodiment, the nuclease (e.g. endonuclease) and the DNA recognition unit (e.g. gRNA) are encoded from different expression vectors whereby each is operably linked to a cis-acting regulator element active in plant cells (e.g., promoter).

As used herein the phrase "plant-expressible" or "active in plant cells" refers to a promoter sequence, including any additional regulatory elements added thereto or contained therein, that is at least capable of inducing, conferring, activating or enhancing expression in a plant cell, tissue or organ, preferably a monocotyledonous or dicotyledonous plant cell, tissue, or organ.

The plant promoter employed can be a constitutive promoter, a tissue specific promoter, an inducible promoter, a chimeric promoter or a developmentally regulated promoter.

Examples of preferred promoters useful for the methods of some embodiments of the invention are presented in Table I, II, III and IV.

TABLE I

Exemplary constitutive promoters for use in the performance of some embodiments of the invention

| Gene Source | Expression Pattern | Reference |
|---|---|---|
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| Rice cyclophilin | constitutive | Bucholz et al, Plant Mol Biol. 25(5): 837-43, 1994 |
| Maize H3 histone | constitutive | Lepetit et al, Mol. Gen. Genet. 231: 276-285, 1992 |
| Actin 2 | constitutive | An et al, Plant J. 10(1); 107121, 1996 |
| CVMV (Cassava Vein Mosaic Virus | constitutive | Lawrenson et al, Gen Biol 16: 258, 2015 |
| U6 (AtU626; TaU6) | constitutive | Lawrenson et al, Gen Biol 16: 258, 2015 |

TABLE II

Exemplary seed-preferred promoters for use in the performance of some embodiments of the invention

| Gene Source | Expression Pattern | Reference |
|---|---|---|
| Seed specific genes | seed | Simon, et al., Plant Mol. Biol. 5. 191, 1985; Scofield, et al., J. Biol. Chem. 262: 12202, 1987; Baszczynski, et al., Plant Mol. Biol. 14: 633, 1990. |
| Brazil Nut albumin | seed | Pearson' et al., Plant Mol. Biol. 18: 235-245, 1992. |
| legumin | seed | Ellis, et al. Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al Plant Mol Biol, 143). 323-32 1990 |
| napA | seed | Stalberg, et al, Planta 199: 515-519, 1996 |
| wheat LMW and HMW, glutenin-1 | endosperm | Mol Gen Genet 216: 81-90, 1989; NAR 17: 461-2, |

TABLE II-continued

Exemplary seed-preferred promoters for use in the performance of some embodiments of the invention

| Gene Source | Expression Pattern | Reference |
|---|---|---|
| Wheat SPA | seed | Albanietal, Plant Cell, 9: 171-184, 1997 |
| wheat a, b and g gliadins | endosperm | EMBO3: 1409-15, 1984 |
| Barley ltrl promoter | endosperm | |
| barley B1, C, D hordein | endosperm | Theor Appl Gen 98: 1253-62, 1999; Plant J 4: 343-55, 1993; Mol Gen Genet 250: 750-60, 1996 |
| Barley DOF | endosperm | Mena et al, The Plant Journal, 116(1): 53-62, 1998 |
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885-889, 1998 |
| rice -globulin Glb-1 | endosperm | Wu et al, Plant Cell Physiology 398) 885-889, 1998 |
| rice OSH1 | emryo | Sato et al, Proc. Nati. Acad. Sci. USA, 93: 8117-8122 |
| rice alpha-globulin REB/OHP-1 | endosperm | Nakase et al. Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| sorgum gamma- kafirin | endosperm | PMB 32: 1029-35, 1996 |
| KNOX | emryo | Postma-Haarsma ef al, Plant Mol. Biol. 39: 257-71, 1999 |
| rice oleosin | Embryo and aleuton | Wu et at, J. Biochem., 123: 386, 1998 |
| sunflower oleosin | Seed (embryo and dry seed) | Cummins, et al., Plant Mol. Biol. 19: 873-876, 1992 |

TABLE III

Exemplary flower-specific promoters for use in the performance of the invention

| Gene Source | Expression Pattern | Reference |
|---|---|---|
| AtPRP4 | flowers | www(dot)salus(dot) medium(dot)edu/m mg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala- 3 | flowers | |

TABLE IV

Alternative rice promoters for use in the performance of the invention

| PRO # | Gene | Expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer of embryo + calli |
| PR00081 | putative caffeoyl- CoA 3-0 methyltransferase | shoot |
| PR00087 | prolamine RM9 | strong in endosperm |

TABLE IV-continued

Alternative rice promoters for use in the performance of the invention

| PRO # | Gene | Expression |
|---|---|---|
| PR00090 | prolamine RP6 | strong in endosperm |
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 strong root | |
| PR00111 | uclacyanin 3-like protein | weak discrimination center/ shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha- globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |

TABLE IV-continued

| Alternative rice promoters for use in the performance of the invention | | |
|---|---|---|
| PRO # | Gene | Expression |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSHI | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18 kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2_short (barley) | |
| PR00228 | BLZ-2_long (barley) | |

The inducible promoter is a promoter induced in a specific plant tissue, by a developmental stage or by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

According to one embodiment the promoter is a pathogen-inducible promoter. These promoters direct the expression of genes in plants following infection with a pathogen such as bacteria, fungi, viruses, nematodes and insects. Such promoters include those from pathogenesis-related proteins (PR proteins), which are induced following infection by a pathogen; e.g., PR proteins, SAR proteins, beta-1,3-glucanase, chitinase, etc. See, for example. Redolfi et al. (1983) *Neth. J. Plant Pathol* 89:245-254; Uknes et al. (1992) *Plant Cell* 4:645-656; and Van Loon (1985) *Plant Mol. Virol.* 4:111-116.

According to one embodiment, when more than one promoter is used in the expression vector, the promoters are identical (e.g., all identical, at least two identical).

According to one embodiment, when more than one promoter is used in the expression vector, the promoters are different (e.g., at least two are different, all are different).

According to one embodiment, the promoter in the expression vector includes, but is not limited to, CaMV 35S, 2×CaMV 35S, CaMV 19S, ubiquitin, AtU626 or TaU6.

According to a specific embodiment, the promoter in the expression vector comprises a 35S promoter.

According to a specific embodiment, the promoter in the expression vector comprises a U6 promoter.

Expression vectors may also comprise transcription and translation initiation sequences, transcription and translation terminator sequences and optionally a polyadenylation signal.

According to a specific embodiment, the expression vector comprises a termination sequence, such as but not limited to, a G7 termination sequence, an AtuNos termination sequence or a CaMV-35S terminator sequence.

Plant cells may be transformed stably or transiently with the nucleic acid constructs of some embodiments of the invention. In stable transformation, the nucleic acid molecule of some embodiments of the invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

According to one embodiment, an *agrobacterium*-free expression method is used to introduce foreign genes into plant cells. According to one embodiment, the *agrobacterium*-free expression method is transient. According to a specific embodiment, a bombardment method is used to introduce foreign genes into plant cells. According to another specific embodiment, bombardment of a plant root is used to introduce foreign genes into plant cells. An exemplary bombardment method which can be used in accordance with some embodiments of the invention is discussed in the examples section which follows.

Furthermore, various cloning kits or gene synthesis can be used according to the teachings of some embodiments of the invention.

According to one embodiment the nucleic acid construct is a binary vector. Examples for binary vectors are pBIN19, pBI101, pBinAR, pGPTV, pCAMBIA, pBIB-HYG, pBecks, pGreen or pPZP (Hajukiewicz, P. et al., Plant Mol. Biol. 25, 989 (1994), and Hellens et al, Trends in Plant Science 5, 446 (2000)).

Examples of other vectors to be used in other methods of DNA delivery (e.g. transfection, electroporation, bombardment, viral inoculation as discussed below) are: pGE-sgRNA (Zhang et al. Nat. Comms. 2016 7:12697), pJIT163-Ubi-Cas9 (Wang et al. Nat. Biotechnol 2004 32, 947-951), pICH47742::2x35S-5'UTR-hCas9(STOP)-NOST (Belhan et al. Plant Methods 2013 11; 9(1):39), pAHC25 (Christensen, A. H. & P. H. Quail, 1996. Ubiquitin promoter-based vectors for high-level expression of selectable and/or screenable marker genes in monocotyledonous plants. Transgenic Research 5: 213-218), pHBT-sGFP(S65T)-NOS (Sheen et al. Protein phosphatase activity is required for light-inducible gene expression in maize. EMBO J. 12 (9), 3497-3505 (1993).

According to one embodiment, the method of some embodiments of the invention further comprises introducing into the plant cell donor oligonucleotides.

According to one embodiment, when the modification is an insertion, the method further comprises introducing into the plant cell donor oligonucleotides.

According to one embodiment, when the modification is a deletion, the method further comprises introducing into the plant cell donor oligonucleotides.

According to one embodiment, when the modification is a deletion and insertion (e.g. swapping), the method further comprises introducing into the plant cell donor oligonucleotides.

According to one embodiment, when the modification is a point mutation, the method further comprises introducing into the plant cell donor oligonucleotides.

As used herein, the term "donor oligonucleotides" or "donor oligos" refers to exogenous nucleotides, i.e. externally introduced into the plant cell to generate a precise change in the genome. According to one embodiment, the donor oligonucleotides are synthetic.

According to one embodiment, the donor oligos are RNA oligos.

According to one embodiment, the donor oligos are DNA oligos.

According to one embodiment, the donor oligos are synthetic oligos.

According to one embodiment, the donor oligonucleotides comprise single-stranded donor oligonucleotides (ssODN).

According to one embodiment, the donor oligonucleotides comprise double-stranded donor oligonucleotides (dsODN).

According to one embodiment, the donor oligonucleotides comprise double-stranded DNA (dsDNA).

According to one embodiment, the donor oligonucleotides comprise double-stranded DNA-RNA duplex (DNA-RNA duplex).

According to one embodiment, the donor oligonucleotides comprise double-stranded DNA-RNA hybrid According to one embodiment, the donor oligonucleotides comprise single-stranded DNA-RNA hybrid.

According to one embodiment, the donor oligonucleotides comprise single-stranded DNA (ssDNA).

According to one embodiment, the donor oligonucleotides comprise double-stranded RNA (dsRNA).

According to one embodiment, the donor oligonucleotides comprise single-stranded RNA (ssRNA).

According to one embodiment, the donor oligonucleotides comprise the DNA or RNA sequence for swapping (as discussed above).

According to one embodiment, the donor oligonucleotides are provided in a non-expressed vector format or oligo.

According to one embodiment, the donor oligonucleotides comprise a DNA donor plasmid (e.g. circular or linearized plasmid).

According to one embodiment, the donor oligonucleotides comprise about 50-5000, about 100-5000, about 250-5000, about 500-5000, about 750-5000, about 1000-5000, about 1500-5000, about 2000-5000, about 2500-5000, about 3000-5000, about 4000-5000, about 50-4000, about 100-4000, about 250-4000, about 500-4000, about 750-4000, about 1000-4000, about 1500-4000, about 2000-4000, about 2500-4000, about 3000-4000, about 50-3000, about 100-3000, about 250-3000, about 500-3000, about 750-3000, about 1000-3000, about 1500-3000, about 2000-3000, about 50-2000, about 100-2000, about 250-2000, about 500-2000, about 750-2000, about 1000-2000, about 1500-2000, about 50-1000, about 100-1000, about 250-1000, about 500-1000, about 750-1000, about 50-750, about 150-750, about 250-750, about 500-750, about 50-500, about 150-500, about 200-500, about 250-500, about 350-500, about 50-250, about 150-250, or about 200-250 nucleotides.

According to a specific embodiment, the donor oligonucleotides comprising the ssODN (e.g. ssDNA or ssRNA) comprise about 200-500 nucleotides.

According to a specific embodiment, the donor oligonucleotides comprising the dsODN (e.g. dsDNA or dsRNA) comprise about 250-5000 nucleotides.

According to one embodiment, for gene swapping of an endogenous RNA silencing molecule (e.g. miRNA) with a RNA silencing sequence of choice (e.g. siRNA), the expression vector, ssODN (e.g. ssDNA or ssRNA) or dsODN (e.g. dsDNA or dsRNA) does not have to be expressed in a plant cell and could serve as a non-expressing template. According to a specific embodiment, in such a case only the DNA editing agent (e.g. Cas9/sgRNA modules) need to be expressed if provided in a DNA form.

According to some embodiments, for gene editing of an endogenous non-coding RNA molecule (e.g. RNA silencing molecule) without the use of a nuclease, the DNA editing agent (e.g., gRNA) may be introduced into the eukaryotic cell with our without (e.g. oligonucleotide donor DNA or RNA, as discussed herein).

According to one embodiment, introducing into the plant cell donor oligonucleotides is effected using any of the methods described above (e.g. using the expression vectors or RNP transfection).

According to one embodiment, the gRNA and the DNA donor oligonucleotides are co-introduced into the plant cell (e.g. via bombardment). It will be appreciated that any additional factors (e.g. nuclease) may be co-introduced therewith.

According to one embodiment, the gRNA is introduced into the plant cell prior to the DNA donor oligonucleotides (e.g. within a few minutes or a few hours). It will be appreciated that any additional factors (e.g. nuclease) may be introduced prior to, concomitantly with, or following the gRNA or the DNA donor oligonucleotides.

According to one embodiment, the gRNA is introduced into the plant cell subsequent to the DNA donor oligonucleotides (e.g. within a few minutes or a few hours). It will be appreciated that any additional factors (e.g. nuclease) may be introduced prior to, concomitantly with, or following the gRNA or the DNA donor oligonucleotides.

According to one embodiment, there is provided a composition comprising at least one gRNA and DNA donor oligonucleotides for genome editing.

According to one embodiment, there is provided a composition comprising at least one gRNA, a nuclease (e.g. endonuclease) and DNA donor oligonucleotides for genome editing.

There are various methods of direct DNA transfer into plant cells and the skilled artisan will know which to select. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or gold or tungsten particles, and the microprojectiles are physically accelerated into protoplasts, cells or plant tissues.

Thus, the delivery of nucleic acids may be introduced into a plant cell in embodiments of the invention by any method known to those of skill in the art, including, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301); by acceleration of DNA-coated particles (See, e.g., U.S. Pat. Nos. 5,015,580, 5,550,318, 5,538,880, 6,160,208, 6,399,861, and 6,403,865) and by Nanoparticles, nanocarriers and cell penetrating peptides (WO201126644A2; WO2009046384A1; WO2008148223A1) in the methods to deliver DNA, RNA, Peptides and/or proteins or combinations of nucleic acids and peptides into plant cells.

Other methods of transfection include the use of transfection reagents (e.g. Lipofectin, ThermoFisher), dendrimers (Kukowska-Latallo, J. F. et al., 1996, Proc. Natl. Acad. Sci. USA93, 4897-902), cell penetrating peptides (Mae et al., 2005, Internalisation of cell-penetrating peptides into tobacco protoplasts, Biochimica et Biophysica Acta 1669 (2):101-7) or polyamines (Zhang and Vinogradov, 2010, Short biodegradable polyamines for gene delivery and transfection of brain capillary endothelial cells, J Control Release, 143(3):359-366).

According to a specific embodiment, for introducing DNA into plant cells (e.g. protoplasts) the method comprises polyethylene glycol (PEG)-mediated DNA uptake. For further details see Karesch et al. (1991) Plant Cell Rep. 9:575-578; Mathur et al. (1995) Plant Cell Rep. 14:221-226; Negrutiu et al. (1987) Plant Cell Mol. Biol. 8:363-373. Plant cells (e.g. protoplasts) are then cultured under conditions that allowed them to grow cell walls, start dividing to form a callus, develop shoots and roots, and regenerate whole plants.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the genetically identical transformed plants.

Micropropagation is a process of growing new generation plants from a single piece of tissue that has been excised from a selected parent plant or cultivar. This process permits the mass reproduction of plants having the desired trait. The new generated plants are genetically identical to, and have all of the characteristics of, the original plant. Micropropagation (or cloning) allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by some embodiments of the invention.

Transient transformation can be effected by any of the direct DNA transfer methods described above or by viral infection using modified plant viruses.

Viruses that have been shown to be useful for the transformation of plant hosts include CaMV, TMV, TRV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is a RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of some embodiments of the invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Regardless of the transformation/infection method employed, the present teachings further select transformed cells comprising a genome editing event.

According to a specific embodiment, selection is carried out such that only cells comprising a successful accurate modification (e.g. swapping, insertion, deletion, point mutation) in the specific locus are selected. Accordingly, cells comprising any event that includes a modification (e.g. an insertion, deletion, point mutation) in an unintended locus are not selected.

According to one embodiment, selection of modified cells can be performed at the phenotypic level, by detection of a molecular event, by detection of a fluorescent reporter, or by growth in the presence of selection (e.g., antibiotic).

According to one embodiment, selection of modified cells is performed by analyzing the biogenesis and occurrence of the newly edited non-coding RNA molecule (e.g. the presence of new miRNA version, the presence of novel edited siRNAs, piRNAs, tasiRNAs etc).

According to one embodiment, selection of modified cells is performed by analyzing the silencing activity and/or specificity of the non-coding RNA molecule (e.g. RNA silencing molecule) towards a second target RNA or target RNA of interest by validating at least one phenotype in the plant or the organism that encode the target RNA, e.g. plant leaf coloring, e.g. partial or complete loss of chlorophyll in leaves and other organs (bleaching), presence/absence of narcotic patterns, flower coloring, fruit traits (such as shelf life, firmness and flavor), growth rate, plant size (e.g. dwarfism), crop yield, biotic stress resistance (e.g. disease resistance, nematode mortality, beetle's egg laying rate, or other resistant phenotypes associated with any of bacteria, viruses, fungi, parasites, insects, weeds, and cultivated or native plants), abiotic stress resistance (e.g. heat/cold resistance, drought resistance, salt resistance, resistance to allyl alcohol, or resistant to lack of nutrients e.g. Phosphorus (P)).

According to one embodiment, the silencing specificity of the non-coding RNA molecule is determined genotypically, e.g. by expression of a gene or lack of expression.

According to one embodiment, the silencing specificity of the non-coding RNA molecule is determined phenotypically.

According to one embodiment, a phenotype of the plant is determined prior to a genotype.

According to one embodiment, a genotype of the plant is determined prior to a phenotype.

According to one embodiment, selection of modified cells is performed by analyzing the silencing activity and/or specificity of the non-coding RNA molecule (e.g. RNA silencing molecule) towards a second target RNA or target RNA of interest by measuring a RNA level of the second target RNA or target RNA of interest. This can be performed using any method known in the art, e.g. by Northern blotting, Nuclease Protection Assays, In Situ hybridization, or quantitative RT-PCR.

According to one embodiment, selection of modified cells is performed by analyzing plant cells or clones comprising the DNA editing event also referred to herein as "mutation" or "edit", dependent on the type of editing sought e.g., insertion, deletion, insertion-deletion (Indel), inversion, substitution and combinations thereof.

Methods for detecting sequence alteration are well known in the art and include, but not limited to, DNA and RNA sequencing (e.g., next generation sequencing), electrophoresis, an enzyme-based mismatch detection assay and a hybridization assay such as PCR, RT-PCR, RNase protection, in-situ hybridization, primer extension, Southern blot, Northern Blot and dot blot analysis. Various methods used for detection of single nucleotide polymorphisms (SNPs) can also be used, such as PCR based 17 endonuclease, Hetroduplex and Sanger sequencing, or PCR followed by restriction digest to detect appearance or disappearance of unique restriction site/s.

Another method of validating the presence of a DNA editing event e.g., Indels comprises a mismatch cleavage assay that makes use of a structure selective enzyme (e.g. endonuclease) that recognizes and cleaves mismatched DNA.

According to one embodiment, selection of transformed cells is effected by flow cytometry (FACS) selecting transformed cells exhibiting fluorescence emitted by the fluorescent reporter. Following FACS sorting, positively selected pools of transformed plant cells, displaying the fluorescent marker are collected and an aliquot can be used for testing the DNA editing event as discussed above.

In cases where antibiotic selection marker was used, following transformation plant cell clones are cultivated in the presence of selection (e.g., antibiotic) until they develop into colonies i.e., clones and micro-calli. A portion of the cells of the calli are then analyzed (validated) for the DNA editing event, as discussed above.

Thus, according to one embodiment of the invention, the method further comprises validating in the transformed cells complementarity of the endogenous non-coding RNA molecule (e.g. RNA silencing molecule) towards the second target RNA.

As mentioned above, following modification of the gene encoding the non-coding RNA molecule (e.g. RNA silencing molecule), the non-coding RNA molecule (e.g. RNA silencing molecule) comprises at least about 30%, 33%, 40%, 50%, 60%, 70%, 80%, 85%, 90%, 91%, 92%, 93%, 94%, 95%, 96%, 97%, 98%, 99% or even 100% complementarity towards the sequence of the second target RNA or target RNA of interest.

The specific binding of designed non-coding RNA molecule with a target RNA of interest can be determined by any method known in the art, such as by computational algorithms (e.g. BLAST) and verified by methods including e.g. Northern blot, In Situ hybridization, QuantiGene Plex Assay etc.

It will be appreciated that positive clones can be homozygous or heterozygous for the DNA editing event. In case of a heterozygous cell, the cell (e.g., when diploid) may comprise a copy of a modified gene and a copy of a non-modified gene of the non-coding RNA molecule (e.g. RNA silencing molecule). The skilled artisan will select the clone for further culturing/regeneration according to the intended use.

According to one embodiment, when a transient method is desired, clones exhibiting the presence of a DNA editing event as desired are further analyzed and selected for the absence of the DNA editing agent, namely, loss of DNA sequences encoding for the DNA editing agent. This can be done, for example, by analyzing the loss of expression of the DNA editing agent (e.g., at the mRNA, protein) e.g., by fluorescent detection of GFP or q-PCR, HPLC.

According to one embodiment, when a transient method is desired, the cells may be analyzed for the absence of the nucleic acid construct as described herein or portions thereof e.g., nucleic acid sequence encoding the DNA editing agent. This can be affirmed by fluorescent microscopy, q-PCR, FACS, and or any other method such as Southern blot, PCR, sequencing, HPLC).

According to one embodiment, the plant is crossed in order to obtain a plant devoid of the DNA editing agent (e.g. of the endonuclease), as discussed below.

Positive clones may be stored (e.g., cryopreserved).

Alternatively, plant cells (e.g., protoplasts) may be regenerated into whole plants first by growing into a group of plant cells that develops into a callus and then by regeneration of shoots (callogenesis) from the callus using plant tissue culture methods. Growth of protoplasts into callus and regeneration of shoots requires the proper balance of plant growth regulators in the tissue culture medium that must be customized for each species of plant.

Protoplasts may also be used for plant breeding, using a technique called protoplast fusion. Protoplasts from different species are induced to fuse by using an electric field or a solution of polyethylene glycol. This technique may be used to generate somatic hybrids in tissue culture.

Methods of protoplast regeneration are well known in the art. Several factors affect the isolation, culture, and regeneration of protoplasts, namely the genotype, the donor tissue and its pre-treatment, the enzyme treatment for protoplast isolation, the method of protoplast culture, the culture, the culture medium, and the physical environment. For a thorough review see Maheshwari et al. 1986 Differentiation of Protoplasts and of Transformed Plant Cells: 3-36. Springer-Verlag, Berlin.

The regenerated plants can be subjected to further breeding and selection as the skilled artisan sees fit.

Thus, embodiments of the invention further relate to plants, plant cells and processed product of plants comprising the non-coding RNA molecule (e.g. RNA silencing molecule) capable of silencing a second target RNA generated according to the present teachings.

According to one aspect of the invention, there is provided a method of producing a plant with reduced expression of a target gene, the method comprising: (a) breeding the plant according to some embodiments of the invention and (b) selecting for progeny plants that have reduced expression of the target RNA of interest or the second target RNA, or progeny that comprises a silencing specificity in the non-coding RNA molecule towards a target RNA of interest, and which do not comprise said DNA editing agent, thereby producing the plant with reduced expression of a target gene.

According to one embodiment, breeding comprises crossing or selfing.

The term "crossing" as used herein refers to the fertilization of female plants (or gametes) by male plants (or gametes). The term "gamete" refers to the haploid reproductive cell (egg or sperm) produced in plants by mitosis from a gametophyte and involved in sexual reproduction, during which two gametes of opposite sex fuse to form a diploid zygote. The term generally includes reference to a pollen (including the sperm cell) and an ovule (including the ovum). "crossing" therefore generally refers to the fertilization of ovules of one individual with pollen from another individual, whereas "selfing" refers to the fertilization of ovules of an individual with pollen from the same individual. Crossing is widely used in plant breeding and results in a mix of genomic information between the two plants crossed one chromosome from the mother and one chromosome from the father. This will result in a new combination of genetically inherited traits.

As mentioned above, the plant may be crossed in order to obtain a plant devoid of undesired factors e.g. DNA editing agent (e.g. endonuclease).

According to one embodiment, there is provided a method of generating a plant with increased stress tolerance, increased yield, increased growth rate or increased yield quality, the method comprising modifying a gene encoding or processed into a non-coding RNA molecule or into a RNA silencing in a plant cell according to the method of some embodiments of the invention, wherein the target RNA of interest is of a gene of the plant conferring sensitivity to stress, decreased yield, decreased growth rate or decreased yield quality thereby generating the plant.

The phrase "stress tolerance" as used herein refers to the ability of a plant to endure a biotic or abiotic stress without suffering a substantial alteration in metabolism, growth, productivity and/or viability.

The phrase "abiotic stress" as used herein refers to the exposure of a plant, plant cell, or the like, to a non-living ("abiotic") physical or chemical agent that has an adverse effect on metabolism, growth, development, propagation, or survival of the plant (collectively, "growth"). An abiotic stress can be imposed on a plant due, for example, to an environmental factor such as water (e.g., flooding, drought, or dehydration), anaerobic conditions (e.g., a lower level of oxygen or high level of $CO_2$), abnormal osmotic conditions (e.g. osmotic stress), salinity, or temperature (e.g., hot/heat, cold, freezing, or frost), an exposure to pollutants (e.g. heavy metal toxicity), anaerobiosis, nutrient deficiency (e.g., nitrogen deficiency or limited nitrogen), atmospheric pollution or UV irradiation.

The phrase "biotic stress" as used herein refers to the exposure of a plant, plant cell, or the like, to a living ("biotic") organism that has an adverse effect on metabolism, growth, development, propagation, or survival of the plant (collectively, "growth"). Biotic stress can be caused by, for example, bacteria, viruses, fungi, parasites, beneficial and harmful insects, weeds, and cultivated or native plants.

The phrase "yield" or "plant yield" as used herein refers to increased plant growth (growth rate), increased crop growth, increased biomass, and/or increased plant product production (including grain, fruit, seeds, etc.).

According to one embodiment, in order to generate a plant with increased stress tolerance, increased yield, increased growth rate or increased yield quality, the non-coding RNA molecule is designed to target a RNA of interest being of a gene of the plant conferring sensitivity to stress, decreased yield, decreased growth rate or decreased yield quality.

According to one embodiment, exemplary susceptibility plant genes to be targeted (e.g. knocked out) include, but are not limited to, the susceptibility S-genes, such as those residing at genetic loci known as MLO (Mildew Lucus O).

According to one embodiment, the plants generated by the present method comprise increased stress tolerance, increased yield, increased yield quality, increased growth rate, by at least about 10%, 20%, 30%, 40%, 50%, 60%, 70%, 80%, 90%, 95% or 100% as compared to plants not generated by the present methods.

Any method known in the art for assessing increased stress tolerance may be used in accordance with the present invention. Exemplary methods of assessing increased stress tolerance include, but are not limited to, downregulation of PagSAP1 in poplar for increased salt stress tolerance as described in Yoon, S K., Bae, E K., Lee, H. et al. Trees (2018) 32: 823. www(dot)doi(dot)org/10.1007/s00468-018-1675-2), and increased drought tolerance in tomato by downregulation of SlbZIP38 (Pan Y et al. Genes 2017, 8, 402: doi:10.3390/genes8120402, incorporated herein by reference.

Any method known in the art for assessing increased yield may be used in accordance with the present invention. Exemplary methods of assessing increased yield include, but are not limited to, reduced DST expression in rice as described in Ar-Rafi Md. Faisal, et al, AJPS>Vol. 8 No. 9, August 2017 DOI: 10.4236/ajps.2017.89149; and downregulation of BnFTA in canola resulted in increased yield as described in Wang Y et al., Mol Plant. 2009 January; 2(1): 191-200.doi: 10.1093/mp/ssn088), both incorporated herein by reference.

Any method known in the art for assessing increased growth rate may be used in accordance with the present invention. Exemplary methods of assessing increased growth rate include, but are not limited to, reduced expression of BIG BROTHER in *Arabidopsis* or GA2-OXIDASE results in enhance growth and biomass as described in Marcelo de Freitas Lima et al. Biotechnology Research and Innovation (2017)1,14-25, incorporated herein by reference.

Any method known in the art for assessing increased yield quality may be used in accordance with the present invention. Exemplary methods of assessing increased yield quality include, but are not limited to, down regulation of OsCKX2 in rice results in production of more tillers, more grains, and the grains were heavier as described in Yeh S_Y et al. Rice (N Y). 2015; 8: 36; and reduce OMT levels in many plants, which result in altered lignin accumulation, increase the digestibility of the material for industry purposes as described in Verma S R and Dwivedi U N. South African Journal of Botany Volume 91, March 2014, Pages 107-125, both incorporated herein by reference.

According to one embodiment, the method further enables generation of a plant comprising increased sweetness, increased sugar content, increased flavor, improved ripening control, increased water stress tolerance, increased heat stress tolerance, and increased salt tolerance. One of skill in the art will know how to utilize the methods described herein to choose target RNA sequences for modification.

According to one embodiment, there is provided a method of generating a pathogen tolerant or resistant plant, the method comprising modifying a gene encoding or processed into a non-coding RNA molecule or into a RNA silencing molecule in a plant cell according to the method of some embodiments of the invention, wherein the target RNA of interest is of a gene of the plant conferring sensitivity to the pathogen, thereby generating the pathogen tolerant or resistant plant.

According to one embodiment, there is provided a method of generating a pathogen tolerant or resistant plant, the method comprising modifying a gene encoding or processed into a non-coding RNA molecule or into a RNA silencing molecule in a plant cell according to the method of some embodiments of the invention, wherein the target RNA of interest is of a gene of the pathogen, thereby generating the pathogen tolerant or resistant plant.

According to one embodiment, there is provided a method of generating a pest tolerant or resistant plant, the method comprising modifying a gene encoding or processed into a non-coding RNA molecule or into a RNA silencing molecule in a plant cell according to the method of some embodiments of the invention, wherein the target RNA of interest is of a gene of the pest, thereby generating the pest tolerant or resistant plant.

As used herein the term "pathogen" refers to an organism that negatively affect plants by colonizing, damaging, attacking, or infecting them. Thus, pathogen may affect the growth, development, reproduction, harvest or yield of a plant. This includes organisms that spread disease and/or damage the host and/or compete for host nutrients. Plant pathogens include, but are not limited to, fungi, oomycetes, bacteria, viruses, viroids, virus-like organisms, phytoplasmas, protozoa, nematodes, insects and parasitic plants.

Non-limiting examples of pathogens include, but are not limited to, Roundheaded Borer such as long horned borers; psyllids such as red gum lerp psyllids (*Glycaspis brimblecombei*), blue gum psyllid, spotted gum lerp psyllids, lemon gum lep psyllids; tortoise beetles; snout beetles; leaf beetles; honey fungus; *Thaumastocoris peregrinus*; sessile gall wasps (Cynipidae) such as *Leptocybe invasa, Ophelimus maskelli* and Selitrichodes globules; Foliage-feeding caterpillars such as Omnivorous looper and Orange *tortrix*; Glassy-winged sharpshooter, and Whiteflies such as Giant whitefly. Other non-limiting examples of pathogens include Aphids such as *Chaitophorus* spp., Cloudywinged cottonwood and *Periphyllus* spp.; Armored scales such as Oystershell scale and San Jose scale; Carpenterworm; Clearwing moth borers such as American hornet moth and Western poplar clearwing; Flatheaded borers such as Bronze birch borer and Bronze poplar borer; Foliage-feeding caterpillars such as Fall webworm, Fruit-tree leafroller, Redhumped caterpillar, Satin moth caterpillar, Spiny elm caterpillar, Tent caterpillar, Tussock moths and Western tiger swallowtail; Foliage miners such as Poplar shield bearer, Gall and blister mites such as Cottonwood gall mite; Gall aphids such as Poplar petiolegall aphid; Glassy-winged sharpshooter, Leaf beetles and flea beetles; Mealybugs; Poplar and willow borer, Roundheaded borers; Sawflies; Soft scales such as Black scale, Brown soft scale, Cottony maple scale and European fruit lecanium; Treehoppers such as Buffalo treehopper, and True bugs such as Lace bugs and *Lygus* bugs.

Other non-limiting examples of viral plant pathogens include, but are not limited to Species: Pea early-browning virus (PEBV), Genus: Tobravirus. Species: Pepper ringspot virus (PepRSV), Genus: Tobravirus. Species: Watermelon mosaic virus (WMV), Genus: Potyvirus and other viruses from the Potyvirus Genus. Species: Tobacco mosaic virus Genus (TMV), Tobamovirus and other viruses from the Tobamovirus Genus. Species: Potato virus X Genus (PVX), Potexvirus and other viruses from the Potexvirus Genus. Thus the present teachings envisage targeting of RNA as well as DNA viruses (e.g. Gemini virus or Bigeminivirus). Geminiviridae viruses which may be targeted include, but are not limited to, *Abutilon* mosaic bigeminivirus, *Ageratum* yellow vein bigeminivirus, Bean calico mosaic bigeminivirus, Bean golden mosaic bigeminivirus, Bhendi yellow vein mosaic bigeminivirus, Cassava African mosaic bigeminivirus, Cassava Indian mosaic bigeminivirus, Chino del tomaté bigeminivirus, Cotton leaf crumple bigeminivirus, Cotton leaf curl bigeminivirus, Croton yellow vein mosaic bigeminivirus, *Dolichos* yellow mosaic bigeminivirus, *Euphorbia* mosaic bigeminivirus, Horsegram yellow mosaic bigeminivirus, Jatropha mosaic bigeminivirus, Lima bean golden mosaic bigeminivirus, Melon leaf curl bigeminivirus, Mung bean yellow mosaic bigeminivirus, Okra leaf-curl bigeminivirus, Pepper hausteco bigeminivirus, Pepper Texas bigeminivirus, Potato yellow mosaic bigeminivirus, Rhynchosia mosaic bigeminivirus, Serrano golden mosaic bigeminivirus, Squash leaf curl bigeminivirus, Tobacco leaf curl bigeminivirus, Tomato Australian leafcurl bigeminivirus, Tomato golden mosaic bigeminivirus, Tomato Indian leafcurl bigeminivirus, Tomato leaf crumple bigeminivirus, Tomato mottle bigeminivirus, Tomato yellow leaf curl bigeminivirus. Tomato yellow mosaic bigeminivirus, Watermelon chlorotic stunt bigeminivirus and Watermelon curly mottle bigeminivirus.

As used herein the term "pest" refers to an organism which directly or indirectly harms the plant. A direct effect includes, for example, feeding on the plant leaves. Indirect effect includes, for example, transmission of a disease agent (e.g. a virus, bacteria, etc.) to the plant. In the latter case the pest serves as a vector for pathogen transmission. Exemplary pests include, but are not limited to, beetles, psylids, insects, nematodes, snails.

According to one embodiment, the pathogen is a nematode. Exemplary nematodes include, but are not limited to, the burrowing nematode (*Radopholus similis*), *Caenorhabditis elegans, Radopholus arabocoffeae, Pratylenchus coffeae*, root-knot nematode (*Meloidogyne* spp.), cyst nematode (*Heterodera* and *Globodera* spp.), root lesion nematode (*Pratylenchus* spp.), the stem nematode (*Ditylenchus dipsaci*), the pine wilt nematode (*Bursaphelenchus xylophilus*), the reniform nematode (*Rotylenchulus reniformis*), *Xiphinema index, Nacobbus aberrans* and *Aphelenchoides besseyi.*

According to one embodiment, the pathogen is a fungus. Exemplary fungi include, but are not limited to, *Fusarium oxysporum, Leptosphaeria maculans* (*Phoma* lingam), *Sclerotinia sclerotiorum, Pyricularia grisea, Gibberella fujikuroi* (*Fusarium moniliforme*), *Magnaporthe oryzae, Botrytis cinereal, Puccinia* spp., *Fusarium graminearum, Blumeria*

*graminis. Mycosphaerella graminicola, Colletotrichum* spp., *Ustilago maydis, Melamtpsora lini, Phakopsora pachyrhizi* and *Rhizoctonia solani.*

According to one embodiment, in order to generate a pathogen resistant or tolerant plant, the non-coding RNA molecule is designed to target a RNA of interest being of a gene of the plant conferring sensitivity to a pathogen.

According to one embodiment, an exemplary plant gene to be targeted includes, but is not limited to, the gene eIF4E which confers sensitivity to viral infection in cucumber.

According to one embodiment, in order to generate a pathogen resistant or tolerant plant, the non-coding RNA molecule is designed to target a RNA of interest being of a gene of the pathogen.

Determination of the plant or pathogen target genes may be achieved using any method known in the art such as by routine bioinformatics analysis.

According to one embodiment, the nematode pathogen gene comprises the *Radopholus similis* genes Calreticulin13 (CRT) or collagen 5 (col-5).

According to one embodiment, the fungi pathogen gene comprises the *Fusarium oxysporum* genes FOW2, FRP1, and OPR.

According to one embodiment, the pathogen gene includes, for example, vacuolar ATPase (vATPase), dvssj1 and dvssj2, α-tubulin and snf7.

According to a specific embodiment, when the plant is a *Brassica napus* (rapeseed), the target RNA of interest includes, but is not limited to, a gene of *Leptosphaeria maculans* (*Phoma* lingam) (causing e.g. *Phoma* stem canker) (e.g. as set forth in GenBank Accession No: AM933613.1); a gene of Flea beetle (*Phyllotreta* vittula or Chrysomelidae, e.g. as set forth in GenBank Accession No: KT959245.1); or a gene of by *Sclerotinia sclerotiorum* (causing e.g. *Sclerotinia* stem rot) (e.g. as set forth in GenBank Accession No: NW_001820833.1).

According to a specific embodiment, when the plant is a *Citrus* x *sinensis* (Orange), the target RNA of interest includes, but is not limited to, a gene of *Citrus* Canker (CCK) (e.g. as set forth in GenBank Accession No: AE008925); a gene of Candidatus Liberibacter spp. (causing e.g. *Citrus* greening disease) (e.g. as set forth in GenBank Accession No: CP001677.5); or a gene of *Armillaria* root rot (e.g. as set forth in GenBank Accession No: KY389267.1).

According to a specific embodiment, when the plant is a *Elaeis guineensis* (Oil palm), the target RNA of interest includes, but is not limited to, a gene of *Ganoderma* spp. (causing e.g. Basal stem rot (BSR) also known as *Ganoderma* butt rot) (e.g. as set forth in GenBank Accession No: U56128.1), a gene of Nettle Caterpillar or a gene of any one of *Fusarium* spp., *Phytophthora* spp., *Pythium* spp., *Rhizoctonia solani* (causing e.g. Root rot).

According to a specific embodiment, when the plant is a *Fragaria vesca* (Wild strawberry), the target RNA of interest includes, but is not limited to, a gene of *Verticillium* dahlia (causing e.g. *Verticillium* Wilt) (e.g. as set forth in GenBank Accession No: DS572713.1); or a gene of *Fusarium oxysporum* f. sp. *fragariae* (causing e.g. *Fusarium* wilt) (e.g. as set forth in GenBank Accession No: KR855868.1);

According to a specific embodiment, when the plant is a *Glycine max* (Soybean), the target RNA of interest includes, but is not limited to, a gene of *P. pachyrhizi* (causing e.g. Soybean rust, also known as Asian rust) (e.g. as set forth in GenBank Accession No: DQ026061.1); a gene of Soybean Aphid (e.g. as set forth in GenBank Accession No: KJ451424.1); a gene of Soybean Dwarf Virus (SbDV) (e.g. as set forth in GenBank Accession No: NC_003056.1); or a gene of Green Stink Bug (*Acrosternum hilare*) (e.g. as set forth in GenBank Accession No: NW_020110722.1).

According to a specific embodiment, when the plant is a *Gossypium raimondii* (Cotton), the target RNA of interest includes, but is not limited to, a gene of *Fusarium oxysporum* f. sp. vasinfectum (causing e.g. *Fusarium* wilt) (e.g. as set forth in GenBank Accession No: JN416614.1); a gene of Soybean Aphid (e.g. as set forth in GenBank Accession No: KJ451424.1); or a gene of Pink bollworm (*Pectinophora gossypiella*) (e.g. as set forth in GenBank Accession No: KU550964.1).

According to a specific embodiment, when the plant is a *Oryza sativa* (Rice), the target RNA of interest includes, but is not limited to, a gene of *Pyricularia grisea* (causing e.g. Rice Blast) (e.g. as set forth in GenBank Accession No: AF027979.1); a gene of *Gibberella fujikuroi* (*Fusarium moniliforme*) (causing e.g. Bakanae Disease) (e.g. as set forth in GenBank Accession No: AY862192.1); or a gene of a Stem borer, e.g. Scirpophaga incertulas Walker—Yellow Stem Borer, S. innota Walker—White Stem Borer, *Chilo suppressalis* Walker—Striped Stem Borer, Sesa-mia inferens Walker—Pink Stem Borer (e.g. as set forth in GenBank Accession No: KF290773.1).

According to a specific embodiment, when the plant is a *Solanum lycopersicum* (Tomato), the target RNA of interest includes, but is not limited to, a gene of *Phytophthora infestans* (causing e.g. Late blight) (e.g. as set forth in GenBank Accession No: AY855210.1); a gene of a whitefly *Bemisia tabaci* (e.g. Gennadius, e.g. as set forth in GenBank Accession No: KX390870.1); or a gene of Tomato yellow leaf curl geminivirus (TYLCV) (e.g. as set forth in GenBank Accession No: LN846610.1).

According to a specific embodiment, when the plant is a *Solanum tuberosum* (Potato), the target RNA of interest includes, but is not limited to, a gene of *Phytophthora infestans* (causing e.g. Late Blight) (e.g., as set forth in GenBank Accession No: AY050538.3); a gene of *Erwinia* spp. (causing e.g. Blackleg and Soft Rot) (e.g. as set forth in GenBank Accession No: CP001654.1); or a gene of Cyst Nematodes (e.g. *Globodera pallida* and *G. rostochiensis*) (e.g. as set forth in GenBank Accession No: KF963519.1).

According to a specific embodiment, when the plant is a *Theobroma cacao* (Cacao), the target RNA of interest includes, but is not limited to, a gene of a gene of basidiomycete *Moniliophthora roreri* (causing e.g. Frosty Pod Rot) (e.g. as set forth in GenBank Accession No: LATX01001521.1); a gene of *Moniliophthora perniciosa* (causing e.g. Witches' Broom disease); or a gene of Mirids e.g. *Distantiella theobroma* and *Sahlbergella singularis, Helopeltis* spp, *Monalonion* specie.

According to a specific embodiment, when the plant is a *Vitis vinifera* (Grape or Grapevine), the target RNA of interest includes, but is not limited to, a gene of closterovirus GVA (causing e.g. Rugose wood disease) (e.g. as set forth in GenBank Accession No: AF007415.2); a gene of Grapevine leafroll virus (e.g. as set forth in GenBank Accession No: FJ436234.1); a gene of Grapevine fanleaf degeneration disease virus (GFLV) (e.g. as set forth in GenBank Accession No: NC_003203.1); or a gene of Grapevine fleck disease (GFkV) (e.g. as set forth in GenBank Accession No: NC_003347.1).

According to a specific embodiment, when the plant is a *Zea mays* (Maize also referred to as corn), the target RNA of interest includes, but is not limited to, a gene of a Fall Armyworm (e.g. *Spodoptera frugiperda*) (e.g. as set forth in GenBank Accession No: AJ488181.3); a gene of European corn borer (e.g. as set forth in GenBank Accession No:

GU329524.1); or a gene of Northern and western corn rootworms (e.g. as set forth in GenBank Accession No: NM_001039403.1).

According to a specific embodiment, when the plant is a sugarcane, the target RNA of interest includes, but is not limited to, a gene of a Internode Borer (e.g. *Chilo* Saccharifagus *Indicus*), a gene of a *Xanthomonas* Albileneans (causing e.g. Leaf Scald) or a gene of a Sugarcane Yellow Leaf Virus (SCYLV).

According to a specific embodiment, when the plant is a wheat, the target RNA of interest includes, but is not limited to, a gene of a *Puccinia striiformis* (causing e.g. stripe rust) or a gene of an Aphid.

According to a specific embodiment, when the plant is a barley, the target RNA of interest includes, but is not limited to, a gene of a *Puccinia bordei* (causing e.g. Leaf rust), a gene of *Puccinia striiformis* f. sp. *Hordei* (causing e.g. stripe rust), or a gene of an Aphid.

According to a specific embodiment, when the plant is a sunflower, the target RNA of interest includes, but is not limited to, a gene of a *Puccinia helianthi* (causing e.g. Rust disease); a gene of Boerema *macdonaldii* (causing e.g. *Phoma* black stem); a gene of a Seed weevil (e.g. red and gray), e.g. *Smicronyx fulvus* (red); *Smicronyx sordidus* (gray); or a gene of *Sclerotinia sclerotiorum* (causing e.g. *Sclerotinia* stalk and head rot disease).

According to a specific embodiment, when the plant is a rubber plant, the target RNA of interest includes, but is not limited to, a gene of a *Microcyclus ulei* (causing e.g. South American leaf blight (SALB)); a gene of *Rigidoporus microporus* (causing e.g. White root disease); a gene of *Ganoderma pseudoferreum* (causing e.g. Red root disease).

According to a specific embodiment, when the plant is an apple plant, the target RNA of interest includes, but is not limited to, a gene of *Neonectria ditissima* (causing e.g. Apple Canker), a gene of *Podosphaera leucotricha* (causing e.g. Apple Powdery Mildew), or a gene of *Venturia inaequalis* (causing e.g. Apple Scab).

Exemplary endogenous non-coding RNA molecules which may be modified to target the RNA of interest (e.g. a gene of a pathogen), exemplary sequences of gRNA (i.e. a DNA editing agent) which may be used to modify the endogenous non-coding RNA molecules, and exemplary nucleotide sequences for redirecting a silencing specificity of the endogenous non-coding RNA molecule towards the target RNA of interest are provided in Table 1B, hereinbelow.

TABLE 1B

Examples of GEiGS oligo designs to generate different traits in various hosts

| | Oligo info | oligo_seq | seq difference from wt | Sg_seq | pam_difference | sgRNA_ strand |
|---|---|---|---|---|---|---|
| Host, trait and miRNA-template<br>Host (bold);<br>*Pathogen/pest/disease* (*italic*) | | Sequence of GEIGS oligo, consisting of the precursor sequence with its corresponding mature replaced by a siRNA targeting the desired molecule - SEQ ID NO: | Number of nucleotide changes between the wild type precursor and the GeiGs oligo | Sequence of the CRISPR/cas9 small guide RNA targeting the precursor sequence for swapping - SEQ ID NO: | Number of nucleotide changes between the wild type precursor and the GEiGS sequence that fall in the PAM region of the sgRNA | |
| Brassica napus (rapeseed)<br>*AM933613.1/ Phoma stem canker (caused by leptosphaeria maculans or phoma lingam - fungal pathogen)* | | | | | | |
| bna-MIR169e | Max change/ perfect structure/ trait-specific SIRNA | 103 | 132 | 235 | 3 | rv |
| bna-MIR156d | Min change/ perfect structure/ trait-specific SIRNA | 104 | 25 | 236 | 1 | fw |
| bna-MIR169e | Max change/ altered structure/ trait-specific SIRNA | 105 | 128 | 237 | 3 | rv |
| bna-MIR169e | Max change/ perfect structure/ non-specific SIRNA | 106 | 131 | 238 | 3 | rv |
| *KT959245.1/ Flea beetle (Phyllotreta vittula or Chrysomelidae)* | | | | | | |
| bna-MIR169c | Max change/ perfect structure/ trait-specific SIRNA | 107 | 138 | 239 | 3 | rv |

TABLE 1B-continued

Examples of GEiGS oligo designs to generate different traits in various hosts

| | Oligo info | oligo_seq | seq difference from wt | Sg_seq | pam_difference | sgRNA_ strand |
|---|---|---|---|---|---|---|
| bna-MIR156d | Min change/ perfect structure/ trait-specific SIRNA | 108 | 29 | 240 | 1 | fw |
| bna-MIR156b | Max change/ altered structure/ trait-specific SIRNA | 109 | 76 | 241 | 1 | fw |
| bna-MIR169e | Max change/ perfect structure/ non-specific siRNA | 110 | 133 | 242 | 3 | rv |
| *NW_001820833.1/ Sclerotinia stem rot (caused by Sclerotinia sclerotiorum, a fungal pathogen)* | | | | | | |
| bna-MIR169e | Max change/ perfect structure/ trait-specific SIRNA | 111 | 130 | 243 | 3 | rv |
| bna-MIR390b | Min change/ perfect structure/ trait-specific SIRNA | 112 | 23 | 244 | 3 | fw |
| bna-MIR156b | Max change/ altered structure/ trait-specific SIRNA | 113 | 68 | 245 | 1 | fw |
| bna-MIR169e | Max change/ perfect structure/ non-specific SIRNA | 114 | 135 | 246 | 3 | rv |
| Citrus x sinensis (Orange) *AE008925/Citrus Canker (CCK)* | | | | | | |
| csi-MIR167c | Max change/ perfect structure/ trait-specific SIRNA | 115 | 173 | 247 | 3 | fw |
| csi-MIR156a | Min change/ perfect structure/ trait-specific siRNA | 116 | 24 | 248 | 3 | rv |
| csi-MIR167c | Max change/ altered structure/ trait-specific siRNA | 117 | 150 | 249 | 3 | fw |
| csi-MIR167c | Max change/ perfect structure/ non-specific SIRNA | 118 | 173 | 250 | 2 | fw |
| *CP001677.5/Citrus greening disease caused by a vector-transmitted pathogen (Candidatus Liberibacter* spp.) | | | | | | |
| csi-MIR164a | Max change/ perfect structure/ trait-specific SIRNA | 119 | 115 | 251 | 2 | rv |
| csi-MIR482f | Min change/ perfect structure/ trait-specific SIRNA | 120 | 22 | 252 | 2. | rv |
| csi-MIR398a | Max change/ altered structure/ trait-specific SIRNA | 121 | 88 | 253 | 3 | fw |

TABLE 1B-continued

Examples of GEiGS oligo designs to generate different traits in various hosts

| | Oligo info | oligo_seq | seq difference from wt | Sg_seq | pam_difference | sgRNA_ strand |
|---|---|---|---|---|---|---|
| csi-MIR164a | Max change/ perfect structure/ non-specific SIRNA | 122 | 119 | 254 | 3 | rv |
| *KY389267.1/Armillaria root rot* | | | | | | |
| csi-MIR167c | Max change/ perfect structure/ trait-specific SIRNA | 123 | 168 | 255 | 3 | fw |
| csi-MIR171a | Min change/ perfect structure/ trait-specific SIRNA | 124 | 21 | 256 | 3 | rv |
| csi-MIR167c | Max change/ altered structure/ trait-specific siRNA | 125 | 144 | 257 | 1 | fw |
| csi-MIR167c | Max change/ perfect structure/ non-specific SIRNA | 126 | 182 | 258 | 3 | fw |
| Elaeis guineensis (Oil palm) *U56128.1/Basal stem rot (BSR) also known as Ganoderma butt rot (Ganoderma* spp.) | | | | | | |
| egu-MIR172c | Max change/ perfect structure/ trait-specific SIRNA | 127 | 89 | 259 | 1 | rv |
| egu-MIR172c | Min change/ perfect structure/ trait-specific SIRNA | 128 | 53 | 260 | 1 | rv |
| egu-MIR172c | Max change/ altered structure/ trait-specific SIRNA | 129 | 74 | 261 | 1 | rv |
| egu-MIR172c | Max change/ perfect structure/ non-specific SIRNA | 130 | 94 | 262 | 1 | rv |
| Fragaria vesca (Wild strawberry) *DS572713.1/ Verticillium Wilt (Verticillium dahlia)* | | | | | | |
| fve-MIR159c | Max change/ perfect structure/ trait-specific SiRNA | 131 | 100 | 263 | 3 | fw |
| fve-MIR160b | Min change/ perfect structure/ trait-specific SIRNA | 132 | 22 | 264 | 3 | rv |
| fve-MIR166a | Max change/ altered structure/ trait-specific SIRNA | 133 | 56 | 265 | 3 | fw |
| fve-MIR164b | Max change/ perfect structure/ non-specific SIRNA | 134 | 95 | 266 | 3 | fw |
| *KR855868.1/Fusarium wilt (Fusarium oxysporum f.sp. fragariae)* | | | | | | |
| fve-MIR159c | Max change/ perfect structure/ trait-specific SIRNA | 135 | 97 | 267 | 3 | fw |

TABLE 1B-continued

Examples of GEiGS oligo designs to generate different traits in various hosts

| | Oligo info | oligo_seq | seq difference from wt | Sg_seq | pam_difference | sgRNA_ strand |
|---|---|---|---|---|---|---|
| fve-MIR167b | Min change/ perfect structure/ trait-specific siRNA | 136 | 17 | 268 | 1 | rv |
| fve-MIR169a | Max change/ altered structure/ trait-specific SIRNA | 137 | 69 | 269 | 3 | rv |
| fve-MIR164b | Max change/ perfect structure/ non-specific SIRNA | 138 | 94 | 270 | 3 | fw |
| Glycine max (Soybean) *DQ026061.1/Soybean rust caused by P. pachyrhizi (also known as Asian rust)* | | | | | | |
| gma-MIR167c | Max change/ perfect structure/ trait-specific SIRNA | 139 | 166 | 271 | 3 | rv |
| gma-MIR1511 | Min change/ perfect structure/ trait-specific SIRNA | 140 | 23 | 272 | 3 | fw |
| gma-MIR167c | Max change/ altered structure/ trait-specific SiRNA | 141 | 141 | 273 | 3 | rv |
| gma-MIR167c | Max change/ perfect structure/ non-specific SIRNA | 142 | 163 | 274 | 3 | rv |
| *KJ451424.1/Soybean Aphid* | | | | | | |
| gma-MIR167c | Max change/ perfect structure/ trait-specific SIRNA | 143 | 163 | 275 | 3 | rv |
| gma-MIR168a | Min change/ perfect structure/ trait-specific SIRNA | 144 | 23 | 276 | 0 | rv |
| gma-MIR167c | Max change/ altered structure/ trait-specific SIRNA | 145 | 132 | 277 | 3 | rv |
| gma-MIR167c | Max change/ perfect structure/ non-specific SIRNA | 146 | 161 | 278 | 3 | rv |
| *NC_003056.1/Soybean Dwarf Virus (SbDV)* | | | | | | |
| gma-MIR167c | Max change/ perfect structure/ trait-specific SIRNA | 147 | 165 | 279 | 3 | rv |
| gma-MIR1516a | Min change/ perfect structure/ trait-specific SIRNA | 148 | 23 | 280 | 1 | fw |
| gma-MIR167c | Max change/ altered structure/ trait-specific SIRNA | 149 | 135 | 281 | 3 | rv |
| gma-MIR167c | Max change/ perfect structure/ non-specific siRNA | 150 | 163 | 282 | 3 | rv |

TABLE 1B-continued

Examples of GEiGS oligo designs to generate different traits in various hosts

| | Oligo info | oligo_seq | seq difference from wt | Sg_seq | pam_difference | sgRNA_strand |
|---|---|---|---|---|---|---|
| *NW_020110722.1/ Green Stink Bug (Acrosternum hilare)* | | | | | | |
| gma-MIR167c | Max change/ perfect structure/ trait-specific siRNA | 151 | 158 | 283 | 3 | rv |
| gma-MIR162a | Min change ! perfect structure/ trait-specific SIRNA | 152 | 22 | 284 | 1 | rv |
| gma-MIR167c | Max change/ altered structure/ trait-specific SIRNA | 153 | 135 | 285 | 3 | rv |
| gma-MIR167c | Max change/ perfect structure/ non-specific SIRNA | 154 | 164 | 286 | 3 | rv |
| Gossypium raimondii (Cotton) *JN416614.1/Fusarium wilt (Fusarium oxysporum f.sp. vasinfectum)* | | | | | | |
| gra-MIR8637 | Max change/ perfect structure/ trait-specific SiRNA | 155 | 154 | 287 | 3 | rv |
| gra-MIR7486e | Min change/ perfect structure/ trait-specific SIRNA | 156 | 2 | 288 | 3 | fw |
| gra-MIR8633 | Max change/ altered structure/ trait-specific SIRNA | 157 | 58 | 289 | 3 | fw |
| gra-MIR8635 | Max change/ perfect structure/ non-specific SIRNA | 158 | 149 | 290 | 3 | fw |
| *KJ451424.1/Soybean Aphid* | | | | | | |
| gra-MIR8637 | Max change/ perfect structure/ trait-specific SIRNA | 159 | 153 | 291 | 3 | rv |
| gra-MIR157a | Min change/ perfect structure/ trait-specific SIRNA | 160 | 16 | 292 | 1 | fw |
| gra-MIR8636 | Max change/ altered structure/ trait-specific SiRNA | 161 | 62 | 293 | 3 | fw |
| gra-MIR8637 | Max change/ perfect structure/ non-specific SIRNA | 162 | 149 | 294 | 3 | rv |
| *KU550964.1/Pink bollworm (Pectinophora gossypiella)* | | | | | | |
| gra-MIR8637 | Max change/ perfect structure/ trait-specific SIRNA | 163 | 155 | 295 | 3 | rv |
| gra-MIR157a | Min change/ perfect structure/ trait-specific SIRNA | 164 | 21 | 296 | 1 | fw |
| gra-MIR8644 | Max change/ altered structure/ trait-specific SIRNA | 165 | 53 | 297 | 3 | rv |

TABLE 1B-continued

Examples of GEiGS oligo designs to generate different traits in various hosts

| | Oligo info | oligo_seq | seq difference from wt | Sg_seq | pam_difference | sgRNA_ strand |
|---|---|---|---|---|---|---|
| gra-MIR8635 | Max change/ perfect structure/ non-specific SiRNA | 166 | 154 | 298 | 3 | fw |
| Oryza sativa (Rice) *AF027979.1/Rice Blast (fungal disease caused by Pyricularia grisea)* | | | | | | |
| osa-MIR166b | Max change/ perfect structure/ trait-specific SIRNA | 167 | 105 | 299 | 1 | fw |
| osa-MIR156e | Min change/ perfect structure/ trait-specific SIRNA | 168 | 2.1 | 300 | 0 | fw |
| osa-MIR160b | Max change/ altered structure/ trait-specific SiRNA | 169 | 59 | 301 | 3 | rv |
| osa-MIR166b | Max change/ perfect structure/ non-specific SiRNA | 170 | 100 | 302 | 3 | fw |
| *AY862192.1/Bakanae Disease (fungal disease caused by Fusarium moniliforme and Gibberella fujikuroi)* | | | | | | |
| osa-MIR166b | Max change/ perfect structure/ trait-specific SIRNA | 171 | 100 | 303 | 3 | fw |
| osa-MIR160c | Min change/ perfect structure/ trait-specific SiRNA | 172 | 22 | 304 | 1 | rv |
| osa-MIR156j | Max change/ altered structure/ trait-specific SIRNA | 173 | 68 | 305 | 1 | rv |
| osa-MIR166b | Max change/ perfect structure/ non-specific SIRNA | 174 | 104 | 306 | 3 | fw |
| *KF290773.1/Stem borer (Scirpophaga incertulas Walker - Yellow Stem Borer, S. innoto Walker - White Stem Borer, Chilo suppressalis Walker Striped Stem Borer, Sesamia inferens Walker - Pink Stem Borer* | | | | | | |
| osa-MIR166b | Max change/ perfect structure/ trait-specific SIRNA | 175 | 100 | 307 | 1 | fw |
| osa-MIR156j | Min change/ perfect structure/ trait-specific SIRNA | 176 | 21 | 308 | 3 | rv |
| osa-MIR160b | Max change/ altered structure/ trait-specific SIRNA | 177 | 57 | 309 | 3 | rv |
| osa-MIR166b | Max change/ perfect structure/ non-specific SIRNA | 178 | 103 | 310 | 3 | fw |

TABLE 1B-continued

Examples of GEiGS oligo designs to generate different traits in various hosts

| | Oligo info | oligo_seq | seq difference from wt | Sg_seq | pam_difference | sgRNA_ strand |
|---|---|---|---|---|---|---|
| Solanum lycopersicum (Tomato) *AY855210.1/Late blight (Phytophthora infestans)* | | | | | | |
| sly-MIR319b | Max change/ perfect structure/ trait-specific SIRNA | 179 | 143 | 311 | 3 | fw |
| sly-MIR156b | Min change/ perfect structure/ trait-specific SiRNA | 180 | 24 | 312 | 0 | fw |
| sly-MIR395a | Max change/ altered structure/ trait-specific SIRNA | 181 | 75 | 313 | 3 | fw |
| sly-MIR319b | Max change/ perfect structure/ non-specific siRNA | 182 | 145 | 314 | 3 | fw |
| *KX390870.1/whitefly Bemisia tabaci (Gennadius)* | | | | | | |
| sly-MIR319b | Max change/ perfect structure/ trait-specific SIRNA | 183 | 144 | 315 | 3 | fw |
| sly-MIR391 | Min change/ perfect structure/ trait-specific SiRNA | 184 | 16 | 316 | 3 | fw |
| sly-MIR319c | Max change/ altered structure/ trait-specific SiRNA | 185 | 79 | 317 | 1 | rv |
| sly-MIR319b | Max change/ perfect structure/ non-specific SIRNA | 186 | 138 | 318 | 3 | fw |
| *LN846610.1/Tomato yellow leaf curl geminivirus (TYLCV)* | | | | | | |
| sly-MIR319b | Max change/ perfect structure/ trait-specific SIRNA | 187 | 141 | 319 | 3 | fw |
| sly-MIR156b | Min change/ perfect structure/ trait-specific SIRNA | 188 | 24 | 320 | 0 | fw |
| sly-MIR395a | Max change/ altered structure/ trait-specific SIRNA | 189 | 81 | 321 | 3 | fw |
| sly-MIR319b | Max change/ perfect structure/ non-specific SiRNA | 190 | 143 | 322 | 3 | fw |
| Solanum tuberosum (Potato) *AY050538.3/Late Blight (Phytophthora infestans)* | | | | | | |
| stu-MIR6022 | Max change/ perfect structure/ trait-specific SIRNA | 191 | 110 | 323 | 1 | fw |
| stu-MIR7988 | Min change/ perfect structure/ trait-specific SIRNA | 192 | 19 | 324 | 1 | rv |

TABLE 1B-continued

Examples of GEiGS oligo designs to generate different traits in various hosts

| | Oligo info | oligo_seq | seq difference from wt | Sg_seq | pam_difference | sgRNA_ strand |
|---|---|---|---|---|---|---|
| stu-MIR482d | Max change/ altered structure/ trait-specific SIRNA | 193 | 50 | 325 | 3 | rv |
| stu-MIR6022 | Max change/ perfect structure/ non-specific SIRNA | 194 | 106 | 326 | 1 | fw |
| *CP001654.1/Blackleg and Soft Rot* (*Erwinia* spp.) | | | | | | |
| stu-MIR6022 | Max change/ perfect structure/ trait-specific SIRNA | 195 | 110 | 327 | 1 | fw |
| stu-MIR7988 | Min change/ perfect structure/ trait-specific SIRNA | 196 | 16 | 328 | 1 | rv |
| stu-MIR482d | Max change/ altered structure/ trait-specific siRNA | 197 | 50 | 329 | 2 | rv |
| stu-MIR6022 | Max change/ perfect structure/ non-specific SIRNA | 198 | 104 | 330 | 1 | fw |
| *KF963519.1/Cyst Nematodes* (*Globodera pallida and G.rostochiensis*) | | | | | | |
| stu-MIR6022 | Max change/ perfect structure/ trait-specific SIRNA | 199 | 107 | 331 | 1 | fw |
| stu-MIR7985 | Min change/ perfect structure/ trait-specific SIRNA | 200 | 20 | 332 | 3 | fw |
| stu-MIR6024 | Max change/ altered structure/ trait-specific SIRNA | 201 | 49 | 333 | 0 | rv |
| stu-MIR6022 | Max change/ perfect structure/ non-specific SIRNA | 202 | 107 | 334 | 1 | fw |
| Theobroma cacao (Cacao) *LATX01001521.1/Frosty Pod Rot caused by the basidiomycete Moniliophthora roreri* | | | | | | |
| tcc-MIR169b | Max change/ perfect structure/ trait-specific SIRNA | 203 | 100 | 335 | 3 | fw |
| tcc-MIR167a | Min change/ perfect structure/ trait-specific SIRNA | 204 | 25 | 336 | 3 | rv |
| tcc-MIR167b | Max change/ altered structure/ trait-specific SIRNA | 205 | 52 | 337 | 1 | fw |
| tcc-MIR169b | Max change/ perfect structure/ non-specific SIRNA | 206 | 104 | 338 | 3 | fw |

TABLE 1B-continued

| Examples of GEiGS oligo designs to generate different traits in various hosts | | | | | | |
|---|---|---|---|---|---|---|
| | Oligo info | oligo_seq | seq difference from wt | Sg_seq | pam_difference | sgRNA_ strand |
| Vitis vinifera (Grape) *AF007415.2/Rugose wood disease (closterovirus GVA)* | | | | | | |
| vvi-MIR167a | Max change/ perfect structure/ trait-specific SIRNA | 207 | 154 | 339 | 3 | fw |
| vvi-MIR164b | Min change/ perfect structure/ trait-specific siRNA | 208 | 22 | 340 | 3 | fw |
| vvi-MIR167a | Max change/ altered structure/ trait-specific SIRNA | 209 | 108 | 341 | 3 | fw |
| vvi-MIR167a | Max change/ perfect structure/ non-specific SIRNA | 210 | 153 | 342 | 2. | fw |
| *FJ436234.1/Grapevine leafroll virus* | | | | | | |
| vvi-MIR167a | Max change/ perfect structure/ trait-specific SIRNA | 211 | 152 | 343 | 2 | fw |
| vvi-MIR167c | Min change/ perfect structure/ trait-specific siRNA | 212 | 20 | 344 | 3 | rv |
| vvi-MIR167a | Max change/ altered structure/ trait-specific SIRNA | 213 | 118 | 345 | 2 | fw |
| vvi-MIR167a | Max change/ perfect structure/ non-specific SIRNA | 214 | 152 | 346 | 3 | fw |
| *NC_003203.1/Grapevine fanleaf degeneration disease virus (GFLV) - a nepovirus* | | | | | | |
| vvi-MIR167a | Max change/ perfect structure/ trait-specific SIRNA | 215 | 158 | 347 | 2 | fw |
| vvi-MIR166h | Min change/ perfect structure/ trait-specific SIRNA | 216 | 19 | 348 | 3 | fw |
| vvi-MIR167a | Max change/ altered structure/ trait-specific SIRNA | 217 | 118 | 349 | 2. | fw |
| Vvi-MIR167a | Max change/ perfect structure/ non-specific SIRNA | 218 | 156 | 350 | 3 | fw |
| *NC_003347.1/Grapevine fleck disease (GFkV)* | | | | | | |
| vvi-MIR167a | Max change/ perfect structure/ trait-specific SIRNA | 219 | 161 | 351 | 2 | fw |
| vvi-MIR166b | Min change/ perfect structure/ trait-specific SIRNA | 220 | 19 | 352 | 3 | fw |
| vvi-MIR167a | Max change/ altered structure/ trait-specific SIRNA | 221 | 127 | 353 | 2 | fw |

TABLE 1B-continued

Examples of GEiGS oligo designs to generate different traits in various hosts

| | Oligo info | oligo_seq | seq difference from wt | Sg_seq | pam_difference | sgRNA_ strand |
|---|---|---|---|---|---|---|
| vvi-MIR167a | Max change/ perfect structure/ non-specific SiRNA | 222 | 157 | 354 | 2 | fw |
| Zea mays (Maize) *AJ488181.3/Foll Armyworm* (*Spodoptera frugiperda*) | | | | | | |
| zma-MIR166a | Max change/ perfect structure/ trait-specific SIRNA | 223 | 100 | 355 | 0 | fw |
| zma-MIR160c | Min change/ perfect structure/ trait-specific SIRNA | 224 | 20 | 356 | 2 | fw |
| zma-MIR156f | Max change/ altered structure/ trait-specific siRNA | 225 | 64 | 357 | 0 | fw |
| zma-MIR1668 | Max change/ perfect structure/ non-specific SIRNA | 226 | 101 | 358 | 3 | fw |
| *GU329524.1/European corn borer* | | | | | | |
| zma-MIR166a | Max change/ perfect structure/ trait-specific SIRNA | 227 | 103 | 359 | 1 | fw |
| zma-MIR166h | Min change/ perfect structure/ trait-specific SIRNA | 228 | 20 | 360 | 1 | rv |
| zma-MIR171f | Max change/ altered structure/ trait-specific SIRNA | 229 | 62. | 361 | 3 | rv |
| zma-MIR166a | Max change/ perfect structure/ non-specific SIRNA | 230 | 106 | 362 | 3 | fw |
| *NM_001039403.1/ Northern and wertern corn rootworms* | | | | | | |
| zma-MIR166a | Max change/ perfect structure/ trait-specific SIRNA | 231 | 107 | 363 | 0 | fw |
| zma-MIR172d | Min change/ perfect structure/ trait-specific SIRNA | 232 | 20 | 364 | 3 | rw |
| zma-MIR166a | Max change/ altered structure/ trait-specific SIRNA | 233 | 73 | 365 | 1 | fw |
| zma-MIR1668 | Max change/ perfect structure/ non-specific SIRNA | 234 | 105 | 366 | 3 | fw |

Table 1B provides example GeiGS oligos designed against a variety of targets in several host organisms. For each host-target combination, four oligos are provided: minimum sequence changes with matching structure and efficient siRNA; maximum sequence changes with matching structure and efficient siRNA; maximum sequence changes and non-matching structure and efficient siRNA; and maximum sequence changes with matching structure and inefficient siRNA.

According to one embodiment, the plants generated by the present method are more resistant or tolerant to pathogens by at least about 10%, 20%, 30%, 40%, 50%, 60%, 70%, 80%, 90%, 95% or 100% as compared to plants not generated by the present methods (i.e. as compared to wild type plants).

Any method known in the art for assessing tolerance or resistance to a pathogen of a plant may be used in accordance with the present invention. Exemplary methods include, but are not limited to, reducing MYB46 expression in *Arabidopsis* which results in enhance resistance to *Botrytis cinereal* as described in Ramírez V1, García-Andrade J, Vera P., Plant Signal Behav. 2011 June; 6(6):911-3. Epub 2011 Jun. 1; or downregulation of HCT in alfalfa promotes activation of defense to response in the plant as described in Gallego-Giraldo L. et al. New Phytologist (2011) 190: 627-639 doi: 10.1111/j.1469-8137.2010.03621.x), both incorporated herein by reference.

According to one embodiment, there is provided a method of generating a herbicide resistant plant, the method comprising modifying a gene encoding or processed into a non-coding RNA molecule or into a RNA silencing molecule in a plant cell according to the methods of some embodiments of the invention, wherein the target RNA of interest is of a gene of the plant conferring sensitivity to the herbicide, thereby generating the herbicide resistant plant.

According to one embodiment, the herbicides target pathways that reside within plastids (e.g. within the chloroplast).

Thus to generate herbicide resistant plants, the non-coding RNA molecule is designed to target a RNA of interest including, but not limited to, the chloroplast gene psbA (which codes for the photosynthetic quinone-binding membrane protein $Q_B$, the target of the herbicide atrazine) and the gene for EPSP synthase (a nuclear protein, however, its overexpression or accumulation in the chloroplast enables plant resistance to the herbicide glyphosate as it increases the rate of transcription of EPSPs as well as by a reduced turnover of the enzyme).

According to one embodiment, the plants generated by the present method are more resistant to herbicides by at least about 10%, 20%, 30%, 40%, 50%, 60%, 70%, 80%, 90%, 95% or 100% as compared to plants not generated by the present methods.

According to one embodiment, there is provided a plant generated according to the method of some embodiments of the invention.

According to one embodiment, plant is non-genetically modified (non-GMO).

According to one embodiment, there is provided a seed of the plant generated according to the method of some embodiments of the invention.

Designing GEiGS with minimal nucleotide modifications/edits in the endogenous non-coding RNA can be achieved using in silico methods, which are based on bioinformatics tools that are well known to the skilled artisan.

According to one embodiment, such a method is effected as follows:

The following information should be available: a) Target sequence to be silenced by Gene Editing induced Gene Silencing (GEiGS) ("target"); b) Choosing whether the GEiGS (i.e. the non-coding RNA with modified silencing activity and/or specificity) would be expressed ubiquitously (e.g. constitutively) or specifically (e.g. expression specific to a certain tissue, developmental stage, stress, heat/cold shock etc.).

Submitting this information to publicly or inhouse available miRNA datasets (e.g. small RNA sequencing, genomic sequences, microarrays etc.) so as to filter (i.e. elect) only relevant miRNAs that match the input criteria: miRNAs that are expressed according to the requirement(s) described above, such as miRbase (Kozommara and Griffiths-Jones (2014)), tasRNAdb (Zhang Changqing, et al. (2013)) and mirEx 2.0 (Zielezinski, Andrzej et al. "mirEX 2.0—an Integrated Environment for Expression Profiling of Plant microRNAs." BMC Plant Biology 15 (2015): 144. PMC. Web. 15 Sep. 2018).

Using publically available tools, a list of potent target-specific siRNA sequences may be generated. The miRNAs may be aligned against the potent siRNA sequences and the most homologous miRNAs may be elected. Filtered miRNAs may have a similar sequence in the same orientation like the potent siRNAs.

Modifying the naturally mature miRNAs sequences, which are scored to have high homology to target-specific potent siRNAs, to perfectly match the target's sequence. This modification may occur in one mature miRNA strand with the highest target homology (e.g. could be either the original miRNA guide or passenger strand). Such 100% complementary to the target can potentially turn the miRNA sequence into a siRNA.

Minimal GE may be achieved by filtering miRNA sequences with naturally occurring high homology (reverse complement) to the target.

Using the primary modified miRNA genes to generate ssDNA oligos (e.g. 200-500 nt ssDNA long) and dsDNA fragments (e.g. 250-5000 nt dsDNA fragments only or cloned within plasmids) based on the genomic DNA sequences that flank the modified miRNA precursor sequence (pre-miRNA). The modified miRNA's guide strand (silencing strand) sequence may be designed to be 100% complementary to the target.

Modifying the sequence of the other miRNA gene region to preserve the original (unmodified) miRNA precursor and mature structure, through keeping the same base pairing profile.

Designing sgRNAs to specifically target the original unmodified miRNA gene (specific to the genomic miRNA loci), and not the modified version (i.e. the oligo/fragment sequences).

Analyzing the comparative restriction enzyme site between the modified and the original miRNA gene and summarizing the differential restriction sites. Such a detection system is based on PCR that is followed by restriction enzyme digestion and gel electrophoresis.

Validating as discussed in detail above.

Examining the targeting of the non-coding RNA towards other targets (e.g. "off target effect"), using in silico methods, when the endogenous non-coding RNA (e.g. miRNA) comprises naturally occurring high homology with the target (e.g. 60-90%), so as to obtain specific silencing to of the target of interest.

Minimally modifying the endogenous non-coding RNA (e.g. miRNA) to boost its potency to silence the target of interest.

Validating GEiGS outcome of the primary minimally edited miRNA genes to generate candidate refined minimally edited miRNAs. An experimentally effective primary GEiGS outcome (the primary minimally edited miRNA genes) is considered as a miRNA(s) with a guide or passenger strand that is modified to match the target by 100%.

Generating several guide or passenger strand sequences that are gradually reverted back into the original sequence (as illustrated in FIG. 11).

Keeping the seed sequence in a way that there are at least 5 matches out of the seven seed nucleotides (nucleotides 2-8 from the 5' terminus).

Testing the various candidate 'refined minimally edited miRNA genes' for target silencing efficiency. Choosing the gene GE-mediated knock-in that provides the highest silencing with the minimal miRNA sequence modification.

Testing potential "off target effects" of refined minimally edited miRNA candidates. A significant prediction for "off target effects" affects the final evaluation of the refined minimally edited miRNA genes.

Testing the less refined minimally edited miRNA gene candidates based on the experimental validation.

As used herein the term “about” refers to ±10%.

The terms “comprises”, “comprising”, “includes”, “including”, “having” and their conjugates mean “including but not limited to”.

The term “consisting of” means “including and limited to”.

The term “consisting essentially of” means that the composition, method or structure may include additional ingredients, steps and/or parts, but only if the additional ingredients, steps and/or parts do not materially alter the basic and novel characteristics of the claimed composition, method or structure.

As used herein, the singular form “a”, “an” and “the” include plural references unless the context clearly dictates otherwise. For example, the term “a compound” or “at least one compound” may include a plurality of compounds, including mixtures thereof.

Throughout this application, various embodiments of this invention may be presented in a to range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases “ranging/ranges between” a first indicate number and a second indicate number and “ranging/ranges from” a first indicate number “to” a second indicate number are used herein interchangeably and are meant to include the first and second indicated numbers and all the fractional and integral numerals therebetween.

As used herein the term “method” refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term “treating” includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence to format or a RNA sequence format. For example, SEQ ID NOs: 1-4 are expressed in a DNA sequence format (e.g., reciting T for thymine), but it can refer to either a DNA sequence that corresponds to an gRNA nucleic acid sequence, or the RNA sequence of a RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, “Molecular Cloning: A laboratory Manual” Sambrook et al., (1989); “Current Protocols in Molecular Biology” Volumes I-m Ausubel, R. M., ed. (1994); Ausubel et al., “Current Protocols in Molecular Biology”, John Wiley and Sons, Baltimore, Maryland (1989); Perbal, “A Practical Guide to Molecular Cloning”, John Wiley & Sons, New York (1988): Watson et al., “Recombinant DNA”, Scientific American Books, New York; Birren et al. (eds) “Genome Analysis: A Laboratory Manual Series”, Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; “Cell Biology: A Laboratory Handbook”, Volumes I-III Cellis, J. E., ed. (1994); “Current Protocols in Immunology” Volumes I-m Coligan J. E., ed. (1994); Stites et al. (eds), “Basic and Clinical Immunology” (8th Edition), Appleton & Lange, Norwalk, CT (1994); Mishell and Shiigi (eds), “Selected Methods in Cellular Immunology”, W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; “Oligonucleotide Synthesis” Gait, M. J., ed. (1984); “Nucleic Acid Hybridization” Hames, B. D., and Higgins S. J., eds. (1985); “Transcription and Translation” Hames, B. D., and Higgins S. J., Eds. (1984); “Animal Cell Culture” Freshney, R. I., ed. (1986); “Immobilized Cells and Enzymes” IRL Press, (1986); “A Practical Guide to Molecular Cloning” Perbal, B., (1984) and “Methods in Enzymology” Vol. 1-317, Academic Press; “PCR Protocols: A Guide To Methods And Applications”, Academic Press, San Diego, CA to (1990); Marshak et al., “Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

*Arabidopsis* Cell Culture

*Arabidopsis thaliana* (ecotype Landsberg erecta) cell cultures were maintained in 100 mL of liquid growth medium (4.4 g/L Murashige and Skoog (MS) salts with vitamins [Duchefa, Haarlem, The Netherlands], 30 g/L sucrose, 0.5 mg/L 1-Naphthaleneacetic acid (NAA) and 0.5 mg/L 6-Benzylaminopurine (BAP) at 25° C., 16 hour photoperiod and gentle agitation (100 rpm). Every week 6 ml of culture was transferred to fresh medium.

Plant Growth

*Arabidopsis thaliana* (ecotype Colombia-0) seedlings were surface sterilized and grown on plates containing MS medium supplemented with 0.8 g/L agar at 20° C. in 16 hour photoperiod.

Stable Transformation of *Arabidopsis* Cell Culture

*Agrobacterium* carrying the pK7WGF2 plasmid were grown in LB medium supplemented with 100 mg/L spectinomycin at 28° C. to an OD of 0.8. Bacteria were collected by centrifugation and resuspended in the same amount of plant cell culture medium. Four days after transfer to fresh medium, 4 ml of *Arabidopsis* cells were incubated with 0.1 mL of the *Agrobacterium* suspension in a Petri dish at 25° C. in the dark with gentle agitation (130 rpm). After 48 hours, the cells were collected by centrifugation and washed five times with cell culture medium to remove most of the bacteria. Finally, cells were resuspended in 2 ml of cell culture medium and plates onto a petri dish containing cell culture medium supplemented with 0.4% Phytagel, 500 mg/L timenten and 50 mg/L kanamycin. The dishes were stored at 25° C. in the dark until calli formation was observed, usually after 2 or 3 weeks Banana Embryogenic Calli:

Banana embryogenic callus is developed from an initial explant such as immature male flowers or shoot tip as described by Ma [Ma S. S., *Proceedings of Symposium on Tissue culture of horticultural crops*, Taipei, Taiwan, 8-9 Mar. 1988, pp. 181-188] and Schoofs [Schoofs H., *The origin of embryogenic cells in Musa*. PhD thesis, KULeuven, Belgium (1997)]. Embryogenic cell suspensions are initiated from freshly developed highly embryogenic calli in liquid medium. 80% of the medium is refreshed every 12-14 days until the initiated cell suspension is fully established (6- to 9 months).

Coffee Embryonic Calli:

Coffee embryonic calli is obtained as previously described [Etienne, H., *Protocol for somatic embryogenesis in woody plants* (2005) Springer. p. 167-1795]. Briefly, young leaves are surface sterilized, cut into 1 $cm^2$ pieces and placed on half strength semi solid MS medium supplemented with 2.26 μM 2,4-dichlorophenoxyacetic acid (2,4-D), 4.92 μM indole-3-butyric acid (IBA) and 9.84 μM isopentenyladenine (iP) for one month. Explants are then transferred to half strength semisolid MS medium containing 4.52 μM 2,4-D and 17.76 μM 6-benzylaminopurine (6-BAP) for 6 to 8 months until regeneration of embryogenic calli. Embryogenic calli are maintained on MS media supplemented with 5 μM 6-BAP.

Cell suspension cultures are generated from embryogenic calli as previously described [Acuna, J. R. and M. de Pena, *Plant Cell Reports* (1991) 10(6): p. 345-348]. Embryogenic calli (30 g/l) are placed in liquid MS medium supplemented with 13.32 μM 6-BAP. Flasks are placed in a shaking incubator (110 rpm) at 28° C. The cell suspension is sub-cultured/passaged every two to four weeks until fully established. Cell suspension cultures are maintained in liquid MS medium with 4.44 μM 6-BAP.

Computational Pipeline to Generate GEiGS Templates

The computational GEiGS pipeline applies biological metadata and enables an automatic generation of GEiGS DNA templates that are used to minimally edit non-coding RNA genes (e.g. miRNA genes), leading to a new gain of function. i.e. redirection of their silencing capacity to target sequence of interest.

As illustrated in FIG. 9, the pipeline starts with filling and submitting input: a) target sequence to be silenced by GEiGS; b) the host organism to be gene edited and to express the GEiGS; c) one can choose whether the GEiGS would be expressed ubiquitously or not. If specific GEiGS expression is required, one can choose from a few options (expression specific to a certain tissue, developmental stage, stress, heat/cold shock etc).

When all the required input is submitted, the computational process begins with searching among miRNA datasets (e.g. small RNA sequencing, microarray etc.) and filtering only relevant miRNAs that match the input criteria. Next, the selected mature miRNA sequences are aligned against the target sequence and miRNA with the highest complementary levels are filtered. These naturally target-complementary mature miRNA sequences are then modified to perfectly match the target's sequence. Then, the modified mature miRNA sequences are run through an algorithm that predicts siRNA potency and the top 20 with the highest silencing score are filtered. These final to modified miRNA genes are then used to generate 200-500 nt ssDNA or 250-5000 nt dsDNA sequences as follows:

200-500 nt ssDNA oligos and 250-5000 nt dsDNA fragments are designed based on the genomic DNA sequence that flanks the modified miRNA. The pre-miRNA sequence is located in the center of the oligo. The modified miRNA's guide strand (silencing) sequence is 100% complementary to the target. However, the sequence of the modified passenger miRNA strand is further modified to preserve the original (unmodified) miRNA structure, keeping the same base pairing profile.

Next, differential sgRNAs are designed to specifically target the original unmodified miRNA gene, and not the modified swapping version. Finally, comparative restriction enzyme site analysis is performed between the modified and the original miRNA gene and differential restriction sites are summarized.

Therefore, the pipeline output includes:

a) 200-500 nt ssDNA oligo or 250-5000 nt dsDNA fragment sequence with minimally modified miRNA
b) 2-3 differential sgRNAs that target specifically the original miRNA gene and not the modified
c) List of differential restriction enzyme sites among the modified and original miRNA gene Target Genes Phytoene desaturase gene (PDS Rationale:

PDS is an essential gene in the chlorophyll biosynthesis pathway and loss of PDS function in plants results in albino phenotype [Fan et al., *Sci Rep* (2015) 5:12217]. When used as a target gene in genome editing (GE) strategy or RNAi, positively edited plants are easily identified by partial or complete loss of chlorophyll in leaves and other organs (bleaching).

Methods:

miRNAs with ubiquitous expression profile are chosen (depends on the application, one might choose miRNAs with expression profile that is specific to a certain tissue, developmental stage, temperature, stress etc).

miRNAs are modified to siRNA targeting the PDS gene from *Arabidopsis* (see Table 1A, below). Following transfection and FACS sorting (RFP/GFP are used for identifying positive Cas9/sgRNA transfection events), protocolonies (or calli) are transferred into solid regeneration to media (half strength MS+B5 vitamins, 20 g/l sucrose, 0.8% agar) until shoots are regenerated. Loss of pigmentation in these shoots indicates loss of function of the PDS gene and correct GE. No albino phenotype is observed in the control plantlets transfected with an oligo carrying random sequence.

Green Fluorescent Protein (GFP) Gene

Rationale:

GFP is a protein composed of 238 amino acid residues (26.9 kDa) that exhibits bright green fluorescence when exposed to light in the blue to ultraviolet range. Although many other marine organisms have similar green fluorescent proteins, GFP traditionally refers to the protein first isolated from the jellyfish *Aequorea victoria*. The GFP from *A. victoria* has a major excitation peak at a wavelength of 395 nm and a minor one at 475 nm. Its emission peak is at 509 nm, which is in the lower green portion of the visible spectrum. The fluorescence quantum yield (QY) of GFP is 0.79. The GFP from the sea pansy (*Renilla reniformis*) has a single major excitation peak at 498 nm. GFP makes for an excellent tool in many areas of biology due to its ability to form internal chromophores without requiring any accessory cofactors, gene products, or enzymes/substrates other than molecular oxygen.

Methods:

miRNAs with ubiquitous expression profile are chosen (depends on the application, one might choose miRNAs with expression profile that is specific to a certain tissue, developmental stage, temperature, stress etc).

miRNAs are modified into siRNA targeting the GFP gene (see Table 1A, below). Following transfection FACS sorting is performed, isolating mCherry-expressing protoplasts (mCherry is used for identifying positive Cas9/sgRNA transfection events) with no or low GFP signal. In the control (oligo with non-target siRNA sequence), all protoplasts express mCherry and GFP. Next, candidate successful GE protoplast (mCherry positive and GFP negative) are regenerated into plants for further analyses. Protoplasts are also qualitatively documented under the microscope. For quantification analysis and ratios FACS analysis was used.

TABLE 1A

| Target Genes IDs | | |
|---|---|---|
| Gene name | Query sequence ID | Query sequence organism |
| PDS | NM_001340908.1 (SEQ ID NO: 25) NM_117498 (SEQ ID NO: 26) | *Arabidopsis* |
| ADH1 | NC_003070.9 | *Arabidopsis* |
| eGFP | AFA52654 (SEQ ID NO: 27) | *Aequorea victoria* |

siRNA Design

Target-specific siRNAs are designed by publically available siRNA-designers such as ThermoFisher Scientific's "BLOCK-iT™ RNAi Designer" and Invivogen's "Find siRNA sequences".

sgRNAs Design sgRNAs are designed to target the endogenous miRNA genes using the publically available sgRNA designer, as previously described in Park et al., *Bioinformatics* (2015) 31(24): 4014-4016. Two sgRNAs are designed for each cassette, but a single sgRNA is expressed per cell to initiate gene swapping. sgRNAs correspond to the pre-miRNA sequence that is modified post swapping.

In order to maximize the chance of efficient sgRNA choice, two different publicly available algorithms (CRISPER Design: www(dot)crispr(dot)mit(dot)edu:8079/ and CHOPCHOP: www(dot)chopchop(dot)cbu(dot)uib (dot)no/) are used and the top scoring sgRNA from each algorithm is selected.

Swapping ssDNA Oligo Design:

400 b ssDNA oligo is designed based on the genomic DNA sequence of the miRNA gene. The pre-miRNA sequence is located in the center of the oligo. Next, the double stranded siRNA sequences are swapped with the mature miRNA sequences in a way that the guide (silencing) siRNA strand is kept 100% complementary to the target. The sequence of the passenger siRNA strand is modified to preserve the original miRNA structure, keeping the same base pairing profile.

Swapping Plasmid DNA Design 4000 bp dsDNA fragment is designed based on the genomic DNA sequence of the miRNA gene. The pre-miRNA sequence is located in the center of the dsDNA fragment. Next, the double stranded siRNA sequences are swapped with the mature miRNA sequences in a way that the guide (silencing) siRNA strand is kept 100% complementary to the target. The sequence of the passenger siRNA strand is modified to preserve the original miRNA structure, keeping the same base pairing profile. Finally, the fragment is cloned into a standard vector (e.g. pBluescript).

Lone Plasmids for Swapping:

Plasmid-1: GEiGS_mir173_si-GFP_1 (SEQ ID NO: 31)
to Plasmid-2: GEiGS_mir173_si-GFP_2 (SEQ ID NO: 32)
Plasmid-3: GEiGS_mir173_si-PDS_1 (SEQ ID NO: 33)
Plasmid-4: GEiGS_mir173_si-PDS_2 (SEQ ID NO: 34)
Plasmid-5: GEiGS_mir390a_si-GFP_1 (SEQ ID NO: 35)
Plasmid-6: GEiGS_mir390a_si-GFP_2 (SEQ ID NO: 36)
Plasmid-7: GEiGS_mir390a_si-PDS_1 (SEQ ID NO: 37)
Plasmid-8: GEiGS_mir390a_si-PDS_2 (SEQ ID NO: 38)

```
sgRNAs sequences:
Arabidopsis mir-390A:
                                        (SEQ ID NO: 1)
1. CTATCCATCCTGAGTTTCATTGG;

                                        (SEQ ID NO: 2)
2. AAGAATCTGTAAAGCTCAGGAGG;

Arabidopsis mir-173:
                                        (SEQ ID NO: 3)
1. CTTGCAGAGAGAAATCACAGTGG;

                                        (SEQ ID NO: 4)
2. GCTTACACAGAGAATCACAGAGG;
```

List of Endogenous miRNA that are Swapped:

1. *Arabidopsis* mir-390A
2. *Arabidopsis* mir-173 ssDNA Oligos Used for Gene Swapping:

Oligo-1: GEiGS_mir173_si-GFP_1 (5'→3') (SEQ ID NO: 5)

Oligo-2: GEiGS_mir173_si-GFP_2 (5'→3') (SEQ ID NO: 6)

Oligo-3: GEiGS_mir173_si-PDS_1 (5'→3') (SEQ ID NO: 7)

Oligo-4: GEiGS_mir173_si-PDS_2 (5'→3') (SEQ ID NO: 8)

Oligo-5: GEiGS_mir390a_si-GFP_1 (5'→3') (SEQ ID NO: 9)

Oligo-6: GEiGS_mir390a_si-GFP_2 (5'→3') (SEQ ID NO: 10)

Oligo-7: GEiGS_mir390a_si-PDS_1 (5'→3') (SEQ ID NO: 11)

Oligo-8: GEiGS_mir390a_si-PDS_2 (5'-+3') (SEQ ID NO: 12)

sgRNA Cloning

The transfection plasmid utilized was composed of 4 modules comprising of 1) mCherry driven by the CsVMV promoter terminated by a G7 termination sequence;
2) 2×35S::hCas9-35S-ter i.e. hCas9 driven by the 35S promoter terminated by AtuNos termination sequence;
3) AtU6-26 and/or U6 synthetic promoter driving sgRNA for guide 1;

Plasmid Design

For transient expression, a plasmid containing three transcriptional units is used. The first to transcriptional unit contains CsVMV promoter driving expression of mCherry and the G7 terminator. The next transcriptional unit consists of 2×-35S promoter-driving expression of Cas9 and the 35S terminator. The third contains the *Arabidopsis* U6 promoter expressing sgRNA to target miRNA genes (each vector comprises a single sgRNAs).

Design and Cloning of CRISPR/CAS9 to Target miR-173 and miR-390 and Introducing SWAPs to Target GFP, AtPDS3 and AtADH1

The present inventors have designed changes in the sequences of mature miR-173 and miR-390, in their genomic context, to target GFP, AtPDS3 or AtADH1, by producing small RNA that reverse complements the target genes, visualized in FIGS. 12A-G and 13A-G. In addition, to maintain the secondary structure of the miRNA precursor transcript, further changes in the pri-miRNA were carried out, as specified in FIGS. 12A-G, 13A-G, 14A-D and 15A-D and Table 2 (below). These fragments were cloned into PUC plasmids and named DONORs and the DNA fragments are referred as SWAPs. For sequences for modifying miR-173—SWAP1 and SWAP2 to target GFP, SWAP3 and SWAP4 to target AtPDS3 and SWAP9 and SWAP10 to target AtADH1 (see Table 2, below). For sequences for modifying miR-390—SWAP5 and SWAP6 to target GFP, SWAP7 and SWAP8 to target AtPDS3 and SWAP11 and SWAP12 to target AtADH1 (see Table 2, below).

Guide RNAs targeting miR-173 and miR-390 were introduced into CRISPR/CAS9 vector system in order to generate a DNA cleavage in the desired miRNA loci. These were co-introduced to the plants with the DONOR vectors via gene bombardment protocol, to introduce desired modifications through Homologous DNA Repair (HDR). These guide RNAs are specified in Table 2, below, and illustrated in FIGS. 12A and 13A.

TABLE 2

Sequences and oligos used in the experiments

| SEQ ID NO: | Aim |
|---|---|
| 39 | miR173 |
| 40 | miR390 |
| 41 | sgRNA sequence used for miR173 targeting in CRISPR/CAS9 system- GEiGS#4 |
| 42 | sgRNA sequence used for miR173 targeting in CRISPR/CAS9 system- GEiGS#5 |
| 43 | sgRNA sequence used for miR390 targeting in CRISPR/CAS9 system- GEiGS#1 |
| 44 | sgRNA sequence used for miR390 targeting in CRISPR/CAS9 system- GEiGS#3 |
| 45 | mature GEiGS-siRNA targeting GFP- used in SWAP5 (based on miR390) and in SWAP1 (based on miR173) |
| 46 | Complementary strand of mature GEiGS-siRNA targeting GFP- used in SWAP5 (based on miR390) and in SWAP1 (based on miR173) |
| 47 | mature GEiGS-siRNA targeting GFP- used in SWAP6 (based on miR390) and in SWAP2 (based on miR173) |
| 48 | Complementary strand of mature GEiGS-siRNA targeting GFP- used in SWAP6 (based on miR390) and in SWAP2 (based on miR173) |
| 49 | mature GEiGS-siRNA targeting AtPDS3- used in SWAP7 (based on miR390) and in SWAP3 (based on miR173) |
| 50 | Complementary strand of mature GEiGS-siRNA targeting AtPDS3- used in SWAP7 (based on miR390) and in SWAP3 (based on miR173) |
| 51 | mature GEiGS-siRNA targeting AtPDS3- used in SWAP8 (based on miR390) and in SWAP4 (based on miR173) |
| 52 | Complementary strand of mature GEiGS-siRNA targeting AtPDS3- used in SWAP8 (based on miR390) and in SWAP4 (based on miR173) |
| 53 | mature GEiGS-siRNA targeting AtADH1- used in SWAP11 (based on miR390) and in SWAP9 (based on miR173) |
| 54 | Complementary strand of mature GEiGS-siRNA targeting AtADH1- used in SWAP11 (based on miR390) and in SWAP9 (based on miR173) |
| 55 | mature GEiGS-siRNA targeting AtADH1- used in SWAP12 (based on miR390) and in SWAP10 (based on miR173) |
| 56 | Complementary strand of mature GEiGS-siRNA targeting AtADH1- used in SWAP12 (based on miR390) and in SWAP10 (based on miR173) |
| 57 | Primary transcript of miR173 (pri-miR173) |
| 58 | Primary transcript of SWAP1 (used in Donor vector for targeting GFP) |
| 59 | Primary transcript of SWAP2 (used in Donor vector for targeting GFP) |
| 60 | Primary transcript of SWAP3 (used in Donor vector for targeting PDS3) |
| 61 | Primary transcript of SWAP4 (used in Donor vector for targeting PDS3) |

TABLE 2-continued

| Sequences and oligos used in the experiments | |
|---|---|
| SEQ ID NO: | Aim |
| 62 | Primary transcript of SWAP9 (used in Donor vector for targeting ADH1) |
| 63 | Primary transcript of SWAP10 (used in Donor vector for targeting ADH1) |
| 64 | Primary transcript of miR390 (pri-miR390) |
| 65 | Primary transcript of SWAP5 (used in Donor vector for targeting GFP) |
| 66 | Primary transcript of SWAP6 (used in Donor vector for targeting GFP) |
| 67 | Primary transcript of SWAP7 (used in Donor vector for targeting PDS3) |
| 68 | Primary transcript of SWAP8(used in Donor vector for targeting PDS3) |
| 69 | Primary transcript of SWAP11 (used in Donor vector for targeting ADH1) |
| 70 | Primary transcript of SWAP12 (used in Donor vector for targeting ADH1) |
| 71 | Sequence of miR173 loci |
| 72 | Oligo sequence of SWAP1 (used in Donor vector for modification of miR173 for targeting GFP) |
| 73 | Oligo sequence of SWAP2 (used in Donor vector for modification of miR173 for targeting GFP) |
| 74 | Oligo sequence of SWAP3 (used in Donor vector for modification of miR173 for targeting PDS3) |
| 75 | Oligo sequence of SWAP4 (used in Donor vector for modification of miR173 for targeting PDS3) |
| 76 | Oligo sequence of SWAP9 (used in Donor vector for modification of miR173 for targeting ADH1) |
| 77 | Oligo sequence of SWAP10 (used in Donor vector for modification of miR173 for targeting ADH1) |
| 78 | Oligo sequence of miR390 loci |
| 79 | Oligo sequence of SWAP5 (used in Donor vector for modification of miR390 for targeting GFP) |
| 80 | Oligo sequence of SWAP6 (used in Donor vector for modification of miR390 for targeting GFP) |
| 81 | Oligo sequence of SWAP7 (used in Donor vector for modification of miR390 for targeting PDS3) |
| 82 | Oligo sequence of SWAP8(used in Donor vector for modification of miR390 for targeting PDS3) |
| 83 | Oligo sequence of SWAP11 (used in Donor vector for modification of miR390 for targeting ADH1) |
| 84 | Oligo sequence of SWAP12 (used in Donor vector for modification of miR390 for targeting ADH1) |
| 85 | qRT for housekeeping gene- 18S expression (NC_037304)- Forward primer |
| 86 | qRT for housekeeping gene- 18S expression (NC_037304)- Reverse primer |
| 87 | qRT for analysis of PDS3 expression (AT4G14210)- Forward primer |
| 88 | qRT for analysis of PDS3 expression (AT4G14210)- Reverse primer |
| 89 | qRT for analysis of ADH1 expression (AT1G77120)- Forward primer |
| 90 | qRT for analysis of ADH1 expression (AT1G77120)- Reverse primer |
| 91 | Forward primer for internal amplification of miR390 and its modified versions |
| 92 | Reverse primer for internal amplification of miR390 and its modified versions |
| 93 | Forward primer for external amplification of miR390 and its modified versions- primary reaction |
| 94 | Reverse for external amplification of miR390 and its modified versions- primary reaction |
| 95 | Forward primer for external amplification of miR390 and its modified versions- nested reaction |
| 96 | Reverse for external amplification of miR390 and its modified versions- nested reaction |
| 97 | Forward primer for internal amplification of miR173 and its modified versions |
| 98 | Reverse primer for internal amplification of miR173 and its modified versions |
| 99 | Forward primer for external amplification of miR173 and its modified versions- primary reaction |
| 100 | Reverse for external amplification of miR173 and its modified versions- primary reaction |
| 101 | Forward primer for external amplification of miR173 and its modified versions- nested reaction |
| 102 | Reverse for external amplification of miR173 and its modified versions- nested reaction |

Protoplasts Isolation

Protoplasts were isolated by incubating plant material (e.g. leaves, calli, cell suspensions) in a digestion solution (I % cellulase, 0.5% macerozyme, 0.5% driselase, 0.4 M mannitol, 154 mM NaCl, 20 mM KCl, 20 mM MES pH 5.6, 10 mM CaCl2) for 4-24 hours at room temperature and gentle shaking. After digestion, remaining plant material was washed with W5 solution (154 mM NaCl, 125 mM CaCl2), 5 mM KCl, 2 mM MES pH5.6) and protoplasts suspension was filtered through a 40 μm strainer. After centrifugation at 80 g for 3 minutes at room temperature, protoplasts were resuspended in 2 ml W5 buffer and precipitated by gravity in ice. The final protoplast pellet was resuspended in 2 ml of MMg (0.4 M mannitol, 15 mM MgCl2, 4 mM MES pH 5.6) and protoplast concentration was determined using a hemocytometer. Protoplasts viability was estimated using Trypan Blue staining.

Polyethylene Glycol (PEG)-Mediated Plasmid Transfection

PEG-transfection of protoplasts was effected using a modified version of the strategy reported by Wang [Wang et al., *Scientia Horticulturae* (2015) 191: p. 82-89]. Protoplasts were resuspended to a density of 2-5×$10^6$ protoplasts/ml in MMg solution. 100-200 μl of protoplast suspension was added to a tube containing the plasmid. The plasmid:protoplast ratio greatly affects transformation efficiency therefore a range of plasmid concentrations in protoplast suspension, 5-300 μg/μl, were assayed. PEG solution (100-200 μl) was added to the mixture and incubated at 23° C. for various lengths of time ranging from 10-60 minutes. PEG4000 concentration was optimized, a range of 20-80% PEG4000 in 200-400 mM mannitol. 100-500 mM $CaCl_2$ solution was assayed. The protoplasts were then washed in W5 and centrifuged at 80 g for 3 minutes, prior resuspension in 1 ml W5 and incubated in the dark at 23° C. After incubation for 24-72 hours fluorescence was detected by microscopy.

FACS Sorting of Fluorescent Protein-Expressing Cells 24-72 hours after plasmid/RNA delivery, cells were collected and sorted for fluorescent protein expression using a flow cytometer in order to enrich for mCherry/Editing agent expressing cells as previously described [Chiang et al., *Sci Rep* (2016) 6: 24356]. This enrichment step allows bypassing antibiotic selection and collecting only cells transiently expressing the fluorescent protein, Cas9 and the sgRNA. These cells can be further tested for editing of the target gene by HR yielding to successful swapping events and loss of the corresponding gene expression.

Bombardment and Plant Regeneration

*Arabidopsis* Root Preparation:

Chlorine gas sterilized *Arabidopsis* (cv. Col-0) seeds were shown on MS minus sucrose plates and vernalised for three days in the dark at 4° C., followed by germination vertically at 25° C. in constant light. After two weeks, roots were excised into 1 cm root segments and placed on Callus Induction Media (CIM: ½ MS with B5 vitamins, 2% glucose, pH 5.7, 0.8% agar, 2 mg/l IAA, 0.5 mg/l 2,4-D, 0.05 mg/l kinetin) plates. Following six days incubation in the dark, at 25° C., the root segments were transferred onto filter paper discs and placed onto CIMM plates, (½ MS without vitamins, 2% glucose, 0.4 M mannitol, pH 5.7 and 0.8% agar) for 4-6 hours, in preparation for bombardment.

Bombardment

Plasmid constructs were introduced into the root tissue via the PDS-1000/He Particle Delivery (Bio-Rad; PDS-1000/He System #1652257), several preparative steps, outlined below, were required for this procedure to be carried out.

Gold Stock Preparation 40 mg of 0.6 μm gold (Bio-Rad; Cat: 1652262) was mixed with 1 ml of 100% ethanol, pulse centrifuged to pellet and the ethanol removed. This wash procedure was repeated another two times.

Once washed the pellet was resuspended in 1 ml of sterile distilled water and dispensed into 1.5 ml tubes of 50 μl aliquot working volumes.

Bead Preparation

In short, the following was performed:

A single tube was sufficient gold to bombard 2 plates of *Arabidopsis* roots, (2 shots per plate), therefore each tube was distributed between 4 (1,100 psi) Biolistic Rupture disks (Bio-Rad; Cat: 1652329).

Bombardments requiring multiple plates of the same sample, tubes were combined and volumes of DNA and CaCl2)/spermidine mixture adjusted accordingly, in order to maintain sample consistency and minimize overall preparations.

The following protocol summarises the process of preparing one tube of gold, these should be adjusted according to number of tubes of gold used.

All subsequent processes were carried out at 4° C. in an Eppendorf thermomixer.

Plasmid DNA samples were prepared, each tube comprising 11 μg of DNA added at a concentration of 1000 ng/μl 1) 493 μl ddH2O was added to 1 aliquot (7 μl) of spermidine (Sigma-Aldrich; S0266), giving to a final concentration of 0.1 M spermidine. 1250 μl 2.5M $CaCl_2$) was added to the spermidine mixture, vortexed and placed on ice.
2) A tube of pre-prepared gold was placed into the thermomixer, and rotated at a speed of 1400 rpm.
3) 11 μl of DNA was added to the tube, vortexed, and placed back into the rotating thermomixer.
4) To bind, DNA/gold particles, 70 μl of spermidine $CaCl_2$ mixture was added to each tube (in the thermomixer).
5) The tubes were vigorously vortexed for 15-30 seconds and placed on ice for about 70-80 seconds.
6) The mixture was centrifuged for 1 minute at 7000 rpm, the supernatant was removed and placed on ice.
7) 500 μl 100% ethanol was added to each tube and the pellet was resuspended by pipetting and vortexed.
8) The tubes were centrifuged at 7000 rpm for 1 minute.
9) The supernatant was removed and the pellet resuspended in 50 μl 100% ethanol, and stored on ice.

Macro Carrier Preparation

The following was performed in a laminar flow cabinet:

1) Macro carriers (Bio-Rad; 1652335), stopping screens (Bio-Rad; 1652336), and macro carrier disk holders were sterilized and dried.
2) Macro carriers were placed flatly into the macro carrier disk holders.
3) DNA coated gold mixture was vortexed and spread (5 pl) onto the center of each Biolistic Rupture disk.

Ethanol was allowed to evaporate.

PDS-1000 (Helium Particle Delivery System)

In short, the following was performed:

The regulator valve of the helium bottle was adjusted to at least 1300 psi incoming pressure. Vacuum was created by pressing vac/vent/hold switch and holding the fire switch for 3 seconds. This ensured helium was bled into the pipework.

1100 psi rupture disks were placed into isopropanol and mixed to remove static.

1) One rupture disk was placed into the disk retaining cap.
2) Microcarrier launch assembly was constructed (with a stopping screen and a gold containing microcarrier).
3) Petri dish *Arabidopsis* root callus was placed 6 cm below the launch assembly.
4) Vacuum pressure was set to 27 inches of Hg (mercury) and helium valve was opened (at approximately 1100 psi).
5) Vacuum was released; microcarrier launch assembly and the rupture disk retaining cap were removed.
6) Bombardment on the same tissue (i.e. each plate was bombarded 2 times).
7) Bombarded roots were subsequently placed on CIM plates, in the dark, at 25° C., for additional 24 hours.

Co-Bombardments

When bombarding GEiGS plasmids combinations, 5 μg (1000 ng/μl) of the sgRNA plasmid was mixed with 8.5 μg (1000 ng/μl) swap plasmid and 11 μl of this mixture was added to the sample. If bombarding with more GEiGS plasmids at the same time, the concentration ratio of sgRNA plasmids to swap plasmids used was 1:1.7 and 11 μg (1000 ng/μl) of this mixture was added to the sample. If co-bombarding with plasmids not associated with GEiGS swapping, equal ratios were mixed and 11 μg (1000 ng/μl) of the mixture was added to each sample.

Plant Regeneration

For shoot regeneration, modified protocol from Valvekens et al. [Valvekens, D. et al., *Proc Nal Acad Sci USA* (1988) 85(15): 5536-5540] was carried out. Bombarded roots were placed on Shoot Induction Media (SIM) plates, which included ½ MS with B5 vitamins, 2% glucose, pH 5.7, 0.8% agar, 5 mg/l 2 iP, 0.15 mg/I IAA. Plates were left in 16 hours light at 25° C.—8 hours dark at 23° C. cycles. After 10 days, plates were transferred to MS plates with 3% sucrose, 0.8% agar for a week, then transferred to fresh similar plates. Once plants regenerated, they were excised from the roots and placed on MS plates with 3% sucrose, 0.8% agar, until analysed.

Colony Formation and Plant Regeneration

The fluorescent protein positive cells were partly sampled and used for DNA extraction and genome editing (GE) testing and partly plated at high dilution in liquid medium to allow colony formation for 28-35 days. Colonies were picked, grown and split into two aliquots. One aliquot was used for DNA extraction and genome editing (GE) testing and CRISPR DNA-free testing (see below), while the others were kept in culture until their status was verified. Only the ones clearly showing to be GE and CRISPR DNA-free were selected forward. Colonies were grown in culture medium in for about 6-10 weeks. Protocolonies (or calli) were subcultured into regeneration media (e.g. half strength MS+B5 vitamins, 20 g/l sucrose). Regenerated plantlets were placed on solidified media (0.8% agar) at a low light intensity at 28° C. After 2 months, plantlets were transferred to soil to and placed in a glasshouse at 80-100% humidity.

Virus Inoculation and DNA Delivery to *Arabidopsis* Seedlings

Sap from *Arabidopsis* leaves infected with TuMV infectious clone p35S::TuMV-GFP (0.1 mg/ml) are used for mechanical inoculations.

Plant Propagation

Clones that were sequenced and predicted to have lost the expression of the target genes and found to be free of the CRISPR system DNA/RNA were propagated for generation in large quantities and in parallel were differentiated to generate seedlings from which functional assay is performed to test the desired trait.

Phenotypic Analysis

As described above, such as by looking at the pigmentation, florescence or morphology dependent on the target gene.

Allyl Alcohol Selection

For selection of plants with allyl alcohol, 10 days post bombardment, roots were placed on SIM media. Roots were immersed in 30 mM allyl alcohol (Sigma-Aldrich, US) for 2 hours. Then the roots were washed three times with MS media, and placed on MS plates with 3% sucrose, 0.8% agar. Regeneration process was carried on as previously described.

Genotyping

Tissue samples were treated and amplicons amplified in accordance to the manufacturers recommendations. MyTaq Plant-PCR Kit (BioLine BIO 25056) for short internal amplification and Phire Plant Direct PCR Kit (Thermo Scientific; F-130WH) for longer external amplifications. Oligos used for these amplifications are specified in Table 2, above. Different modifications in the miRNA loci were identified through different digestion patterns of the amplicons, as follows:

For modifications of miR-390—internal amplicon was 978 base pairs long, and for external amplification it was 2629 base pairs. For the identification of swap 7, digestion with NlaIII resulted in a fragment size of 636 base pairs, while in the wt version it was cleaved to 420 and 216 long fragments. For the identification of swap 8, digestion with Hpy188I resulted in fragments size of 293 and 339 base pairs, while in the wt version this site was absent and resulted in a 632-long fragment. For the identification of swaps 11 and 12, digestion with BccI resulted in a fragment size of 662 base pairs, while in the wt version it was cleaved to 147 and 417 long fragments.

For modifications of miR-173—internal amplicon was 574 base pairs long, and for nested external amplification it was 466 base pairs. For the identification of swap 3, digestion with BslI resulted in fragments size of 217 and 249 base pairs in the external amplicon and 317 and 149 in the internal one. In the wt version this site was absent and resulted in a 466-long fragment in the external to amplicon and 574 in the internal reaction. For the identification of swap 4, digestion with BtsαI resulted in fragments size of 212 and 254 base pairs in the external amplicon and 212 and 362 in the internal one. In the wt version, this site was absent and resulted in a 466-long fragment in the external amplicon and 574 in the internal reaction. For the identification of swap 9, digestion with NlaIII resulted in fragments size of 317 and 149 base pairs in the external amplicon and 317 and 244 in the internal one. In the wt version, this site was absent and resulted in a 466-long fragment in the external amplicon and 561 in the internal reaction. For the identification of swap 10, digestion with NlaIII resulted in fragments size of 375 and 91 base pairs in the external amplicon and 375 and 186 in the internal one. In the wt version, this site was absent and resulted in a 466-long fragment in the external amplicon and 561 in the internal reaction.

DNA and RNA Isolation

Samples were harvested into liquid nitrogen and stored in −80° C. until processed. Grinding of tissue was carried out in tubes placed in dry ice, using plastic Tissue Grinder Pestles (Axygen. US). Isolation of DNA and total RNA from ground tissue was carried out using RNA/DNA Purification kit (cat. 48700; Norgen Biotek Corp., Canada), according to manufacturer's instructions. In the case of low 260/230 ratio (<1.6), of the RNA fraction, isolated RNA was precipitated overnight in −20° C., with 1 μl glycogen (cat. 10814010; Invitrogen, US) 10% V/V sodium acetate, 3 M pH 5.5 (cat. AM9740, Invitrogen, US) and 3 times the volume of ethanol. The solution was centrifuged for 30 minutes in maximum speed, at 4° C. This was followed by two washes with 70% ethanol, airdrying for 15 minutes and resuspending in Nuclease-free water (cat. 10977035; Invitrogen, US).

Reverse Transcription (RT) and Quantitative Real-Time PCR (qRT-PCR)

One microgram of isolated total RNA was treated with DNase I according to manufacturer's manual (AMPD1; Sigma-Aldrich. US). The sample was reverse transcribed, following the instructor's manual of High-Capacity cDNA Reverse Transcription Kit (cat 4368814; Applied Biosystems, US).

For gene expression, Quantitative Real Time PCR (qRT-PCR) analysis was carried out on CFX96 Touch™ Real-Time PCR Detection System (BioRad, US) and SYBR® Green JumpStart™ Taq ReadyMix™ (S4438, Sigma-Aldrich, US), according to manufacturer's' protocols, and analysed with Bio-RadCFX manager program (version 3.1). For the analysis of AtADH1 (AT1G77120) the following primer set was used: Forward GTTGAGAGTGTTG-GAGAAGGAG SEQ ID NO: 367 and reverse CTCGGTGTTGATCCTGAGAAG SEQ ID NO: 368; For the analysis of APDS3 (AT4G14210), the following primer set was used: Forward GTACTGCTGGTCCTTTGCAG SEQ to ID NO: 369 and reverse AGGAGCACTACG-GAAGGATG SEQ ID NO: 370; For endogenous calibration gene, the 18S ribosomal RNA gene (NC_037304) was used—Forward ACACCCTGGGAATTGGTTT SEQ ID NO: 371 and reverse GTATGCGCCAATAAGACCAC SEQ ID NO: 372.

Example 1A

Genome Editing Induced Gene Silencing (GEiGS)

In order to design GEiGS oligos, template non-coding RNA molecules (precursors) that are processed and give raise to derivate small silencing RNA molecules (matures) are required. Two sources of precursors and their corresponding mature sequences were used for generating GEiGS oligos. For miRNAs, sequences were obtained from the miRBase database [Kozomara, A. and Griffiths-Jones, S., *Nucleic Acids Res* (2014) 42: D68, ÄìD73], tasiRNA precursors and matures were obtained from the tasiRNAdb database [Zhang, C. et al, *Bioinformatics* (2014) 30: 1045, Äì1046].

Silencing targets were chosen in a variety of host organisms (see Table 1B, above), siRNAs were designed against these targets using the siRNArules software [Holen, T., *RNA* (2006) 12: 1620, Äì1625.]. Each of these siRNA molecules was used to replace the mature sequences present in each precursor, generating “naive” GEiGS oligos. The structure of these naive sequences was adjusted to approach the structure of the wild type precursor as much as possible using the ViennaRNA Package v2.6 [Lorenz, R. et al., ViennaRNA Package 2.0. Algorithms for Molecular Biology (2011) 6: 26]. After the structure adjustment, the number of sequences and secondary structure changes between the wild type and the modified oligo were calculated. These calculations are essential to identify potentially functional GEiGS oligos that require minimal sequence changes with respect to the wild type.

CRISPR/cas9 small guide RNAs (sgRNAs) against the wild type precursors were generated using the CasOT software [Xiao, A. et al., *Bioinformatics* (2014) 30: 1180, Äì182] (see Table 1B, above), sgRNAs were selected where the modifications applied to generate the GEiGS oligo affect the PAM region of the sgRNA, rendering it ineffective against the modified oligo.

Example 1B

Gene Silencing of Endogenous Plant Gene—PDS

In order to establish a high-throughput screening for quantitative evaluation of endogenous gene silencing using Genome Editing Induced Gene Silencing (GEiGS), the present inventors considered several potential visual markers. The present inventors chose to focus on genes involved in pigment accumulation, such as those encoding for phytoene desaturase (PDS). Silencing of PDS to causes photobleaching (FIG. 2B) which allows to use it as robust seedling screening after gene editing as proof-of-concept (POC). FIGS. 2A-C show a representative experiment with *N. benthamiana* and *Arabidopsis* plants silenced for PDS. Plants show the characteristic photobleaching phenotype observed in plants with diminished amounts of carotenoids.

In the POC experiment, choosing siRNAs was carried out as follows:

In order to initiate the RNAi machinery in *Arabidopsis* or *Nicotiana benthamiana* against the PDS gene using GEiGS application, there is a need to identify effective 21-24 bp siRNA targeting PDS. Two approaches are used in order to find active siRNA sequences: 1) screening the literature—since PDS silencing is a well-known assay in many plants, the present inventors are identifying well characterized short siRNA sequences in different plants that might be 100% match to the gene in *Arabidopsis* or *Nicotiana benthamiana*. 2) There are many public algorithms that are being used to predict which siRNA will be effective in initiating gene silencing to a given gene. Since the predictions of these algorithms are not 100%, the present inventors are using only sequences that are the outcome of at least two different algorithms.

In order to use siRNA sequences that silence the PDS gene, the present inventors are swapping them with a known endogenous non-coding RNA gene sequence using the CRISPR/Cas9 system (e.g. changing a miRNA sequence, changing a long dsRNA sequence, creating antisense RNA, changing tRNA etc.). There are many databases of characterized non-coding RNAs e.g. miRNAs; the present inventors are choosing several known *Arabidopsis* or *Nicotiana benthamiana* endogenous non-coding RNAs e.g. miRNAs with different expression profiles (e.g. low constitutive expression, highly expressed, induced in stress etc.). For example, in order to swap the endogenous miRNA sequence with siRNA targeting PDS gene, the present inventors are using the HR approach (Homologous Recombination). Using HR, two options are contemplated: using a donor ssDNA oligo sequence of around 250-500 nt which includes, for example, the modified miRNA sequence in the middle or using plasmids carrying 1 Kb-4 Kb insert which is almost 100% identical to the miRNA surrounding in the plant genome except the 2×21 bp of the miRNA and the *miRNA that is changed to the siRNA of the PDS (500-2000 bp up and downstream the siRNA, as illustrated in FIG. 1). The transfection includes the following constructs: CRISPR: Cas9/GFP sensor to track and enrich for positive transformed cells, gRNAs that guides the Cas9 to produce a double stranded break (DSB) which is repaired by HR depending on the insertion vector/oligo. The insertion vector/oligo contains two continuous regions of homology surrounding the targeted locus that are replaced (i.e. miRNA) and is modified to carry the mutation of interest (i.e. siRNA). If plasmid is used, the targeting construct comprises or is free from restriction enzymes-recognition sites and is used as a template for homologous recombination ending with the replacement of the miRNA with the siRNA of choice. After transfection to protoplasts, FACS is used to enrich for Cas9/sgRNA-transfected events, protoplasts are regenerated to plants and bleached seedlings are screened and scored (see FIG. 1). As control, protoplasts are transfected with an oligo carrying a random non-PDS targeting sequence. The positive edited plants are expected to produce siRNA sequences targeting PDS and therefore PDS gene is silenced and seedling are seen as white compared to the control with no gRNA. It is important to note that after the swap, the edited miRNA will still be processed as miRNA because the original base-pairing profile is kept. However, the newly edited processed miRNA has a high complementary to the target (e.g. 100%), and therefore, in practice, the newly edited small RNA will act as siRNA.

Example 2

Gene Silencing of “Endogenous” Transgene—GFP

Another quick and robust approach to check the efficiency of GEiGS is by silencing a transgene which is also a marker gene like GFP (green fluorescent protein). There are few easy options to assess the effectiveness of the GFP silencing in the cell, e.g. FACS analysis, PCR and microscopy. In order to show POC of GFP silencing using GEiGS, the present inventors are using a transgenic *Arabidopsis* or tobacco lines stably expressing GFP. Protoplasts from GFP expressing plants are used with GEiGS methodology to modify endogenous non-coding RNA e.g. miRNA to act as siRNA potent to initiate the RNA silencing mechanism targeting the GFP gene. The positive edited plants are expected to be silenced for GFP expression as illustrated in FIGS. 3A-D. Furthermore, GFP silencing in plants is well characterized and there are many available short RNA sequences (siRNA) that can be utilized to initiate GFP silencing. Therefore, for gene swapping, the present inventors are using publically available tools to generate siRNA specific to GFP or are using known siRNA molecules available from the literature.

In order to use siRNA sequences that will silence the GFP gene, the present inventors are swapping them with a known endogenous non-coding RNA e.g. miRNA gene sequence using the CRISPR/Cas9 system (e.g. changing a miRNA sequence, changing a long dsRNA sequence, creating antisense RNA, changing tRNA etc.). There are many databases of characterized non-coding RNAs e.g. miRNAs, the present inventors are choosing several known *Arabidopsis* or *Nicotiana benthamiana* non-coding RNAs e.g. miRNAs with different expression profiles (e.g. low constitutive expression, highly expressed, induced in stress etc.). For example, in order to swap the endogenous miRNA sequence with siRNA, the present inventors are using the HR approach. In HR two options are contemplated: using a donor oligo sequence of around 250-500 bp which includes, for example, to the siRNA sequence in the middle or using plasmids expressing 1 Kb-4 Kb insert which is almost 100% identical to the miRNA surrounding in the plant genome except the 2×21 bp of the miRNA and the *miRNA that are changed to the siRNA of the GFP (500-2000 bp up and downstream the siRNA, see FIG. 1). The transfection includes the following constructs: CRISPR:Cas9/RFP sensor to track and enrich for positive transformed cells using e.g. FACS analysis, gRNAs that guides the Cas9 to produce a DSB which is repaired by HR depending on the insertion vector/oligo. The insertion vector contains two continuous regions of homology surrounding the targeted locus that are replaced (i.e. miRNA) and is modified to carry the mutation of interest (i.e. siRNA). The targeting construct comprises or is free from restriction enzymes-recognition sites and is used as a template for homologous recombination ending with the replacement of the miRNA with the siRNA of choice. After transfection to protoplasts, FACS is used to enrich for positive transfected events (using the red fluorescent protein (RFP) marker), enriched protoplasts are scored for GFP silencing under a microscope (FIG. 4). The positive edited protoplasts are expected to produce siRNA sequences targeting GFP and therefore GFP expression of the transgene is expected to be silenced as compared to control protoplasts. GFP is a faster method than PDS since the two last steps of recovery and regeneration are not necessary, the scoring can be done on the protoplasts/cells level.

Example 3

Gene Silencing of Exogenous Transgene—GFP in *Arabidopsis*

In addition to the former example of GFP silencing, another way to demonstrate the efficiency of GEiGS is by silencing a marker gene like GFP (green fluorescent protein) in a transient GFP transformation assay. In this example, first plant cells (e.g. *Arabidopsis*) are treated using GEiGS to express small siRNA molecules targeting GFP (method for utilizing siGFP are discussed in Example 2 above). Control protoplasts (e.g. GEiGS-PDS) and edited protoplasts using GEiGS (expressing siGFP) are then transfected with a plasmid expressing separately two markers (sensor) GFP+RFP. Protoplast which express only RFP but not GFP in the GEiGS treatment are the results of GFP silencing due to siGFP expression (as illustrated in FIG. 5).

Example 4

Immunized Plants to Virus Infection, Silencing of Exogenous Virus Gene (Using GFP as Marker)

In order to prove that GEiGS is a robust method for plant immunization with the ability to knock down exogenous genes, the present inventors are providing an example of silencing of a virus gene. There are various viruses that infect different plant species and that can be used in the present to POC: TuMV, CMV, TMV etc.

Turnip mosaic virus (TuMV) is transmitted non-persistently by aphids and causes prevalent diseases of cruciferous crops in many parts of the world. TuMV genome, which is single-stranded, is a positive-sense RNA molecule of approximately 10,000 nt (accession number NC_002509). TuMV has the same typical potyvirus genetic organization previously discussed by Urcuqui-Inchima et al. [Urcuqui-Inchima et al., *Virus Res.* (2001) 74: 157-175]. The symptoms of TuMV are mottling in broad, yellow, circular, and irregular areas. The oldest leaves often become bright yellow all over. The lamina often becomes necrotic. Extensive use was made of TuMV-GFP and suppressor-deficient TuMV-AS9-GFP to expose antiviral silencing activities in *Arabidopsis*. Wild-type plants were immune to TuMV-AS9-GFP, but immunity was effectively suppressed by loss of DCL2 and DCL4, indicating that TuMV normally masks the effects of a siRNA dependent antiviral response [Hernan Garcia-Ruiz et al., *The Plant Cell* (2010) 22: 481-496].

Cucumber mosaic virus (CMV) is a plant pathogenic virus in the family Bromoviridae. It is the type member of the plant virus genus, Cucumovirus. This virus has a worldwide distribution and a very wide host range. In fact it has the reputation of having the widest host range of any known plant virus. It can be transmitted from plant to plant both mechanically by sap and by aphids in a stylet-borne fashion. This virus was first found in cucumbers (*Cucumis sativus*) showing mosaic symptoms in 1934, hence the name Cucumber mosaic. An expression CMV-based expression vector that utilizes the mutant 3a MP for CP-independent cell-to-cell movement was developed. This new vector [Fujiki et al., *Virology* (2008) 381(1): 136-142] was incorporated into an *agrobacterium* binary vector and delivered into plants via agroinfiltration. The results demonstrate that this novel CMV-based expression vector holds great promise for recombinant protein production.

Tobacco mosaic virus (TMV), a single-stranded RNA virus that commonly infects solanaceous plants, a plant family that includes many species such as petunias, tomatoes and tobacco. The virus causes a mosaic pattern of brown spots on the surface of leaves. The virus doesn't usually cause the plant to die, but can seriously stunt its growth. Lower leaves can suffer from 'mosaic burn' in hot and dry weather, where large areas of the leaf die. This virus cannot get into plants on its own. Plants are usually infected via plant wounds after human handling or via contaminated equipment. Once inside the plant, the virus releases its genetic code (RNA). The plant gets confused by this code, mistaking it for its own, and starts to produce virus proteins. Virus-based expression systems in plants are particularly attractive versus alternative transient expression systems due to the high level of gene multiplication and concomitant elevated levels of expression achievable within a short period of time while minimizing impairment of host activities. TMV is one of the most extensively studied plant viruses and has thus become a natural choice for vector development. TMV-based vectors have led to recombinant protein yield as high as 80% of total soluble protein. Agroinfection is inexpensive and reproducible, making it a preferred method of delivering viral expression vectors into plant tissues as part of the T-DNA of a binary vector carried by *Agrobacterium tumefaciens.*

The present inventors are using TuMV-GFP for infection of *Arabidopsis* or TMV-GFP for tobacco plants. In order to create plants resistant to virus infection, the present inventors are using an engineered virus that expresses GFP upon plant infection. Using such a virus will enable to use the same constructs as described in Example 3, above. The difference being that now the GFP is expressed from the virus infection. Control plants that are infected with virus-GFP (CMV or TMV) show expression of GFP under the microscope (FIG. 6) however, GEiGS plants engineered to express siRNA GFP are expected to show reduced levels of GFP (FIG. 6). Accordingly, generating GEiGS plants with no GFP expression after infection with Virus-GFP will demonstrate that RNAi silencing of exogenous gene was achieved and that GEiGS is an effective method to immune plants against viruses and potentially other pathogens. There are few easy options to assess the effectiveness of the GFP silencing in the cell, such as the use FACS analysis, PCR and microscopy. GFP silencing in plants is well characterized and there are many available short RNA sequences (siRNA) that are active in initiating GFP silencing. Therefore, for gene swapping, the present inventors are using a few known siRNA molecules available from the literature.

In order to use siRNA sequences that will silence the GFP gene, the present inventors are swapping them with a known endogenous non-coding RNA e.g. miRNA gene sequence using the CRISPR/Cas9 system (as discussed above, there are many other options to introduce these siRNA sequences, like changing long dsRNA sequences, creating antisense RNA, changing tRNA etc.). There are many databases of characterized endogenous non-coding RNA e.g. miRNAs, the present inventors are choosing several known *Arabidopsis* or *Nicotiana benthamiana* non-coding RNA e.g. miRNAs with different expression profiles (e.g. low constitutive expression, highly expressed, induced in stress etc.). For example, in order to swap the endogenous miRNA sequence with siRNA, the present inventors are using the HR approach. In HR two options are contemplated: using a donor oligo sequence of around 250-500 bp which includes, for example, the siRNA sequence in the middle or using plasmids expressing 1 Kb-4 Kb insert which is almost 100% identical to the miRNA surrounding in the plant genome except the 2×21 bp of the miRNA and the *miRNA that are changed to the siRNA of the GFP (500-2000 bp up and downstream the siRNA, see FIG. 1). The transfection includes the following constructs: CRISPR:Cas9/RFP sensor to track and enrich for positive transformed cells using e.g. FACS analysis, gRNAs that guides the Cas9 to produce a DSB which is repaired by HR depending on the insertion vector/oligo. The insertion vector contains two continuous regions of homology surrounding the targeted locus that are replaced (i.e. miRNA) and is modified to carry the mutation of interest (i.e. siRNA). The targeting construct comprises or is free from restriction enzymes-recognition sites and is used as a template for homologous recombination ending with the replacement of the miRNA with the siRNA of choice. After transfection to protoplasts, FACS is used to enrich for positive transfected events, protoplasts are regenerated to plants and plants are infected with the virus by mechanical inoculations. Plants are scored for GFP silencing under microscope (as described in FIG. 6). The positive edited protoplasts with GEiGS are expected to produce siRNA sequences targeting GFP and therefore the virus GFP gene expression is expected to be silenced compared to control unedited plants.

Example 5

Banana Plant Resistant to Nematode

The damage to banana productivity due to nematodes is tremendous, reaching up to 50% of yield loss in untreated soils. The problem is accentuated in traditional banana plantations where mono cropping is a common practice. Banning of nematicides like methyl bromide in various parts of the world exacerbated the problem and leaves farmers with inappropriate and unreliable alternatives. *Radopholus similis*, the burrowing nematode, is the most economically important nematode parasite of banana in the world. Infection by burrowing nematode causes toppling disease of banana, yellows disease of pepper and spreading decline of *Citrus*. These diseases are the result of burrowing nematode infection destroying root tissue, leaving plants with little to no support or ability to take up water and translocate nutrients. Because of the damage that it causes to *Citrus*, ornamentals and other agricultural industries, worldwide, burrowing nematode is one of the most regulated nematode plant pests (FIG. 7).

RNA interference (RNAi) has emerged as an invaluable gene-silencing tool for functional analysis in a wide variety of organisms, particularly the free-living model nematode *Caenorhabditis elegans*. An increasing number of studies have described its application to plant parasitic nematodes. Genes expressed in a range of cell types are silenced when nematodes take up double stranded RNA (dsRNA) or short interfering RNAs (siRNAs) that elicit a systemic RNAi response. Extensive siRNA studies with *C. elegans* suggest that successfully preventing nematodes from completing their life cycle is attributed to silencing genes that are expressed early in embryonic development. In *R. similis* such candidate genes might be Calreticulin13 (CRT) or the gene collagen 5 (col-5). CRT is a Ca2'-binding multifunctional protein that plays key roles in the parasitism, immune evasion, reproduction and pathogenesis of many animal parasites and plant nematodes. Therefore, CRT is a promising target for controlling *R. similis*. Col-5 belongs to the collagen genes of nematodes encode proteins that have a diverse range of functions. Among their most abundant products are the cuticular collagens, which include about 80% of the proteins present in the nematode cuticle. The structures of these collagens have been found to be strikingly similar in the free-living and parasitic nematode species studied so far, and the genes that encode them appear to constitute a large multigene family whose expression is subject to developmental regulation.

By utilizing GEiGS, the present inventors are creating banana plants expressing siRNA molecules that are transmitted from their roots to nematodes upon feeding, and subsequently induce the silencing of nematode genes. The silencing of genes essential for succession in the life cycle inhibits nematode propagation and abolishes damages caused by nematodes. The present inventors are changing a few banana endogenous non-coding RNA e.g. miRNA sequences with short sequences from the CRT or the col-5 genes. GEiGS is used in Banana protoplasts that are regenerated to plantlets and are then screened with different nematodes for resistance.

Example 6

Banana Plant Resistant to *Fusarium oxysporum*

The genus *Fusarium* includes several species of fungi that are broadly spread in soil and organic substrates worldwide. *Fusarium oxysporum* is one of the most relevant species of this genus and is the causal agent of root rots, damping-off and wilt diseases in more than 100 plants species, including a wide range of economically important horticultural crops, flowers, trees, and a number of field crops such as cabbage, banana, and cotton. *Fusarium oxysporum* is a devastating pathogen causing extensive yield losses in a variety of crops and development of sustainable, environmentally friendly methods to improve crop resistance is crucial. *F. oxysporum* consists of over 120 forma specialis of pathogenic strains determined by their primary host plants. All strains of *F. oxysporum* are saprophytic, being able to grow and survive for long periods on organic matter in soil making it very difficult to control. Its pathogenic life cycle starts with spore germination upon recognition of a suitable host. Once the hyphae is formed, the pathogen enters its host by directly penetrating the roots and colonizes it within the xylem by producing microconidia which leads to mycelium formation. Colonization and toxin production by the pathogen results in blockage of the host vascular system, causing characteristic disease symptoms including vasculature yellowing, vein clearing, chlorosis, and necrosis in leaf veins and leaves, leaf detachment and wilting. After the plant dies, the fungus sporulates on the decayed leaf surfaces. *F. oxysporum* is most prevalent in tropical and subtropical regions and it is expected that its geographical range will extend due to climate change. Current control methods for *Fusarium* wilt are very limited with crop rotations being ineffective due to the large host range and its persistence in soil. Management of *Fusarium* wilt is mainly done through cultural practices and farm hygiene which only reduce the transmission of inoculum while soil sterilization can only be performed in glasshouses. Soil fumigation using broad-spectrum biocides such as methyl bromide is expensive and has many hazardous effects on the environment.

Hu z, have used Host-Delivered RNA interference technology to partially silence three different genes (FOW2, FRP1, and OPR) in the hemi-biotrophic fungus *F. oxysporum* f. sp. *conglutinans* [Hu et al., *Front Chem.* (2015) 20 (3):1]. Expression of double stranded RNA (dsRNA) molecules targeting fungal pathogen genes was achieved in a number of transgenic *Arabidopsis* lines. *F. oxysporum* infecting the transgenic lines displayed substantially reduced mRNA levels on all three targeted genes, with an average of 75, 83, and 72% reduction for FOW2, FRP1, and OPR, respectively. The silencing of pathogen genes had a clear positive effect on the ability of the transgenic lines to fight infection. All transgenic lines displayed enhanced resistance to *F. oxysporum* with delayed disease symptom development, especially FRP1 and OPR lines. Survival rates after fungal infection were higher in the transgenic lines compared to control wild type plants which consistently showed survival rates of 10%, with FOW2 lines showing 25% survival; FRP1 lines 30-50% survival and OPR between 45 and 70% survival. The down-regulation effect was specific for the targeted genes without unintended effects in related genes (Hu Z. (2015) supra). It was shown that in fungi, both long and short dsRNAs are equally internalized and induce RNAi to silence target genes.

The present inventors are utilizing GEiGS in order to create Banana plants resistant to *F. oxysporum* by changing few endogenous non-coding RNA e.g. miRNAs sequences to specifically target the fungi genes like FOW2. FRP1 and OPR. Edited Protoplasts are regenerated to plantlets and are challenged with *F. oxysporum* in a controlled environment, resistant plants are verified to express the relevant siRNA.

Example 7

Coffee Tree Resistant to Nematode

*Coffea* is a genus of flowering plants whose seeds, called coffee beans, are used to make various coffee beverages and products. It is a member of the family Rubiaceae. They are shrubs or small trees native to tropical and southern Africa and tropical Asia. Coffee ranks as one of the world's most valuable and widely traded commodity crops and is an important export product of several countries, including those in Central and South America, the Caribbean and Africa. A steady decline in coffee production has been attributed to biotic and socio-economic constraints. Among the less studied biotic constraints are nematodes.

Plant-parasitic nematodes are regarded as a severe constraint to coffee production in the world and especially in Vietnam (FIG. 8). The dominant and most important species are *Radopholus arabocofeae* and *Pratylenchus coffeae*. Both species are responsible for the death of plants younger than 5 years old. Traditionally, the main method to control *P. coffeae* is by chemical means there is no particular control strategy against *R. arabocoffeae.*

The present inventors are utilizing GEiGS strategy (as described in Example 5 above) to create *Coffea canephora* (*Robusta*) trees expressing siRNA molecules that are transmitted from their roots to nematodes upon feeding, and subsequently inducing the silencing of nematode genes. The silencing of genes essential for succession in the life cycle inhibits nematode propagation and abolishes damages caused by nematodes. The present inventors are thus changing a few endogenous non-coding RNA e.g. miRNA sequences with short sequences from the nematode genes. GEiGS is used in coffee protoplasts that are regenerated to plantlets and then screened with different nematodes for resistance.

Example 8

Generation of Plants with Modified Endogenous miRNA to Target Different Genes

Minimal modifications in the genomic loci of a miRNA, in its recognition sequence (which will mature to a miRNA) can lead to a new system to regulate new genes, in a non-transgenic manner. Therefore, an *agrobacterium*-free transient expression method was used, to introduce these modifications by bombardment of *Arabidopsis* roots, and their regeneration for further analysis. The present inventors had chosen to target two genes, PDS3 and ADH1 in *Arabidopsis* plants.

Carotenoids play an important role in many physiological processes in plants and the phytoene desaturase gene (PDS3) encodes one of the important enzymes in the carotenoid biosynthesis pathway, its silencing produces an albino/bleached phenotype. Accordingly, plants with reduced expression of PDS3 exhibit reduced chlorophyll levels, up to complete albino and dwarfism.

Alcohol dehydrogenase (ADH1) comprises a group of dehydrogenase enzymes which catalyse the interconversion between alcohols and aldehydes or ketones with the concomitant reduction of NAD+ or NADP+. The principal metabolic purpose for this enzyme is the breakdown of alcoholic toxic substances within tissues. Plants harbouring reduced ADH1 expression exhibit increase tolerance to allyl alcohol. Accordingly, plants with reduced ADH1 are resistant to the toxic effect of allyl alcohol, therefore their regeneration was carried out with allyl alcohol selection.

Two well-established miRNAs were chosen to be modified, miR-173 and miR-390, that were previously shown to be expressed throughout plant development [Zielezinski A et al., *BMC Plant Biology* (2015) 15: 144]. To introduce the modification, a 2-component system was used. First, the CRISPR/CAS9 system was used, to generate a cleavage in the miR-173 and miR-390 loci, through designed specific guide RNAs (FIGS. 12A and 13A; and Table 2, above), to promote homologous DNA repair (HDR) in the site. Second, A DONOR sequence, with the desired modification of the miRNA sequence, to target the newly assigned genes, was introduced as a template for the HDR (FIGS. 12A-G, 13A-G, 14A-D and 15A-D; Table 2, above). In addition, since the secondary structure of the primary transcript of the miRNA (pri-miRNA) is important for the correct biogenesis and activity of the mature miRNA, further modifications were introduced in the complementary strand in the pri-miRNA and analysed in mFOLD (www(dot)unafold(dot)rna (dot)Albany(dot)edu) for structure conservation (FIGS. 12A-G and 13A-G). In total, two guides were designed for each miRNA loci, and two different DONOR sequences (modified miRNA sequences) were designed for each gene (FIGS. 14A-D and 15A-D, and Table 2, above).

Example 9

Bombardment and Plant Regeneration

GEiGS constructs were bombarded into pre-prepared roots (as discussed in detail in the materials and experimental procedures section, above) and regenerated. Plantlets were selected via bleached phenotype for PDS3 transformants and survival on allyl alcohol treatment for ADH1 transformants. In order to validate Swap compared to no Swap, i.e. retained wild type, these plants were subsequently screened for insertion through specific primers spanning the modified region followed by restriction digest (FIG. 16).

Example 10

Genotype Validation of Phenotype Selection

As discussed above, the Proof of Concept (POC) for the gene editing system was established using well known phenotypic traits, Phytoene desaturase (PDS3) and Alcohol desaturase (ADH1) as targets.

As mentioned above, plants harbouring reduced ADH1 expression exhibit increase tolerance to allyl alcohol. Therefore, bombarded plants for modified miRNA to target ADH1 were regenerated in media containing 30 mM allyl alcohol and compared to the regeneration rate of control plants. 118 GEiGS #3+SWAP11 allyl alcohol selected plants survived, compared to 51 control plants on allyl alcohol media (data not shown). Of the selected GEiGS #3+SWAP11, 5 were shown to harbour the DONOR (data not shown). The large amount of plants regenerating in the DONOR-treated plants, might be due to transient expression, during the bombardment process, as well.

Thus, PDS3 and ADH1 selection through bleached phenotype (FIG. 16) and allyl alcohol selection (FIG. 17), respectively, give an ideal means for transformed plantlet selection for genotyping.

Swap region of 4 kb was assessed primarily through internal primers and specific amplicon differentiation of original wild type to insertion via restriction enzyme digestion variation.

ADH1 (FIG. 17) showed a comparative genotype of allyl alcohol selected plants with the expected DONOR presence restriction pattern when compared to restricted and non-restricted DONOR plasmid. PDS3 (FIG. 16) showed a comparison of bombarded samples phenotypes with and without DONOR and their respective differential restriction enzyme digestion patterns compared to that of restricted and non-restricted DONOR plasmid. These results provided a clear association of PDS3 albino/bleached phenotype to the expected restriction pattern. Subsequent external PCR combining specific internal, within the Swap region, in conjunction with external primer, outside and specific to the genomic region to swap into was carried out (data not shown). Further validation of the Swap was obtained through Sanger sequencing of the PCR amplicons, in order to assess heterozygous, homozygous, or presence of DONOR Swap (data not shown).

Example 11

Modified miRNA Reduce the Expression of their New Target Gene

In order to verify the potential of the modified miRNAs in the GEiGS system to down regulate the expression of their newly designated targets, gene expression analysis was carried out using qRT-PCR (quantitative Real-Time PCR). RNA was extracted and reverse transcribed, from the positively identified regenerated plants and compared to regenerated plants, treated in parallel, but were not introduced with the relevant modifying constructs. In the case, where miR-173 was modified to target PDS3 (GEiGS #4+SWAP4), a reduction of 83% in the gene expression level, on average, was observed (FIG. 18). In plants with modified miR-390 to target ADH1 (GEiGS #3+SWAP11), a similar change in gene expression was observed, 82% of the levels in the control plants (FIG. 19). Taken together, these results substantiate the gene editing methods of modifying endogenous miRNAs to successfully target new genes and reduce their expression, by replacing the target recognition sequence in the miRNA transcript in the endogenous locus.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of modifying a gene encoding or processed into a non-coding RNA molecule having no RNA silencing activity in a plant cell, the method comprising introducing into the plant cell a DNA editing agent conferring a silencing specificity of said non-coding RNA molecule towards a target RNA of interest, thereby modifying the gene encoding or processed into the non-coding RNA molecule.

2. The method of claim 1, wherein the gene encoding or processed into the non-coding RNA molecule is endogenous to the plant cell.

3. The method of claim 1, wherein said modifying said gene encoding or processed into said non-coding RNA molecule comprises imparting said non-coding RNA molecule with at least 45% complementarity towards said target RNA of interest.

4. The method of claim 1 wherein said silencing specificity of said non-coding RNA molecule is determined:
i) by measuring a RNA or protein level of said target RNA of interest;
ii) phenotypically, optionally wherein said determined phenotypically is effected by determination of at least one plant phenotype selected from the group consisting of plant a leaf coloring, a flower coloring, a growth rate, a plant size, a crop yield, a fruit trait, a biotic stress resistance, and an abiotic stress resistance; and/or
iii) genotypically, optionally wherein a plant phenotype is determined prior to a plant genotype or a plant genotype is determined prior to a plant phenotype.

5. The method of claim 1, wherein said non-coding RNA molecule is processed from a precursor.

6. The method of claim 5, wherein the modification results in said non-coding RNA molecule being a RNA interference (RNAi) molecule selected from the group consisting of a small interfering RNA (siRNA), a short hairpin RNA (shRNA), a microRNA (miRNA), a Piwi-interacting RNA (piRNA) and trans-acting siRNA (tasiRNA).

7. The method of claim 1, wherein said non-coding RNA molecule is selected from the group consisting of a small nuclear RNA (snRNA), a small nucleolar RNA (snoRNA), a long non-coding RNA (lncRNA), a ribosomal RNA (rRNA), transfer RNA (tRNA), a repeat-derived RNA, and a transposable element RNA.

8. The method of claim 6, wherein said RNAi molecule is designed such that a sequence of said RNAi molecule is modified to preserve originality of structure and to be recognized by cellular RNAi factors.

9. The method of claim 1, wherein said modifying said gene is effected by a modification selected from the group consisting of a deletion, an insertion, a point mutation, and a combination thereof, and/or wherein said modification:
i) is in a stem region of said non-coding RNA molecule;
ii) is in a loop region of said non-coding RNA molecule;
iii) is in a non-structured region of said non-coding RNA molecule;
iv) is in a stem region and a loop region of said non-coding RNA molecule;
v) is in a stem region, a loop region, and a non-structured region of said non-coding RNA molecule; and/or
iv) comprises a modification of at most 200 nucleotides.

10. The method of claim 9, wherein said method further comprises introducing into the plant cell donor oligonucleotides.

11. The method of claim 1, wherein said DNA editing agent comprises at least one gRNA operatively linked to a plant expressible promoter.

12. The method of claim 1, wherein said DNA editing agent does not comprise an endonuclease, or wherein said DNA editing agent comprises an endonuclease, and optionally wherein said endonuclease comprises Cas9.

13. The method of claim 1, wherein said DNA editing agent is of a DNA editing system selected from the group consisting of a meganuclease, a zinc finger nucleases (ZFN), a transcription-activator like effector nuclease (TALEN), and CRISPR, optionally wherein said DNA editing agent is applied to the cell as DNA, RNA or RNP.

14. The method of claim 1, wherein said DNA editing agent is linked to a reporter for monitoring expression in a plant cell, optionally wherein said reporter is a fluorescent protein.

15. The method of claim 1, wherein said target RNA of interest is endogenous to the plant cell, or wherein said target RNA of interest is exogenous to the plant cell.

16. A method of producing a plant with reduced expression of a target gene, the method comprising:
(a) breeding a plant comprising a plant cell generated according to the method of claim 1, optionally wherein said breeding comprises crossing or selfing; and
(b) selecting for progeny plants that have reduced expression of said target RNA of interest, or progeny that comprises a silencing specificity in said non-coding RNA molecule towards a target RNA of interest, and which do not comprise said DNA editing agent,
thereby producing said plant with reduced expression of a target gene.

17. A method of generating a plant with a phenotype selected from the group consisting of increased stress tolerance, increased yield, increased growth rate, increased yield quality, pathogen tolerance, pathogen resistance, pest tolerance, pest resistance, and herbicide resistance, the method comprising modifying a gene encoding or processed into a non-coding RNA molecule in a plant cell according to claim 1, wherein said target RNA of interest is of a gene selected from the group consisting of:
i) a gene of the of the plant conferring sensitivity to stress, decreased yield, decreased growth rate, decreased yield quality, sensitivity to said pathogen, sensitivity to said pest, or sensitivity to said herbicide;
ii) a gene of the pathogen; and
iii) a gene of the pest;
thereby generating the plant.

18. The method of claim 1, wherein following introducing into the plant cell the DNA editing agent, the plant cell is heterozygous for the modification.

19. The method of claim 1, wherein the DNA editing agent generates two or more double stranded DNA breaks in the gene encoding or processed into the non-coding RNA molecule.

* * * * *

SEQUENCE LISTING

```
Sequence total quantity: 417
SEQ ID NO: 1            moltype = DNA  length = 23
FEATURE                 Location/Qualifiers
source                  1..23
                        mol_type = unassigned DNA
                        organism = Arabidopsis thaliana
SEQUENCE: 1
ctatccatcc tgagtttcat tgg                                            23

SEQ ID NO: 2            moltype = DNA  length = 23
FEATURE                 Location/Qualifiers
source                  1..23
                        mol_type = unassigned DNA
                        organism = Arabidopsis thaliana
SEQUENCE: 2
aagaatctgt aaagctcagg agg                                            23

SEQ ID NO: 3            moltype = DNA  length = 23
FEATURE                 Location/Qualifiers
source                  1..23
                        mol_type = unassigned DNA
                        organism = Arabidopsis thaliana
SEQUENCE: 3
cttgcagaga gaaatcacag tgg                                            23

SEQ ID NO: 4            moltype = DNA  length = 23
FEATURE                 Location/Qualifiers
source                  1..23
                        mol_type = unassigned DNA
                        organism = Arabidopsis thaliana
SEQUENCE: 4
gcttacacag agaatcacag agg                                            23

SEQ ID NO: 5            moltype = DNA  length = 400
FEATURE                 Location/Qualifiers
misc_feature            1..400
                        note = Oligo-1: GEiGS_mir173_si-GFP_1
source                  1..400
                        mol_type = other DNA
                        organism = synthetic construct
SEQUENCE: 5
gcataaaaaa gtcaacaaaa cttaaagcgg cggtctcatc gtaatctcag cccaataccc  60
tattttcctc tcccctatat aaatactttc ttcttctact gatcttcttc tcacaaataa  120
acccaaatat atcaatctac tgtgttggtg attaagtact taagtcgtgc tgcttcatgt  180
ggagtggtca aaaaagttgt agttttctta aagtctcttt cctctccaca taagcaggac  240
gagttaagag cttgctccct aaacttatct ctctgatgat ttaatgttag agatcttcgt  300
aaatctatgt gtttgataga tctgatgcgt tttttgagtt gatgatttga ttatttttca  360
ctggaaagta tctcattagg gtaacgataa tgttttatgg                          400

SEQ ID NO: 6            moltype = DNA  length = 400
FEATURE                 Location/Qualifiers
misc_feature            1..400
                        note = Oligo-2: GEiGS_mir173_si-GFP_2
source                  1..400
                        mol_type = other DNA
                        organism = synthetic construct
SEQUENCE: 6
gcataaaaaa gtcaacaaaa cttaaagcgg cggtctcatc gtaatctcag cccaataccc  60
tattttcctc tcccctatat aaatactttc ttcttctact gatcttcttc tcacaaataa  120
acccaaatat atcaatctac tgtgttggtg attaagtact tagttgtact ccagcttgtg  180
ccagtggtca aaaaagttgt agttttctta aagtctcttt cctctggcaa agctgcagta  240
caactaagag cttgctccct aaacttatct ctctgatgat ttaatgttag agatcttcgt  300
aaatctatgt gtttgataga tctgatgcgt tttttgagtt gatgatttga ttatttttca  360
ctggaaagta tctcattagg gtaacgataa tgttttatgg                          400

SEQ ID NO: 7            moltype = DNA  length = 400
FEATURE                 Location/Qualifiers
misc_feature            1..400
                        note = Oligo-3: GEiGS_mir173_si-PDS_1
source                  1..400
                        mol_type = other DNA
                        organism = synthetic construct
SEQUENCE: 7
gcataaaaaa gtcaacaaaa cttaaagcgg cggtctcatc gtaatctcag cccaataccc  60
tattttcctc tcccctatat aaatactttc ttcttctact gatcttcttc tcacaaataa  120
```

-continued

```
acccaaatat atcaatctac tgtgttggtg attaagtact ttatccacac aaactacctg  180
caagtggtca aaaaagttgt agttttctta aagtctcttt cctcttgcag tagttagtgt  240
ggataaagag cttgctccct aaacttatct ctctgatgat ttaatgttag agatcttcgt  300
aaatctatgt gtttgataga tctgatgcgt tttttgagtt gatgatttga ttattttca   360
ctggaaagta tctcattagg gtaacgataa tgttttatgg                        400

SEQ ID NO: 8            moltype = DNA  length = 400
FEATURE                 Location/Qualifiers
misc_feature            1..400
                        note = Oligo-4: GEiGS_mir173_si-PDS_2
source                  1..400
                        mol_type = other DNA
                        organism = synthetic construct
SEQUENCE: 8
gcataaaaaa gtcaacaaaa cttaaagcgg cggtctcatc gtaatctcag cccaataccc  60
tattttcctc tcccctatat aaatactttc ttcttctact gatcttcttc tcacaaataa  120
acccaaatat atcaatctac tgtgttggtg attaagtact ttgacaatcc agccaatcca  180
gcagtggtca aaaaagttgt agttttctta aagtctcttt cctctgctga ttggcaggat  240
tgtcaaagag cttgctccct aaacttatct ctctgatgat ttaatgttag agatcttcgt  300
aaatctatgt gtttgataga tctgatgcgt tttttgagtt gatgatttga ttattttca   360
ctggaaagta tctcattagg gtaacgataa tgttttatgg                        400

SEQ ID NO: 9            moltype = DNA  length = 400
FEATURE                 Location/Qualifiers
misc_feature            1..400
                        note = Oligo-5: GEiGS_mir390a_si-GFP_1
source                  1..400
                        mol_type = other DNA
                        organism = synthetic construct
SEQUENCE: 9
agaggagatg acgtgtgttc cttcgaaccc gagttttgtt cgtctataaa tagcaccttc  60
tcttctcctt cttcctcact tccatctttt tagcttcact atctctctat aatcggtttt  120
atctttctct aagtcacaac ccaaaaaaac aaagtagaga agaatctgta aagtcgtgct  180
gcttcatgtg gatgatgatc acattcgtta tctatttttt ccacatgaag aagcacgact  240
tgattggctc ttcttactac aatgaaaaag gccgaggcaa aacgcctaaa atcacttgag  300
aatcaattct ttttactgtc catttaagct atcttttata aacgtgtctt attttctatc  360
tcttttgttt aaactaagaa actatagtat tttgtctaaa                        400

SEQ ID NO: 10           moltype = DNA  length = 400
FEATURE                 Location/Qualifiers
misc_feature            1..400
                        note = Oligo-6: GEiGS_mir390a_si-GFP_2
source                  1..400
                        mol_type = other DNA
                        organism = synthetic construct
SEQUENCE: 10
agaggagatg acgtgtgttc cttcgaaccc gagttttgtt cgtctataaa tagcaccttc  60
tcttctcctt cttcctcact tccatctttt tagcttcact atctctctat aatcggtttt  120
atctttctct aagtcacaac ccaaaaaaac aaagtagaga agaatctgta agttgtactc  180
cagcttgtgc catgatgatc acattcgtta tctatttttt ggcacaagct tgagtacaac  240
tgattggctc ttcttactac aatgaaaaag gccgaggcaa aacgcctaaa atcacttgag  300
aatcaattct ttttactgtc catttaagct atcttttata aacgtgtctt attttctatc  360
tcttttgttt aaactaagaa actatagtat tttgtctaaa                        400

SEQ ID NO: 11           moltype = DNA  length = 400
FEATURE                 Location/Qualifiers
misc_feature            1..400
                        note = Oligo-7: GEiGS_mir390a_si-PDS_1
source                  1..400
                        mol_type = other DNA
                        organism = synthetic construct
SEQUENCE: 11
agaggagatg acgtgtgttc cttcgaaccc gagttttgtt cgtctataaa tagcaccttc  60
tcttctcctt cttcctcact tccatctttt tagcttcact atctctctat aatcggtttt  120
atctttctct aagtcacaac ccaaaaaaac aaagtagaga agaatctgta tatccacaca  180
aactacctgc aatgatgatc acattcgtta tctatttttt tgcaggtagt gtgtgtggat  240
agattggctc ttcttactac aatgaaaaag gccgaggcaa aacgcctaaa atcacttgag  300
aatcaattct ttttactgtc catttaagct atcttttata aacgtgtctt attttctatc  360
tcttttgttt aaactaagaa actatagtat tttgtctaaa                        400

SEQ ID NO: 12           moltype = DNA  length = 400
FEATURE                 Location/Qualifiers
misc_feature            1..400
                        note = Oligo-8: GEiGS_mir390a_si-PDS_2
source                  1..400
                        mol_type = other DNA
                        organism = synthetic construct
SEQUENCE: 12
agaggagatg acgtgtgttc cttcgaaccc gagttttgtt cgtctataaa tagcaccttc  60
```

-continued

```
tcttctcctt cttcctcact tccatctttt tagcttcact atctctctat aatcggtttt  120
atctttctct aagtcacaac ccaaaaaaac aaagtagaga agaatctgta tgacaatcca  180
gccaatccag catgatgatc acattcgtta tctatttttt gctggattgg atggattgtc  240
agattggctc ttcttactac aatgaaaaag gccgaggcaa aacgcctaaa atcacttgag  300
aatcaattct ttttactgtc catttaagct atcttttata aacgtgtctt attttctatc  360
tcttttgttt aaactaagaa actatagtat tttgtctaaa                        400

SEQ ID NO: 13          moltype = DNA  length = 1005
FEATURE                Location/Qualifiers
misc_feature           1..1005
                       note = CaMV-35S-promoter nucleic acid sequence
source                 1..1005
                       mol_type = other DNA
                       organism = synthetic construct
SEQUENCE: 13
tttggagagg acaggcttct tgagatcctt caacaattac caacaacaac aaacaacaaa  60
caacattaca attactattt acaattacag tcgactctag aggatccatg gtgagcaagg  120
gcgaggagct gttcaccggg gtggtgccca tcctggtcga gctggacggc gacgtaaacg  180
gccacaagtt cagcgtgaga ggcgagggcg agggcgatgc caccaacggc aagctgaccc  240
tgaagttcat ctgcaccacc ggcaagctgc ccgtgccctg gcccaccctc gtgaccaccc  300
tgacctacgg cgtgcagtgc ttcagccgct accccgacca catgaagcag cacgacttct  360
tcaagtccgc catgcccgaa ggctacgtcc aggagcgcac catctcttc aaggacgacg  420
gcacttacaa gacccgcgcc gaggtgaagt tcgagggcga caccctggtg aaccgcatcg  480
agctgaaggg catcgacttc aaggaggacg gcaacatcct ggggcacaag ctggagtaca  540
acttcaacag ccacaacgtc tatatcactg ccgacaagca gaagaacggc atcaaggcca  600
acttcaagat ccgccacaac gttgaggacg gcagcgtgca gctcgccgac cactaccagc  660
agaacacccc catcggcgac ggccccgtgc tgctgcccga caaccactac ctgagcaccc  720
agtccgttct gagcaaagac cccaacgaga agcgcgatca catggtcctg ctggagttcg  780
tgaccgccgc cgggatcact ctcggcatgg acgagctgta caagtaaagc ggccgcccgg  840
ctgcagatcg ttcaaacatt tggcaataaa gtttcttaag attgaatcct gttgccggtc  900
ttgcgatgat tatcatataa tttctgttga attacgttaa gcatgtaata attaacatgt  960
aatgcatgac gttatttatg agatgggttt ttatgattag agtcc                  1005

SEQ ID NO: 14          moltype = DNA  length = 855
FEATURE                Location/Qualifiers
misc_feature           1..855
                       note = NOS terminator nucleic acid sequence
source                 1..855
                       mol_type = other DNA
                       organism = synthetic construct
SEQUENCE: 14
gctcgtccat gccgagagtg atcccggcgg cggtcacgaa ctccagcagg accatgtgat  60
cgcgcttctc gttggggtct ttgctcagaa cggactgggt gctcaggtag tggttgtcgg  120
gcagcagcac ggggccgtcg ccgatggggg tgttctgctg gtagtggtcg gcgagctgca  180
cgctgccgtc ctcaacgttg tggcggatct tgaagttggc cttgatgccg ttcttctgct  240
tgtcggcagt gatatagacg ttgtggctgt tgaagttgta ctccagcttg tgccccagga  300
tgttgccgtc ctccttgaag tcgatgccct tcagctcgat gcggttcacc agggtgtcgc  360
cctcgaactt cacctcggcg cgggtcttgt aagtgccgtc gtccttgaaa gagatggtgc  420
gctcctggac gtagccttcg ggcatggcgg acttgaagaa gtcgtgctgc ttcatgtggt  480
cggggtagcg gctgaagcac tgcacgccgt aggtcagggt ggtcacgagg gtgggccagg  540
gcacgggcag cttgccggtg gtgcagatga acttcagggt cagcttgccg ttggtggcat  600
cgccctcgcc ctcgcctctc acgctgaact tgtggccgtt tacgtcgccg tccagctcga  660
ccaggatggg caccaccccg gtgaacagct cctcgccctt gctcaccatg gatcctctag  720
agtcgactgt aattgtaaat agtaattgta atgttgtttg ttgtttgttg ttgttggtaa  780
ttgttgaagg atctcaagaa gcctgtcctc tccaaatgaa atgaacttcc ttatatagag  840
gaagggtctt gcgaa                                                   855

SEQ ID NO: 15          moltype = DNA  length = 215
FEATURE                Location/Qualifiers
misc_feature           1..215
                       note = CaMV-35S terminator nucleic acid sequence
source                 1..215
                       mol_type = other DNA
                       organism = synthetic construct
SEQUENCE: 15
cgctctgtca tcgttacaat caacatgcta ccctccgcga gatcatccgt gtttcaaacc  60
cggcagctta gttgccgttc ttccgaatag catcggtaac atgagcaaag tctgccgcct  120
tacaacggct ctcccgctga cgccgtcccg gactgatggg ctgcctgtat cgagtggtga  180
ttttgtgccg agctgccggt cggggagctg ttggc                             215

SEQ ID NO: 16          moltype = DNA  length = 216
FEATURE                Location/Qualifiers
misc_feature           1..216
                       note = G7-ter nucleic acid sequence
source                 1..216
                       mol_type = other DNA
                       organism = synthetic construct
SEQUENCE: 16
gatcccccgt cgacagctag ctatatcatc aatttatgta ttacacataa tatcgcactc  60
```

-continued

```
agtctttcat ctacggcaat gtaccagctg atataatcag ttattgaaat atttctgaat  120
ttaaacttgc atcaataaat ttatgttttt gcttggacta taatacctga cttgttattt  180
tatcaataaa tatttaaact atatttcttt caagat                            216

SEQ ID NO: 17          moltype = DNA  length = 516
FEATURE                Location/Qualifiers
misc_feature           1..516
                       note = CsVMV promoter nucleic acid sequence
source                 1..516
                       mol_type = other DNA
                       organism = synthetic construct
SEQUENCE: 17
ccagaaggta attatccaag atgtagcatc aagaatccaa tgtttacggg aaaaactatg  60
gaagtattat gtaagctcag caagaagcag atcaatatgc ggcacatatg caacctatgt  120
tcaaaaatga agaatgtaca gatacaagat cctatactgc cagaatacga agaagaatac  180
gtagaaattg aaaaagaaga accaggcgaa gaaaagaatc ttgatgacgt aagcactgac  240
gacaacaatg aaaagaagaa gataaggtcg gtgattgtga aagagacata gaggacacat  300
gtaaggtgga aaatgtaagg gcggaaagta accttatcac aaaggaatct tatcccccac  360
tacttatcct tttatatttt tccgtgtcat ttttgccctt gagttttcct atataaggaa  420
ccaagttcgg catttgtgaa aacaagaaaa aatttggtgt aagctatttt ctttgaagta  480
ctgaggatac aacttcagag aaatttgtaa gtttgt                            516

SEQ ID NO: 18          moltype = DNA  length = 636
FEATURE                Location/Qualifiers
source                 1..636
                       mol_type = unassigned DNA
                       organism = Arabidopsis thaliana
SEQUENCE: 18
gtcgacgagt cagtaataaa cggcgtcaaa gtggttgcag ccggcacaca cgagtcgtgt  60
ttatcaactc aaagcacaaa tacttttcct caacctaaaa ataaggcaat tagccaaaaa  120
caactttgcg tgtaaacaac gctcaataca cgtgtcattt tattattagc tattgcttca  180
ccgccttagc tttctcgtga cctagtcgtc ctcgtctttt cttcttcttc ttctataaaa  240
caatacccaa agagctcttc ttcttcacaa ttcagatttc aatttctcaa aatcttaaaa  300
actttctctc aattctctct accgtgatca aggtaaattt ctgtgttcct tattctctca  360
aaatcttcga ttttgttttc gttcgatccc aatttcgtat atgttctttg gtttagattc  420
tgttaatctt agatcgaaga cgattttctg ggtttgatcg ttagatatca tcttaattct  480
cgattagggt ttcatagata tcatccgatt tgttcaaata atttgagttt tgtcgaataa  540
ttactcttcg atttgtgatt tctatctaga tctggtgtta gtttctagtt tgtgcgatcg  600
aatttgtaga ttaatctgag tttttctgat taacag                            636

SEQ ID NO: 19          moltype = DNA  length = 4140
FEATURE                Location/Qualifiers
misc_feature           1..4140
                       note = pco_Cas9_NLS nucleic acid sequence
source                 1..4140
                       mol_type = other DNA
                       organism = synthetic construct
SEQUENCE: 19
atggataaga agtactctat cggactcgat atcggaacta actctgtggg atgggctgtg  60
atcaccgatg agtacaaggt gccatctaag aagttcaagg ttctcggaaa caccgatagg  120
cactctatca agaaaaacct tatcggtgct ctcctcttcg attctggtga aactgctgag  180
gctaccagac tcaagagaac cgctagaaga aggtacacca gaagaaagaa caggatctgc  240
tacctccaag agatcttctc taacgagatg gctaaagtgg atgattcatt cttccacagg  300
ctcgaagagt cattcctcgt ggaagaagat aagaagcacg agaggcaccc tatcttcgga  360
aacatcgttg atgaggtggc ataccacgag aagtacccta ctatctacca cctcagaaag  420
aagctcgttg attctactga taaggctgat ctcaggctca tctacctcgc tctcgctcac  480
atgatcaagt tcagaggaca cttcctcatc gagggtgatc tcaaccctga taactctgat  540
gtggataagt tgttcatcca gctcgtgcag acctacaacc agcttttcga agagaaccct  600
atcaacgctt caggtgtgga tgctaaggct atcctctctg ctaggctctc taagtcaaga  660
aggcttgaga acctcattgc tcagctccct ggtgagaaga agaacggact tttcggaaac  720
ttgatcgctc tctctctcgg actcacccct aacttcaagt ctaacttcga tctcgctgag  780
gatgcaaagc tccagctctc aaaggatacc tacgatgatg atctcgataa cctcctcgct  840
cagatcggag atcagtacgc tgatttgttc ctcgctgcta agaacctctc tgatgctatc  900
ctcctcagtg atatcctcag agtgaacacc gagatcacca aggctccact ctcagcttct  960
atgatcaaga gatacgatga gcaccaccag gatctcacac ttctcaaggc tcttgttaga  1020
cagcagctcc cagagaagta caaagagatt ttcttcgatc agtctaagaa cggatacgct  1080
ggttacatcg atggtggtgc atctcaagaa gagttctaca agttcatcaa gcctatcctc  1140
gagaagatgg atggaaccga ggaactcctc gtgaagctca atagagagga tcttctcaga  1200
aagcagagga ccttcgataa cggatctatc cctcatcaga tccacctcgg agagttgcac  1260
gctatcctta gaaggcaaga ggatttctac ccattcctca aggataacag ggaaaagatt  1320
gagaagattc tcaccttcag aatcccttac tacgtgggac ctctcgctag aggaaactca  1380
agattcgctt ggatgaccag aaagtctgag gaaaccatca ccccttggaa cttcgaagag  1440
gtggtggata agggtgctag tgctcagtct ttcatcgaga ggatgaccaa cttcgataag  1500
aaccttccaa acgagaaggt gctccctaag cactctttgc tctacgagta cttcaccgtg  1560
tacaacgagt tgaccaaggt taagtacgtg accgagggaa tgaggaagcc tgcttttttg  1620
tcaggtgagc aaaagaaggc tatcgttgat ctcttgttca agaccaacag aaaggtgacc  1680
gtgaagcagc tcaaagagga ttacttcaag aaaatcgagt gcttcgattc agttgagatt  1740
tctggtgttg aggataggtt caacgcatct ctcggaacct accacgatct cctcaagatc  1800
attaaggata aggatttctt ggataacgag gaaaacgagg atatcttgga ggatatcgtt  1860
```

-continued

```
cttaccctca ccctctttga agatagagag atgattgaag aaaggctcaa gacctacgct  1920
catctcttcg atgataaggt gatgaagcag ttgaagagaa gaagatacac tggttgggga  1980
aggctctcaa gaaagctcat taacggaatc agggataagc agtctggaaa gacaatcctt  2040
gatttcctca agtctgatgg attcgctaac agaaacttca tgcagctcat ccacgatgat  2100
tctctcacct ttaaagagga tatccagaag gctcaggttt caggacaggg tgatagtctc  2160
catgagcata tcgctaacct cgctggatct cctgcaatca agaagggaat cctccagact  2220
gtgaaggttg tggatgagtt ggtgaaggtg atgggaaggc ataagcctga gaacatcgtg  2280
atcgaaatgg ctagagagaa ccagaccact cagaagggac agaagaactc tagggaaagg  2340
atgaagagga tcgaggaagg tatcaaagag cttggatctc agatcctcaa agagcaccct  2400
gttgagaaca ctcagctcca gaatgagaag ctctacctct actacctcca gaacggaagg  2460
gatatgtatg tggatcaaga gttggatatc aacaggctct ctgattacga tgttgatcat  2520
atcgtgccac agtcattctt gaaggatgat tctatcgata acaaggtgct caccaggtct  2580
gataagaaca ggggtaagag tgataacgtg ccaagtgaag aggttgtgaa gaaaatgaag  2640
aactattgga ggcagctcct caacgctaag ctcatcactc agagaaagtt cgataacttg  2700
actaaggctg agaggggagg actctctgaa ttggataagg caggattcat caagaggcag  2760
cttgtggaaa ccaggcagat cactaagcac gttgcacaga tcctcgattc taggatgaac  2820
accaagtacg atgagaacga taagttgatc agggaagtga aggttatcac cctcaagtca  2880
aagctcgtgt ctgatttcag aaaggatttc caattctaca aggtgaggga aatcaacaac  2940
taccaccacg ctcacgatgc ttaccttaac gctgttgttg gaaccgctct catcaagaag  3000
tatcctaagc tcgagtcaga gttcgtgtac ggtgattaca aggtgtacga tgtgaggaag  3060
atgatcgcta agtctgagca agagatcgga aaggctaccg ctaagtattt cttctactct  3120
aacatcatga atttcttcaa gaccgagatt accctcgcta acggtgagat cagaaagagg  3180
ccactcatcg agacaaacgg tgaaacaggt gagatcgtgt gggataaggg aagggatttc  3240
gctaccgtta gaaaggtgct ctctatgcca caggtgaaca tcgttaagaa aaccgaggtg  3300
cagaccggtg gattctctaa agagtctatc ctccctaaga ggaactctga taagctcatt  3360
gctaggaaga aggattggga ccctaagaaa tacggtggtt tcgattctcc taccgtggct  3420
tactctgttc tcgttgtggc taaggttgag aagggaaaga gtaagaagct caagtctgtt  3480
aaggaacttc tcggaatcac tatcatggaa aggtcatctt tcgagaagaa cccaatcgat  3540
ttcctcgagg ctaagggata caaagaggtt aagaaggatc tcatcatcaa gctcccaaag  3600
tactcactct tcgaactcga gaacggtaga aagaggatgc tcgcttctgc tggtgagctt  3660
caaaagggaa acgagcttgc tctcccatct aagtacgtta actttcttta cctcgcttct  3720
cactacgaga agttgaaggg atctccagaa gataacgagc agaagcaact tttcgttgag  3780
cagcacaagc actacttgga tgagatcatc gagcagatct ctgagttctc taaaagggtg  3840
atcctcgctg atgcaaacct cgataaggtg ttgtctgctt acaacaagca cagagataag  3900
cctatcaggg aacaggcaga gaacatcatc catctcttca cccttaccaa cctcggtgct  3960
cctgctgctt tcaagtactt cgatacaacc atcgatagga agagatacac ctctaccaaa  4020
gaagtgctcg atgctaccct catccatcag tctatcactg gactctacga gactaggatc  4080
gatctctcac agctcggtgg tgattcaagg gctgatccta agaagaagag gaaggtttga  4140
```

```
SEQ ID NO: 20          moltype = DNA  length = 263
FEATURE                Location/Qualifiers
misc_feature           1..263
                       note = AtuNos ter nucleic acid sequence
source                 1..263
                       mol_type = other DNA
                       organism = synthetic construct
SEQUENCE: 20
gtcaagcaga tcgttcaaac atttggcaat aaagtttctt aagattgaat cctgttgccg  60
gtcttgcgat gattatcata taatttctgt tgaattacgt taagcatgta ataattaaca  120
tgtaatgcat gacgttattt atgagatggg tttttatgat tagagtcccg caattataca  180
tttaatacgc gatagaaaac aaaatatagc gcgcaaacta ggataaatta tcgcgcgcgg  240
tgtcatctat gttactagat cga                                          263
```

```
SEQ ID NO: 21          moltype = DNA  length = 1147
FEATURE                Location/Qualifiers
misc_feature           1..1147
                       note = Synthetic construct clone eGFP-OsP5SM_E/R eGFP
                        (eGFP) gene
source                 1..1147
                       mol_type = other DNA
                       organism = synthetic construct
SEQUENCE: 21
atgtctagag tgagcaaggg cgaggagctg ttcaccgggg tggtgcccat cctggtcgag  60
ctggacggcg acgtaaacgg ccacaagttc agcgtgtccg gcgagggcga gggcgatgcc  120
acctacggca agctgaccct gaagttcatc tgcaccaccg gcaagctgcc cgtgccctgg  180
cccaccctcg tgaccaccct gacctacggc gtgcagtgct tcagccgcta ccccgaccac  240
atgaagcagc acgacttctt caagtccgcc atgcccgaag gctacgtcca ggaggtagat  300
ttatgcatcc tcttgtcatg agaagtcgaa ttgttcccat tctgtgtgtt gcagctacag  360
atggagatac atagagatac tcgtggattt tgcttagtgt tgagttttgt tctggttgtg  420
aactaaaagt ttatacattt gcaggaaata aatagccttt tgtttaaatc aaaaggtctt  480
acctatgtta gtgtgaagca ttggatccca aagaactcca aaatgcgatg aggcatattt  540
aatcttgtct ggactagtaa caggttggga tgaccacctg tgaagctcca acaggattgc  600
ctcctcacgc aatgtttgag gtctgatgtt caatagcttg ttttgtttca ctttgctttg  660
gactttcttt tcgccaatga gctatgtttc tgatggtttt cactcttttg gtgtgtagag  720
aaccatcttc ttcaaggacg acggcaacta caagacccgc gccgaggtga agttcgaggg  780
cgacaccctg gtgaaccgca tcgagctgaa gggcatcgac ttcaaggagg acggcaacac  840
ctggggcaca agctggagta caactacaac agccacaacg tctatatcat ggccgacaag  900
cagaagaagg catcaaggtg aacttcaaga tccgccacaa catcgaggac ggcagcgtgc  960
agctcgccga ccactacagc agaacacccc catcggcgac ggccccgtgc tgctgcccga  1020
```

-continued

```
caaccactac ctgagcaccc agtccgccct gagcaaagac cccaacgaga agcgcgatca  1080
catggtcctg ctggagttcg tgaccgccgc cgggatcact ctcggcatgg acgagctgta  1140
caagtaa                                                            1147

SEQ ID NO: 22          moltype = DNA  length = 2074
FEATURE                Location/Qualifiers
source                 1..2074
                       mol_type = unassigned DNA
                       organism = Arabidopsis thaliana
SEQUENCE: 22
caattatgtg ttaaagatac aaacttttgt ctgatttgct tccaccggtt tcacctaaga  60
tactcaattt tcttactttt tgtgtgtttt gtaattctaa ttcttttata gcttcaattt  120
ttagattcat tgaagcagtt gtgagttaag ttggagaaaa tggttgtgtt tgggaatgtt  180
tctgcggcga atttgcctta tcaaaacggg tttttggagg cactttcatc tggaggttgt  240
gaactaatgg gacatagctt tagggttccc acttctcaag cgcttaagac aagaacaagg  300
aggaggagta ctgctggtcc tttgcaggta gtttgtgtgg atattccaag gccagagcta  360
gagaacactg tcaatttctt ggaagctgct agtttatctg catccttccg tagtgctcct  420
cgtcctgcta agcctttgaa agttgtaatt gctggtgctg gattggctgg attgtcaact  480
gcaaagtacc tggctgatgc aggccacaaa cctctgttgc ttgaagcaag agatgttctt  540
ggtggaaaga tagctgcatg gaaggatgaa gatggggact ggtatgagac tggtttacat  600
attttcttcg gtgcttatcc gaatgtgcag aatttatttg gagaacttgg gatcaatgat  660
cggttgcagt ggaaggaaca ctccatgatt tttgctatgc caagtaaacc tggagaattt  720
agtagatttg acttcccaga tgtcctacca gcacccttaa atggtatttg ggctattttg  780
cggaacaacg agatgctgac atggccagag aaaataaagt ttgctattgg acttttgcca  840
gccatggtcg gcggtcaggc ttatgttgag gcccaagatg gtttatcagt caaagaatgg  900
atggaaaagc agggagtacc tgagcgcgtg accgacgagg tgtttattgc catgtcaaag  960
gcgctaaact ttataaaccc tgatgaactg tcaatgcaat gcattttgat agctttgaac  1020
cggtttcttc aggaaaaaca tggttccaag atggcattct tggatggtaa tcctccggaa  1080
aggctttgta tgccagtagt ggatcatatt cgatcactag gtggggaagt gcaacttaat  1140
tctaggataa agaaaattga gctcaatgac gatggcacgg ttaagagttt cttactcact  1200
aatggaagca ctgtcgaagg agacgcttat gtgtttgccg ctccagtcga tatcctgaag  1260
ctccttttac cagatccctg gaaagaaata ccgtacttca agaaattgga taaattagtt  1320
ggagtaccag ttattaatgt tcatatatgg tttgatcgaa aactgaagaa cacatatgat  1380
cacctactct ttagcagaag taaccttctg agcgtgtatg ccgacatgtc cttaacttgt  1440
aaggaatatt acgatcctaa ccggtcaatg ctggagctag tatttgcacc agcagaggaa  1500
tggatatcac ggactgattc tgacatcata gatgcaacaa tgaaagaact tgagaaactc  1560
ttccctgatg aaatctcagc tgaccaaagc aaagctaaaa ttctgaagta ccatgtcgtt  1620
aagactccaa gatctgtgta caagaccatc ccaaactgtg aaccatgtcg tcctctacaa  1680
agatcaccta ttgaaggatt ctacttagct ggagattaca caaaacagaa gtacttagct  1740
tccatggaag gcgctgtcct ctctggcaaa ttctgctctc agtctattgt tcaggattac  1800
gagctactgg ctgcgtctgg accaagaaag ttgtcggagg caacagtatc atcatcatga  1860
gaagaggaca aaacttaaag atgatttgct tgtaagcatt attatttgtg tataaatctc  1920
attgcaatcc aaacttaacc ttactctctt cagtaaatga atctcacaga tttgacatct  1980
cacgtttctg tcaattttat aatttttaaa aagtaattac tgtcgacctt ttgtaatcat  2040
agtgatttat cattatgtct ctctttttaa aacc                              2074

SEQ ID NO: 23          moltype = DNA  length = 1419
FEATURE                Location/Qualifiers
source                 1..1419
                       mol_type = unassigned DNA
                       organism = Arabidopsis thaliana
SEQUENCE: 23
ggagcatctt cattcttaag atatgaagat aatcttcaaa aggcccctgg gaatctgaaa  60
gaagagaagc aggcccattt atatgggaaa gaacaatagt atttcttata taggcccatt  120
taagttgaaa acaatcttca aaagtcccac atcgcttaga taagaaaacg aagctgagtt  180
tatatacagc tagagtcgaa gtagtgattg tgagacggat atcaatacgc aaaccgcctc  240
tccccgcgcg ttggccgatt cattaatgca gctggcacga caggtttccc gactggaaag  300
cgggcagtga gcgcaacgca attaatgtga gttagctcac tcattaggca ccccaggctt  360
tacactttat gcttccggct cgtatgttgt gtggaattgt gagcggataa caatttcaca  420
catactagag aaagaggaga aatactagat ggcttcctcc gaggacgtta tcaaagagtt  480
catgcgtttc aaagttcgta tggaaggttc cgttaacggt cacgagttcg aaatcgaagg  540
tgaaggtgaa ggtcgtccgt acgaaggtac ccagaccgct aaactgaaag ttaccaaagg  600
tggtccgctg ccgttcgctt gggacatcct gtccccgcag ttccagtacg gttccaaagc  660
ttacgttaaa cacccggctg acatcccgga ctacctgaaa ctgtccttcc cggaaggttt  720
caaatgggaa cgtgttatga acttcgagga cggtggtgtt gttaccgtta cccaggactc  780
ctccctgcaa gacggtgagt tcatctacaa agttaaactg cgtggtacca acttcccgtc  840
cgacggtccg gttatgcaga aaaaaaccat gggttgggaa gcttccaccg aacgtatgta  900
cccggaggac ggtgctctga aaggtgaaat caaaatgcgt ctgaaactga aagacggtgg  960
tcactacgac gctgaagtta aaaccaccta catggctaaa aaaccggttc agctgccggg  1020
tgcttacaaa accgacatca aactggacat cacctcccac aacgaggact acaccatcgt  1080
tgaacagtac gaacgtgctg aaggtcgtca ctccaccggt gcttaataac gctgatagtg  1140
ctagtgtaga tcgctactag agccaggcat caaataaaac gaaaggctca gtcgaaagac  1200
tgggcctttc gttttatctg ttgtttgtcg gtgaacgctc tctactagag tcacactggc  1260
tcaccttcgg gtgggccttt ctgcgtttat acgtctcagt tttagagcta gaaatagcaa  1320
gttaaaataa ggctagtccg ttatcaactt gaaaaagtgg caccgagtcg gtgctttttt  1380
tctagaccca gctttcttgt acaaagttgg cattacgct                         1419

SEQ ID NO: 24          moltype = DNA  length = 1286
FEATURE                Location/Qualifiers
```

-continued

```
misc_feature            1..1286
                        note = U6III-synthetic pol 3 promoter for sgRNA expression
source                  1..1286
                        mol_type = other DNA
                        organism = synthetic construct
SEQUENCE: 24
ggagtatgat caaaagtccc acatcgatca ggtgatatat agcagcttag tttatataat  60
gatagagtcg acatagcgat tgggagacgc aatacgcaaa ccgcctctcc ccgcgcgttg  120
gccgattcat taatgcagct ggcacgacag gtttcccgac tggaaagcgg gcagtgagcg  180
caacgcaatt aatgtgagtt agctcactca ttaggcaccc caggctttac actttatgct  240
tccggctcgt atgttgtgtg gaattgtgag cggataacaa tttcacacat actagagaaa  300
gaggagaaat actagatggc ttcctccgag gacgttatca aagagttcat gcgtttcaaa  360
gttcgtatgg aaggttccgt taacggtcac gagttcgaaa tcgaaggtga aggtgaaggt  420
cgtccgtacg aaggtaccca gaccgctaaa ctgaaagtta ccaaaggtgg tccgctgccg  480
ttcgcttggg acatcctgtc cccgcagttc cagtacggtt ccaaagctta cgttaaacac  540
ccggctgaca tcccggacta cctgaaactg tccttcccgg aaggtttcaa atgggaacgt  600
gttatgaact tcgaggacgg tggtgttgtt accgttaccc aggactcctc cctgcaagac  660
ggtgagttca tctacaaagt taaactgcgt ggtaccaact tcccgtccga cggtccggtt  720
atgcagaaaa aaaccatggg ttgggaagct tccaccgaac gtatgtaccc ggaggacggt  780
gctctgaaag gtgaaatcaa aatgcgtctg aaactgaaag acggtggtca ctacgacgct  840
gaagttaaaa ccacctacat ggctaaaaaa ccggttcagc tgccgggtgc ttacaaaacc  900
gacatcaaac tggacatcac ctcccacaac gaggactaca ccatcgttga acagtacgaa  960
cgtgctgaag gtcgtcactc caccggtgct taataacgct gatagtgcta gtgtagatcg  1020
ctactagagc caggcatcaa ataaaacgaa aggctcagtc gaaagactgg gcctttcgtt  1080
ttatctgttg tttgtcggtg aacgctctct actagagtca cactggctca ccttcgggtg  1140
ggcctttctg cgtttatacg tctccgtttt agagctagaa atagcaagtt aaaataaggc  1200
tagtccgtta tcaacttgaa aaagtggcac cgagtcggtg cttttttttct agacccagct  1260
ttcttgtaca aagttggcat tacgct                                     1286

SEQ ID NO: 25           moltype = DNA  length = 2074
FEATURE                 Location/Qualifiers
source                  1..2074
                        mol_type = unassigned DNA
                        organism = Arabidopsis thaliana
SEQUENCE: 25
caattatgtg ttaaagatac aaacttttgt ctgatttgct tccaccggtt tcacctaaga  60
tactcaattt tcttactttt tgtgtgtttt gtaattctaa ttcttttata gcttcaattt  120
ttagattcat tgaagcagtt gtgagttaag ttggagaaaa tggttgtgtt tgggaatgtt  180
tctgcggcga atttgcctta tcaaaacggg tttttggagg cactttcatc tggaggttgt  240
gaactaatgg gacatagctt tagggttccc acttctcaag cgcttaagac aagaacaagg  300
aggaggagta ctgctggtcc tttgcaggta gtttgtgtgg atattccaag gccagagcta  360
gagaacactg tcaatttctt ggaagctgct agtttatctg catccttccg tagtgctcct  420
cgtcctgcta agcctttgaa agttgtaatt gctggtgctg gattggctgg attgtcaact  480
gcaaagtacc tggctgatgc aggccacaaa cctctgttgc ttgaagcaag agatgttctt  540
ggtggaaaga tagctgcatg gaaggatgaa gatggggact ggtatgagac tggtttacat  600
attttcttcg gtgcttatcc gaatgtgcag aatttatttg gagaacttgg gatcaatgat  660
cggttgcagt ggaaggaaca ctccatgatt tttgctatgc caagtaaacc tggagaattt  720
agtagatttg acttcccaga tgtcctacca gcacccttaa atggtatttg ggctattttg  780
cggaacaacg agatgctgac atggccagag aaaataaagt ttgctattgg acttttgcca  840
gccatggtcg gcggtcaggc ttatgttgag gcccaagatg gtttatcagt caaagaatgg  900
atggaaaagc agggagtacc tgagcgcgtg accgacgagg tgtttattgc catgtcaaag  960
gcgctaaact ttataaaccc tgatgaactg tcaatgcaat gcattttgat agctttgaac  1020
cggtttcttc aggaaaaaca tggttccaag atggcattct tggatggtaa tcctccggaa  1080
aggctttgta tgccagtagt ggatcatatt cgatcactag gtggggaagt gcaacttaat  1140
tctaggataa agaaaattga gctcaatgac gatggcacgg ttaagagttt cttactcact  1200
aatggaagca ctgtcgaagg agacgcttat gtgtttgccg ctccagtcga tatcctgaag  1260
ctccttttac cagatccctg gaaagaaata ccgtacttca agaaattgga taaattagtt  1320
ggagtaccag ttattaatgt tcatatatgg tttgatcgaa aactgaagaa cacatatgat  1380
cacctactct ttagcagaag taaccttctg agcgtgtatg ccgacatgtc cttaacttgt  1440
aaggaatatt acgatcctaa ccggtcaatg ctggagctag tatttgcacc agcagaggaa  1500
tggatatcac ggactgattc tgacatcata gatgcaacaa tgaaagaact tgagaaactc  1560
ttccctgatg aaatctcagc tgaccaaagc aaagctaaaa ttctgaagta ccatgtcgtt  1620
aagactccaa gatctgtgta caagaccatc ccaaactgtg aaccatgtcg tcctctacaa  1680
agatcaccta ttgaaggatt ctacttagct ggagattaca caaaacagaa gtacttagct  1740
tccatggaag gcgctgtcct ctctggcaaa ttctgctctc agtctattgt tcaggattac  1800
gagctactgg ctgcgtctgg accaagaaag ttgtcggagg caacagtatc atcatcatga  1860
gaagaggaca aaacttaaag atgatttgct tgtaagcatt attatttgtg tataaatctc  1920
attgcaatcc aaacttaacc ttactctctt cagtaaatga atctcacaga tttgacatct  1980
cacgtttctg tcaattttat aatttttaaa aagtaattac tgtcgacctt ttgtaatcat  2040
agtgatttat cattatgtct ctctttttaa aacc                            2074

SEQ ID NO: 26           moltype = DNA  length = 2290
FEATURE                 Location/Qualifiers
source                  1..2290
                        mol_type = unassigned DNA
                        organism = Arabidopsis thaliana
SEQUENCE: 26
ctttggtggg caaaaacata ttagctgaga ggtcaatttc tttttcccct aaaccaaatt  60
acgttgagat gcatggtctc tctctactca attaaccaaa taaggaaaag aatcatatgg  120
```

-continued

```
tcatcaattc gtaaatcaaa attttaattt gtgtggtatt taatccatct acatgtttcg  180
taagcaacaa aagagcttgg tctgaaaacc aaacaagacc atatgggcac tcgaatactc  240
cattttgtta tcggctactt ccactagcct cctccttcgc tgcgtctcct gtttctctac  300
ttcacgatta ctcgctagat tcattgaagc agttgtgagt taagttggag aaaatggttg  360
tgtttgggaa tgtttctgcg gcgaatttgc cttatcaaaa cgggtttttg gaggcacttt  420
catctggagg ttgtgaacta atgggacata gctttagggt tcccacttct caagcgctta  480
agacaagaac aaggaggagg agtactgctg gtcctttgca ggtagtttgt gtggatattc  540
caaggccaga gctagagaac actgtcaatt tcttggaagc tgctagttta tctgcatcct  600
tccgtagtgc tcctcgtcct gctaagcctt tgaaagttgt aattgctggt gctggattgg  660
ctggattgtc aactgcaaag tacctggctg atgcaggcca caaacctctg ttgcttgaag  720
caagagatgt tcttggtgga aagatagctg catggaagga tgaagatggg gactggtatg  780
agactggttt acatattttc ttcggtgctt atccgaatgt gcagaattta tttggagaac  840
ttgggatcaa tgatcggttg cagtggaagg aacactccat gatttttgct atgccaagta  900
aacctggaga atttagtaga tttgacttcc cagatgtcct accagcaccc ttaaatggta  960
tttgggctat tttgcggaac aacgagatgc tgacatggcc agagaaaata aagtttgcta  1020
ttggactttt gccagccatg gtcggcggtc aggcttatgt tgaggcccaa gatggtttat  1080
cagtcaaaga atggatggaa aagcagggag tacctgagcg cgtgaccgac gaggtgttta  1140
ttgccatgtc aaaggcgcta aactttataa accctgatga actgtcaatg caatgcattt  1200
tgatagcttt gaaccggttt cttcaggaaa aacatggttc caagatggca ttcttggatg  1260
gtaatcctcc ggaaaggctt tgtatgccag tagtggatca tattcgatca ctaggtgggg  1320
aagtgcaact taattctagg ataaagaaaa ttgagctcaa tgacgatggc acggttaaga  1380
gtttcttact cactaatgga agcactgtcg aaggagacgc ttatgtgttt gccgctccag  1440
tcgatatcct gaagctcctt ttaccagatc cctggaaaga aataccgtac ttcaagaaat  1500
tggataaatt agttggagta ccagttatta atgttcatat atggtttgat cgaaaactga  1560
agaacacata tgatcaccta ctctttagca gaagtaacct tctgagcgtg tatgccgaca  1620
tgtccttaac ttgtaaggaa tattacgatc ctaaccggtc aatgctggag ctagtatttg  1680
caccagcaga ggaatggata tcacggactg attctgacat catagatgca acaatgaaag  1740
aacttgagaa actcttccct gatgaaatct cagctgacca aagcaaagct aaaattctga  1800
agtaccatgt cgttaagact ccaagatctg tgtacaagac catcccaaac tgtgaaccat  1860
gtcgtcctct acaaagatca cctattgaag gattctactt agctggagat tacacaaaac  1920
agaagtactt agcttccatg gaaggcgctg tcctctctgg caaattctgc tctcagtcta  1980
ttgttcagga ttacgagcta ctggctgcgt ctggaccaag aaagttgtcg gaggcaacag  2040
tatcatcatc atgagaagag gacaaaactt aaagatgatt tgcttgtaag cattattatt  2100
tgtgtataaa tctcattgca atccaaactt aaccttactc tcttcagtaa atgaatctca  2160
cagatttgac atctcacgtt tctgtcaatt ttataatttt taaaaagtaa ttactgtcga  2220
ccttttgtaa tcatagtgat ttatcattat gtctctcttt ttaaaacctt ttctggtaca  2280
aattataaaa                                                         2290

SEQ ID NO: 27          moltype = AA  length = 241
FEATURE                Location/Qualifiers
REGION                 1..241
                       note = eGFP [synthetic construct] amino acid sequence
source                 1..241
                       mol_type = protein
                       organism = synthetic construct
SEQUENCE: 27
MSRVSKGEEL FTGVVPILVE LDGDVNGHKF SVSGEGEGDA TYGKLTLKFI CTTGKLPVPW  60
PTLVTTLTYG VQCFSRYPDH MKQHDFFKSA MPEGYVQERT IFFKDDGNYK TRAEVKFEGD  120
TLVNRIELKG IDFKEDGNIL GHKLEYNYNS HNVYIMADKQ KNGIKVNFKI RHNIEDGSVQ  180
LADHYQQNTP IGDGPVLLPD NHYLSTQSAL SKDPNEKRDH MVLLEFVTAA GITLGMDELY  240
K                                                                  241

SEQ ID NO: 28          moltype = RNA  length = 107
FEATURE                Location/Qualifiers
source                 1..107
                       mol_type = unassigned RNA
                       organism = Arabidopsis thaliana
SEQUENCE: 28
gtagagaaga atctgtaaag ctcaggaggg atagcgccat gatgatcaca ttcgttatct  60
attttttggc gctatccatc ctgagtttca ttggctcttc ttactac                107

SEQ ID NO: 29          moltype = RNA  length = 102
FEATURE                Location/Qualifiers
source                 1..102
                       mol_type = unassigned RNA
                       organism = Arabidopsis thaliana
SEQUENCE: 29
taagtacttt cgcttgcaga gagaaatcac agtggtcaaa aaagttgtag ttttcttaaa  60
gtctctttcc tctgtgattc tctgtgtaag cgaaagagct tg                     102

SEQ ID NO: 30          moltype = DNA  length = 711
FEATURE                Location/Qualifiers
misc_feature           1..711
                       note = nucleic acid sequence encoding mCherry
source                 1..711
                       mol_type = other DNA
                       organism = synthetic construct
SEQUENCE: 30
atggtgagca agggcgagga ggataacatg gccatcatca aggagttcat gcgcttcaag  60
```

```
gtgcacatgg agggctccgt gaacggccac gagttcgaga tcgagggcga gggcgagggc  120
cgcccctacg agggcaccca gaccgccaag ctgaaggtga ccaagggtgg cccccctgccc  180
ttcgcctggg acatcctgtc ccctcagttc atgtacggct ccaaggccta cgtgaagcac  240
cccgccgaca tccccgacta cttgaagctg tccttccccg agggcttcaa gtgggagcgc  300
gtgatgaact tcgaggacgg cggcgtggtg accgtgaccc aggactcctc cctgcaggac  360
ggcgagttca tctacaaggt gaagctgcgc ggcaccaact tcccctccga cggcccagta  420
atgcagaaga aaaccatggg ctgggaggcc tcctccgagc ggatgtaccc cgaggacggc  480
gccctgaagg gcgagatcaa gcagaggctg aagctgaagg acggcggcca ctacgacgct  540
gaggtcaaga ccacctacaa ggccaagaag cccgtgcagc tgcccggcgc ctacaacgtc  600
aacatcaagt tggacatcac ctcccacaac gaggactaca ccatcgtgga acagtacgaa  660
cgcgccgagg gccgccactc caccggcggc atggacgagc tgtacaagtg a           711

SEQ ID NO: 31           moltype = DNA  length = 4100
FEATURE                 Location/Qualifiers
misc_feature            1..4100
                        note = Plasmid-1: GEiGS_ mir173_si-GFP_1
source                  1..4100
                        mol_type = other DNA
                        organism = synthetic construct
SEQUENCE: 31
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaatacctta acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac attttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac tttttttttt  1440
ttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aattttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact taagtcgtgc tgcttcatgt ggagtggtca aaaaagttgt  2100
agttttctta aagtctcttt cctctccaca taagcaggac gagttaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
```

-continued

```
aagatatagg aacatgtaat catgcggctc tccatacaat acatcttgtt gacaaagttc  3600
ccaagacctc attctacaaa ccaatgtttc ttttttcttt ttctttttgg tgatagtttt  3660
tgcaatcaaa tgttgtaaaa ctatgattgg aaatactact gtattttacc gaaaacttta  3720
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtctttttta ggatttgttg  3960
atttttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                              4100

SEQ ID NO: 32          moltype = DNA  length = 4100
FEATURE                Location/Qualifiers
misc_feature           1..4100
                       note = Plasmid-2: GEiGS_ mir173_si-GFP_2
source                 1..4100
                       mol_type = other DNA
                       organism = synthetic construct
SEQUENCE: 32
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaatacctta acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac atttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaattg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac ttttttttt  1440
ttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aattttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact tagttgtact ccagcttgtg ccagtggtca aaaaagttgt  2100
agttttctta aagtctcttt cctctggcaa agctgcagta caactaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
aagatatagg aacatgtaat catgcggctc tccatacaat acatcttgtt gacaaagttc  3600
```

-continued

```
ccaagacctc attctacaaa ccaatgtttc ttttttcttt ttctttttgg tgatagtttt  3660
tgcaatcaaa tgttgtaaaa ctatgattgg aaatactact gtattttacc gaaaacttta  3720
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtcttttttta ggatttgttg  3960
atttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                              4100

SEQ ID NO: 33          moltype = DNA  length = 4100
FEATURE                Location/Qualifiers
misc_feature           1..4100
                       note = Plasmid-3: GEiGS_ mir173_si-PDS_1
source                 1..4100
                       mol_type = other DNA
                       organism = synthetic construct
SEQUENCE: 33
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaataccttta acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac attttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac tttttttttt  1440
tttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aattttttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact ttatccacac aaactacctg caagtggtca aaaaagttgt  2100
agttttctta aagtctcttt cctcttgcag tagttagtgt ggataaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgtttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
aagatatagg aacatgtaat catgcggctc tccatacaat acatcttgtt gacaaagttc  3600
ccaagacctc attctacaaa ccaatgtttc ttttttcttt ttctttttgg tgatagtttt  3660
```

-continued

```
tgcaatcaaa tgttgtaaaa ctatgattgg aaatactact gtattttacc gaaaacttta  3720
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtcttttttta ggatttgttg  3960
attttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                              4100

SEQ ID NO: 34          moltype = DNA  length = 4100
FEATURE                Location/Qualifiers
misc_feature           1..4100
                       note = Plasmid-4: GEiGS_ mir173_si-PDS_2
source                 1..4100
                       mol_type = other DNA
                       organism = synthetic construct
SEQUENCE: 34
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaatacctta acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac attttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac ttttttttt  1440
ttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aattttttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact ttgacaatcc agccaatcca gcagtggtca aaaaagttgt  2100
agttttctta aagtctcttt cctctgctga ttggcaggat tgtcaaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgtttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
aagatatagg aacatgtaat catgcggctc tccatacaat acatcttgtt gacaaagttc  3600
ccaagacctc attctacaaa ccaatgtttc tttttttcttt ttctttttgg tgatagtttt  3660
tgcaatcaaa tgttgtaaaa ctatgattgg aaatactact gtattttacc gaaaacttta  3720
```

```
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtctttttta ggatttgttg  3960
atttttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                              4100

SEQ ID NO: 35          moltype = DNA  length = 4000
FEATURE                Location/Qualifiers
misc_feature           1..4000
                       note = Plasmid-5: GEiGS_ mir390a _si-GFP_1
source                 1..4000
                       mol_type = other DNA
                       organism = synthetic construct
SEQUENCE: 35
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
cacttttatg agaaaatgta tcttaaaaaa tgttattcat caaagcttag atgcgctata  240
ggggaacata atcattattt gaaaagaacc aattcaaata tttttttttt taagagttaa  300
aatcctatat aacataacca tccaaacttt gggcatgaac acaacaatat ttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aatttttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcattttct gttaacatat atggaaaaaa caaacttcac cgttatttac  1200
ctgaatttac ctatttgggt aagaattgta cctctggacc tctagtattt tatatacacc  1260
taaaaatata attttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatattttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tataggggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta aagtcgtgct gcttcatgtg gatgatgatc  2100
acattcgtta tctatttttt ccacatgaag aagcacgact tgattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tgggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
```

-continued gagaggatag gtcttcttct tctgtaattt gctgggaccg caagtcatgt gaggctgctc 3840
tgctgatgct gcacggcgtc gcaactctct caataaattc ttttaactaa cgctccaatt 3900
ttcgatgtaa attggctgac ttcaattcta tgccttactc ttgtactcta tgtttcttta 3960
tctattaaaa tccaactctg cttttgaacc caaaaaacaa 4000

SEQ ID NO: 36 moltype = DNA length = 4000
FEATURE Location/Qualifiers
misc_feature 1..4000
note = Plasmid-6: GEiGS_ mir390a _si-GFP_2
source 1..4000
mol_type = other DNA
organism = synthetic construct
SEQUENCE: 36
accctcattg attttggtgg ccaaactctt gatcgtattc ttttaggaac agtaattaat 60
tttaaatttg agaaaaatgt agtgatgaaa gtgagatata tgggacgcac tattgaaagc 120
attgtccaca ccgcatgatg tgagattgat gtgaatatgg taactaataa cacccagact 180
cacttttatg agaaaatgta tcttaaaaaa tgttattcat caaagcttag atgcgctata 240
ggggaacata atcattattt gaaaagaacc aattcaaata tttttttttt taagagttaa 300
aatcctatat aacataacca tccaaacttt gggcatgaac acaacaatat tttttttcgt 360
ttttgataaa ttctttcaat tgcaatcaaa acttaccagc tatacaaatg tttgctgcat 420
ccaatctaat acaccgttaa acaataaaat ttgttatctc tcaaatctga tcatctattc 480
caacctgact gttttattct agtattttaa ggccaggtat aacgaaaaca aagaaaaaag 540
ttcagcgacc aagacatttt gacatcaggc tcaaacggtc aaacccacga aaacttttac 600
ctcatttctt aaccacgcag tgttatttga atagccttaa taggctaata caaaacaaca 660
agccatcgat tacagtttta actataatat tacaaaatct taaaccaaaa caagaaaaga 720
tatatattcc gtaaaattaa aataatattt ttaatatagt cattatgtaa gttagctctt 780
tcgacaaaat cattataaat taggccattt tgtaagttag ttcttttatc gacaagccat 840
tataacttag gtaattttgt aagttagctg gactataacc aatttttttg tttcacatct 900
agagtataaa acacatatat attgaccgta caactttagt caaattagaa actctgtttt 960
atctgcagaa aagaaaaaaa aagaggatga attatgtaaa tacttcagga ttagaaataa 1020
tgtcatcgta tatctcttga tatgaataca tattttactt gactagtacc gtagtcggca 1080
ggaaaatgac acaaacaacc atctaaaaag ataaagtaag aactaaaaag tcttgacatt 1140
cattagttta atcattttct gttaacatat atggaaaaaa caaacttcac cgttatttac 1200
ctgaatttac ctatttgggt aagaattgta cctctggacc tctagtattt tatatacacc 1260
taaaaatata attttggtcg ggaaaatata actctgttta attaattaaa ttttcagtat 1320
tgtgtaagtg taattataga aatcaatttt atccgcgtaa caaaataata taaaattata 1380
ctttcaaatc cacgaatata tattgtgaag tctcatagtt tgcaaataag cattggtctt 1440
cggccgacaa aaaaaaaagc attggtcttc gaatattttg aatatcggac caatggtata 1500
taattaataa tatgtggtat ataaatacat atttatttaa atcacaatag gatatgcaat 1560
gtgtgtatat atacatatac gtaattaaag tccgggttaa actgatagca tatattataa 1620
tagatgcatc tataattgtt cgtcaacaaa agcattatca tgtattttga attaagcttc 1680
cttcatttct gtgaatcaaa aggcctcaga agaagaaact aaagtcaaac aatcaacggg 1740
atccaataaa tcacatctgg actatatagt atcaatactt tccacactaa aaaagctaag 1800
aaatttaata aatacattat tataggggggg aaaaaaaggt agtcatcaga tatatatttt 1860
ggtaagaaaa tatagaaatg aataatttca cgtttaacga agaggagatg acgtgtgttc 1920
cttcgaaccc gagttttgtt cgtctataaa tagcaccttc tcttctcctt cttcctcact 1980
tccatctttt tagcttcact atctctctat aatcggtttt atctttctct aagtcacaac 2040
ccaaaaaaac aaagtagaga agaatctgta agttgtactc cagcttgtgc catgatgatc 2100
acattcgtta tctatttttt ggcacaagct tgagtacaac tgattggctc ttcttactac 2160
aatgaaaaag gccgaggcaa aacgcctaaa atcacttgag aatcaattct ttttactgtc 2220
catttaagct atcttttata aacgtgtctt attttctatc tcttttgttt aaactaagaa 2280
actatagtat tttgtctaaa acaaaacatg aaagaacaga ttagatctca tctttagtct 2340
ctttctccgg tgcagtcagc caccgtcggg taagtttcat ctgtatttta ttaattaatt 2400
acaattatta gtgttcttat taccgttttg gtaaaattag ttaattaatg tcggtccaaa 2460
cattctaaac caattattct gaaaagggtg aacgccaatc agttatatac aatattctta 2520
cattaaagta gaatcggaga tgttacatac taaccaaaag ttacatatac tagtatcatt 2580
ttctttaaga tttgtttagg atttactcac tttatagtgc tcgcggttgg ggtcagggta 2640
agtggggaac agatatgctc tgcatgaacc acgtggacca acatgcatat acacagttac 2700
atttattttt tctagtaggt tcatttgcaa attttccagt atcttgtatg ttatcttcat 2760
ggtgagtttt ttggtcgcat attcttggtg attcttcttc tacgttttca ctttcttctt 2820
cagagacctt attaatatgt taattgcatg aatttatgta acattcaaga aaaagagatc 2880
gaatacaaga aaccggaaat ttaatttcta atttgaattc tatgcatgtt tgtttctttg 2940
ccaatttagt acgaatatat ttatggtccg gagttctaac caaagatagt tgctctgtat 3000
atagaagtta tacatctcgc ttgtttaaac taaataacta tttagtttgt cttggtagtc 3060
cagtgacttt ctgcaaacat tgggatttat aatatagtca aaacgttggg atatgtagta 3120
ttcattttcg ttgtaaaaat cattatattt tgcaaaggtt gcaacgtaaa acgttgtatt 3180
gaatttagga gaaagtagcc atttacaatg aattttagtg acaaactgtt gtatacagcc 3240
tgtgccacta agtatgtcta tatctaaatt tggaatggat gataaccagt attggtcaat 3300
aatggataat ttggtattta gaattactaa tttggtattt tagtgacaaa ctgttgtatg 3360
gaatttagga gaacgcgttc ccaagctata tattatatgt atttcattct ttcatatgtt 3420
atattatgaa ttgttataaa aaagaccaat gagcaacggt ttaaggttta atcagtaatc 3480
gatccgacca atcatataca agttcctaac acatcttcta actactgagt aaaatagtaa 3540
tgctattaca aaggtttttt cttttcaaaa tacagcctaa tgctactaca aaattctaat 3600
gttataaaat aatcatagga gaagtaaacc ccggtattta attaatacct tacaaactta 3660
cattattgat aaagttgaat gaagagttat atggtccatt tagtattatt tacttaatat 3720
gatactagtg ttagacgtgt tactgtattt caacgtgcat aatcaggttg ttcaaaaaga 3780
gagaggatag gtcttcttct tctgtaattt gctgggaccg caagtcatgt gaggctgctc 3840
tgctgatgct gcacggcgtc gcaactctct caataaattc ttttaactaa cgctccaatt 3900
ttcgatgtaa attggctgac ttcaattcta tgccttactc ttgtactcta tgtttcttta 3960

```
tctattaaaa tccaactctg cttttgaacc caaaaaacaa                      4000

SEQ ID NO: 37          moltype = DNA  length = 4000
FEATURE                Location/Qualifiers
misc_feature           1..4000
                       note = Plasmid-7: GEiGS_ mir390a _si-PDS_1
source                 1..4000
                       mol_type = other DNA
                       organism = synthetic construct
SEQUENCE: 37
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
cacttttatg agaaaatgta tcttaaaaaa tgttattcat caaagcttag atgcgctata  240
ggggaacata atcattattt gaaaagaacc aattcaaata tttttttttt taagagttaa  300
aatcctatat aacataacca tccaaacttt gggcatgaac acaacaatat ttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aattttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcattttct gttaacatat atggaaaaaa caaacttcac cgttatttac  1200
ctgaatttac ctatttgggt aagaattgta cctctggacc tctagtattt tatatacacc  1260
taaaaatata attttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatattttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tatagggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta tatccacaca aactacctgc aatgatgatc  2100
acattcgtta tctatttttt tgcaggtagt gtgtgtggat agattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tgggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
gagaggatag gtcttcttct tctgtaattt gctgggaccg caagtcatgt gaggctgctc  3840
tgctgatgct gcacggcgtc gcaactctct caataaattc ttttaactaa cgctccaatt  3900
ttcgatgtaa attggctgac ttcaattcta tgccttactc ttgtactcta tgtttcttta  3960
tctattaaaa tccaactctg cttttgaacc caaaaaacaa                      4000

SEQ ID NO: 38          moltype = DNA  length = 4000
```

-continued

```
FEATURE                Location/Qualifiers
misc_feature           1..4000
                       note = Plasmid-8: GEiGS_ mir390a _si-PDS_2
source                 1..4000
                       mol_type = other DNA
                       organism = synthetic construct
SEQUENCE: 38
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
cacttttatg agaaaatgta tcttaaaaaa tgttattcat caaagcttag atgcgctata  240
ggggaacata atcattattt gaaaagaacc aattcaaata tttttttttt taagagttaa  300
aatcctatat aacataacca tccaaacttt gggcatgaac acaacaatat tttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aattttttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcattttct gttaacatat atggaaaaaa caaacttcac cgttatttac  1200
ctgaatttac ctatttgggt aagaattgta cctctggacc tctagtattt tatatacacc  1260
taaaaatata attttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatattttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tatagggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta tgacaatcca gccaatccag catgatgatc  2100
acattcgtta tctatttttt gctggattgg atggattgtc agattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tgggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
gagaggatag gtcttcttct tctgtaattt gctgggaccg caagtcatgt gaggctgctc  3840
tgctgatgct gcacggcgtc gcaactctct caataaattc ttttaactaa cgctccaatt  3900
ttcgatgtaa attggctgac ttcaattcta tgccttactc ttgtactcta tgtttcttta  3960
tctattaaaa tccaactctg cttttgaacc caaaaaacaa                        4000

SEQ ID NO: 39          moltype = DNA  length = 22
FEATURE                Location/Qualifiers
misc_feature           1..22
                       note = Single strand oligonucleotide
```

```
source                  1..22
                        mol_type = other DNA
                        organism = synthetic construct
SEQUENCE: 39
ttcgcttgca gagagaaatc ac                                            22

SEQ ID NO: 40           moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 40
aagctcagga gggatagcgc c                                             21

SEQ ID NO: 41           moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 41
cttgcagaga gaaatcacag tgg                                           23

SEQ ID NO: 42           moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 42
gcttacacag agaatcacag agg                                           23

SEQ ID NO: 43           moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 43
aagaatctgt aaagctcagg agg                                           23

SEQ ID NO: 44           moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 44
ctatccatcc tgagtttcat tgg                                           23

SEQ ID NO: 45           moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 45
aagtcgtgct gcttcatgtg g                                             21

SEQ ID NO: 46           moltype = DNA  length = 22
FEATURE                 Location/Qualifiers
misc_feature            1..22
                        note = Single strand oligonucleotide
source                  1..22
                        mol_type = other DNA
                        organism = synthetic construct
SEQUENCE: 46
ccacataagc aggacgagtt aa                                            22

SEQ ID NO: 47           moltype = DNA  length = 21
FEATURE                 Location/Qualifiers
misc_feature            1..21
```

```
                          note = Single strand oligonucleotide
source                    1..21
                          mol_type = other DNA
                          organism = synthetic construct
SEQUENCE: 47
agttgtactc cagcttgtgc c                                                21

SEQ ID NO: 48             moltype = DNA  length = 21
FEATURE                   Location/Qualifiers
misc_feature              1..21
                          note = Single strand oligonucleotide
source                    1..21
                          mol_type = other DNA
                          organism = synthetic construct
SEQUENCE: 48
gcaaagctgc agtacaacta a                                                21

SEQ ID NO: 49             moltype = DNA  length = 21
FEATURE                   Location/Qualifiers
misc_feature              1..21
                          note = Single strand oligonucleotide
source                    1..21
                          mol_type = other DNA
                          organism = synthetic construct
SEQUENCE: 49
tatccacaca aactacctgc a                                                21

SEQ ID NO: 50             moltype = DNA  length = 21
FEATURE                   Location/Qualifiers
misc_feature              1..21
                          note = Single strand oligonucleotide
source                    1..21
                          mol_type = other DNA
                          organism = synthetic construct
SEQUENCE: 50
gcagtagtta gtgtggataa a                                                21

SEQ ID NO: 51             moltype = DNA  length = 21
FEATURE                   Location/Qualifiers
misc_feature              1..21
                          note = Single strand oligonucleotide
source                    1..21
                          mol_type = other DNA
                          organism = synthetic construct
SEQUENCE: 51
tgacaatcca gccaatccag c                                                21

SEQ ID NO: 52             moltype = DNA  length = 21
FEATURE                   Location/Qualifiers
misc_feature              1..21
                          note = Single strand oligonucleotide
source                    1..21
                          mol_type = other DNA
                          organism = synthetic construct
SEQUENCE: 52
ctgattggca ggattgtcaa a                                                21

SEQ ID NO: 53             moltype = DNA  length = 21
FEATURE                   Location/Qualifiers
misc_feature              1..21
                          note = Single strand oligonucleotide
source                    1..21
                          mol_type = other DNA
                          organism = synthetic construct
SEQUENCE: 53
taaagatcgg caacacatga t                                                21

SEQ ID NO: 54             moltype = DNA  length = 19
FEATURE                   Location/Qualifiers
misc_feature              1..19
                          note = Single strand oligonucleotide
source                    1..19
                          mol_type = other DNA
                          organism = synthetic construct
SEQUENCE: 54
tcagtgttgg cgatcttta                                                   19

SEQ ID NO: 55             moltype = DNA  length = 21
FEATURE                   Location/Qualifiers
```

```
misc_feature           1..21
                       note = Single strand oligonucleotide
source                 1..21
                       mol_type = other DNA
                       organism = synthetic construct
SEQUENCE: 55
tgacctttct tgggtttagc c                                            21

SEQ ID NO: 56          moltype = DNA  length = 19
FEATURE                Location/Qualifiers
misc_feature           1..19
                       note = Single strand oligonucleotide
source                 1..19
                       mol_type = other DNA
                       organism = synthetic construct
SEQUENCE: 56
gctaacccat gaaaggtca                                               19

SEQ ID NO: 57          moltype = DNA  length = 102
FEATURE                Location/Qualifiers
misc_feature           1..102
                       note = Single strand oligonucleotide
source                 1..102
                       mol_type = other DNA
                       organism = synthetic construct
SEQUENCE: 57
taagtacttt cgcttgcaga gagaaatcac agtggtcaaa aaagttgtag ttttcttaaa  60
gtctctttcc tctgtgattc tctgtgtaag cgaaagagct tg                     102

SEQ ID NO: 58          moltype = DNA  length = 102
FEATURE                Location/Qualifiers
misc_feature           1..102
                       note = Single strand oligonucleotide
source                 1..102
                       mol_type = other DNA
                       organism = synthetic construct
SEQUENCE: 58
taagtactta agtcgtgctg cttcatgtgg agtggtcaaa aaagttgtag ttttcttaaa  60
gtctctttcc tctccacata agcaggacga gttaagagct tg                     102

SEQ ID NO: 59          moltype = DNA  length = 102
FEATURE                Location/Qualifiers
misc_feature           1..102
                       note = Single strand oligonucleotide
source                 1..102
                       mol_type = other DNA
                       organism = synthetic construct
SEQUENCE: 59
taagtactta gttgtactcc agcttgtgcc agtggtcaaa aaagttgtag ttttcttaaa  60
gtctctttcc tctggcaaag ctgcagtaca actaagagct tg                     102

SEQ ID NO: 60          moltype = DNA  length = 102
FEATURE                Location/Qualifiers
misc_feature           1..102
                       note = Single strand oligonucleotide
source                 1..102
                       mol_type = other DNA
                       organism = synthetic construct
SEQUENCE: 60
taagtacttt atccacacaa actacctgca agtggtcaaa aaagttgtag ttttcttaaa  60
gtctctttcc tcttgcagta gttagtgtgg ataaagagct tg                     102

SEQ ID NO: 61          moltype = DNA  length = 102
FEATURE                Location/Qualifiers
misc_feature           1..102
                       note = Single strand oligonucleotide
source                 1..102
                       mol_type = other DNA
                       organism = synthetic construct
SEQUENCE: 61
taagtacttt gacaatccag ccaatccagc agtggtcaaa aaagttgtag ttttcttaaa  60
gtctctttcc tctgctgatt ggcaggattg tcaaagagct tg                     102

SEQ ID NO: 62          moltype = DNA  length = 102
FEATURE                Location/Qualifiers
misc_feature           1..102
                       note = Single strand oligonucleotide
source                 1..102
                       mol_type = other DNA
```

```
                        organism = synthetic construct
SEQUENCE: 62
taagtacttt aaagatcggc aacacatgat agtggtcaaa aaagttgtag ttttcttaaa     60
gtctctttcc tctgatcagt gttggcgatc tttaagagct tg                       102

SEQ ID NO: 63           moltype = DNA   length = 102
FEATURE                 Location/Qualifiers
misc_feature            1..102
                        note = Single strand oligonucleotide
source                  1..102
                        mol_type = other DNA
                        organism = synthetic construct
SEQUENCE: 63
taagtacttt gacctttctt gggtttagcc agtggtcaaa aaagttgtag ttttcttaaa     60
gtctctttcc tctgggctaa cccatgaaag gtcaagagct tg                       102

SEQ ID NO: 64           moltype = DNA   length = 107
FEATURE                 Location/Qualifiers
misc_feature            1..107
                        note = Single strand oligonucleotide
source                  1..107
                        mol_type = other DNA
                        organism = synthetic construct
SEQUENCE: 64
gtagagaaga atctgtaaag ctcaggaggg atagcgccat gatgatcaca ttcgttatct     60
atttttggc gctatccatc ctgagtttca ttggctcttc ttactac                   107

SEQ ID NO: 65           moltype = DNA   length = 107
FEATURE                 Location/Qualifiers
misc_feature            1..107
                        note = Single strand oligonucleotide
source                  1..107
                        mol_type = other DNA
                        organism = synthetic construct
SEQUENCE: 65
gtagagaaga atctgtaaag tcgtgctgct tcatgtggat gatgatcaca ttcgttatct     60
attttttcca catgaagaag cacgacttga ttggctcttc ttactac                  107

SEQ ID NO: 66           moltype = DNA   length = 107
FEATURE                 Location/Qualifiers
misc_feature            1..107
                        note = Single strand oligonucleotide
source                  1..107
                        mol_type = other DNA
                        organism = synthetic construct
SEQUENCE: 66
gtagagaaga atctgtaagt tgtactccag cttgtgccat gatgatcaca ttcgttatct     60
attttttggc acaagcttga gtacaactga ttggctcttc ttactac                  107

SEQ ID NO: 67           moltype = DNA   length = 107
FEATURE                 Location/Qualifiers
misc_feature            1..107
                        note = Single strand oligonucleotide
source                  1..107
                        mol_type = other DNA
                        organism = synthetic construct
SEQUENCE: 67
gtagagaaga atctgtatat ccacacaaac tacctgcaat gatgatcaca ttcgttatct     60
attttttgc aggtagtgtg tgtggataga ttggctcttc ttactac                   107

SEQ ID NO: 68           moltype = DNA   length = 107
FEATURE                 Location/Qualifiers
misc_feature            1..107
                        note = Single strand oligonucleotide
source                  1..107
                        mol_type = other DNA
                        organism = synthetic construct
SEQUENCE: 68
gtagagaaga atctgtatga caatccagcc aatccagcat gatgatcaca ttcgttatct     60
attttttgct ggattggatg gattgtcaga ttggctcttc ttactac                  107

SEQ ID NO: 69           moltype = DNA   length = 107
FEATURE                 Location/Qualifiers
misc_feature            1..107
                        note = Single strand oligonucleotide
source                  1..107
                        mol_type = other DNA
                        organism = synthetic construct
SEQUENCE: 69
```

-continued

```
gtagagaaga atctgtataa agatcggcaa cacatgatat gatgatcaca ttcgttatct  60
attttttatc atgtgttacc gatctttaca ttggctcttc ttactac               107

SEQ ID NO: 70          moltype = DNA  length = 107
FEATURE                Location/Qualifiers
misc_feature           1..107
                       note = Single strand oligonucleotide
source                 1..107
                       mol_type = other DNA
                       organism = synthetic construct
SEQUENCE: 70
gtagagaaga atctgtatga cctttcttgg gtttagccat gatgatcaca ttcgttatct  60
atttttggc taaaccccag aaaggtcaca ttggctcttc ttactac                107

SEQ ID NO: 71          moltype = DNA  length = 4100
FEATURE                Location/Qualifiers
misc_feature           1..4100
                       note = Single strand oligonucleotide
source                 1..4100
                       mol_type = other DNA
                       organism = synthetic construct
SEQUENCE: 71
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaataccttta acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac attttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac tttttttttt  1440
ttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aattttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact ttcgcttgca gagagaaatc acagtggtca aaaaagttgt  2100
agttttctta aagtctcttt cctctgtgat tctctgtgta agcgaaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
```

-continued

```
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
aagatatagg aacatgtaat catgcggctc tccatacaat acatcttgtt gacaaagttc  3600
ccaagacctc attctacaaa ccaatgtttc tttttctttt ttctttttgg tgatagtttt  3660
tgcaatcaaa tgttgtaaaa ctatgattgg aaatactact gtattttacc gaaaacttta  3720
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtcttttttta ggatttgttg  3960
atttttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                              4100

SEQ ID NO: 72           moltype = DNA  length = 4100
FEATURE                 Location/Qualifiers
misc_feature            1..4100
                        note = Single strand oligonucleotide
source                  1..4100
                        mol_type = other DNA
                        organism = synthetic construct
SEQUENCE: 72
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaataccttta acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac attttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac tttttttttt  1440
ttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aatttttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact taagtcgtgc tgcttcatgt ggagtggtca aaaaagttgt  2100
agtttctta aagtctcttt cctctccaca taagcaggac gagttaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
```

```
gtagagcatt catagtgtct tgccaatatg gtgtgatcaa cgaagtttga caaaaccgtg  3540
aagatatagg aacatgtaat catgcggctc tccatacaat acatcttgtt gacaaagttc  3600
ccaagacctc attctacaaa ccaatgtttc tttttcttt ttctttttgg tgatagtttt  3660
tgcaatcaaa tgttgtaaaa ctatgattgg aaatactact gtattttacc gaaaacttta  3720
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtcttttta ggatttgttg  3960
attttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                               4100

SEQ ID NO: 73          moltype = DNA  length = 4100
FEATURE                Location/Qualifiers
misc_feature           1..4100
                       note = Single strand oligonucleotide
source                 1..4100
                       mol_type = other DNA
                       organism = synthetic construct
SEQUENCE: 73
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaataccttat acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac attttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac ttttttttt  1440
tttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aattttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact tagttgtact ccagcttgtg ccagtggtca aaaaagttgt  2100
agttttctta aagtctcttt cctctggcaa agctgcagta caactaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
```

-continued

```
aagatatagg aacatgtaat catgcggctc tccatacaat acatcttgtt gacaaagttc  3600
ccaagacctc attctacaaa ccaatgtttc tttttttcttt ttctttttgg tgatagtttt  3660
tgcaatcaaa tgttgtaaaa ctatgattgg aaatactact gtattttacc gaaaacttta  3720
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtcttttttta ggatttgttg  3960
attttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                              4100

SEQ ID NO: 74          moltype = DNA  length = 4100
FEATURE                Location/Qualifiers
misc_feature           1..4100
                       note = Single strand oligonucleotide
source                 1..4100
                       mol_type = other DNA
                       organism = synthetic construct
SEQUENCE: 74
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaatacctta acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac atttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac ttttttttt  1440
tttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aattttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact ttatccacac aaactacctg caagtggtca aaaaagttgt  2100
agttttctta aagtctcttt cctcttgcag tagttagtgt ggataaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
aagatatagg aacatgtaat catgcggctc tccatacaat acatcttgtt gacaaagttc  3600
```

```
ccaagacctc attctacaaa ccaatgtttc ttttttcttt ttctttttgg tgatagtttt  3660
tgcaatcaaa tgttgtaaaa ctatgattgg aaatactact gtattttacc gaaaacttta  3720
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttatttg tttcatatta tagaatgtct tggaaagttc tatgtaaatt  3900
taaatgtatt tagtaacttg tgacgatttt atattatgta gtcttttta ggatttgttg  3960
attttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                               4100
```

```
SEQ ID NO: 75          moltype = DNA  length = 4100
FEATURE                Location/Qualifiers
misc_feature           1..4100
                       note = Single strand oligonucleotide
source                 1..4100
                       mol_type = other DNA
                       organism = synthetic construct
SEQUENCE: 75
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaatacctta acgcttcgtt tgctggaatg tgtaccacca ttagtagaag  420
aaagtataat aagactatta atgcaagaga tttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac attttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac tttttttttt  1440
tttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aattttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact ttgacaatcc agccaatcca gcagtggtca aaaaagttgt  2100
agttttctta aagtctcttt cctctgctga ttggcaggat tgtcaaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
aagatatagg aacatgtaat catgcggctc tccatacaat acatcttgtt gacaaagttc  3600
ccaagacctc attctacaaa ccaatgtttc ttttttcttt ttctttttgg tgatagtttt  3660
```

```
tgcaatcaaa tgttgtaaaa ctatgattgg aaatactact gtattttacc gaaaacttta  3720
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtcttttttta ggatttgttg  3960
attttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                              4100

SEQ ID NO: 76          moltype = DNA  length = 4100
FEATURE                Location/Qualifiers
misc_feature           1..4100
                       note = Single strand oligonucleotide
source                 1..4100
                       mol_type = other DNA
                       organism = synthetic construct
SEQUENCE: 76
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaatacctta acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac attttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac tttttttttt  1440
ttttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aattttttttg ccatttgatt ggttagtata ggagaattta  1620
aaaacgacga taaggtttag gtaaattatt tcatttgaaa ataattgagc accgttaata  1680
attttcatcc ataaaataat atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact ttaaagatcg gcaacacatg atagtggtca aaaaagttgt  2100
agttttctta aagtctcttt cctctgatca gtgttggcga tctttaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgtttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
aagatatagg aacatgtaat catgcggctc tccatacaat acatcttgtt gacaaagttc  3600
ccaagacctc attctacaaa ccaatgtttc tttttttcttt ttcttttttgg tgatagtttt  3660
tgcaatcaaa tgttgtaaaa ctatgattgg aaatactact gtattttacc gaaaacttta  3720
```

```
ttatatatag tcattaacac tcattaccaa tcacataatc aatagtctat tttgattata  3780
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtctttttta ggatttgttg  3960
atttttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                             4100

SEQ ID NO: 77           moltype = DNA  length = 4100
FEATURE                 Location/Qualifiers
misc_feature            1..4100
                        note = Single strand oligonucleotide
source                  1..4100
                        mol_type = other DNA
                        organism = synthetic construct
SEQUENCE: 77
cacttatcat ttagacagta gattttaaat ttgtatttac aatttcaaaa ctgaaattca  60
tttgtaatca aagaaaaaca aaacaagaaa agggaggagg agtgggattt gggttgctta  120
acagtattat atatacacgt cgttagttaa tcaataaatt atgagcaggt gtagtagcta  180
tgaacatggt tttaccaaat tggtaaattc atgtcattgt tgtagcactt tagcgaggcc  240
agcaaaatgg cgttcttgga aagggcatgg cggcccgtgg ccgccaggga tatgtgtgca  300
gctagaagga ttagaaggag taacttcacc tttttgtaga aactgtaaat tgccaagacg  360
ctcgtttggt aaataccttta acgcttcgtt tgctggaatg tgtaccacca ttagtagaag  420
aaagtataat aagactatta atgcaagaga ttttttcata ttccttttct aagagtagaa  480
tggaatgaat aaatgaatga atgaaatagg gtttttcttg tttagatcct gtcgcacccg  540
agaataatag aagctgaatt aattggtgaa gagttttatg gtggcgatgt tgtatttata  600
gagggaaatg atttcaagtt tacaatggga tttttaattt gttttgttga ctattatctt  660
gcggagagat cttgactgtt gacatgtatg tagtgtttgt tattaaaata aatgcatttt  720
tgtagacccg attcttaaat atgttaggca tggtcaaatt gttagactgt aaaagcttga  780
gtagagacat cggtcaactt tgtttacaag aattctctat aaaatattat acaaattgat  840
cggtagaaat tagatggaac attttgaatt aatgtttgac aatgtataaa ttggtttggt  900
caatatctag gaatgaaaac aagagctgct tcaaagttgt tccattctta agtatacata  960
gaggtggctt gatgggaagt ttcatggaag tgtagtttta tatctacttc caaattcgtt  1020
gatctgtttc ttatctcaag ctaaacatgt ttagaaaaga tgtgttaaaa acatgtgaca  1080
aaaaaagagt caaatgtttg gcaaacaagg tacttagatt tttggcatct attcaaatat  1140
aatagaatcc caaaattatg atatttgtca atcaaatttg aaaaaaaaaa aaaaaaaaaa  1200
aaagattcta caaaagatca aacgtattgc cgtagattta tcataatttt aattctttca  1260
cactaccact agtccactac catatagtga tgagataatc cataatcata aataagatat  1320
aactttcgaa ttcttgtttt tgttgcctca aagttgttgg atcattattt tttacgtaaa  1380
tgtggcttaa tgagaattta tgtttgtggg aattgtagtt tgcttccaac tttttttttt  1440
ttttttttgaa cacgtagttt gcttccaact tagtttatct ttttcttatt tcaagttaaa  1500
catgtaaaaa aacatgtgac gacgaaattc aatcagttcc tccaatgttt ggcagaagcc  1560
aaatctttgg taaacaaagt aatttttttg ccatttgatt ggttagtata ggagaattta  1620
aaaacgacga taaggtttag gtaaattatt tcatttgaaa ataattgagc accgttaata  1680
attttcatcc ataaaatatt atttcaaaga tgatatttga tccccattaa attcattcgt  1740
aaccaaaaaa aagttatgaa aaaagagtgg tcgtgtgagt tgcccaagca ccattataat  1800
aaaaaataaa ataattagca agtaataagg aataaaatcc tgtaattata gctgaaaaag  1860
gaaaaatatt tggagaccgt cagattcgaa tctgaacaaa gcataaaaaa gtcaacaaaa  1920
cttaaagcgg cggtctcatc gtaatctcag cccaataccc tattttcctc tcccctatat  1980
aaatactttc ttcttctact gatcttcttc tcacaaataa acccaaatat atcaatctac  2040
tgtgttggtg attaagtact ttgacctttc ttgggtttag ccagtggtca aaaaagttgt  2100
agtttctta aagtctcttt cctctgggct aacccatgaa aggtcaagag cttgctccct  2160
aaacttatct ctctgatgat ttaatgttag agatcttcgt aaatctatgt gtttgataga  2220
tctgatgcgt tttttgagtt gatgatttga ttatttttca ctggaaagta tctcattagg  2280
gtaacgataa tgttttatgg atttggttgt ataacagatc catgaaatct tgactggtta  2340
taaaatctga ataatgtatt tcaatttgga gattcggtga taaaaattac tgatttacga  2400
atgacattta tatcgataga tgagtttgct gatttggttg ttaaattgat aaatcaagga  2460
catgagaaac tgtttttgta tgctaatttg tccatggaat aaaattggga ggtgaggacc  2520
gtgagggtag tcaggaaacc ttaatattga agttgatgtt gaaccaacaa atctgcccaa  2580
aaatgataaa agttgatgcc gagcccacaa attttgatga caatcgataa gcccaagccc  2640
aaaaggcatc tgtacctgag cccattattc tttcattact agcaaaaagg atgcattaga  2700
gaccccggtg tagtaaattg acctcacaat tcactattgt attgtatacg tacatttcaa  2760
gcgtaattaa accctcatat ttttatacgc tttaaatata attggccttt aattagctca  2820
aataaactag atgtcgtacg tgatcacggt ggatgaaatc aatggtatta tgaaaagact  2880
gtacatgatt tcaaatattt taatgtggtc gtaaaaattg ttgtttatag tggaaattga  2940
agacaacaac gttactgaaa cacatacaga ttgaaatttc gatcatttac ttgcaaagtg  3000
ttaccgtgga ggcgtggcgt ggacgtaagg taccataatg gtttgtgtta cagtcacgcc  3060
actacactcg aattcaagct accatattat aatacgttgt tgattagaaa aaatagtcgc  3120
caattttctt taaaacaaat ttcagttttt atttgtcagc aaaaaaaact tactaacaca  3180
acggaagaac acaaaaatta gggagttgct cacagagcaa aagtaataga aatgggaaaa  3240
gctaatatac gtccgagtag gaaactaatc ttgcaaaaac tgatgaaagc aatcagaagc  3300
cttgacgttt gtctggagag aggaattgtg ttttggatca ctttgttcag tttgttgtgg  3360
atcgtcttcc gttacgttct caccaaaaat atttcataat gaaacaaaaa aattaattaa  3420
taatggtagc ttagaatgcc aagttgagaa cagatttgca gtttgtcccg gaatgatcaa  3480
gtagagcatt catagtgtct tgccaatatg gtgtgatcaa cgaagtttga caaaaccgtg  3540
aagatatagg aacatgtaat catgcggctc tccatacaat acatcttgtt gacaaagttc  3600
ccaagacctc attctacaaa ccaatgtttc ttttttcttt ttctttttgg tgatagtttt  3660
tgcaatcaaa tgttgtaaaa ctatgattgg aaatactact gtattttacc gaaaacttta  3720
ttatatatag tcattaacac tcattaccaa tcacataatc aatagtctat tttgattata  3780
```

```
caacttttaa acaataaaga catgtttata cagatttggt ttaaattagt actccctata  3840
ttttagaaaa ttttattttg tttcatatta tagaatgtct tggaaagttc tatgtaaatt  3900
taaatgtatt tagtaacttg tgacgatttt atattatgta gtctttttta ggatttgttg  3960
atttttttaaa ataaattttt taaagaaaaa aaacaaatta ttttaataaa catgccttta  4020
ccttatacag tttatatttt gaaagagaga tagtatgttt taggatatat ttaaagaaaa  4080
aaaaataact ctttaattta                                              4100

SEQ ID NO: 78          moltype = DNA  length = 4000
FEATURE                Location/Qualifiers
misc_feature           1..4000
                       note = Single strand oligonucleotide
source                 1..4000
                       mol_type = other DNA
                       organism = synthetic construct
SEQUENCE: 78
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
cacttttatg agaaaatgta tcttaaaaaa tgttattcat caaagcttag atgcgctata  240
ggggaacata atcattattt gaaaagaacc aattcaaata tttttttttt taagagttaa  300
aatcctatat aacataacca tccaaacttt gggcatgaac acaacaatat ttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aattttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcattttct gttaacatat atggaaaaaa caaacttcac cgttatttac  1200
ctgaatttac ctatttgggt aagaattgta cctctggacc tctagtattt tatatacacc  1260
taaaaatata attttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatatttttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tataggggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta aagctcagga gggatagcgc catgatgatc  2100
acattcgtta tctatttttt ggcgctatcc atcctgagtt tcattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tgggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
gagaggatag gtcttcttct tctgtaattt gctgggaccg caagtcatgt gaggctgctc  3840
```

-continued

```
tgctgatgct gcacggcgtc gcaactctct caataaattc ttttaactaa cgctccaatt  3900
ttcgatgtaa attggctgac ttcaattcta tgccttactc ttgtactcta tgtttcttta  3960
tctattaaaa tccaactctg cttttgaacc caaaaaacaa                        4000

SEQ ID NO: 79          moltype = DNA  length = 4000
FEATURE                Location/Qualifiers
misc_feature           1..4000
                       note = Single strand oligonucleotide
source                 1..4000
                       mol_type = other DNA
                       organism = synthetic construct
SEQUENCE: 79
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
cacttttatg agaaaatgta tcttaaaaaa tgttattcat caaagcttag atgcgctata  240
ggggaacata atcattattt gaaaagaacc aattcaaata tttttttttt taagagttaa  300
aatcctatat aacataacca tccaaacttt gggcatgaac acaacaatat ttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aattttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcattttct gttaacatat atggaaaaaa caaacttcac cgttatttac  1200
ctgaatttac ctatttgggt aagaattgta cctctggacc tctagtattt tatatacacc  1260
taaaaatata atttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatattttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tataggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta aagtcgtgct gcttcatgtg gatgatgatc  2100
acattcgtta tctatttttt ccacatgaag aagcacgact tgattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tgggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
gagaggatag gtcttcttct tctgtaattt gctgggaccg caagtcatgt gaggctgctc  3840
tgctgatgct gcacggcgtc gcaactctct caataaattc ttttaactaa cgctccaatt  3900
ttcgatgtaa attggctgac ttcaattcta tgccttactc ttgtactcta tgtttcttta  3960
tctattaaaa tccaactctg cttttgaacc caaaaaacaa                        4000
```

```
SEQ ID NO: 80          moltype = DNA  length = 4000
FEATURE                Location/Qualifiers
misc_feature           1..4000
                       note = Single strand oligonucleotide
source                 1..4000
                       mol_type = other DNA
                       organism = synthetic construct
SEQUENCE: 80
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
cacttttatg agaaaatgta tcttaaaaaa tgttattcat caaagcttag atgcgctata  240
ggggaacata atcattattt gaaaagaacc aattcaaata ttttttttt taagagttaa  300
aatcctatat aacataacca tccaaacttt gggcatgaac acaacaatat tttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aattttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcattttct gttaacatat atggaaaaaa caaacttcac cgttatttac  1200
ctgaatttac ctatttgggt aagaattgta cctctggacc tctagtattt tatatacacc  1260
taaaaatata attttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatattttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tataggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta agttgtactc cagcttgtgc catgatgatc  2100
acattcgtta tctatttttt ggcacaagct tgagtacaac tgattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
gagaggatag gtcttcttct tctgtaattt gctgggaccg caagtcatgt gaggctgctc  3840
tgctgatgct gcacggcgtc gcaactctct caataaattc ttttaactaa cgctccaatt  3900
ttcgatgtaa attggctgac ttcaattcta tgccttactc ttgtactcta tgtttcttta  3960
tctattaaaa tccaactctg cttttgaacc caaaaaacaa                        4000

SEQ ID NO: 81          moltype = DNA  length = 4000
FEATURE                Location/Qualifiers
```

```
misc_feature            1..4000
                        note = Single strand oligonucleotide
source                  1..4000
                        mol_type = other DNA
                        organism = synthetic construct
SEQUENCE: 81
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
cacttttatg agaaaatgta tcttaaaaaa tgttattcat caaagcttag atgcgctata  240
ggggaacata atcattattt gaaaagaacc aattcaaata tttttttttt taagagttaa  300
aatcctatat aacataacca tccaaacttt gggcatgaac acaacaatat ttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aattttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcatttct gttaacatat atggaaaaaa caaacttcac cgttatttac  1200
ctgaatttac ctatttgggt aagaattgta cctctggacc tctagtattt tatatacacc  1260
taaaaatata attttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatattttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tatagggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta tatccacaca aactacctgc aatgatgatc  2100
acattcgtta tctattttt tgcaggtagt gtgtgtggat agattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tgggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
gagaggatag gtcttcttct tctgtaattt gctgggaccg caagtcatgt gaggctgctc  3840
tgctgatgct gcacggcgtc gcaactctct caataaattc ttttaactaa cgctccaatt  3900
ttcgatgtaa attggctgac ttcaattcta tgccttactc ttgtactcta tgtttcttta  3960
tctattaaaa tccaactctg cttttgaacc caaaaaacaa                        4000

SEQ ID NO: 82           moltype = DNA  length = 4000
FEATURE                 Location/Qualifiers
misc_feature            1..4000
                        note = Single strand oligonucleotide
source                  1..4000
```

```
                       mol_type = other DNA
                       organism = synthetic construct
SEQUENCE: 82
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
cacttttatg agaaaatgta tcttaaaaaa tgttattcat caaagcttag atgcgctata  240
ggggaacata atcattattt gaaaagaacc aattcaaata ttttttttt taagagttaa  300
aatcctatat aacataacca tccaaacttt gggcatgaac acaacaatat tttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aatttttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcattttct gttaacatat atggaaaaaa caaacttcac cgttatttac  1200
ctgaatttac ctatttgggt aagaattgta cctctggacc tctagtattt tatatacacc  1260
taaaaatata attttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatattttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tataggggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta tgacaatcca gccaatccag catgatgatc  2100
acattcgtta tctatttttt gctggattgg atggattgtc agattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tgggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
gagaggatag gtcttcttct tctgtaattt gctgggaccg caagtcatgt gaggctgctc  3840
tgctgatgct gcacggcgtc gcaactctct caataaattc ttttaactaa cgctccaatt  3900
ttcgatgtaa attggctgac ttcaattcta tgccttactc ttgtactcta tgtttcttta  3960
tctattaaaa tccaactctg cttttgaacc caaaaaacaa                       4000

SEQ ID NO: 83          moltype = DNA  length = 4000
FEATURE                Location/Qualifiers
misc_feature           1..4000
                       note = Single strand oligonucleotide
source                 1..4000
                       mol_type = other DNA
                       organism = synthetic construct
SEQUENCE: 83
```

```
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
cacttttatg agaaaatgta tcttaaaaaa tgttattcat caaagcttag atgcgctata  240
ggggaacata atcattattt gaaaagaacc aattcaaata tttttttttt taagagttaa  300
aatcctatat aacataacca tccaaacttt gggcatgaac acaacaatat tttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aattttttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcattttct gttaacatat atggaaaaaa caaacttcac cgttatttac  1200
ctgaatttac ctatttgggt aagaattgta cctctggacc tctagtattt tatatacacc  1260
taaaaatata attttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatattttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tataggggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta taaagatcgg caacacatga tatgatgatc  2100
acattcgtta tctatttttt atcatgtgtt accgatcttt acattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tgggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
gagaggatag gtcttcttct tctgtaattt gctgggaccg caagtcatgt gaggctgctc  3840
tgctgatgct gcacggcgtc gcaactctct caataaattc ttttaactaa cgctccaatt  3900
ttcgatgtaa attggctgac ttcaattcta tgccttactc ttgtactcta tgtttcttta  3960
tctattaaaa tccaactctg cttttgaacc caaaaaacaa  4000
```

```
SEQ ID NO: 84          moltype = DNA  length = 4000
FEATURE                Location/Qualifiers
misc_feature           1..4000
                       note = Single strand oligonucleotide
source                 1..4000
                       mol_type = other DNA
                       organism = synthetic construct
SEQUENCE: 84
accctcattg attttggtgg ccaaactctt gatcgtattc ttttaggaac agtaattaat  60
tttaaatttg agaaaaatgt agtgatgaaa gtgagatata tgggacgcac tattgaaagc  120
attgtccaca ccgcatgatg tgagattgat gtgaatatgg taactaataa cacccagact  180
```

-continued

```
cacttttatg agaaaatgta tcttaaaaaa tgttattcat caaagcttag atgcgctata  240
ggggaacata atcattattt gaaaagaacc aattcaaata tttttttttt taagagttaa  300
aatcctatat aacataacca tccaaacttt gggcatgaac acaacaatat tttttttcgt  360
ttttgataaa ttctttcaat tgcaatcaaa acttaccagc tatacaaatg tttgctgcat  420
ccaatctaat acaccgttaa acaataaaat ttgttatctc tcaaatctga tcatctattc  480
caacctgact gttttattct agtattttaa ggccaggtat aacgaaaaca aagaaaaaag  540
ttcagcgacc aagacatttt gacatcaggc tcaaacggtc aaacccacga aaacttttac  600
ctcatttctt aaccacgcag tgttatttga atagccttaa taggctaata caaaacaaca  660
agccatcgat tacagtttta actataatat tacaaaatct taaaccaaaa caagaaaaga  720
tatatattcc gtaaaattaa aataatattt ttaatatagt cattatgtaa gttagctctt  780
tcgacaaaat cattataaat taggccattt tgtaagttag ttcttttatc gacaagccat  840
tataacttag gtaattttgt aagttagctg gactataacc aatttttttg tttcacatct  900
agagtataaa acacatatat attgaccgta caactttagt caaattagaa actctgtttt  960
atctgcagaa aagaaaaaaa aagaggatga attatgtaaa tacttcagga ttagaaataa  1020
tgtcatcgta tatctcttga tatgaataca tattttactt gactagtacc gtagtcggca  1080
ggaaaatgac acaaacaacc atctaaaaag ataaagtaag aactaaaaag tcttgacatt  1140
cattagttta atcattttct gttaacatat atggaaaaaa caaacttcac cgttatttac  1200
ctgaatttac ctatttgggt aagaattgta cctctggacc tctagtattt tatatacacc  1260
taaaaatata attttggtcg ggaaaatata actctgttta attaattaaa ttttcagtat  1320
tgtgtaagtg taattataga aatcaatttt atccgcgtaa caaaataata taaaattata  1380
ctttcaaatc cacgaatata tattgtgaag tctcatagtt tgcaaataag cattggtctt  1440
cggccgacaa aaaaaaaagc attggtcttc gaatattttg aatatcggac caatggtata  1500
taattaataa tatgtggtat ataaatacat atttatttaa atcacaatag gatatgcaat  1560
gtgtgtatat atacatatac gtaattaaag tccgggttaa actgatagca tatattataa  1620
tagatgcatc tataattgtt cgtcaacaaa agcattatca tgtattttga attaagcttc  1680
cttcatttct gtgaatcaaa aggcctcaga agaagaaact aaagtcaaac aatcaacggg  1740
atccaataaa tcacatctgg actatatagt atcaatactt tccacactaa aaaagctaag  1800
aaatttaata aatacattat tataggggg aaaaaaaggt agtcatcaga tatatatttt  1860
ggtaagaaaa tatagaaatg aataatttca cgtttaacga agaggagatg acgtgtgttc  1920
cttcgaaccc gagttttgtt cgtctataaa tagcaccttc tcttctcctt cttcctcact  1980
tccatctttt tagcttcact atctctctat aatcggtttt atctttctct aagtcacaac  2040
ccaaaaaaac aaagtagaga agaatctgta tgacctttct tgggtttagc catgatgatc  2100
acattcgtta tctatttttt ggctaaaccc cagaaaggtc acattggctc ttcttactac  2160
aatgaaaaag gccgaggcaa aacgcctaaa atcacttgag aatcaattct ttttactgtc  2220
catttaagct atcttttata aacgtgtctt attttctatc tcttttgttt aaactaagaa  2280
actatagtat tttgtctaaa acaaaacatg aaagaacaga ttagatctca tctttagtct  2340
ctttctccgg tgcagtcagc caccgtcggg taagtttcat ctgtatttta ttaattaatt  2400
acaattatta gtgttcttat taccgttttg gtaaaattag ttaattaatg tcggtccaaa  2460
cattctaaac caattattct gaaaagggtg aacgccaatc agttatatac aatattctta  2520
cattaaagta gaatcggaga tgttacatac taaccaaaag ttacatatac tagtatcatt  2580
ttctttaaga tttgtttagg atttactcac tttatagtgc tcgcggttgg ggtcagggta  2640
agtggggaac agatatgctc tgcatgaacc acgtggacca acatgcatat acacagttac  2700
atttattttt tctagtaggt tcatttgcaa attttccagt atcttgtatg ttatcttcat  2760
ggtgagtttt ttggtcgcat attcttggtg attcttcttc tacgttttca ctttcttctt  2820
cagagacctt attaatatgt taattgcatg aatttatgta acattcaaga aaaagagatc  2880
gaatacaaga aaccggaaat ttaatttcta atttgaattc tatgcatgtt tgtttctttg  2940
ccaatttagt acgaatatat ttatggtccg gagttctaac caaagatagt tgctctgtat  3000
atagaagtta tacatctcgc ttgtttaaac taaataacta tttagtttgt cttggtagtc  3060
cagtgacttt ctgcaaacat tgggatttat aatatagtca aaacgttggg atatgtagta  3120
ttcattttcg ttgtaaaaat cattatattt tgcaaaggtt gcaacgtaaa acgttgtatt  3180
gaatttagga gaaagtagcc atttacaatg aattttagtg acaaactgtt gtatacagcc  3240
tgtgccacta agtatgtcta tatctaaatt tggaatggat gataaccagt attggtcaat  3300
aatggataat ttggtattta gaattactaa tttggtattt tagtgacaaa ctgttgtatg  3360
gaatttagga gaacgcgttc ccaagctata tattatatgt atttcattct ttcatatgtt  3420
atattatgaa ttgttataaa aaagaccaat gagcaacggt ttaaggttta atcagtaatc  3480
gatccgacca atcatataca agttcctaac acatcttcta actactgagt aaaatagtaa  3540
tgctattaca aaggtttttt cttttcaaaa tacagcctaa tgctactaca aaattctaat  3600
gttataaaat aatcatagga gaagtaaacc ccggtattta attaatacct tacaaactta  3660
cattattgat aaagttgaat gaagagttat atggtccatt tagtattatt tacttaatat  3720
gatactagtg ttagacgtgt tactgtattt caacgtgcat aatcaggttg ttcaaaaaga  3780
gagaggatag gtcttcttct tctgtaattt gctgggaccg caagtcatgt gaggctgctc  3840
tgctgatgct gcacggcgtc gcaactctct caataaattc ttttaactaa cgctccaatt  3900
ttcgatgtaa attggctgac ttcaattcta tgccttactc ttgtactcta tgtttcttta  3960
tctattaaaa tccaactctg cttttgaacc caaaaaaacaa                        4000
```

```
SEQ ID NO: 85          moltype = DNA  length = 19
FEATURE                Location/Qualifiers
misc_feature           1..19
                       note = Single strand oligonucleotide
source                 1..19
                       mol_type = other DNA
                       organism = synthetic construct
SEQUENCE: 85
acaccctggg aattggttt                                               19

SEQ ID NO: 86          moltype = DNA  length = 20
FEATURE                Location/Qualifiers
misc_feature           1..20
                       note = Single strand oligonucleotide
```

```
source                 1..20
                       mol_type = other DNA
                       organism = synthetic construct
SEQUENCE: 86
gtatgcgcca ataagaccac                                              20

SEQ ID NO: 87          moltype = DNA  length = 20
FEATURE                Location/Qualifiers
misc_feature           1..20
                       note = Single strand oligonucleotide
source                 1..20
                       mol_type = other DNA
                       organism = synthetic construct
SEQUENCE: 87
gtactgctgg tcctttgcag                                              20

SEQ ID NO: 88          moltype = DNA  length = 20
FEATURE                Location/Qualifiers
misc_feature           1..20
                       note = Single strand oligonucleotide
source                 1..20
                       mol_type = other DNA
                       organism = synthetic construct
SEQUENCE: 88
aggagcacta cggaaggatg                                              20

SEQ ID NO: 89          moltype = DNA  length = 22
FEATURE                Location/Qualifiers
misc_feature           1..22
                       note = Single strand oligonucleotide
source                 1..22
                       mol_type = other DNA
                       organism = synthetic construct
SEQUENCE: 89
gttgagagtg ttggagaagg ag                                           22

SEQ ID NO: 90          moltype = DNA  length = 21
FEATURE                Location/Qualifiers
misc_feature           1..21
                       note = Single strand oligonucleotide
source                 1..21
                       mol_type = other DNA
                       organism = synthetic construct
SEQUENCE: 90
ctcggtgttg atcctgagaa g                                            21

SEQ ID NO: 91          moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 91
agcttccttc atttctgtga atc                                          23

SEQ ID NO: 92          moltype = DNA  length = 21
FEATURE                Location/Qualifiers
misc_feature           1..21
                       note = Single strand oligonucleotide
source                 1..21
                       mol_type = other DNA
                       organism = synthetic construct
SEQUENCE: 92
ctgttcccca cttaccctga c                                            21

SEQ ID NO: 93          moltype = DNA  length = 21
FEATURE                Location/Qualifiers
misc_feature           1..21
                       note = Single strand oligonucleotide
source                 1..21
                       mol_type = other DNA
                       organism = synthetic construct
SEQUENCE: 93
ctcctcatct gattccttct c                                            21

SEQ ID NO: 94          moltype = DNA  length = 21
FEATURE                Location/Qualifiers
misc_feature           1..21
```

-continued

```
                        note = Single strand oligonucleotide
source                  1..21
                        mol_type = other DNA
                        organism = synthetic construct
SEQUENCE: 94
ctgttcccca cttaccctga c                                              21

SEQ ID NO: 95           moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 95
gtgtgtggaa agtttatcaa cac                                            23

SEQ ID NO: 96           moltype = DNA  length = 27
FEATURE                 Location/Qualifiers
misc_feature            1..27
                        note = Single strand oligonucleotide
source                  1..27
                        mol_type = other DNA
                        organism = synthetic construct
SEQUENCE: 96
gttagtatgt aacatctccg attctac                                        27

SEQ ID NO: 97           moltype = DNA  length = 20
FEATURE                 Location/Qualifiers
misc_feature            1..20
                        note = Single strand oligonucleotide
source                  1..20
                        mol_type = other DNA
                        organism = synthetic construct
SEQUENCE: 97
agagtggtcg tgtgagttgc                                                20

SEQ ID NO: 98           moltype = DNA  length = 25
FEATURE                 Location/Qualifiers
misc_feature            1..25
                        note = Single strand oligonucleotide
source                  1..25
                        mol_type = other DNA
                        organism = synthetic construct
SEQUENCE: 98
ccagtcaaga tttcatggat ctgtt                                          25

SEQ ID NO: 99           moltype = DNA  length = 28
FEATURE                 Location/Qualifiers
misc_feature            1..28
                        note = Single strand oligonucleotide
source                  1..28
                        mol_type = other DNA
                        organism = synthetic construct
SEQUENCE: 99
ctaacataat cgagaacaga tggaagac                                       28

SEQ ID NO: 100          moltype = DNA  length = 32
FEATURE                 Location/Qualifiers
misc_feature            1..32
                        note = Single strand oligonucleotide
source                  1..32
                        mol_type = other DNA
                        organism = synthetic construct
SEQUENCE: 100
ttctcatgtc cttgatttat caatttaaca ac                                  32

SEQ ID NO: 101          moltype = DNA  length = 20
FEATURE                 Location/Qualifiers
misc_feature            1..20
                        note = Single strand oligonucleotide
source                  1..20
                        mol_type = other DNA
                        organism = synthetic construct
SEQUENCE: 101
agagtggtcg tgtgagttgc                                                20

SEQ ID NO: 102          moltype = DNA  length = 26
FEATURE                 Location/Qualifiers
```

```
misc_feature          1..26
                      note = Single strand oligonucleotide
source                1..26
                      mol_type = other DNA
                      organism = synthetic construct
SEQUENCE: 102
cgcatcagat ctatcaaaca cataga                                    26

SEQ ID NO: 103        moltype = RNA  length = 277
FEATURE               Location/Qualifiers
misc_feature          1..277
                      note = Single strand oligonucleotide
source                1..277
                      mol_type = other RNA
                      organism = synthetic construct
SEQUENCE: 103
gctactctgg tgaaccatcg ttggccatgc ttgccttatt ctcccatggc aatcttacta  60
cggccgtagg aaacttctcc ggacaagcga ataggcttca cagactctac gaaaacccct  120
aaaacaaaca ctaacaaagg gactgaagag cctaccacca cccaatgcgt cgattactga  180
cgcacgtacg tggtcagcga aggcgctgag ctcgtggtat tggcagcggt gaacagaata  240
atcaaacaag ccaacggtgg tatcatccag aacatct                         277

SEQ ID NO: 104        moltype = RNA  length = 110
FEATURE               Location/Qualifiers
misc_feature          1..110
                      note = Single strand oligonucleotide
source                1..110
                      mol_type = other RNA
                      organism = synthetic construct
SEQUENCE: 104
cgcaaagaaa gaggaggagg atgatgagta aacaaatgca ctctgcatgt tcgatgcaca  60
tgcatctctt gcttgctcat tgatccatct ttcttgctcc ggcaccgagt            110

SEQ ID NO: 105        moltype = RNA  length = 277
FEATURE               Location/Qualifiers
misc_feature          1..277
                      note = Single strand oligonucleotide
source                1..277
                      mol_type = other RNA
                      organism = synthetic construct
SEQUENCE: 105
gaatctgttc tcatcttttc cttaggggtg tttacctgtt ctgccacgtt atctcttctt  60
tccttgattc cgacggaacc aaataatagt ggccaggaca gacagacaac gaaaacccaa  120
aaaacaaaca cgaacaatgt tagtcaattc tggcgtccaa cataacgcat gcaacacgta  180
tgcgcggacg ttgggagtgg aagcattcgc cggaaggaaa cagcaaaggt gaagagaata  240
gagagtgcgt tgaggaggag gatgatgagt aatgacg                         277

SEQ ID NO: 106        moltype = RNA  length = 277
FEATURE               Location/Qualifiers
misc_feature          1..277
                      note = Single strand oligonucleotide
source                1..277
                      mol_type = other RNA
                      organism = synthetic construct
SEQUENCE: 106
gaccaggtta tgaccccgtg ggttcaagac atgccactag cagccgagct aagcctgccg  60
tcactaaaca acctttgtct agagaatacg ctatgctaca aataagcgac gaaaacccta  120
caaacaatct ccaacaacgc tcgttaatag tatactgccg cgaattgcgc taaacactag  180
cgcatgcaag cggcgagctt acgagctccg atgacggtaa cgccaaggtc gaagtgctgg  240
ttcatattgg gattcgtggg gttcactaat ccgccct                         277

SEQ ID NO: 107        moltype = RNA  length = 277
FEATURE               Location/Qualifiers
misc_feature          1..277
                      note = Single strand oligonucleotide
source                1..277
                      mol_type = other RNA
                      organism = synthetic construct
SEQUENCE: 107
ggcccaggta cgatggagtc cattcaggac ttgctagcaa cgcacgcgag gggcgattgg  60
tgtgtcattg aggcttagcg acagataata tataacataa gacgtcctac gaaaaaccta  120
caaacaaaca ctaacaaagg aagtcaagtg ttatcaacct catctagctt ctagaacaga  180
agctcccacg aggtgagtgt aggcattcgc aatattgata ggtaactggc gaatcgttgc  240
tccaaatcag gatggattct attcgatatt tagagaa                         277

SEQ ID NO: 108        moltype = RNA  length = 110
FEATURE               Location/Qualifiers
misc_feature          1..110
                      note = Single strand oligonucleotide
```

```
source                  1..110
                        mol_type = other RNA
                        organism = synthetic construct
SEQUENCE: 108
cgcaaagaaa ctcaaagaaa attttcgata aacaaatgca cttcgcatga acgatgcgtt  60
tgcatccctt gcttgttgaa gtatttatct ttgaggctcc ggcaccgatt            110

SEQ ID NO: 109          moltype = RNA  length = 208
FEATURE                 Location/Qualifiers
misc_feature            1..208
                        note = Single strand oligonucleotide
source                  1..208
                        mol_type = other RNA
                        organism = synthetic construct
SEQUENCE: 109
ttggtgggag ggctaggctg gcggtacgtt attctgaaaa aatattacgg acgtgatgca  60
agcacatatg gatgttgcat gacacggccg gtgcatgtga acaaaaacaa aaccaaggca  120
aaagagcgag agagagagca tgcattgcaa atctgtcgtg tttttttatg ggtggcagcc  180
accctggatg cggcatcctt cagaccga                                     208

SEQ ID NO: 110          moltype = RNA  length = 277
FEATURE                 Location/Qualifiers
misc_feature            1..277
                        note = Single strand oligonucleotide
source                  1..277
                        mol_type = other RNA
                        organism = synthetic construct
SEQUENCE: 110
gctacggtta tggccctacg ggtacgagac gagctgatgt cacccgagtt actcctacat  60
acgctgtatc caacggatcc agagacaata ggggtcaaga ttacgagata gaaaacccag  120
cacacaatat tgaacatttt tttagagttg atccacacca catcgtgcag ttaacacaat  180
tgcaagcacg tggtgagcgc agacgttcga ctgtatgtaa agacaaagtc gaaatgatgt  240
ttctcatcgg tattcgtggg gttcactaat cctatcc                           277

SEQ ID NO: 111          moltype = RNA  length = 277
FEATURE                 Location/Qualifiers
misc_feature            1..277
                        note = Single strand oligonucleotide
source                  1..277
                        mol_type = other RNA
                        organism = synthetic construct
SEQUENCE: 111
gcatctttgc gtccgtcttc cgtgctcgac ttgccggtac ccgccatgac aaacctccga  60
gctatgtgta gtgcctaccc atataacacc catctctaaa cgtattctaa gaaaaaccac  120
aaaacaatcg cgaacaaggg aggcgactag agatccacct catcgagctt tgactactaa  180
agctgctacg gggtcgggta agggcccgag gagtttggaa agtaagtggt gaaggggtgc  240
tacagatttg tatggaagat gagactgcaa aagtacc                           277

SEQ ID NO: 112          moltype = RNA  length = 105
FEATURE                 Location/Qualifiers
misc_feature            1..105
                        note = Single strand oligonucleotide
source                  1..105
                        mol_type = other RNA
                        organism = synthetic construct
SEQUENCE: 112
gaagagaaga atctgtaaag tttagaaagg ataaacaaac cacgatcaca cacatcgata  60
tacttttgtt tgtccattct gagcttcact ggctcttctt acttc                  105

SEQ ID NO: 113          moltype = RNA  length = 208
FEATURE                 Location/Qualifiers
misc_feature            1..208
                        note = Single strand oligonucleotide
source                  1..208
                        mol_type = other RNA
                        organism = synthetic construct
SEQUENCE: 113
tcggtcgggt agttacgctg gcatcgattg atggatagta ataataaagt cagtcttgcg  60
agcacagatg gatgtatcat cacaccacct gtggatgact acaaaaagaa aaccaaggca  120
aaagagcgag agagagagcc cgcagggcaa cggtttcgtt gttactatac cgttgcagcc  180
accgtaaaac ctccctctgc cgaaccga                                     208

SEQ ID NO: 114          moltype = RNA  length = 277
FEATURE                 Location/Qualifiers
misc_feature            1..277
                        note = Single strand oligonucleotide
source                  1..277
                        mol_type = other RNA
                        organism = synthetic construct
```

```
SEQUENCE: 114
gagtcggtta tggccctgtg aattcaggtc atgcgtccct ctgcctagtg aagccacccc  60
tcgctgggga tgtcgtccac agagaacaga acggtctgca gacgcactac gaaaaccatt  120
gaaactagcc caaacaaagt gggtcaccag attgccagct cgcggtgctc acagaacgtg  180
agcaggaaag ggttgaggcc atggtctcgt ccgaggggta agccacagtg gaaaagaggg  240
aacataatgg gattcgtggg gttcactaat ccttgca                           277

SEQ ID NO: 115         moltype = RNA  length = 341
FEATURE                Location/Qualifiers
misc_feature           1..341
                       note = Single strand oligonucleotide
source                 1..341
                       mol_type = other RNA
                       organism = synthetic construct
SEQUENCE: 115
aacgagatgc caacttctca agattgcaaa agcaaccagc tagtacgttg gtacacacca  60
atgggataac cggtcagcaa ttagatcctg ttaccatcaa caggatccga gggctcatcc  120
ccgatgagga atcggatcgg ccatcagatc tcgagcaaga accaagaggt ctgccggtat  180
atctccttag aatccaaaca cgaccagggt tggacccgtt ccttcctcgc ccccaaaaag  240
taagggcgga ggaatgagtt cctggttgtt tcagggagag aatcagcatc atcggcgttg  300
attggtaccg gctttgcagc tggaggggtt ggcaactcgc c                      341

SEQ ID NO: 116         moltype = RNA  length = 103
FEATURE                Location/Qualifiers
misc_feature           1..103
                       note = Single strand oligonucleotide
source                 1..103
                       mol_type = other RNA
                       organism = synthetic construct
SEQUENCE: 116
agagagagct acaggccggc gctggagagc atacgcaggt aattttatta gaaaataact  60
ttgcaggtgc gtgctctcta agcgtcggcc tgcgccatct tgg                    103

SEQ ID NO: 117         moltype = RNA  length = 341
FEATURE                Location/Qualifiers
misc_feature           1..341
                       note = Single strand oligonucleotide
source                 1..341
                       mol_type = other RNA
                       organism = synthetic construct
SEQUENCE: 117
tgggggaggg tccaggcatc agggatgaaa agcaagcagc taccctgttg agacagttcg  60
acaatactac cctaaagcag tgtgattgaa ttactgagaa tttgatcctt ggactcgttg  120
caagcgagca aaagttgggg atgtaacttc gcgaggaagc aggaagcgga gtcatgggtt  180
atcgccagat aaaccaagca cttcgtcagc cccagggtga cctatgtggc ccccgaaaat  240
taagggccta ggtcacgttg tgacggagtt tactggtggg tttgatgagc tcagtatgtc  300
aagggaccca tggttcgtga tagtgtctgg acctaccccg t                      341

SEQ ID NO: 118         moltype = RNA  length = 341
FEATURE                Location/Qualifiers
misc_feature           1..341
                       note = Single strand oligonucleotide
source                 1..341
                       mol_type = other RNA
                       organism = synthetic construct
SEQUENCE: 118
agagtgattt attcgtgggg ttcactaatc cgtaagcaac gctgatgcca tcataggatg  60
gtaatgaagc cggatagata caagttgcta tttccaataa tagcaaccat ggaggctgcg  120
cagcagctca aatggttcgg ggtcagatca tcgggcaatg acgaagatga tcataggggt  180
agcgcgtgag aagccaacca cgctctgcga tcgagcctta actcgagcgc ccacaaaaag  240
gaagggtgga gttaagcctt gtagagcgtt tccgcgcgtg gtagtacagc cgcgcagtat  300
tacgactcct gtggttagta agtccgcgag taagacactg g                      341

SEQ ID NO: 119         moltype = RNA  length = 239
FEATURE                Location/Qualifiers
misc_feature           1..239
                       note = Single strand oligonucleotide
source                 1..239
                       mol_type = other RNA
                       organism = synthetic construct
SEQUENCE: 119
gcggaggtca agttctcctc attataaaca tgaaggtgtc tctcgtccta acacacagcg  60
atcaacaaaa agtaactaac ccacacatat ggtagaaacc aaaaccataa cgtggatacc  120
cttattctgc gtataagttt gacaaaattc gggggaagga accatgtttg tattgggcgg  180
agcaagcgcg tggctcctag agcacgtcgg ccacaaagca cgttggggac caagaacgg   239

SEQ ID NO: 120         moltype = RNA  length = 94
FEATURE                Location/Qualifiers
misc_feature           1..94
```

```
                         note = Single strand oligonucleotide
source                   1..94
                         mol_type = other RNA
                         organism = synthetic construct
SEQUENCE: 120
gggaagtctt ggattgtgga gaatttaaaa agaaataact ttcgtcacga acgaaagcaa  60
ttatttttta acaccaccac agcctaagat tttc                              94

SEQ ID NO: 121           moltype = RNA  length = 225
FEATURE                  Location/Qualifiers
misc_feature             1..225
                         note = Single strand oligonucleotide
source                   1..225
                         mol_type = other RNA
                         organism = synthetic construct
SEQUENCE: 121
caacagaaga gacacccccg aggagagaac ctgctcatct ttaatgtttt ttttgaaaac  60
ctgaccagcg ccgctcctgc ctgcaacaac catccatcag aacaaaaagt tcgtatggcg  120
aaaggccatt gatggtgggc aggtctcccc ttggggaagt ctagcgtcaa cgagctgggg  180
tctgatggtt tcacaattgc taaaacttgt gcttcaggtg acaaa                  225

SEQ ID NO: 122           moltype = RNA  length = 239
FEATURE                  Location/Qualifiers
misc_feature             1..239
                         note = Single strand oligonucleotide
source                   1..239
                         mol_type = other RNA
                         organism = synthetic construct
SEQUENCE: 122
ggggagagca tggattcgtg gttcctgtgg atagccccgc acataatcgc acttcgtccc  60
ataaacaaaa acaaaagaaa ccacacaacc tgtagaaacc aaaacaggtg gcaccgatca  120
cgacccggtg ccgccgctca gacatgagtt atgtgtacac agattcgtgg ggttcactaa  180
tcctaaccac ccagctcgta gcgggtcggg cgtatcactt gggatcggct caagatcgg   239

SEQ ID NO: 123           moltype = RNA  length = 341
FEATURE                  Location/Qualifiers
misc_feature             1..341
                         note = Single strand oligonucleotide
source                   1..341
                         mol_type = other RNA
                         organism = synthetic construct
SEQUENCE: 123
accgtgagat ttttgaggtg agcgagggta gtcaaacaga cgatggtcag taatattatt  60
ggcgctacgc cctttatgta ccatggtgcg ggccgggatt cgtatcacct ggaatcattt  120
cgaatgatga aaggggaggg attagaacgt acgaccaact agcaagtgtg ttgagggatc  180
atctccttta gctccaatca ctagcacagg atgtccttgc tctattctgc ccccaaaaat  240
aaagggcata gggtaaagac tgtgttagtg ctagggagac attcttaagc gctgcatagg  300
aatcggtcct tctaccctct tgatctcaaa gatcacacgt a                      341

SEQ ID NO: 124           moltype = RNA  length = 96
FEATURE                  Location/Qualifiers
misc_feature             1..96
                         note = Single strand oligonucleotide
source                   1..96
                         mol_type = other RNA
                         organism = synthetic construct
SEQUENCE: 124
gacaactggt tattggtgcg gggcgttaag aaaacggtgc tcaatacttt ttgagctccg  60
ctttctgaac gttctgtatt gataacgagt gccacg                            96

SEQ ID NO: 125           moltype = RNA  length = 341
FEATURE                  Location/Qualifiers
misc_feature             1..341
                         note = Single strand oligonucleotide
source                   1..341
                         mol_type = other RNA
                         organism = synthetic construct
SEQUENCE: 125
cgtgggagat aaaattattt ttgatacact agagagcatc tacagttaaa ataaagattt  60
tgagtagcac cccacaggtt tcagtacttt tggctaaata aaagtaccag gttttctttc  120
ctaaagaata attggtgggg gactaagatc tcgcgcaatt atgaagaggt ctgtgggatc  180
agctccctcg aagccaatca cgcttaaggg cccaactaga tcgtctcggc cccctaaaac  240
gaagggttac ggtttacttg cttgagcgtt tcagggggtg atgcgttacc aacggagacg  300
tatgggtccc gcagtgtggg atggtggttt tattacccaa g                      341

SEQ ID NO: 126           moltype = RNA  length = 341
FEATURE                  Location/Qualifiers
misc_feature             1..341
                         note = Single strand oligonucleotide
```

```
source                 1..341
                       mol_type = other RNA
                       organism = synthetic construct
SEQUENCE: 126
gctgggaggg gttagtggag ttacacggat gggaaccacc ctaccttgat ataaacatat  60
taaccataga cagagaggga gaaggtctct ggtcatgctc agagacccaa ggggtctatt  120
ctatagacga attgctttgt aggtgttggc tcgcgaaact aaaaagagtt gagtcgggaa  180
atcgccagat tgaccaatct cacacattgg ggtaacggga ccatcctcgc ccacaaaaag  240
gaagggcggt ggtcctatta ggtgtgtggc gactggcgag ggttcgcagc tacgcagtgg  300
atcgttcccg acattcgtgg ggttcactaa tcctacccac a                      341

SEQ ID NO: 127         moltype = RNA  length = 193
FEATURE                Location/Qualifiers
misc_feature           1..193
                       note = Single strand oligonucleotide
source                 1..193
                       mol_type = other RNA
                       organism = synthetic construct
SEQUENCE: 127
gggttcttcc agaagggcgg acaaccaacg gcgaccgccc cctagggacc ccaggcggac  60
gttaagttag gatttcccat ttacattcgg atgggatgtg ggcgagccgc cgtcacgaaa  120
acggcggcag cgccaagagc gctggacgtt cgcagaagac agaacctggt tgctcgctct  180
tctggaagaa cct                                                     193

SEQ ID NO: 128         moltype = RNA  length = 193
FEATURE                Location/Qualifiers
misc_feature           1..193
                       note = Single strand oligonucleotide
source                 1..193
                       mol_type = other RNA
                       organism = synthetic construct
SEQUENCE: 128
gggtttttc agaagggtgg acatccatcg cccatctccg cttgtgcccc ccaggagaag  60
ggtacgccag gatttcggat agagtgacct attcgaggag tttccgccgc tgcctcgaaa  120
gcagcggctg ctccaactga gcagaagaag ctcttaaaac agaacctgga tgctcgctct  180
tctggaagaa cct                                                     193

SEQ ID NO: 129         moltype = RNA  length = 193
FEATURE                Location/Qualifiers
misc_feature           1..193
                       note = Single strand oligonucleotide
source                 1..193
                       mol_type = other RNA
                       organism = synthetic construct
SEQUENCE: 129
gggttctttc aggagggtga acatcccacg ccgacctctc attattgccc ccaggaggat  60
ggtacaactg gtcgtctatt tgaagtgcta agtggaggtg ccccggctgc tgacccgaaa  120
tcagcagcag ctccaaaaga gctggggggg cgctgaatcc agaaccggga tgctcgctct  180
tctggaagaa cct                                                     193

SEQ ID NO: 130         moltype = RNA  length = 193
FEATURE                Location/Qualifiers
misc_feature           1..193
                       note = Single strand oligonucleotide
source                 1..193
                       mol_type = other RNA
                       organism = synthetic construct
SEQUENCE: 130
gcggtggtat tgctttttca tcagcctgcg cccatcacac cagggggcag acatgtgaag  60
ggcaatacag gactactagc ttaaagacgg gctggttggg tagcagctgc aggcgcgaaa  120
tctgcagccg ccccaaaagg gcgggggctg cccacaaggc agaacaaggc tgttggaggg  180
gtaatgccat tgc                                                     193

SEQ ID NO: 131         moltype = RNA  length = 216
FEATURE                Location/Qualifiers
misc_feature           1..216
                       note = Single strand oligonucleotide
source                 1..216
                       mol_type = other RNA
                       organism = synthetic construct
SEQUENCE: 131
gggaatcaga catggcgaga tttcatcggg atctggggcg agggcgaggg cgtgacagtg  60
gggagcgcag tcgatacatg caccaggcac acccagtatc gccttggaaa gcaaggcgca  120
ctgggtccgc cggatgcatg tgacgagtgc aacgcgcccg ctgcaagcat cgcgactcgt  180
tccagattcc gatgattctc cgtcgcactg atgccc                            216

SEQ ID NO: 132         moltype = RNA  length = 89
FEATURE                Location/Qualifiers
misc_feature           1..89
```

```
                        note = Single strand oligonucleotide
source                  1..89
                        mol_type = other RNA
                        organism = synthetic construct
SEQUENCE: 132
catgctatcg gtgcttcgta cggtatttgc agagagcaca tcgaacaccg atggcctccg  60
tggatgtcgt atgtggtgcc gttagtatg                                    89

SEQ ID NO: 133          moltype = RNA  length = 142
FEATURE                 Location/Qualifiers
misc_feature            1..142
                        note = Single strand oligonucleotide
source                  1..142
                        mol_type = other RNA
                        organism = synthetic construct
SEQUENCE: 133
gcggcctgaa acaccgtttg attggtgtgc tggggtcaac gtgtccaatg ccagaagacg  60
tcagcaaggg aagaacaggt gttcctgggc gatgaacgcg ttggtgcttc tacatcaacc  120
gaaggtaaac tttcacgcaa cg                                           142

SEQ ID NO: 134          moltype = RNA  length = 186
FEATURE                 Location/Qualifiers
misc_feature            1..186
                        note = Single strand oligonucleotide
source                  1..186
                        mol_type = other RNA
                        organism = synthetic construct
SEQUENCE: 134
gtggcgtgac ctgagcaagt attcgtgggg ttcactaatc ctgaccgacc cttgcgcagg  60
ccaggcgtcc atgattggta agtcacccca caaagtgcaa gaccagaatg gacagccagg  120
ttgccttaac cagcagaggg tcggcgagcg ttggtgagga ccgccgatgc atgaccacca  180
cgccac                                                             186

SEQ ID NO: 135          moltype = RNA  length = 216
FEATURE                 Location/Qualifiers
misc_feature            1..216
                        note = Single strand oligonucleotide
source                  1..216
                        mol_type = other RNA
                        organism = synthetic construct
SEQUENCE: 135
tggatacacg cgtgggaaga tctggtcttc ttgaccggtc ttggttaggt catgacgggg  60
gtccgcgcag tccactcagg cgctcggcac ccccgctacc ttcacggaaa gtgtgaagcg  120
gcggggcagc cagtcgcctg agaggagtgc aacgcagccc ccgcaagaat aacagaggac  180
tggtcaagaa gactattctg tttcggagtg tagcca                            216

SEQ ID NO: 136          moltype = RNA  length = 83
FEATURE                 Location/Qualifiers
misc_feature            1..83
                        note = Single strand oligonucleotide
source                  1..83
                        mol_type = other RNA
                        organism = synthetic construct
SEQUENCE: 136
tacgtatatt gtgtagttaa tttactcagg tgtgtgtggg gttacggtgc acctccaata  60
gtgaagacta tcagcatcac gta                                          83

SEQ ID NO: 137          moltype = RNA  length = 140
FEATURE                 Location/Qualifiers
misc_feature            1..140
                        note = Single strand oligonucleotide
source                  1..140
                        mol_type = other RNA
                        organism = synthetic construct
SEQUENCE: 137
cccggagttt gtgggcaagt ccgctcgtac gacttcaagg aacagcctcc gaaaacagga  60
gtacatgtga gatagaataa ttcctgggcc ggctccctgt tgtcttgttg tgcgaacaag  120
acatgccggg agctcccggg                                              140

SEQ ID NO: 138          moltype = RNA  length = 186
FEATURE                 Location/Qualifiers
misc_feature            1..186
                        note = Single strand oligonucleotide
source                  1..186
                        mol_type = other RNA
                        organism = synthetic construct
SEQUENCE: 138
aaggtgggag tggagagaga attcgtgggg ttcactaatc ctcactagct ctggccctag  60
aggtgacacc cggatatgga aagctccaca cggtgagaca gccgtaacgg gtgctcaact  120
```

-continued

```
tgggcagagc cagccgggag ctagccagag ttggtggaag ccgccagttc actagctgcc  180
cacctt                                                              186

SEQ ID NO: 139         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 139
tttgcgaggc tagcaactgg attctactat ataaaaacac agacttggaa tcatgtcacc  60
caccaggact ctccgagaat ccccgtccga aagacatgaa cgggtggaaa aagactctca  120
atcatcgacg acaagctaac acaaggtatc cagtaaggta ctctaaagga ggttgatgtg  180
atggagcact gtagaacacg tgctaaactc acatcgacta aagatgagtg ttcaaggtcg  240
tcaagtatcc gagccaggat acaaacgact cacacatatt ggtcctatac cctaaaggat  300
accctccgaa agggcaattc ggacagcaaa agctgtgttt tcctatatgg tagatgtggt  360
tgttagccac gcaaa                                                    375

SEQ ID NO: 140         moltype = RNA  length = 99
FEATURE                Location/Qualifiers
misc_feature           1..99
                       note = Single strand oligonucleotide
source                 1..99
                       mol_type = other RNA
                       organism = synthetic construct
SEQUENCE: 140
tcagcgtatg tagtaggctc tgcttcatca agtggtcttg tgttcaaatt cagctccaag  60
cacatggtca actggattct actatatatg tgaatataa                         99

SEQ ID NO: 141         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 141
cttgcgaggt cagcgtgtcc atccaactta tgtaatgctc ccatgcaatg tttgtccacc  60
ccagaggcct tattttaaag ctgatgctac cagggcaaaa aatggtgaaa aacccatcta  120
gacaattccg atatccaact tcaaggcttc caggtagtat cacgaaacgt gaaacacgtg  180
aaggatcttt gcagagcatg ggataaaatc acgtgttttg gtctggagtt tccaatgaca  240
tcaagtcgca gagccatgcg acaaatgtta cagataaatt gcagtgaata cgacaaggaa  300
gccctcctga cggttaatca gggcggcccg taggggggtat tccattcggg ctcttatgcg  360
cgttgaccac gcaat                                                    375

SEQ ID NO: 142         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 142
aaagagaggg attcgtgggg ttcactaatc cgttagcctc acacccctta ttccctcacc  60
tctcatgcct tagaatgaag caccagtcac tagagggaaa aaaggcgaaa aacccttcca  120
aacaatagtg agcaccaaac ccaaggtaag cagctggtag cttgaagcaa gttatacggg  180
gcggaaaaca gaagatctcg ttttaaaccc ccgtataaga accaagagcg ctcactggcc  240
ccaagtttct gagccaagaa acaagggtca cagctgtgtt gttgctacta caagaagttt  300
acccaccaga aggccaatct ggttagcacg gggtggggct accacgggtt agtaagtctg  360
cggatcccac tcttc                                                    375

SEQ ID NO: 143         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 143
attgtgaggc caaacagaag attaaggggt tgtctaccgc tcacctatta ctgtcacacc  60
tagcatgccc agaacctgtg caccctccac aagtgatagc aatggcgaaa aaaccatcca  120
accaacagtg ctccagaaaa ccaaggcttc caggacggat ctctaaggga gacaataggg  180
tgggatatat gaagatcatt gtataaaggt cctgttgtgc cagtaggttc cacaccctct  240
ccaataggct gagccaagct taaagagagg ccgacggaac gtatacaatt cattaaggaa  300
gcccactagt agcgcaagct agtcaccaga gggagcggta gccacaattc cttatgtttt  360
gtttggtcac acaaa                                                    375

SEQ ID NO: 144         moltype = RNA  length = 125
```

-continued

```
FEATURE                Location/Qualifiers
misc_feature           1..125
                       note = Single strand oligonucleotide
source                 1..125
                       mol_type = other RNA
                       organism = synthetic construct
SEQUENCE: 144
cactgtgcgg tctctaatac gactgttcag agtgatgaac cggtttccgc gcggaacgga  60
ggagcgggcg ccggcgccga attggatcgt tcctctgagc agctgtatcg gaggccgcgg  120
tgaac                                                              125

SEQ ID NO: 145         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 145
tttgagaggc caggaaggat attacgatga tgaatcccac atacttgatt gttactcacc  60
ttgcaagccc accgtgtgag ctcccaccat tagagtaact gtaggggaaa aaacctagac  120
ttcaactgac cttcacaaac acaaggtttc cagtcggtat cactaacggt gataaaagtt  180
tcggtacctt ctagaagatg ggtaaaaaaa acttttattg atttagagca aacactttat  240
gcaatggtca gagccatgac caaatatgga cagacttgtt gtaacaaata cggaaaggaa  300
acccaccaca agggcaatgt ggtaagcaaa agatgtggga tcctcattgt cgtggctcct  360
tcttggtcac tcaac                                                   375

SEQ ID NO: 146         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 146
gatgagaggt ttggaggggt aatgccattg cgttgcacac atacttccac tttgcccacc  60
cctcatggcg ccgacggcac caccagcaaa tagggcaaac agagaccaaa aattcttata  120
cacaaacact cgcggcaaat acaaggtaac cagtgagggc gaccaaaggt ttgtctagcg  180
agggtactcg gcagagctag ggtaaaagtt gctggacacg taactgacat cgaaagatct  240
gcaagtgtct gagccaagac ataatagatc cggaggatgt gggtccagct cccaaaggtt  300
acccaccagg aggacaactt ggtcatcata agatgtgtgc gccatgtggt ggcttctctt  360
tccaaaccac tcata                                                   375

SEQ ID NO: 147         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 147
aacgagaggt atgataaaac atgcttatga atgaaatcac tcactgcgcc cattcccaac  60
ccggatgcct tatgatgaag cacgcgattc gagggaatga attagggata aagctaacta  120
cgcaaactaa taccacaaag tcaaggttgc cagaggggaa cacgaaccgt gataagagag  180
gaggctcgcc gtagaacgcg tgggaaaact tctcttatga gacttgtgag aacaattacc  240
acaagatccc gagccaggga tcaatggtga ccgagtctta ggagcaattc cactaaggta  300
acccacccga agggcaattg ggtaatcaac aggagtggtt tgccatttgt aagatctttt  360
gtcgtatcac tcgtc                                                   375

SEQ ID NO: 148         moltype = RNA  length = 111
FEATURE                Location/Qualifiers
misc_feature           1..111
                       note = Single strand oligonucleotide
source                 1..111
                       mol_type = other RNA
                       organism = synthetic construct
SEQUENCE: 148
catgtttgga tactagttaa tattaatgtt taaagctact ctacaaaaaa tatatgatat  60
atttccggta gagtagcttt aaatattgat attggctagt atccaaacag a           111

SEQ ID NO: 149         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 149
tttgggaggt ctagttaata ttaatgttta atttaatctc agactattat ttgtcacacc  60
```

-continued

```
actaatgcct gaggctcaag caccagaaat aagtgacaac attggtgtaa aatccagcct  120
cccaagtcaa atcgaacaat tcaaggctgc cagatagtct cactaagggt ggttaaagcg  180
agggtggcgt gtagaacacc gtcaaaaatc gctttagcgc gtcgagattt cgcaatatct  240
tcaagtctct gagccaagag ataaaagata cccaagaaat gtcgttaaga ccataaggca  300
gcccacctga agggcaatca ggttatcatt agctggggtt gccagttgtg ctccacgttg  360
agtggatcac ccaac                                                  375

SEQ ID NO: 150         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 150
gacgtgaggt ttggaggggt aatgccattg cgtaaacccc cgactcagaa ttctcccacc  60
gcacagcgca agctccttac gtcctgacaa gagggagaac attggggaaa aagccagcca  120
cacaagtaac taaagcaaaa tgaaggtgtc cagaaacttc ccccaagggg gtaaaacgtg  180
tggggttgcc gaagatcgtg cgacaaagac acgttttagg gtttcgagcg cgcaattact  240
ccaagtgact gagccaagtt ataagagtga ccgaagcgtt ggaatgagga gcttaggggc  300
acccgcctgg agggcaaccg ggcaagcagg agcgggggtt tccacgcggt ggcttctccc  360
tctgaatcac acgtg                                                  375

SEQ ID NO: 151         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 151
gtagcgaggt cgaatcttgt ttataactta agtttgtcgc taacctggcg cagtctcacc  60
tcaccagcca tagactatag ctcctgtcat aagagattga aatggttaaa aacccataca  120
tacaaatctg atacccaaac tcaaggattc caggaagtat ggccaatggt caattcagtc  180
atgggtcaca gcagagctcg tggcaaactg actggattac acttaggttt cccagtcacg  240
tcaactgtcc gagccaggac agaaacgtga ggcacgaagc gtaacggata catcaaggaa  300
tccctcctga aggacaatta gggcaacaaa ggtagcggca gccacttggg ttgaaccgag  360
gttcgatcac gctag                                                  375

SEQ ID NO: 152         moltype = RNA  length = 102
FEATURE                Location/Qualifiers
misc_feature           1..102
                       note = Single strand oligonucleotide
source                 1..102
                       mol_type = other RNA
                       organism = synthetic construct
SEQUENCE: 152
gtgaagccac tggatggatc ggttcaatcc tctcttccgg aatcgttgtt gaacataaga  60
acctagaatc gaggattaaa cttatttatt tagcgctcac tc                    102

SEQ ID NO: 153         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 153
gttgtgaggg cgaatcttgt ttataactta actaaatcac ccactcaagt ctgcgtcacc  60
actcatattt taggctaagg taccaggcca tagacgtagt aatggagaaa aaaccatcga  120
atcaaaacta ccctacaaaa ccaaggtttc cgatgagtat cactacgagt gaaaatagct  180
ggggagttta gaagatctgg ggctaaaacg gctgttttgc cctttgagta tacattgtct  240
gcaagagtct gagccaagac tcaacagata ccgagatact ggaatgaata cccaaaggaa  300
accctcccta agggcaatag gggcaccacg aggggtggtt tccagttggg ttgggtgaag  360
attcgctcac gcaaa                                                  375

SEQ ID NO: 154         moltype = RNA  length = 375
FEATURE                Location/Qualifiers
misc_feature           1..375
                       note = Single strand oligonucleotide
source                 1..375
                       mol_type = other RNA
                       organism = synthetic construct
SEQUENCE: 154
gatgtgagta attcgtgggg ttcactaatc cggttaccac agacagccta atgacacacc  60
acacatgcca agccgcttag cacctgccac aagtgttata aacgccgaaa aatgcgtcaa  120
cacaaccatt tgaaccaaag acaaggtacc cagcaagtat ctccaaagga ggaataagtg  180
agggtgtccg agagactcgg ggcaaaaatt acttgttcag cgttggtgtt cgcattctca  240
ccaagctcct gagccaagga gcaagtgaga ctcaggaaca gtaaaaaata cctgaagggt  300
```

-continued

```
accctccacg aggacaacgt gggcatgacc tgctgtggta gctccgggtt ggtaagtctg  360
cggattacac gcata                                                   375

SEQ ID NO: 155         moltype = RNA  length = 367
FEATURE                Location/Qualifiers
misc_feature           1..367
                       note = Single strand oligonucleotide
source                 1..367
                       mol_type = other RNA
                       organism = synthetic construct
SEQUENCE: 155
agtaccgagg gaaacgagat gctgctcata taatggcgga tagccccaac ttcacaacta  60
tcgggccttc cggtgcacga gcggaggttc ttagagctag caagtccctc ggtaagattc  120
cacagcctgt gggacagcta ctcacagggc cctaccggac agctggaagt agacttggta  180
tgcctgacgt aacagaccag ttactcagac agccaaatcc atatcgtaca aatgatagga  240
aagagggatc ttaccgaggg aaccaattaa ctctaagaac cctcactaag tgaccgggag  300
agctggtagt tatggattga gggctaaaag ctattgtatg ggtagcattc tgtttccctc  360
gatactg                                                            367

SEQ ID NO: 156         moltype = RNA  length = 87
FEATURE                Location/Qualifiers
misc_feature           1..87
                       note = Single strand oligonucleotide
source                 1..87
                       mol_type = other RNA
                       organism = synthetic construct
SEQUENCE: 156
cacgtcagca cgacaggatg ccaatgcaaa aaaacgtgtc cttgagggcg cgtttttttg  60
cattggcatc ctgtcacgct gacgtgg                                     87

SEQ ID NO: 157         moltype = RNA  length = 168
FEATURE                Location/Qualifiers
misc_feature           1..168
                       note = Single strand oligonucleotide
source                 1..168
                       mol_type = other RNA
                       organism = synthetic construct
SEQUENCE: 157
ggaggacaac atgccaatgc aaaaaaagtt ttggtagaag gagacggtac gcagagcaga  60
agaggaacgg tggacttaac tgagaccatc ttctcctaga taagatctca caaacccctc  120
tccatgcaga tctactaagg atctgctgcg ttggtgtgtt gtcctccc               168

SEQ ID NO: 158         moltype = RNA  length = 372
FEATURE                Location/Qualifiers
misc_feature           1..372
                       note = Single strand oligonucleotide
source                 1..372
                       mol_type = other RNA
                       organism = synthetic construct
SEQUENCE: 158
gtggacggtc attcgtgggg ttcactaatc caaaagaaga ccgcagatcc aaaggacaag  60
ttaagggcca tgttgcccct agacacagag gatggcccgg cggtgtcact gggttagggg  120
aggacctctg ggcgaaggaa atcagagcac acggcctggc tctatcttga acccgtgcat  180
agtaaacggc agatgtgggt aagaacacca cattatgcac gggttggaga cggacccagg  240
ccaaaattcg gaacatggct cccctaacct ggtgacaccg ccaggccata ggggcaaaac  300
atgaccctta attcatctat tgggtccgcg agctccttac ggattagtga actttgcggt  360
tgaccgtgca cc                                                      372

SEQ ID NO: 159         moltype = RNA  length = 367
FEATURE                Location/Qualifiers
misc_feature           1..367
                       note = Single strand oligonucleotide
source                 1..367
                       mol_type = other RNA
                       organism = synthetic construct
SEQUENCE: 159
cgtaccacgg tggcagggag aagagaacga taattgcaaa ttgcccctgc gtctcgcatt  60
acgggctaaa ctgttccggc tagtagggac aatgagctag caagtctatc tgtggttaga  120
aacaccctgt actacaggca agtacgggac cagacatggc agcgtgactc agacggggca  180
cgccagtagt ttcagcccag agacactgac ggccccaacg acataaaaca atttatgcgt  240
aatattctaa ctacagatag aaccaactaa ctcattgttc ccacgagaac ggatagtttg  300
agccgtggtg caagaccaga gggcaaaagg caattgtcgt tctctttttg ttgccgccgt  360
gatacga                                                            367

SEQ ID NO: 160         moltype = RNA  length = 101
FEATURE                Location/Qualifiers
misc_feature           1..101
                       note = Single strand oligonucleotide
source                 1..101
```

```
                         mol_type = other RNA
                         organism = synthetic construct
SEQUENCE: 160
gttgcaaaca gaagattaag gggttagatg atggcgtgca atcaggagtc ttgaagcaat  60
gcatcccact cctttggtct cttgatgctt ctgttttcac c                      101

SEQ ID NO: 161           moltype = RNA  length = 214
FEATURE                  Location/Qualifiers
misc_feature             1..214
                         note = Single strand oligonucleotide
source                   1..214
                         mol_type = other RNA
                         organism = synthetic construct
SEQUENCE: 161
ggctgtcggc ctcgctaggt atgtttaaca atgttatgcc aagcggtggg ccaaaaactc  60
gaaaaacaac ccctttgagg agtaggcgct gcagtcaaac cctgtactcc ccgacgggat  120
ctccgatgag atcggagaca aaacacgggt ctaaaaccga gcatagacac cagggcacaa  180
tattgttaag tgtccttggt ggcaccagcc gccc                              214

SEQ ID NO: 162           moltype = RNA  length = 367
FEATURE                  Location/Qualifiers
misc_feature             1..367
                         note = Single strand oligonucleotide
source                   1..367
                         mol_type = other RNA
                         organism = synthetic construct
SEQUENCE: 162
tgggccaagg tattcgtggg gttcactaat cctcggcaca acgccccttc tccgctgaaa  60
accggcgtaa cattacctgt acgcatgccc atagagcgag ccagccgcac tgtctctacg  120
aacagccagt tttacagcta aaaactgggc cccatccggc agcggaagga ataccaggca  180
tgccgctagg aacagtctag ttccagcgac agcctgaaca cgttcataca agtgaattgt  240
aatatcgtag agacagtgcg gaccaactcc ctctatgggc gcgcctaaaa ggagtgttac  300
agcggttttc gatggaaaga gggcgtaaag ctgagggttg gtgagtcctt tggatacctt  360
gactcat                                                            367

SEQ ID NO: 163           moltype = RNA  length = 367
FEATURE                  Location/Qualifiers
misc_feature             1..367
                         note = Single strand oligonucleotide
source                   1..367
                         mol_type = other RNA
                         organism = synthetic construct
SEQUENCE: 163
ggtaccatgg tgcacagcag tatttgtgta tatgtgccga acgccccctc atctcgtggc  60
aggggcaaat cattcagagg tcgtatggtc tctgtgccag ccagcctttc agccgtccta  120
aataaccagg ttgacagtca caatctgggc accactcgtc agcgagagga acacggggta  180
tgccaatgtt gacaggaaag tcagattgcc ggccctaaca acttcttaca aaagaagtgt  240
aagattagga cggctgaaag gaccaattga cgcggggacc acacaataat ctaatgattt  300
agccctgcca caaggtagga gggcgtaatg cacatgtaca cgaatactgg tgtgcaccat  360
gatacca                                                            367

SEQ ID NO: 164           moltype = RNA  length = 101
FEATURE                  Location/Qualifiers
misc_feature             1..101
                         note = Single strand oligonucleotide
source                   1..101
                         mol_type = other RNA
                         organism = synthetic construct
SEQUENCE: 164
gctgttgggt ggagttccag agtaaagatg agggagtgca attaggagtc ttgaagcaat  60
gcatccccgt ccttttttgct ctggaatctt cattcatcac c                     101

SEQ ID NO: 165           moltype = RNA  length = 148
FEATURE                  Location/Qualifiers
misc_feature             1..148
                         note = Single strand oligonucleotide
source                   1..148
                         mol_type = other RNA
                         organism = synthetic construct
SEQUENCE: 165
agaggagccc ctggtcgatc atggtacgca atgaacgtcg tcatgtatcg acctaaggac  60
aatcggcagt gattaacttt cttaaacaga cccgagcatg acacatggcg accctcatag  120
tgtgcttggg tccgttacgg actccgac                                     148

SEQ ID NO: 166           moltype = RNA  length = 372
FEATURE                  Location/Qualifiers
misc_feature             1..372
                         note = Single strand oligonucleotide
source                   1..372
```

```
                        mol_type = other RNA
                        organism = synthetic construct
SEQUENCE: 166
ggggtcggcc attcgtgggg ttcactaatc caacgtgtga ccggcggggc ggagctcaca  60
tatagtgcct ggtagcctca agagtcggag gtttgcccta ctgtcggtca gtgtttgggg  120
gggacctcct tacgaaggaa aaaggagcaa gcggccaggc tgtataaaga acccttggga  180
ttaacatggc actagcgggt aagaacaccg ctaatttcaa gggttgttta cataccttgg  240
ccaaaagacc aaacacatcc ccccaaacgt tgactggcgg tgaggcagtt gaggctaaac  300
cagacgctat atgcaagcac tgtcccctcg agcagacgac gggttggtgg gtcctgtgat  360
tggccgagcc cc                                                      372

SEQ ID NO: 167          moltype = RNA  length = 206
FEATURE                 Location/Qualifiers
misc_feature            1..206
                        note = Single strand oligonucleotide
source                  1..206
                        mol_type = other RNA
                        organism = synthetic construct
SEQUENCE: 167
gggtgccgaa gcaatccgag gctttttact tgggtgcttg gtcggcaggg aatcaaactc  60
tcgcgtgaat tatgccgttg tcgtcgccct atctcgttcc ggggagccct aaaacctgac  120
taaataatta tagccttcaa tgtgatgagt tgtgatgata gccgaaccaa gggcctgatc  180
aagaagttcc ggacatttcg gcaccc                                       206

SEQ ID NO: 168          moltype = RNA  length = 104
FEATURE                 Location/Qualifiers
misc_feature            1..104
                        note = Single strand oligonucleotide
source                  1..104
                        mol_type = other RNA
                        organism = synthetic construct
SEQUENCE: 168
ggcgcgagct accacaagat gtacggcaaa cggccgggcg tgacggcacc ggcggtcgtg  60
ccgtcgcggc cgcttgctgt atgatctttg tggtagccgg tgcc                   104

SEQ ID NO: 169          moltype = RNA  length = 139
FEATURE                 Location/Qualifiers
misc_feature            1..139
                        note = Single strand oligonucleotide
source                  1..139
                        mol_type = other RNA
                        organism = synthetic construct
SEQUENCE: 169
aaggtccgga accgaacggc aagagagctc ggcaagggcc tgatcaagaa ctcttggatc  60
tcaagccaag gagtgggtgg ctgatggggg ttcttggttc tgtccttatc gagcgggcca  120
agttcacgct atcagcctt                                               139

SEQ ID NO: 170          moltype = RNA  length = 206
FEATURE                 Location/Qualifiers
misc_feature            1..206
                        note = Single strand oligonucleotide
source                  1..206
                        mol_type = other RNA
                        organism = synthetic construct
SEQUENCE: 170
gggggcccat ccaatctgag gattcgtggg gttcactaat ccccccctaaa agtgactcac  60
acgtccgggc gagccttttc gcgatgaccg atctcgagcc ggtgttcacg caaaaacatc  120
ccacgaaagc ttgaatccag ggtgtagtga gctcacgtct ggggagggtt gatgagccat  180
gcgggtcccc agacagatgg gccccc                                       206

SEQ ID NO: 171          moltype = RNA  length = 206
FEATURE                 Location/Qualifiers
misc_feature            1..206
                        note = Single strand oligonucleotide
source                  1..206
                        mol_type = other RNA
                        organism = synthetic construct
SEQUENCE: 171
gggagccccg ccaagatgag gatccgaatt tatgtacctt atcgtcaccc gattacgctc  60
acgggagtcg ccagcttgac tatttcacca agccagatcg agtgatcgcg aaaatcgaaa  120
cgaagtcact ggccagacat tccgtagagc gctgatgccg gatgaatagg gagcatgatc  180
tcggatcccc atccagcggg gctccc                                       206

SEQ ID NO: 172          moltype = RNA  length = 99
FEATURE                 Location/Qualifiers
misc_feature            1..99
                        note = Single strand oligonucleotide
source                  1..99
                        mol_type = other RNA
```

```
                         organism = synthetic construct
SEQUENCE: 172
ggaatggggc tggctgtcac gtcgacactc atctagagca acaaacttct gcgagaggtt  60
gcctatgatg gatgttgatg ttacagccaa ctttattcc                         99

SEQ ID NO: 173           moltype = RNA  length = 165
FEATURE                  Location/Qualifiers
misc_feature             1..165
                         note = Single strand oligonucleotide
source                   1..165
                         mol_type = other RNA
                         organism = synthetic construct
SEQUENCE: 173
tgggggcggg gcgggtacgg gaacacgtaa gctgtgatcg ttgatgttac agccaacttt  60
aagggtgcgg cgggcagtac tcagcggggg ttcttcctcc acccccgggg atggtcggat  120
cgagggaaca tcgcacgtcg cccccgcccg caaccccgc cccta                   165

SEQ ID NO: 174           moltype = RNA  length = 206
FEATURE                  Location/Qualifiers
misc_feature             1..206
                         note = Single strand oligonucleotide
source                   1..206
                         mol_type = other RNA
                         organism = synthetic construct
SEQUENCE: 174
gggagccagt gcaatctgag gattcgtggg gttcactaat cccctcgacg aaatgctcac  60
acctacttac gcttcggcgc tagatcgccc atccaggtcc cctgaccacg caaaaggatc  120
agaagcgcaa gtgaatgacg tgggtggtga gacgttgacg gaggagggtt gatgagtcaa  180
acgagtcccc agacacactg gctccc                                       206

SEQ ID NO: 175           moltype = RNA  length = 206
FEATURE                  Location/Qualifiers
misc_feature             1..206
                         note = Single strand oligonucleotide
source                   1..206
                         mol_type = other RNA
                         organism = synthetic construct
SEQUENCE: 175
gggagcctat ccaaaaggat tggattatg ctggggtttg gcctacttcg agttaggcac   60
acgggtggca tcccgtagac gggttagccg cgaacgattg tccaatccct aaactgtagc  120
aggcgtctgg gatcagccaa cccgtcgtgc tgtgacgtct gtagagctaa agtttagtta  180
aatcttaacc cttcagatgg gctccc                                       206

SEQ ID NO: 176           moltype = RNA  length = 165
FEATURE                  Location/Qualifiers
misc_feature             1..165
                         note = Single strand oligonucleotide
source                   1..165
                         mol_type = other RNA
                         organism = synthetic construct
SEQUENCE: 176
ttggggcggg gcgggatcga gcatatgaaa ggcgagattg aggtctggat agagtttgca  60
cacggcgcgg cggccagcca tcggcgggat gcctgccccc gccgcgtgca agctgctatt  120
ccagatttta tctctcatca ctccctcccg caccccccgc cccga                  165

SEQ ID NO: 177           moltype = RNA  length = 139
FEATURE                  Location/Qualifiers
misc_feature             1..139
                         note = Single strand oligonucleotide
source                   1..139
                         mol_type = other RNA
                         organism = synthetic construct
SEQUENCE: 177
aaggactcgt acaggccggc tagagagcgt aaacttttca tattgtttta ctcttggggc  60
acattccttg gcgtgatagg aggccggggg tggggcggtc tgaggagatg acgcgtgcca  120
aggcccctcg cccctcctt                                               139

SEQ ID NO: 178           moltype = RNA  length = 206
FEATURE                  Location/Qualifiers
misc_feature             1..206
                         note = Single strand oligonucleotide
source                   1..206
                         mol_type = other RNA
                         organism = synthetic construct
SEQUENCE: 178
gggagccgag ccaatcagag gttggagggg taatgccatt gccgacgagt atccaccggc  60
tcgtgtgatc gctccatagc tggtctcccg aggcagtgcg cgggcacgaa caaaacaggc  120
agaagctaga gtgcagtcaa cgtgatgttg gatggggaag gtcgagcgat gacgttgcaa  180
cttcaacccc tgacagttcg gctccc                                       206
```

-continued

```
SEQ ID NO: 179         moltype = RNA  length = 292
FEATURE                Location/Qualifiers
misc_feature           1..292
                       note = Single strand oligonucleotide
source                 1..292
                       mol_type = other RNA
                       organism = synthetic construct
SEQUENCE: 179
gaaccaatgc ggaagatacc aatgcacggt cgcatgtaaa attgggcagt tggtcagttt  60
tgttggggtg aagtcttgcc ccagttagcc gggaggaaag atattacacc cgactcattc  120
tgacgaacgc ctcaggtagt atgcaacctg atactgaggt gaacggcaga atgatgcggg  180
tgtatatatc cacctccgct aactgggcga agacttcact ccaacataac ggacccgctg  240
tcaccggccc atacccgacg tattgggctc tttggtaaca gtggtcgggt tc          292

SEQ ID NO: 180         moltype = RNA  length = 84
FEATURE                Location/Qualifiers
misc_feature           1..84
                       note = Single strand oligonucleotide
source                 1..84
                       mol_type = other RNA
                       organism = synthetic construct
SEQUENCE: 180
ataccgagat aagcagagga agaataatta ggtgctaatt ggaagctgca cctacattcc  60
tttttatctg tttagttttg gtag                                         84

SEQ ID NO: 181         moltype = RNA  length = 199
FEATURE                Location/Qualifiers
misc_feature           1..199
                       note = Single strand oligonucleotide
source                 1..199
                       mol_type = other RNA
                       organism = synthetic construct
SEQUENCE: 181
agggcgtacc aggaggtatg aagcctcgca tgggagatct gcgaggtatt ggggtagact  60
tcgtaaaagg cgcaaacaag ctcgcacaaa agcgtgagga tgatgtagct aaagatgcat  120
aattcaacag cgattcacgc acccagggtg attcgtggac ctcttgttga gagctgtact  180
ttggatagta agacgccct                                               199

SEQ ID NO: 182         moltype = RNA  length = 292
FEATURE                Location/Qualifiers
misc_feature           1..292
                       note = Single strand oligonucleotide
source                 1..292
                       mol_type = other RNA
                       organism = synthetic construct
SEQUENCE: 182
cgccccatga gttagaaacg agttcggggc caaagttcta acacgtaggt tggaaagggt  60
ttggtgaacc ttgcggacac ggaggtcgtg gtcggaggag aattatcgcc cgacgcttgc  120
ccgctaaccc gtgaggtgcc aggaaacgcg atactcacgg gaaggagggt aggttgcggg  180
cgataaattc ggtccggacg acctccgcat tcgtggggtt cactaatccc gttcctacct  240
accccggtca ctgaatggcg aacttggttc taaattacaa ggagaacggg tg          292

SEQ ID NO: 183         moltype = RNA  length = 292
FEATURE                Location/Qualifiers
misc_feature           1..292
                       note = Single strand oligonucleotide
source                 1..292
                       mol_type = other RNA
                       organism = synthetic construct
SEQUENCE: 183
gccccactaa gcttgaagcc attcccgcgt ctcgggagaa aagcgggcgt gggatattta  60
gttgtgctga catgtctagc aacggatgac gaaggttaag aaatatcgcc cgactcgtcc  120
tcacaaacgc cagagcacga acgcaaccgt acactctggc gaatgggggg acgaagcggg  180
cgataatttc acgcctttca tccgttgagg gacatgttag cataataaaa agtccagcgc  240
cctacggtgc ccacaagacg gaatggagtc gagattaaaa tgggacgggg gc          292

SEQ ID NO: 184         moltype = RNA  length = 91
FEATURE                Location/Qualifiers
misc_feature           1..91
                       note = Single strand oligonucleotide
source                 1..91
                       mol_type = other RNA
                       organism = synthetic construct
SEQUENCE: 184
aaggcttgct actgtggagc aatcattctg aacgatagag aaaatgggat ttaatttatc  60
ggtcagaatg atactccaca atactaagcc t                                 91

SEQ ID NO: 185         moltype = RNA  length = 195
```

-continued

```
FEATURE              Location/Qualifiers
misc_feature         1..195
                     note = Single strand oligonucleotide
source               1..195
                     mol_type = other RNA
                     organism = synthetic construct
SEQUENCE: 185
ggagggtacc tagccggctg taacttgtgg actatcggcg gggtaatggg gggcaactag  60
ctgccgaccc attcctccat cccgtccgtg gctacgagag ggtgggcgcg acttggaatg  120
agggaatgga gcgggagata gttggagtcc ccgcccgtgc ctatcctttt caggttgtag  180
cctctgatga gctct                                                   195

SEQ ID NO: 186       moltype = RNA  length = 292
FEATURE              Location/Qualifiers
misc_feature         1..292
                     note = Single strand oligonucleotide
source               1..292
                     mol_type = other RNA
                     organism = synthetic construct
SEQUENCE: 186
gccccactct gacagagacc atgtcgcgca atatgaacaa acggggctga gggaggtggc  60
ttggtggacc ttgcgaaccc ataggtagac gagggtaccg aaaagacgcc cgactctggc  120
atacaaaccc ggttggatcc aagaaatgat aaacgaccgg gaatgggtgc cagaagcggg  180
tgttattttc tcgcccttct atctgtgcat tcgtggggtt cactaatcca gctccatcag  240
ccgacagcat cgccaattgg acatgggttc tgtaggacta agtgcagggg gc          292

SEQ ID NO: 187       moltype = RNA  length = 292
FEATURE              Location/Qualifiers
misc_feature         1..292
                     note = Single strand oligonucleotide
source               1..292
                     mol_type = other RNA
                     organism = synthetic construct
SEQUENCE: 187
ggccccgagg tcttgtgccc aaagacatgt ctgagactcc agggggaagt gggtaattta  60
gtttaaggtg tatgccactc tcaggtaggc gaaggttagg attgcccccc cgacgcaggc  120
ttacaaacgc ggatgggttg acggaagaac agacatccgt gaatgagagt ctgtcacggg  180
ggggacaatc gcaccttcct atctgagctt ggcatatatt ttaaataaaa ctaccaactt  240
tcgaagactt ctgaaagact ttttggcggc aggttctaaa ggtgagcggg tc          292

SEQ ID NO: 188       moltype = RNA  length = 84
FEATURE              Location/Qualifiers
misc_feature         1..84
                     note = Single strand oligonucleotide
source               1..84
                     mol_type = other RNA
                     organism = synthetic construct
SEQUENCE: 188
ttgggatatg ttaggaaata agaaaatcga ggtgctaatt ggaagctgca ccttaggtcc  60
tcttgattcc tagccgtatc tcat                                         84

SEQ ID NO: 189       moltype = RNA  length = 199
FEATURE              Location/Qualifiers
misc_feature         1..199
                     note = Single strand oligonucleotide
source               1..199
                     mol_type = other RNA
                     organism = synthetic construct
SEQUENCE: 189
agggctttca cgggcttcgt aggccttgct aagagatttt ttaaaattaa ctggatgact  60
tagaaaatta cgcaaacaag tagaaataaa cgcatgtgtg gtgcgttgcc aaagaagtgt  120
tccacaaaag atacgcatgc tccatcttag tttgggggac tttcttacga gagcccgaag  180
ctagagggag agaagccct                                               199

SEQ ID NO: 190       moltype = RNA  length = 292
FEATURE              Location/Qualifiers
misc_feature         1..292
                     note = Single strand oligonucleotide
source               1..292
                     mol_type = other RNA
                     organism = synthetic construct
SEQUENCE: 190
gtccccaacc agttgtagcc aattcggatg ctgatggaca acacgtaaga aggatgtggc  60
ttggtgagct ccgcggaccc gtaggttttt gtgggagttg atcgtgatcc cgactcatgc  120
acgcaaacgc aacgggctgt acgaaatcag agaccgttgc gaatgagtgt atgacgcggg  180
attgtcgatc tatcccagga acctgcgcat tcgtggggtt cactaatccg agtccgtctt  240
acctcgccgc gtaaaagtag aattgggggc aacgggtata gacgagaggg gc          292

SEQ ID NO: 191       moltype = RNA  length = 237
```

-continued

```
FEATURE                Location/Qualifiers
misc_feature           1..237
                       note = Single strand oligonucleotide
source                 1..237
                       mol_type = other RNA
                       organism = synthetic construct
SEQUENCE: 191
ctgacccgta catatcgaga gttgtctggc ccgccacagc ccctagcaaa tctcgtcgcg  60
gagccacgcg tagtatggtc gcgagccacg cccgaagcta aaccagaagc accgaaggct  120
acgcgtccct tatacactgt aacggcaccc cgaacacggg aagagggctc cgaaggccga  180
cgagatttcc taggggctgt ggcgggttgg acaactttgg atatgtgccg gtcaggg     237

SEQ ID NO: 192         moltype = RNA  length = 64
FEATURE                Location/Qualifiers
misc_feature           1..64
                       note = Single strand oligonucleotide
source                 1..64
                       mol_type = other RNA
                       organism = synthetic construct
SEQUENCE: 192
cgctgcggag ctcaagaaga accctcttcg aataatccag ggttctttta gggctttgcg  60
gtat                                                              64

SEQ ID NO: 193         moltype = RNA  length = 110
FEATURE                Location/Qualifiers
misc_feature           1..110
                       note = Single strand oligonucleotide
source                 1..110
                       mol_type = other RNA
                       organism = synthetic construct
SEQUENCE: 193
aaagttaggg gagcactagg gttgattggt cgtcacagtt agatctttct gaccctagag  60
acgaaaaagc tgtggcgggt tggacaactt catacctccc aaccatagcg            110

SEQ ID NO: 194         moltype = RNA  length = 237
FEATURE                Location/Qualifiers
misc_feature           1..237
                       note = Single strand oligonucleotide
source                 1..237
                       mol_type = other RNA
                       organism = synthetic construct
SEQUENCE: 194
cgggacagtt cattgcgggg gttggtggac cccacgagtt cccaagcagg agtaggcgca  60
gagtagcttg acgcaaggta ccggcccacg gacgacctca aacagtagag acctaacgcg  120
tcaggctcct atggaaccca tacgaaaccc ccagcagggg aagagtactc tgtagaccgt  180
ctactcctcc ttgggaattc gtggggttca ctaatcccgg cagtgagccg tcccggg     237

SEQ ID NO: 195         moltype = RNA  length = 237
FEATURE                Location/Qualifiers
misc_feature           1..237
                       note = Single strand oligonucleotide
source                 1..237
                       mol_type = other RNA
                       organism = synthetic construct
SEQUENCE: 195
ctgaaccgat cgcaacggag tggtatcatt cactgcctgt cactttcata ttgtggcgca  60
ggtctgcctg tggcatgggc gtgctccaca cagaattcat aacctcttga tccaaacgct  120
gcgggtgacg cattgaaaat gtttctggcc cgaactcggg gaaaaggacc tggaggctgt  180
cgcaatatca aagtgacagg cggtgaatga tgttattcgg ttgcgatccg ttcaggg     237

SEQ ID NO: 196         moltype = RNA  length = 64
FEATURE                Location/Qualifiers
misc_feature           1..64
                       note = Single strand oligonucleotide
source                 1..64
                       mol_type = other RNA
                       organism = synthetic construct
SEQUENCE: 196
accggaagag gtaaatgaat tacctttccg aataatccag gtggtttata tgccttttcc  60
ggat                                                              64

SEQ ID NO: 197         moltype = RNA  length = 110
FEATURE                Location/Qualifiers
misc_feature           1..110
                       note = Single strand oligonucleotide
source                 1..110
                       mol_type = other RNA
                       organism = synthetic construct
SEQUENCE: 197
```

-continued

```
aaggcggggg aagcatctgg acgccggaag aggtaaatga agatcttcca cattggtggg  60
acgaaaatcg tttgctatgt atcatcgtcc cataacttcc aattaggaca             110

SEQ ID NO: 198         moltype = RNA  length = 237
FEATURE                Location/Qualifiers
misc_feature           1..237
                       note = Single strand oligonucleotide
source                 1..237
                       mol_type = other RNA
                       organism = synthetic construct
SEQUENCE: 198
ctgatcagag cattgcgagg gttggtggac cccgcggata cactctctgt caagggccct  60
gagtcgcttg gcggatggtt cgcagcccgc gcgtaggaca aactggagtc accaaacccg  120
ccaggtccat aagcgacgtt tacggaaccc caagcatggg cagaggactc aggaggcggt  180
ccttgataca gagtgtattc gtggggttca ctaatcctgg caatgctccg gtcaggg     237

SEQ ID NO: 199         moltype = RNA  length = 237
FEATURE                Location/Qualifiers
misc_feature           1..237
                       note = Single strand oligonucleotide
source                 1..237
                       mol_type = other RNA
                       organism = synthetic construct
SEQUENCE: 199
cagaacagat ccggacggtt gtgttgtgct tttgctggaa cactagcttt tgtaggccca  60
gcgttccaag gcgcaaggtg acacgctctg tacgaaccta aacccaaagg acctaacgcg  120
tcttggagac tctagactag ggccttattg caagcatgcg cggacgacgc tgaagacggc  180
ctatagaacc tagtgttcca gcaaaagtac agcacaacgg tccggatccg ttctggg     237

SEQ ID NO: 200         moltype = RNA  length = 52
FEATURE                Location/Qualifiers
misc_feature           1..52
                       note = Single strand oligonucleotide
source                 1..52
                       mol_type = other RNA
                       organism = synthetic construct
SEQUENCE: 200
tttggtccca tgttggagct ggtcgcaccc agctccacat ggaagactta cc          52

SEQ ID NO: 201         moltype = RNA  length = 118
FEATURE                Location/Qualifiers
misc_feature           1..118
                       note = Single strand oligonucleotide
source                 1..118
                       mol_type = other RNA
                       organism = synthetic construct
SEQUENCE: 201
aaacaggaaa tgggaagcgg cagaaatgcc attctccgtt tacgttcttc gacgcttccc  60
gctttcctgg gacgtgagta gggaatagtg tttttcccac ttctcaagac cgacccgc    118

SEQ ID NO: 202         moltype = RNA  length = 237
FEATURE                Location/Qualifiers
misc_feature           1..237
                       note = Single strand oligonucleotide
source                 1..237
                       mol_type = other RNA
                       organism = synthetic construct
SEQUENCE: 202
ccgagccgat catgtcgcgg attggtgagc cccacgggtg cacctacgtc atttgtcgct  60
gagtaacatg ctgcaagtga cgcgccctgc ggatattaca aactagagta tactaacgcg  120
gcatgttcgg aagcaacgct tcagaaaccc cgatcacggg cagagtactc gggagcccgg  180
caaatgatct aggtgcattc gtggggttca ctaatccggg atatggtccg ctcgggg     237

SEQ ID NO: 203         moltype = RNA  length = 193
FEATURE                Location/Qualifiers
misc_feature           1..193
                       note = Single strand oligonucleotide
source                 1..193
                       mol_type = other RNA
                       organism = synthetic construct
SEQUENCE: 203
ggtggtgtgt caaaggttcg ctgcctctgc atctaccctc taattgccat atgagaccct  60
aaactaccca agccactgga ataaaaatga ggccgccgtt ccaaccaaaa cgataacata  120
acaaatgtta ttacaagggt gaaaagggcg aagggggggtg ggtgcacggg cgacgcaccg  180
gacgcaccgc cac                                                     193

SEQ ID NO: 204         moltype = RNA  length = 111
FEATURE                Location/Qualifiers
misc_feature           1..111
```

```
                          note = Single strand oligonucleotide
source                    1..111
                          mol_type = other RNA
                          organism = synthetic construct
SEQUENCE: 204
gccgtgcacc cactagcagt tacagtgttc atgaaatcct taacttcctt ccctgtcggg  60
aggatagata ggggtttttg ggtgctgtac ctgttgttgg gatcacgaag a           111

SEQ ID NO: 205            moltype = RNA  length = 138
FEATURE                   Location/Qualifiers
misc_feature              1..138
                          note = Single strand oligonucleotide
source                    1..138
                          mol_type = other RNA
                          organism = synthetic construct
SEQUENCE: 205
gaacgccgca gcgttaaaag ctgcctctgc ctctgcatct atcttcggtt agaaggtgaa  60
ggggggcgcc aagaccgcgg ttctaaccct agctaggtgt agcccgaggg agccagctcc  120
tggcggcttg gggcccca                                                138

SEQ ID NO: 206            moltype = RNA  length = 193
FEATURE                   Location/Qualifiers
misc_feature              1..193
                          note = Single strand oligonucleotide
source                    1..193
                          mol_type = other RNA
                          organism = synthetic construct
SEQUENCE: 206
gcaggcgtcg ccaggggctg ttggaggggt aatgccattg caatggctat aagggactga  60
atactaccga gagcgcggat gccaaaccca agagacagca tctaagacaa cgaagaacca  120
ataaggttct ttaaatcggt aaaaagagcc aagcggtggt attgccattc cattaaccca  180
gtggcgcctg cac                                                     193

SEQ ID NO: 207            moltype = RNA  length = 351
FEATURE                   Location/Qualifiers
misc_feature              1..351
                          note = Single strand oligonucleotide
source                    1..351
                          mol_type = other RNA
                          organism = synthetic construct
SEQUENCE: 207
caggggagtg aagcgagtgc atcttcattc atcgaagcat gcaccttcac attcggaaaa  60
atccccacgg ctggaaccgt ccacccaaca ctaggcagag tcgagcccgc gcggtaccaa  120
atctgggttg gagaataagt cccgggggta gccctccaga gggggcccaa ggccacatga  180
gggatgcgtg caagggaggg acacagcatg gaccggcctg actactattg aaagccgaac  240
gtggatcaga gtcggccgaa ggggcagaat ctacggcccg aatcttgatc caaaccccat  300
agagtcaggg cgccatgggt gggtgaaatc cactcgcttc acacccccac a           351

SEQ ID NO: 208            moltype = RNA  length = 93
FEATURE                   Location/Qualifiers
misc_feature              1..93
                          note = Single strand oligonucleotide
source                    1..93
                          mol_type = other RNA
                          organism = synthetic construct
SEQUENCE: 208
aaaaccaagc tggtgctata atgcacaata aggatcaatc agcacctgga tctgagattc  60
gagttgtgcg ttggcgcacc cacgtggatc cta                               93

SEQ ID NO: 209            moltype = RNA  length = 351
FEATURE                   Location/Qualifiers
misc_feature              1..351
                          note = Single strand oligonucleotide
source                    1..351
                          mol_type = other RNA
                          organism = synthetic construct
SEQUENCE: 209
gctgggaggt cagcgtacaa ctcatgaata tttgaatctc ccaccatccc gaacctctct  60
gaccccatgc ccggtatcga ccaccgatcc acgaagacag accaggccgc ccgattccca  120
atttgtgatc gataaatggg ctcggggttt tcccttagca gggggaccca gtccctagga  180
tggatggggg aatgggtggt aaaagccagg gctaggtctg taatctatac aaaccccaac  240
ggggctagta gtcagctgag gggggaaaac tcatagcctg aatacctagc ctaacaccat  300
agttacaggg ctccctgagg tgttcatatg tgtgcgttga tcacccaccc a           351

SEQ ID NO: 210            moltype = RNA  length = 351
FEATURE                   Location/Qualifiers
misc_feature              1..351
                          note = Single strand oligonucleotide
source                    1..351
```

-continued

```
                         mol_type = other RNA
                         organism = synthetic construct
SEQUENCE: 210
tttgagaggc ttggaggggt aatgccattg cgtgaaacat caaccggtcc cagcatcgaa  60
tggcgcaagt cagggcccgc ccaccgttcc tttgcgatac tccaggccgc ccgatagcca  120
ggcaaagaac gagaaattgg cacgcgtcac gtcccaactg ggagttgcca cgacgaagac  180
cggattggtg taaggggggc agagaacagg gtggtgacct tccatcatct aaagactaac  240
ggggtatcga ctcagctgag gtggtagaaa ccacagcctg aatcagatac ctaacgacat  300
ggggagggtg acccctgacg tggtggcttc tctttccgag ccactcacgc a           351

SEQ ID NO: 211           moltype = RNA  length = 351
FEATURE                  Location/Qualifiers
misc_feature             1..351
                         note = Single strand oligonucleotide
source                   1..351
                         mol_type = other RNA
                         organism = synthetic construct
SEQUENCE: 211
gatgagaggt atgggttttg agacaaaatt tgagaaccga accccatccc accgataaag  60
ggaccgaagt cggctacata gcaccgtctc tacagaatag tccaggccgc ccgtagccca  120
gctgtaagac gagaacatga tgccggtccg cccccatttg gggagatcga atctctagga  180
tggaggttcg gacgggcgac agagatggcg gtgaggacgg gccaccagta aaaatccaac  240
ggggcgttaa gttagcgtag tgggcagaat gcaacgccta agttcaatgc ctaacacctt  300
ggggtttgtg ctccgcctca agttttgctg ggagcccgta ccactcacgc a           351

SEQ ID NO: 212           moltype = RNA  length = 91
FEATURE                  Location/Qualifiers
misc_feature             1..91
                         note = Single strand oligonucleotide
source                   1..91
                         mol_type = other RNA
                         organism = synthetic construct
SEQUENCE: 212
cagtagcagt tggcgccatg atcaagaaga aaacttccct aaacaagcca aggaaagatc  60
ttttcttgtc gtggcctcac ctgttgatgg g                                 91

SEQ ID NO: 213           moltype = RNA  length = 351
FEATURE                  Location/Qualifiers
misc_feature             1..351
                         note = Single strand oligonucleotide
source                   1..351
                         mol_type = other RNA
                         organism = synthetic construct
SEQUENCE: 213
atcgagagtg cagattcttc ttggcgaatt agtgaagcta acaccttctc agccaccaca  60
gaccccaggc cgggacccgt ccaccgatcc accacaagag cccaggccgc ccgtcgccaa  120
cgtggtgatc gagaattcgg cgcggggtca aattccgacg aatggttcga agcccaagga  180
gggatgttag caagggcggt aaataacatg gtgagggtcg tttgcaattt taactctaac  240
gtggttaata tttcgctgag gaggtagaat ccacagccga actacttaac cgaactccat  300
tgagatgacg ttccatgact agttcgggct ggggatctgt acactcgctc a           351

SEQ ID NO: 214           moltype = RNA  length = 351
FEATURE                  Location/Qualifiers
misc_feature             1..351
                         note = Single strand oligonucleotide
source                   1..351
                         mol_type = other RNA
                         organism = synthetic construct
SEQUENCE: 214
aaagagagga attcgtgggg ttcactaatc cttaaaactt ccacctaccc gaacatctct  60
gtctcggcgt ctggatacgt ccactgagcc tgatcgaaag accagaccgc tcgcttccca  120
agatcagctc accacggagg ctgcgaggct agtcaaacgt gacggaccca gtccacaggt  180
gggatggggg tatacgtgtt atagagattg gagttgcctg tctgcgacca aaatccaaac  240
gcgggtttc ggcagctgag ggggaacaac ccatagcctg cagacaaacc cgaacgccgt  300
cgagataggg aaccaatagg ggttagtagg tccgcgaatt tcactctcgc a           351

SEQ ID NO: 215           moltype = RNA  length = 351
FEATURE                  Location/Qualifiers
misc_feature             1..351
                         note = Single strand oligonucleotide
source                   1..351
                         mol_type = other RNA
                         organism = synthetic construct
SEQUENCE: 215
aacccgagtt cagaatctca cttgagattc tgtgaacgat gcacctcgct cccctattcc  60
gaccccagga ccggacccgt ccaccgtcca cggaataaag gccactccgc agaaccccca  120
ctttcgggac gacaaatggt cacggggtct ctggtcatta ccgtgtatgt tgcaattgtg  180
gggatgcgtt gagaataggc aaataccctg gcggtgtgtg tttcagatca caaagcgaac  240
ggggttctga gtgtgccgag gggcataac tcatggccac agtcaagaac ctaaccccat  300
```

```
ttagatacgg acccaggata gggtctcggc ggggttttga acacgggcgc a          351

SEQ ID NO: 216          moltype = RNA  length = 100
FEATURE                 Location/Qualifiers
misc_feature            1..100
                        note = Single strand oligonucleotide
source                  1..100
                        mol_type = other RNA
                        organism = synthetic construct
SEQUENCE: 216
aacagttgag tggggctctg tctgcgtcta gaccactcgc accaagtaca gacataatct  60
gaatgatcta ggcgcagatt ccaccccatc caactcaaca                        100

SEQ ID NO: 217          moltype = RNA  length = 351
FEATURE                 Location/Qualifiers
misc_feature            1..351
                        note = Single strand oligonucleotide
source                  1..351
                        mol_type = other RNA
                        organism = synthetic construct
SEQUENCE: 217
tatggcaggg cagaatctca cttgagattc tgtgaaacaa acaccagctc attctgttca  60
aaccccacgt ctggtaacga ccaccggacc gtgatcacag ttcaggccgc ccgataccca  120
agtcgcgtcc gaaaagtagg cccggggttg gcgctccaaa gcgggaccga gtcctaaggt  180
tggatgtttg taagggtcgg atacatcagg gtgagggctg tctgctttaa aaaacccaac  240
gcgggtttgt cagtgctgag tcgggacaag acacagccat tagcaaaacc cgaacgcgaa  300
agagatagcg ttccctgata gggtcttggc gatgtatggt tcagtcacgc a           351

SEQ ID NO: 218          moltype = RNA  length = 351
FEATURE                 Location/Qualifiers
misc_feature            1..351
                        note = Single strand oligonucleotide
source                  1..351
                        mol_type = other RNA
                        organism = synthetic construct
SEQUENCE: 218
gatgagagct attcgtgggg ttcactaatc cctgaatcac acacctgccc tcccagtccc  60
gccccctagt cagatgacga tcccggccgc ttgatcatag cccaacccgc gtgcagccca  120
cgtcgacggt caaaacttgg cacgggggct ccgcccgatg gcggggttca acccgcaggc  180
aggatgtgtg aatagggagg aagcaccacg gcgagggctg tattcttgat aaaaccaaac  240
ctggagtgca cttggcggag ttggaagaaa gcattgccca attgccactc cgaacgccca  300
agatatagtg ctccgtgagg ggttagtaag cctgcgagta gcactcacac a           351

SEQ ID NO: 219          moltype = RNA  length = 351
FEATURE                 Location/Qualifiers
misc_feature            1..351
                        note = Single strand oligonucleotide
source                  1..351
                        mol_type = other RNA
                        organism = synthetic construct
SEQUENCE: 219
ccggggacgt cacctgtggc ttctaccgca agagaactgc aatccgtatc acgccggaat  60
aaccacaggt ttgggagcgc ccaccgtcca gctgttaaag tccaggccgc ccgtcgccca  120
tgcagcggac gaaaattaag cacgtggttc gcccttacta gggggctcga agccataata  180
cggaattgcg gacgggggc acatatcacg gaacggccct acggcgttga gaacactaag  240
gcggtacttg ataagcccag tgggaaaaat gcagggcctt accacggtac cgaaagcaaa  300
tgcgtagggg cgccgtgttt tgtggtaaac tcacgggtga tgaccctccc a           351

SEQ ID NO: 220          moltype = RNA  length = 99
FEATURE                 Location/Qualifiers
misc_feature            1..99
                        note = Single strand oligonucleotide
source                  1..99
                        mol_type = other RNA
                        organism = synthetic construct
SEQUENCE: 220
gtttttagag gtgaatgctg gatggctcgt cgcattcaca taagaagaag aaatataagt  60
gaaggctgcg aatcgctctt cgtttatctc taatataca                         99

SEQ ID NO: 221          moltype = RNA  length = 351
FEATURE                 Location/Qualifiers
misc_feature            1..351
                        note = Single strand oligonucleotide
source                  1..351
                        mol_type = other RNA
                        organism = synthetic construct
SEQUENCE: 221
cacgtgaggt ccaagccacc atccaagcca agcgaaacaa acacaagccc attagcccct  60
taccccacgg ctgggtccgc ccacagttcc actacgaaag gacaggcagc ccggacccca  120
```

-continued

```
agtagtgaac tagaataagt cccggggtac ccgcgtatac gcgtgatcta atcagcaggt  180
ttgatgtttg taagggaggt atacaacttg gcggttgagt tccactgttc taacactatc  240
ggggtcctaa ttcagccgat ggggaaaaat taacggcctg atttcaggac ccaacgtcac  300
agggagtttg acccagggct tggtttcctt gtggcttgga tcacgcgcgc a           351

SEQ ID NO: 222         moltype = RNA  length = 351
FEATURE                Location/Qualifiers
misc_feature           1..351
                       note = Single strand oligonucleotide
source                 1..351
                       mol_type = other RNA
                       organism = synthetic construct
SEQUENCE: 222
agtgtgagga attcgtgggg ttcactaatc cgggaaactg tcgccttcac ttactgcccg  60
taccccaagt caggaacagt ccacagggcc agtgcgaaag accatgccgc cagcctccca  120
ggcattgccc tacaacgtgg ccaggggtaa agactatcga gttgggccca gcccctatga  180
aggatggcag tcaaggcagg aaatacacgg gaggcgtccg caccatgtcc caatacgaac  240
ggggttcatc atacgctgag ccggtagaag gcatagccgt aggactgaac ctaacaccac  300
gtgtgtgggg gtcccgttcg ggttggtaag tctgcgaatt ccacacaatc a           351

SEQ ID NO: 223         moltype = RNA  length = 213
FEATURE                Location/Qualifiers
misc_feature           1..213
                       note = Single strand oligonucleotide
source                 1..213
                       mol_type = other RNA
                       organism = synthetic construct
SEQUENCE: 223
tgattgtgtg gcttgaggtc cggggtcagc gtccccccgct ccgacccgaa ctagaagtga  60
gtagaagcta gagtgaacgg taccacacag acccgcatct cggaccaacc ctccgcctgc  120
aaccccttcc accccgaccc ccctctcgag gtccgagaca gggcggtggg agacgagggg  180
gcaagaactc cgtactttat ttcacgtaac caa                               213

SEQ ID NO: 224         moltype = RNA  length = 100
FEATURE                Location/Qualifiers
misc_feature           1..100
                       note = Single strand oligonucleotide
source                 1..100
                       mol_type = other RNA
                       organism = synthetic construct
SEQUENCE: 224
aggatttgcc tgggctacag tatggcactc acctagagca acgacagctt gggagggttg  60
cctataaggt ggatgccgta ctttatttca cgtaaatctc                         100

SEQ ID NO: 225         moltype = RNA  length = 167
FEATURE                Location/Qualifiers
misc_feature           1..167
                       note = Single strand oligonucleotide
source                 1..167
                       mol_type = other RNA
                       organism = synthetic construct
SEQUENCE: 225
cggcggccag aatgcgcgca aaaaaaaaaa aaaaaaaaaa gcggcggccg gactgcacct  60
gtggacggcc gccccaaagc gacggagaga cgggttccta accaaggtgt aggagcagcc  120
gccggcgctt ttttttagta gcttttctct tgtcagtctc tcctcca                167

SEQ ID NO: 226         moltype = RNA  length = 213
FEATURE                Location/Qualifiers
misc_feature           1..213
                       note = Single strand oligonucleotide
source                 1..213
                       mol_type = other RNA
                       organism = synthetic construct
SEQUENCE: 226
tgaggattcg tggggttcac taatcccaga cgccgccgct cccccctgag cagggacatc  60
gcccagacct gaggcaacgc ggcgccacca accacccact cgttcccgca ctgaaacatc  120
caccacaacg tacgtagccc cccccacacg gagcgagttc tggcgggcgg agacgagcgg  180
cggagagggt tgatgagccg agtggatccc caa                               213

SEQ ID NO: 227         moltype = RNA  length = 213
FEATURE                Location/Qualifiers
misc_feature           1..213
                       note = Single strand oligonucleotide
source                 1..213
                       mol_type = other RNA
                       organism = synthetic construct
SEQUENCE: 227
cgatttttta tgctttttgg ttcggtcagc cgccgccgcg ccagcccacc tcgtaccccc  60
agaccacacg acgcccacgc agcggcaaca aggcccagcc cgagcccccg caccctcgtc  120
```

-continued

```
ttccacatca accgcagccc cccaccccag gctcgggccc gcccggtcgg tgacgagcgg  180
cgtagaaccg aggcaaagat aataaaaaac cga                               213

SEQ ID NO: 228         moltype = RNA  length = 76
FEATURE                Location/Qualifiers
misc_feature           1..76
                       note = Single strand oligonucleotide
source                 1..76
                       mol_type = other RNA
                       organism = synthetic construct
SEQUENCE: 228
tggttatgac gagcgtgccg tacgagccac ggctgctgct gcgccgccgc gggctacggc  60
actcttttca taatta                                                  76

SEQ ID NO: 229         moltype = RNA  length = 155
FEATURE                Location/Qualifiers
misc_feature           1..155
                       note = Single strand oligonucleotide
source                 1..155
                       mol_type = other RNA
                       organism = synthetic construct
SEQUENCE: 229
atggccgccg gcttagagag tgaaaaaata tatttctgca aaaggcccac cggccgtggg  60
cggcagaatg ccgatttctg cgcctgggag agaggggccc gcgcagcgat aaagcttttg  120
tgggtgtgta tttttacaac cctctctagc ctaca                             155

SEQ ID NO: 230         moltype = RNA  length = 213
FEATURE                Location/Qualifiers
misc_feature           1..213
                       note = Single strand oligonucleotide
source                 1..213
                       mol_type = other RNA
                       organism = synthetic construct
SEQUENCE: 230
cgaggattcg tggggttcac taatccccgc cgcctccgcg ccgcccggcc gcttactccc  60
ttcatccaag cacatgacgc gaaatgaccc actccaagcc ctaccccacg aacctgcgac  120
gactgctaca ccctccgacc cccccccccg ggtagggccc gagagggggg tgacgagagg  180
tgaacaggat tgatgagccg gatgagtccc cga                               213

SEQ ID NO: 231         moltype = RNA  length = 213
FEATURE                Location/Qualifiers
misc_feature           1..213
                       note = Single strand oligonucleotide
source                 1..213
                       mol_type = other RNA
                       organism = synthetic construct
SEQUENCE: 231
acattggttt tactgagtcc gcggggcaga gcccgccgcc atgaagatcc agtataaccc  60
atctagctac tcgagtaccc tgcctccccg acaccaagct cgacccctcg ctccaacgta  120
aacaacagat cccccagccc cccccacctg ggtcgagccc gtgctttggt ggacgagcgg  180
gcgagatctc gcagatttac aaaaactaac gta                               213

SEQ ID NO: 232         moltype = RNA  length = 74
FEATURE                Location/Qualifiers
misc_feature           1..74
                       note = Single strand oligonucleotide
source                 1..74
                       mol_type = other RNA
                       organism = synthetic construct
SEQUENCE: 232
gtgcaggatt gtgagggagc atttccccag ctcgatcatt gcatgattag aagagtttct  60
tcatgttcct gcat                                                    74

SEQ ID NO: 233         moltype = RNA  length = 213
FEATURE                Location/Qualifiers
misc_feature           1..213
                       note = Single strand oligonucleotide
source                 1..213
                       mol_type = other RNA
                       organism = synthetic construct
SEQUENCE: 233
tgagggtgct cgatcacggc cctgggccaa cgccgccgct cccgccccct atcgcctctc  60
cacacaccga tcagcaacac gccgctaccc actcctaacg cgagcccacc cgtccacttc  120
ttcttcaacc gccgcgaccc cccccccccg gctcgtgtcc gagcggtcgg agacgagtgg  180
tggagatcca ggattgtgag ggagcatttc caa                               213

SEQ ID NO: 234         moltype = RNA  length = 213
FEATURE                Location/Qualifiers
misc_feature           1..213
```

-continued

```
                        note = Single strand oligonucleotide
source                  1..213
                        mol_type = other RNA
                        organism = synthetic construct
SEQUENCE: 234
agaggattcg tggggttcac taatccccgc ctccgccgct ccaaccaata gctacaggtc  60
gagaatatag catgctaacc gccgcaacca acgcccatct cgtgccagcc ccacaccatg  120
ccctcctaca gcctcagaca ccccaacagg gtacgagacc gcgcggtcgg agacgagcgg  180
agcaaaggat tgatgagtca gatggatccc cta                               213

SEQ ID NO: 235          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 235
agaaataggc aagtcatcct tgg                                          23

SEQ ID NO: 236          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 236
agaagagagt gagcacacaa agg                                          23

SEQ ID NO: 237          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 237
agaaataggc aagtcatcct tgg                                          23

SEQ ID NO: 238          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 238
agaaataggc aagtcatcct tgg                                          23

SEQ ID NO: 239          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 239
agaaataggc aagtcatcct tgg                                          23

SEQ ID NO: 240          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 240
agaagagagt gagcacacaa agg                                          23

SEQ ID NO: 241          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 241
acagaagata gagagcacta agg                                          23
```

```
SEQ ID NO: 242          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 242
agaaataggc aagtcatcct tgg                                             23

SEQ ID NO: 243          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 243
agaaataggc aagtcatcct tgg                                             23

SEQ ID NO: 244          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 244
aagaatctgt aaagctcagg agg                                             23

SEQ ID NO: 245          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 245
acagaagata gagagcacta agg                                             23

SEQ ID NO: 246          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 246
agaaataggc aagtcatcct tgg                                             23

SEQ ID NO: 247          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 247
cgtagatgaa tggttccatc agg                                             23

SEQ ID NO: 248          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 248
aaaaatgacg ctgacagaag agg                                             23

SEQ ID NO: 249          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 249
```

```
cgtagatgaa tggttccatc agg                                      23

SEQ ID NO: 250          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 250
cgtagatgaa tggttccatc agg                                      23

SEQ ID NO: 251          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 251
aaggtgccgc ggtcatgatg ggg                                      23

SEQ ID NO: 252          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 252
aatcttaggg atgggaggtg tgg                                      23

SEQ ID NO: 253          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 253
aggagtgaac ctgagaacag agg                                      23

SEQ ID NO: 254          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 254
aaggtgccgc ggtcatgatg ggg                                      23

SEQ ID NO: 255          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 255
cgtagatgaa tggttccatc agg                                      23

SEQ ID NO: 256          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 256
agtggcacgt gatattggca cgg                                      23

SEQ ID NO: 257          moltype = DNA  length = 23
FEATURE                 Location/Qualifiers
misc_feature            1..23
                        note = Single strand oligonucleotide
source                  1..23
                        mol_type = other DNA
                        organism = synthetic construct
```

```
SEQUENCE: 257
cgtagatgaa tggttccatc agg                                      23

SEQ ID NO: 258          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 258
cgtagatgaa tggttccatc agg                                      23

SEQ ID NO: 259          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 259
catcatcaag attctcatcc tgg                                      23

SEQ ID NO: 260          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 260
catcatcaag attctcatcc tgg                                      23

SEQ ID NO: 261          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 261
catcatcaag attctcatcc tgg                                      23

SEQ ID NO: 262          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 262
catcatcaag attctcatcc tgg                                      23

SEQ ID NO: 263          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 263
ccgctgcttg tatttcccat tgg                                      23

SEQ ID NO: 264          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 264
caaatggcat acagggagcc agg                                      23

SEQ ID NO: 265          moltype = DNA  length = 23
FEATURE                 Location/Qualifiers
misc_feature            1..23
                        note = Single strand oligonucleotide
source                  1..23
                        mol_type = other DNA
```

```
                        organism = synthetic construct
SEQUENCE: 265
ctgaatgatg atctcggacc agg                                          23

SEQ ID NO: 266          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 266
aaggtgtgag ttgagcaaga tgg                                          23

SEQ ID NO: 267          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 267
ccgctgcttg tatttcccat tgg                                          23

SEQ ID NO: 268          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 268
ctggcagctt caactattgg agg                                          23

SEQ ID NO: 269          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 269
ggaggcaggc aagtcatcct tgg                                          23

SEQ ID NO: 270          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 270
aaggtgtgag ttgagcaaga tgg                                          23

SEQ ID NO: 271          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 271
tgtgatttac cagatcatgc tgg                                          23

SEQ ID NO: 272          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 272
cctcaagcac atggttaacc agg                                          23

SEQ ID NO: 273          moltype = DNA  length = 23
FEATURE                 Location/Qualifiers
misc_feature            1..23
                        note = Single strand oligonucleotide
source                  1..23
```

```
                        mol_type = other DNA
                        organism = synthetic construct
SEQUENCE: 273
tgtgatttac cagatcatgc tgg                                               23

SEQ ID NO: 274          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 274
tgtgatttac cagatcatgc tgg                                               23

SEQ ID NO: 275          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 275
tgtgatttac cagatcatgc tgg                                               23

SEQ ID NO: 276          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 276
cctccattcc gcgcgaaaac cgg                                               23

SEQ ID NO: 277          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 277
tgtgatttac cagatcatgc tgg                                               23

SEQ ID NO: 278          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 278
tgtgatttac cagatcatgc tgg                                               23

SEQ ID NO: 279          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 279
tgtgatttac cagatcatgc tgg                                               23

SEQ ID NO: 280          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 280
gaagctctca aaagagctta tgg                                               23

SEQ ID NO: 281          moltype = DNA  length = 23
FEATURE                 Location/Qualifiers
misc_feature            1..23
                        note = Single strand oligonucleotide
```

-continued

```
source                  1..23
                        mol_type = other DNA
                        organism = synthetic construct
SEQUENCE: 281
tgtgatttac cagatcatgc tgg                                         23

SEQ ID NO: 282          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 282
tgtgatttac cagatcatgc tgg                                         23

SEQ ID NO: 283          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 283
tgtgatttac cagatcatgc tgg                                         23

SEQ ID NO: 284          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 284
gaggtttatc gatcgattca tgg                                         23

SEQ ID NO: 285          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 285
tgtgatttac cagatcatgc tgg                                         23

SEQ ID NO: 286          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 286
tgtgatttac cagatcatgc tgg                                         23

SEQ ID NO: 287          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 287
agcaatccga ctctcaatac agg                                         23

SEQ ID NO: 288          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 288
gcacgacttg ctgacgtgga agg                                         23

SEQ ID NO: 289          moltype = DNA  length = 23
FEATURE                 Location/Qualifiers
misc_feature            1..23
```

```
                         note = Single strand oligonucleotide
source                   1..23
                         mol_type = other DNA
                         organism = synthetic construct
SEQUENCE: 289
ggacaactaa gtgaagaaag agg                                          23

SEQ ID NO: 290           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 290
ggtctcggat cttcaaacgg tgg                                          23

SEQ ID NO: 291           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 291
agcaatccga ctctcaatac agg                                          23

SEQ ID NO: 292           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 292
aagatagaga gcacagatga tgg                                          23

SEQ ID NO: 293           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 293
accggaccct ctaacagtgg agg                                          23

SEQ ID NO: 294           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 294
agcaatccga ctctcaatac agg                                          23

SEQ ID NO: 295           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 295
agcaatccga ctctcaatac agg                                          23

SEQ ID NO: 296           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 296
aagatagaga gcacagatga tgg                                          23

SEQ ID NO: 297           moltype = DNA  length = 23
FEATURE                  Location/Qualifiers
```

```
misc_feature            1..23
                        note = Single strand oligonucleotide
source                  1..23
                        mol_type = other DNA
                        organism = synthetic construct
SEQUENCE: 297
caacattcta gccctacttc tgg                                          23

SEQ ID NO: 298          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 298
ggtctcggat cttcaaacgg tgg                                          23

SEQ ID NO: 299          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 299
aggggaatgt tgtctggctc ggg                                          23

SEQ ID NO: 300          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 300
gacagaagag agtgagcaca cgg                                          23

SEQ ID NO: 301          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 301
catggattgg gctacatgag tgg                                          23

SEQ ID NO: 302          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 302
aggggaatgt tgtctggctc ggg                                          23

SEQ ID NO: 303          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 303
aggggaatgt tgtctggctc ggg                                          23

SEQ ID NO: 304          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 304
agtttgttgc tctagatgag tgg                                          23

SEQ ID NO: 305          moltype = DNA  length = 23
```

```
FEATURE                Location/Qualifiers
misc_feature           1..23
                       note = Single strand oligonucleotide
source                 1..23
                       mol_type = other DNA
                       organism = synthetic construct
SEQUENCE: 305
aaagaggagc gagcacgcgg cgg                                          23

SEQ ID NO: 306         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 306
aggggaatgt tgtctggctc ggg                                          23

SEQ ID NO: 307         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 307
aggggaatgt tgtctggctc ggg                                          23

SEQ ID NO: 308         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 308
tgagagatgc tgacagaaag agg                                          23

SEQ ID NO: 309         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 309
catggattgg gctacatgag tgg                                          23

SEQ ID NO: 310         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 310
aggggaatgt tgtctggctc ggg                                          23

SEQ ID NO: 311         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 311
ttatctgtgc ttggactgaa ggg                                          23

SEQ ID NO: 312         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 312
gatagagagc acgaataatg agg                                          23
```

-continued

```
SEQ ID NO: 313         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 313
aagccttgct gaagtgtttg ggg                                         23

SEQ ID NO: 314         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 314
ttatctgtgc ttggactgaa ggg                                         23

SEQ ID NO: 315         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 315
ttatctgtgc ttggactgaa ggg                                         23

SEQ ID NO: 316         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 316
ctacgcagga gagatgatgc tgg                                         23

SEQ ID NO: 317         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 317
agctcccttc agtccaagca agg                                         23

SEQ ID NO: 318         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 318
ttatctgtgc ttggactgaa ggg                                         23

SEQ ID NO: 319         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 319
ttatctgtgc ttggactgaa ggg                                         23

SEQ ID NO: 320         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 320
gatagagagc acgaataatg agg                                         23
```

```
SEQ ID NO: 321         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 321
aagccttgct gaagtgtttg ggg                                          23

SEQ ID NO: 322         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 322
ttatctgtgc ttggactgaa ggg                                          23

SEQ ID NO: 323         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 323
ggaagggaga atatccagga tgg                                          23

SEQ ID NO: 324         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 324
acaccctgga ttattcgaaa agg                                          23

SEQ ID NO: 325         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 325
gatatgggca tgggcggtgt agg                                          23

SEQ ID NO: 326         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 326
ggaagggaga atatccagga tgg                                          23

SEQ ID NO: 327         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 327
ggaagggaga atatccagga tgg                                          23

SEQ ID NO: 328         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 328
```

```
acaccctgga ttattcgaaa agg                                          23

SEQ ID NO: 329          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 329
gatatgggca tgggcggtgt agg                                          23

SEQ ID NO: 330          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 330
ggaagggaga atatccagga tgg                                          23

SEQ ID NO: 331          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 331
ggaagggaga atatccagga tgg                                          23

SEQ ID NO: 332          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 332
cgcaccgggc ttgcctagaa cgg                                          23

SEQ ID NO: 333          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 333
gagagacgga attgagaaga ggg                                          23

SEQ ID NO: 334          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 334
ggaagggaga atatccagga tgg                                          23

SEQ ID NO: 335          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 335
gaggctatgt gctgcagcca agg                                          23

SEQ ID NO: 336          moltype = DNA  length = 23
FEATURE                 Location/Qualifiers
misc_feature            1..23
                        note = Single strand oligonucleotide
source                  1..23
                        mol_type = other DNA
                        organism = synthetic construct
```

```
SEQUENCE: 336
gaaggaagtt tagatcatgc tgg                                      23

SEQ ID NO: 337         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 337
ctgccagcat gatctatctt tgg                                      23

SEQ ID NO: 338         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 338
gaggctatgt gctgcagcca agg                                      23

SEQ ID NO: 339         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 339
ttgaagctgc cagcatgatc tgg                                      23

SEQ ID NO: 340         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 340
taaaccatgc tggagaagca ggg                                      23

SEQ ID NO: 341         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 341
ttgaagctgc cagcatgatc tgg                                      23

SEQ ID NO: 342         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 342
ttgaagctgc cagcatgatc tgg                                      23

SEQ ID NO: 343         moltype = DNA  length = 23
FEATURE                Location/Qualifiers
misc_feature           1..23
                       note = Single strand oligonucleotide
source                 1..23
                       mol_type = other DNA
                       organism = synthetic construct
SEQUENCE: 343
ttgaagctgc cagcatgatc tgg                                      23

SEQ ID NO: 344         moltype = DNA  length = 23
FEATURE                Location/Qualifiers
misc_feature           1..23
                       note = Single strand oligonucleotide
source                 1..23
                       mol_type = other DNA
```

```
                         organism = synthetic construct
SEQUENCE: 344
tagggaagtt gagatcatgc tgg                                              23

SEQ ID NO: 345           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 345
ttgaagctgc cagcatgatc tgg                                              23

SEQ ID NO: 346           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 346
ttgaagctgc cagcatgatc tgg                                              23

SEQ ID NO: 347           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 347
ttgaagctgc cagcatgatc tgg                                              23

SEQ ID NO: 348           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 348
aatctgaatg atctcggacc agg                                              23

SEQ ID NO: 349           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 349
ttgaagctgc cagcatgatc tgg                                              23

SEQ ID NO: 350           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 350
ttgaagctgc cagcatgatc tgg                                              23

SEQ ID NO: 351           moltype = DNA  length = 23
FEATURE                  Location/Qualifiers
misc_feature             1..23
                         note = Single strand oligonucleotide
source                   1..23
                         mol_type = other DNA
                         organism = synthetic construct
SEQUENCE: 351
ttgaagctgc cagcatgatc tgg                                              23

SEQ ID NO: 352           moltype = DNA  length = 23
FEATURE                  Location/Qualifiers
misc_feature             1..23
                         note = Single strand oligonucleotide
source                   1..23
```

```
                        mol_type = other DNA
                        organism = synthetic construct
SEQUENCE: 352
ataagtgaag gtgtcggacc agg                                           23

SEQ ID NO: 353          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 353
ttgaagctgc cagcatgatc tgg                                           23

SEQ ID NO: 354          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 354
ttgaagctgc cagcatgatc tgg                                           23

SEQ ID NO: 355          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 355
aggggaatgt tgtctggctc ggg                                           23

SEQ ID NO: 356          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 356
agggttgcct ataagatgga tgg                                           23

SEQ ID NO: 357          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 357
agaagagagt gagcacgcat cgg                                           23

SEQ ID NO: 358          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 358
aggggaatgt tgtctggctc ggg                                           23

SEQ ID NO: 359          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 359
aggggaatgt tgtctggctc ggg                                           23

SEQ ID NO: 360          moltype = DNA  length = 23
FEATURE                 Location/Qualifiers
misc_feature            1..23
                        note = Single strand oligonucleotide
```

```
source                  1..23
                        mol_type = other DNA
                        organism = synthetic construct
SEQUENCE: 360
cagccgtggc tcgttcggac cgg                                          23

SEQ ID NO: 361          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 361
agaaggttgt gatattggca cgg                                          23

SEQ ID NO: 362          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 362
aggggaatgt tgtctggctc ggg                                          23

SEQ ID NO: 363          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 363
aggggaatgt tgtctggctc ggg                                          23

SEQ ID NO: 364          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 364
gctggggatg tgaatcttga tgg                                          23

SEQ ID NO: 365          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 365
aggggaatgt tgtctggctc ggg                                          23

SEQ ID NO: 366          moltype = DNA  length = 23
FEATURE                 Location/Qualifiers
misc_feature            1..23
                        note = Single strand oligonucleotide
source                  1..23
                        mol_type = other DNA
                        organism = synthetic construct
SEQUENCE: 366
aggggaatgt tgtctggctc ggg                                          23

SEQ ID NO: 367          moltype = DNA  length = 22
FEATURE                 Location/Qualifiers
misc_feature            1..22
                        note = Single strand oligonucleotide
source                  1..22
                        mol_type = other DNA
                        organism = synthetic construct
SEQUENCE: 367
gttgagagtg ttggagaagg ag                                           22

SEQ ID NO: 368          moltype = DNA  length = 21
FEATURE                 Location/Qualifiers
misc_feature            1..21
```

-continued

```
                        note = Single strand oligonucleotide
source                  1..21
                        mol_type = other DNA
                        organism = synthetic construct
SEQUENCE: 368
ctcggtgttg atcctgagaa g                                     21

SEQ ID NO: 369          moltype = DNA  length = 20
FEATURE                 Location/Qualifiers
misc_feature            1..20
                        note = Single strand oligonucleotide
source                  1..20
                        mol_type = other DNA
                        organism = synthetic construct
SEQUENCE: 369
gtactgctgg tcctttgcag                                       20

SEQ ID NO: 370          moltype = DNA  length = 20
FEATURE                 Location/Qualifiers
misc_feature            1..20
                        note = Single strand oligonucleotide
source                  1..20
                        mol_type = other DNA
                        organism = synthetic construct
SEQUENCE: 370
aggagcacta cggaaggatg                                       20

SEQ ID NO: 371          moltype = DNA  length = 19
FEATURE                 Location/Qualifiers
misc_feature            1..19
                        note = Single strand oligonucleotide
source                  1..19
                        mol_type = other DNA
                        organism = synthetic construct
SEQUENCE: 371
acaccctggg aattggttt                                        19

SEQ ID NO: 372          moltype = DNA  length = 20
FEATURE                 Location/Qualifiers
misc_feature            1..20
                        note = Single strand oligonucleotide
source                  1..20
                        mol_type = other DNA
                        organism = synthetic construct
SEQUENCE: 372
gtatgcgcca ataagaccac                                       20

SEQ ID NO: 373          moltype = DNA  length = 95
FEATURE                 Location/Qualifiers
misc_feature            1..95
                        note = Single strand oligonucleotide
source                  1..95
                        mol_type = other DNA
                        organism = synthetic construct
SEQUENCE: 373
accagaagcg aacatctctt tttagtgttg ttttgttacg acaaagtaga gcttttgtag  60
gcattgggtt gctttagttt cttctcctgc ccttc                      95

SEQ ID NO: 374          moltype = DNA  length = 22
FEATURE                 Location/Qualifiers
misc_feature            1..22
                        note = Single strand oligonucleotide
source                  1..22
                        mol_type = other DNA
                        organism = synthetic construct
SEQUENCE: 374
ttcgcttgca gagagaaatc ac                                    22

SEQ ID NO: 375          moltype = DNA  length = 95
FEATURE                 Location/Qualifiers
misc_feature            1..95
                        note = Single strand oligonucleotide
source                  1..95
                        mol_type = other DNA
                        organism = synthetic construct
SEQUENCE: 375
aacttcttca gcacgacgaa gtacaccagc cccatcgccg acttcgtgac gtgcggcatc  60
cagtcccacc agtgctccca cccggtcccg tgccc                      95
```

-continued

```
SEQ ID NO: 376          moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 376
aagtcgtgct gcttcatgtg g                                            21

SEQ ID NO: 377          moltype = DNA  length = 95
FEATURE                 Location/Qualifiers
misc_feature            1..95
                        note = Single strand oligonucleotide
source                  1..95
                        mol_type = other DNA
                        organism = synthetic construct
SEQUENCE: 377
acaacatcaa catgaggtcg aacacggggt cctacaacgg caggaggaac ttcagctacg  60
ggaagtcgag ctacgccaag tggtcccaca gcggg                             95

SEQ ID NO: 378          moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 378
agttgtactc cagcttgtgc c                                            21

SEQ ID NO: 379          moltype = DNA  length = 95
FEATURE                 Location/Qualifiers
misc_feature            1..95
                        note = Single strand oligonucleotide
source                  1..95
                        mol_type = other DNA
                        organism = synthetic construct
SEQUENCE: 379
aaccttatag gtgtgtttga tggacgtttc ctggtcgtca tgaggaggag gaacaagaac  60
agaattcgcg aactcttcac ccttgggatt tcgat                             95

SEQ ID NO: 380          moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 380
tatccacaca aactacctgc a                                            21

SEQ ID NO: 381          moltype = DNA  length = 95
FEATURE                 Location/Qualifiers
misc_feature            1..95
                        note = Single strand oligonucleotide
source                  1..95
                        mol_type = other DNA
                        organism = synthetic construct
SEQUENCE: 381
acgtcaactg ttaggtcggt taggtcgtgg tcgttaatgt tgaaagtttc cgaatcgtcc  60
tgctcctcgt gatgccttcc tacgtctatt tgatc                             95

SEQ ID NO: 382          moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 382
tgacaatcca gccaatccag c                                            21

SEQ ID NO: 383          moltype = DNA  length = 94
FEATURE                 Location/Qualifiers
misc_feature            1..94
                        note = Single strand oligonucleotide
source                  1..94
                        mol_type = other DNA
```

```
                        organism = synthetic construct
SEQUENCE: 383
gaggccattt ctagccgttg tgtactagag gaccgacttc tagtcagtga ggaagaggtt  60
gtgagagttg ttagggaggt cgaagtaccg gctt                              94

SEQ ID NO: 384          moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 384
taaagatcgg caacacatga t                                            21

SEQ ID NO: 385          moltype = DNA  length = 94
FEATURE                 Location/Qualifiers
misc_feature            1..94
                        note = Single strand oligonucleotide
source                  1..94
                        mol_type = other DNA
                        organism = synthetic construct
SEQUENCE: 385
tgtgaaactg gaaagaaccc aaatcggtgt aagtttcaac gaggattggg tcatctgttt  60
ggtgttgact gttatgtctg gaacagttct cctc                              94

SEQ ID NO: 386          moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 386
tgacctttct tgggtttagc c                                            21

SEQ ID NO: 387          moltype = DNA  length = 87
FEATURE                 Location/Qualifiers
misc_feature            1..87
                        note = Single strand oligonucleotide
source                  1..87
                        mol_type = other DNA
                        organism = synthetic construct
SEQUENCE: 387
ctgattttcg agtctatcct attgtggcga aatagtaact ttgaccttac ggcttctttt  60
tgagttacag agtcgtgtcg cctaggt                                      87

SEQ ID NO: 388          moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 388
aagctcagga gggatagcgc c                                            21

SEQ ID NO: 389          moltype = DNA  length = 87
FEATURE                 Location/Qualifiers
misc_feature            1..87
                        note = Single strand oligonucleotide
source                  1..87
                        mol_type = other DNA
                        organism = synthetic construct
SEQUENCE: 389
aacttcttca gcacgacgaa gtacaccagc cccatcgccg acttcgtgac gtgcggcatc  60
cagtcccacc agtgctccca cccggtc                                      87

SEQ ID NO: 390          moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 390
aagtcgtgct gcttcatgtg g                                            21

SEQ ID NO: 391          moltype = DNA  length = 87
```

-continued

```
FEATURE                Location/Qualifiers
misc_feature           1..87
                       note = Single strand oligonucleotide
source                 1..87
                       mol_type = other DNA
                       organism = synthetic construct
SEQUENCE: 391
acaacatcaa catgaggtcg aacacggggt cctacaacgg caggaggaac ttcagctacg  60
ggaagtcgag ctacgccaag tggtccc                                      87

SEQ ID NO: 392         moltype = DNA  length = 21
FEATURE                Location/Qualifiers
misc_feature           1..21
                       note = Single strand oligonucleotide
source                 1..21
                       mol_type = other DNA
                       organism = synthetic construct
SEQUENCE: 392
agttgtactc cagcttgtgc c                                            21

SEQ ID NO: 393         moltype = DNA  length = 87
FEATURE                Location/Qualifiers
misc_feature           1..87
                       note = Single strand oligonucleotide
source                 1..87
                       mol_type = other DNA
                       organism = synthetic construct
SEQUENCE: 393
aaccttatag gtgtgtttga tggacgtttc ctggtcgtca tgaggaggag gaacaagaac  60
agaattcgcg aactcttcac ccttggg                                      87

SEQ ID NO: 394         moltype = DNA  length = 21
FEATURE                Location/Qualifiers
misc_feature           1..21
                       note = Single strand oligonucleotide
source                 1..21
                       mol_type = other DNA
                       organism = synthetic construct
SEQUENCE: 394
tatccacaca aactacctgc a                                            21

SEQ ID NO: 395         moltype = DNA  length = 87
FEATURE                Location/Qualifiers
misc_feature           1..87
                       note = Single strand oligonucleotide
source                 1..87
                       mol_type = other DNA
                       organism = synthetic construct
SEQUENCE: 395
acgtcaactg ttaggtcggt taggtcgtgg tcgttaatgt tgaaagtttc cgaatcgtcc  60
tgctcctcgt gatgccttcc tacgtct                                      87

SEQ ID NO: 396         moltype = DNA  length = 21
FEATURE                Location/Qualifiers
misc_feature           1..21
                       note = Single strand oligonucleotide
source                 1..21
                       mol_type = other DNA
                       organism = synthetic construct
SEQUENCE: 396
tgacaatcca gccaatccag c                                            21

SEQ ID NO: 397         moltype = DNA  length = 87
FEATURE                Location/Qualifiers
misc_feature           1..87
                       note = Single strand oligonucleotide
source                 1..87
                       mol_type = other DNA
                       organism = synthetic construct
SEQUENCE: 397
gaggccattt ctagccgttg tgtactagag gaccgacttc tagtcagtga ggaagaggtt  60
gtgagagttg ttagggaggt cgaagta                                      87

SEQ ID NO: 398         moltype = DNA  length = 21
FEATURE                Location/Qualifiers
misc_feature           1..21
                       note = Single strand oligonucleotide
source                 1..21
                       mol_type = other DNA
```

-continued

```
                        organism = synthetic construct
SEQUENCE: 398
taaagatcgg caacacatga t                                            21

SEQ ID NO: 399          moltype = DNA  length = 89
FEATURE                 Location/Qualifiers
misc_feature            1..89
                        note = Single strand oligonucleotide
source                  1..89
                        mol_type = other DNA
                        organism = synthetic construct
SEQUENCE: 399
tgtgaaactg gaaagaaccc aaatcggtgt aagtttcaac gaggattggg tcatctgttt  60
ggtgttgact gttatgtctg gaacagttc                                    89

SEQ ID NO: 400          moltype = DNA  length = 21
FEATURE                 Location/Qualifiers
misc_feature            1..21
                        note = Single strand oligonucleotide
source                  1..21
                        mol_type = other DNA
                        organism = synthetic construct
SEQUENCE: 400
tgacctttct tgggtttagc c                                            21

SEQ ID NO: 401          moltype = DNA  length = 416
FEATURE                 Location/Qualifiers
misc_feature            1..416
                        note = Single strand oligonucleotide
source                  1..416
                        mol_type = other DNA
                        organism = synthetic construct
SEQUENCE: 401
aaaacgtaat aagttctttt tgtgtgtgtc tgcaggcaat atcaaaaaca taaccatcat  60
gatgtataga gactgtcggg tccattgtga ggagacattc agtttctctt taaaactcct  120
tcattgaaat agtccggtgt tatccctacc tgagcttagt ttttttttt taattttttt  180
tctgtcctat tgaattattc tattctcttg tccatgttcg acccatccct ttcaaagtat  240
ctcaaccttc tatcgtttta aagactctct cctatctctt tttggtgttg agtatgtgtg  300
tatctctact cctagttcat ttgaatcagt ttttctacct tgtctatccc tcctgagcta  360
atgtttgcat cttcttgttg gtcattgatg tatggttgat ataaattcca aataaa      416

SEQ ID NO: 402          moltype = DNA  length = 416
FEATURE                 Location/Qualifiers
misc_feature            1..416
                        note = Single strand oligonucleotide
source                  1..416
                        mol_type = other DNA
                        organism = synthetic construct
SEQUENCE: 402
aaaacgtaat aagttctttt tgtgtgtgtc tgcaggcaat atcaaaaaca taaccatcat  60
gatgtataga gactgtcggg tccattgtga ggagacattc agtttctctt taaaactcct  120
tcattgaaat agtccggtgt tatccctacc tgagcttagt ttttttttt taattttttt  180
tctgtcctat tgaattattc tattggtcac ttgaccgcca tgacatccct ttcaaagtat  240
ctcaaccttc tatcgtttta aagactctct cctatctctt tttggtgttg agtatgtgtg  300
tatctctact cctagttcat ttgaatcagt ttttctacct tgtctatccc tcctgagcta  360
atgtttgcat cttcttgttg gtcattgatg tatggttgat ataaattcca aataaa      416

SEQ ID NO: 403          moltype = DNA  length = 416
FEATURE                 Location/Qualifiers
misc_feature            1..416
                        note = Single strand oligonucleotide
source                  1..416
                        mol_type = other DNA
                        organism = synthetic construct
SEQUENCE: 403
aaaacgtaat aagttctttt tgtgtgtgtc tgcaggcaat atcaaaaaca taaccatcat  60
gatgtataga gactgtcggg tccattgtga ggagacattc agtttctctt taaaactcct  120
tcattgaaat agtccggtgt tatccctacc tgagcttagt ttttttttt taattttttt  180
tctgtcctat tgaattattc tattttcttg accttgtaag acccatccct ttcaaagtat  240
ctcaaccttc tatcgtttta aagactctct cctatctctt tttggtgttg agtatgtgtg  300
tatctctact cctagttcat ttgaatcagt ttttctacct tgtctatccc tcctgagcta  360
atgtttgcat cttcttgttg gtcattgatg tatggttgat ataaattcca aataaa      416

SEQ ID NO: 404          moltype = DNA  length = 107
FEATURE                 Location/Qualifiers
misc_feature            1..107
                        note = Single strand oligonucleotide
source                  1..107
                        mol_type = other DNA
```

```
                         organism = synthetic construct
SEQUENCE: 404
gtagagaaga atctgtaaag ctcaggaggg atagcgccat gatgatcaca ttcgttatct    60
atttttggc gctatccatc ctgagtttca ttggctcttc ttactac                  107

SEQ ID NO: 405           moltype = DNA   length = 107
FEATURE                  Location/Qualifiers
misc_feature             1..107
                         note = Single strand oligonucleotide
source                   1..107
                         mol_type = other DNA
                         organism = synthetic construct
SEQUENCE: 405
gtagagaaga atctgtaaag tcgtgctgct tcatgtggat gatgatcaca ttcgttatct    60
attttttcca catgaagaag cacgacttga ttggctcttc ttactac                 107

SEQ ID NO: 406           moltype = DNA   length = 107
FEATURE                  Location/Qualifiers
misc_feature             1..107
                         note = Single strand oligonucleotide
source                   1..107
                         mol_type = other DNA
                         organism = synthetic construct
SEQUENCE: 406
gtagagaaga atctgtaagt tgtactccag cttgtgccat gatgatcaca ttcgttatct    60
atttttggc acaagcttga gtacaactga ttggctcttc ttactac                  107

SEQ ID NO: 407           moltype = DNA   length = 107
FEATURE                  Location/Qualifiers
misc_feature             1..107
                         note = Single strand oligonucleotide
source                   1..107
                         mol_type = other DNA
                         organism = synthetic construct
SEQUENCE: 407
gtagagaaga atctgtatat ccacacaaac tacctgcaat gatgatcaca ttcgttatct    60
atttttttgc aggtagtgtg tgtggataga ttggctcttc ttactac                 107

SEQ ID NO: 408           moltype = DNA   length = 107
FEATURE                  Location/Qualifiers
misc_feature             1..107
                         note = Single strand oligonucleotide
source                   1..107
                         mol_type = other DNA
                         organism = synthetic construct
SEQUENCE: 408
gtagagaaga atctgtatga caatccagcc aatccagcat gatgatcaca ttcgttatct    60
attttttgct ggattggatg gattgtcaga ttggctcttc ttactac                 107

SEQ ID NO: 409           moltype = DNA   length = 107
FEATURE                  Location/Qualifiers
misc_feature             1..107
                         note = Single strand oligonucleotide
source                   1..107
                         mol_type = other DNA
                         organism = synthetic construct
SEQUENCE: 409
gtagagaaga atctgtataa agatcggcaa cacatgatat gatgatcaca ttcgttatct    60
atttttatc atgtgttacc gatctttaca ttggctcttc ttactac                  107

SEQ ID NO: 410           moltype = DNA   length = 107
FEATURE                  Location/Qualifiers
misc_feature             1..107
                         note = Single strand oligonucleotide
source                   1..107
                         mol_type = other DNA
                         organism = synthetic construct
SEQUENCE: 410
gtagagaaga atctgtatga cctttcttgg gtttagccat gatgatcaca ttcgttatct    60
atttttggc taaaccccag aaaggtcaca ttggctcttc ttactac                  107

SEQ ID NO: 411           moltype = DNA   length = 102
FEATURE                  Location/Qualifiers
misc_feature             1..102
                         note = Single strand oligonucleotide
source                   1..102
                         mol_type = other DNA
                         organism = synthetic construct
SEQUENCE: 411
```

-continued

```
taagtacttt cgcttgcaga gagaaatcac agtggtcaaa aaagttgtag ttttcttaaa  60
gtctctttcc tctgtgattc tctgtgtaag cgaaagagct tg                     102

SEQ ID NO: 412          moltype = DNA  length = 102
FEATURE                 Location/Qualifiers
misc_feature            1..102
                        note = Single strand oligonucleotide
source                  1..102
                        mol_type = other DNA
                        organism = synthetic construct
SEQUENCE: 412
taagtactta agtcgtgctg cttcatgtgg agtggtcaaa aaagttgtag ttttcttaaa  60
gtctctttcc tctccacata agcaggacga gttaagagct tg                     102

SEQ ID NO: 413          moltype = DNA  length = 102
FEATURE                 Location/Qualifiers
misc_feature            1..102
                        note = Single strand oligonucleotide
source                  1..102
                        mol_type = other DNA
                        organism = synthetic construct
SEQUENCE: 413
taagtactta gttgtactcc agcttgtgcc agtggtcaaa aaagttgtag ttttcttaaa  60
gtctctttcc tctggcaaag ctgcagtaca actaagagct tg                     102

SEQ ID NO: 414          moltype = DNA  length = 102
FEATURE                 Location/Qualifiers
misc_feature            1..102
                        note = Single strand oligonucleotide
source                  1..102
                        mol_type = other DNA
                        organism = synthetic construct
SEQUENCE: 414
taagtacttt atccacacaa actacctgca agtggtcaaa aaagttgtag ttttcttaaa  60
gtctctttcc tcttgcagta gttagtgtgg ataaagagct tg                     102

SEQ ID NO: 415          moltype = DNA  length = 102
FEATURE                 Location/Qualifiers
misc_feature            1..102
                        note = Single strand oligonucleotide
source                  1..102
                        mol_type = other DNA
                        organism = synthetic construct
SEQUENCE: 415
taagtacttt gacaatccag ccaatccagc agtggtcaaa aaagttgtag ttttcttaaa  60
gtctctttcc tctgctgatt ggcaggattg tcaaagagct tg                     102

SEQ ID NO: 416          moltype = DNA  length = 102
FEATURE                 Location/Qualifiers
misc_feature            1..102
                        note = Single strand oligonucleotide
source                  1..102
                        mol_type = other DNA
                        organism = synthetic construct
SEQUENCE: 416
taagtacttt aaagatcggc aacacatgat agtggtcaaa aaagttgtag ttttcttaaa  60
gtctctttcc tctgatcagt gttggcgatc tttaagagct tg                     102

SEQ ID NO: 417          moltype = DNA  length = 102
FEATURE                 Location/Qualifiers
misc_feature            1..102
                        note = Single strand oligonucleotide
source                  1..102
                        mol_type = other DNA
                        organism = synthetic construct
SEQUENCE: 417
taagtacttt gacctttctt gggtttagcc agtggtcaaa aaagttgtag ttttcttaaa  60
gtctctttcc tctgggctaa cccatgaaag gtcaagagct tg                     102
```